(12) United States Patent
Khan et al.

(10) Patent No.: US 7,783,431 B2
(45) Date of Patent: *Aug. 24, 2010

(54) METHODS FOR ANALYZING HIGH DIMENSIONAL DATA FOR CLASSIFYING, DIAGNOSING, PROGNOSTICATING, AND/OR PREDICTING DISEASES AND OTHER BIOLOGICAL STATES

(75) Inventors: Javed Khan, Derwood, MD (US); Markus Ringner, Lund (SE); Carsten Peterson, Lund (SE); Paul Meltzer, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/928,901

(22) Filed: Oct. 30, 2007

(65) Prior Publication Data
US 2009/0035766 A1 Feb. 5, 2009

Related U.S. Application Data

(63) Continuation of application No. 10/133,937, filed on Apr. 25, 2002.

(51) Int. Cl.
*G06F 19/00* (2006.01)
*G06F 17/10* (2006.01)
*G06N 3/00* (2006.01)
*G06G 7/00* (2006.01)
*G06G 7/58* (2006.01)

(52) U.S. Cl. .............................. 702/19; 702/13; 702/15; 703/2; 703/11

(58) Field of Classification Search ....................... None
See application file for complete search history.

(56) References Cited

U.S. PATENT DOCUMENTS

| | | | |
|---|---|---|---|
| 6,794,137 | B2 | 9/2004 | Blumenberg |
| 7,062,384 | B2 | 6/2006 | Rocke et al. |
| 7,229,774 | B2 | 6/2007 | Chinnaiyan et al. |
| 7,341,552 | B2 | 3/2008 | Zhang et al. |
| 7,370,021 | B2 | 5/2008 | Reeve et al. |
| 7,384,736 | B2 | 6/2008 | Hakonarson |
| 7,402,388 | B2 | 7/2008 | Gillis et al. |
| 7,402,399 | B2 | 7/2008 | Mukherjeei et al. |
| 2003/0207278 | A1 | 11/2003 | Khan et al. |
| 2004/0009154 | A1 | 1/2004 | Khan et al. |
| 2008/0181896 | A1 | 7/2008 | Khan et al. |

OTHER PUBLICATIONS

NHGRI Protocol, http://www.nhgri.hih.gov/DIR/LGG/SK/HTML/protocol.html, 27 pages (Apr. 25, 2002).
Furey et al., *Bioinformatics*, 16(10):906-914 (2000).
Herrero et al., *Bioinformatics*, 17(2):126-136 (2001).
Muller et al., *IEEE Transactions on Neural Networks*, 12(2):181-201 (2001).
Raychaudhuri et al., *Trends in Biotechnology*, 19(5):189-193 (2001).
GenBank Accession No. NM_000612, dated Oct. 31, 2000.
Blast Alignment between GenBank Accession No. NM_000612 and SEQ ID No. 72, dated Aug. 16, 2007.
Agilent Technology Webpage, dated Aug. 16, 2007.
Image Consortium Record printed Aug. 15, 2007.
GenBank Accession No. N54901, dated Jan. 28, 1997.
GenBank Sequence Revision History page printed Aug. 15, 2007.
GenCard Database Record IGF2 printed Aug. 15, 2007.
Golub et al., "Molecular Classification of Cancer: Class Discovery and Class Prediction by Gene Expression Monitoring", Science, 286:531-537 (1999).
Gruvberger et al., "Estrogen Receptor Status in Breast Cancer is Associated with Remarkably Distinct Gene Expression Patterns", Cancer Research, 61:5979-5984 (2001).
Kwon et al., "DNA Microarray Data Analysis for Cancer Classification Based on Stepwise Discriminant Analysis and Bayesian Decision Theory", Genome Informatics, 12:252-254 (2001).
Cover page of Nature Medicine, vol. 7, No. 6, Jun. 2001 (received Jun. 15, 2001).
Sequence Alignment printed Sep. 11, 2006.
Image Id. No. record printed Sep. 21, 2006.
Tips for cDNA sequences printed Sep. 21, 2006.
Sperduti et al., "Supervised Neural Networks for the Classification of Structures, IEEE Transaction on Neural Networks", 8(3):714-735 (1997).
Khan et al., "Classification and diagnostic prediction of cancers using gene expression profiling and artificial neural networks", Nature Medicine, 7(6):673-679 (2001).
Peterson et al., "JETNET 3.0—A versatile artificial neural network package", Computer Physics Communications, 81:185-220 (1994).
Tusher et al., "Significance analysis of microarrays applied to the ionizing radiation response", PNAS, 98(9):5116-5121 (2001).
Van Gelder et al., "Amplified RNA synthesized from limited quantities of heterogeneous cDNA", Proc. Natl. Acad. Sci. USA, 87(5):1663-1667 (1990).
Ancoca et al., "On the statistical assessment of classifiers using DNA microarray data", BMC Bioinformatics, 7:387 (2006).
Chen et al., "Diagnosis of the Small Round Blue Cell Tumors Using Multiplex Polymerase Chain Reaction", Journal of Molecular Diagnostics, 9(1):80-88 (2007).
Kim et al., "ECgene: genome annotation for alternative splicing", Nucleic Acids Research, 33:D75-D79 (2005).

(Continued)

Primary Examiner—Lori A Clow
(74) Attorney, Agent, or Firm—Merchant & Gould P.C.

(57) ABSTRACT

A method of diagnosing, predicting, or prognosticating about a disease that includes obtaining experimental data, wherein the experimental data is high dimensional data, filtering the data, reducing the dimensionality of the data through use of one or more methods, training a supervised pattern recognition method, ranking individual data points from the data, wherein the ranking is dependent on the outcome of the supervised pattern recognition method, choosing multiple data points from the data, wherein the choice is based on the relative ranking of the individual data points, and using the multiple data points to determine if an unknown set of experimental data indicates a diseased condition, a predilection for a diseased condition, or a prognosis about a diseased condition.

11 Claims, 9 Drawing Sheets

OTHER PUBLICATIONS

Mateos et al., "Supervised Neural Networks for Clustering Conditions in DNA Array Data after Reducing Noise by Clustering Gene Expression Profiles", *Microarray data analysis II*, Kluwer Academic Publ., pp. 91-103 (2002).

Raychaudhuri et al., Pacific Symposium on Biocomputing (2000) pp. 455-466.

Li et al., Human Pathology, 2008, 39:1792-1801.

Wang et al., Human Genetics, 2006, 120:297-300.

U.S. Appl. No. 10/133,937 Office Action dated Jan. 22, 2009.

U.S. Appl. No. 10/159,563 Office Action dated Feb. 12, 2009.

U.S. Appl. No. 11/981,502 Restriction Requirement mailed Oct. 2, 2009.

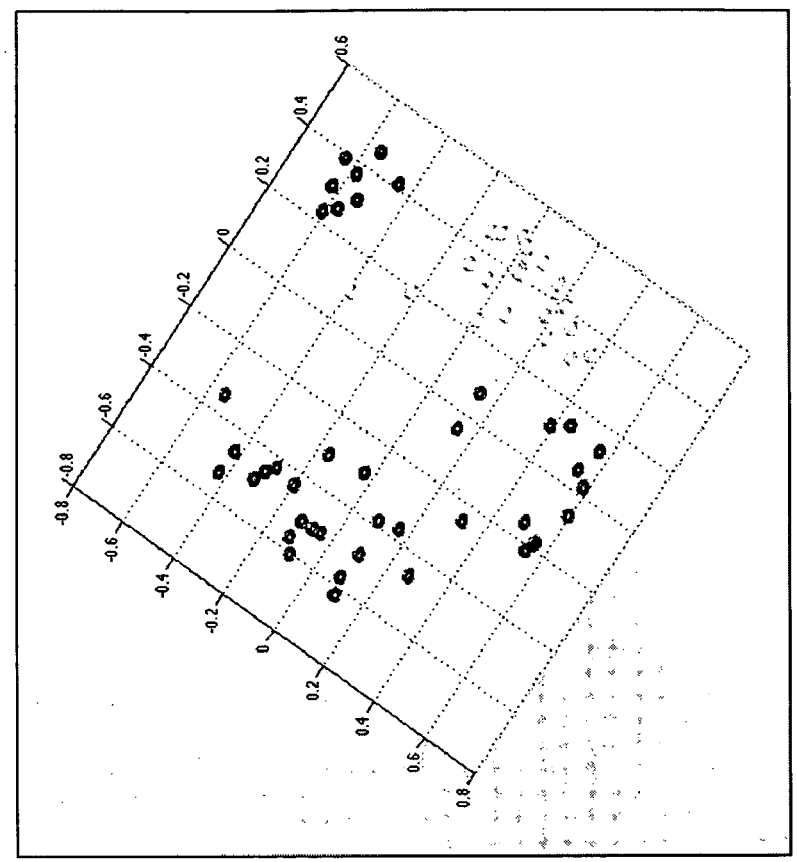
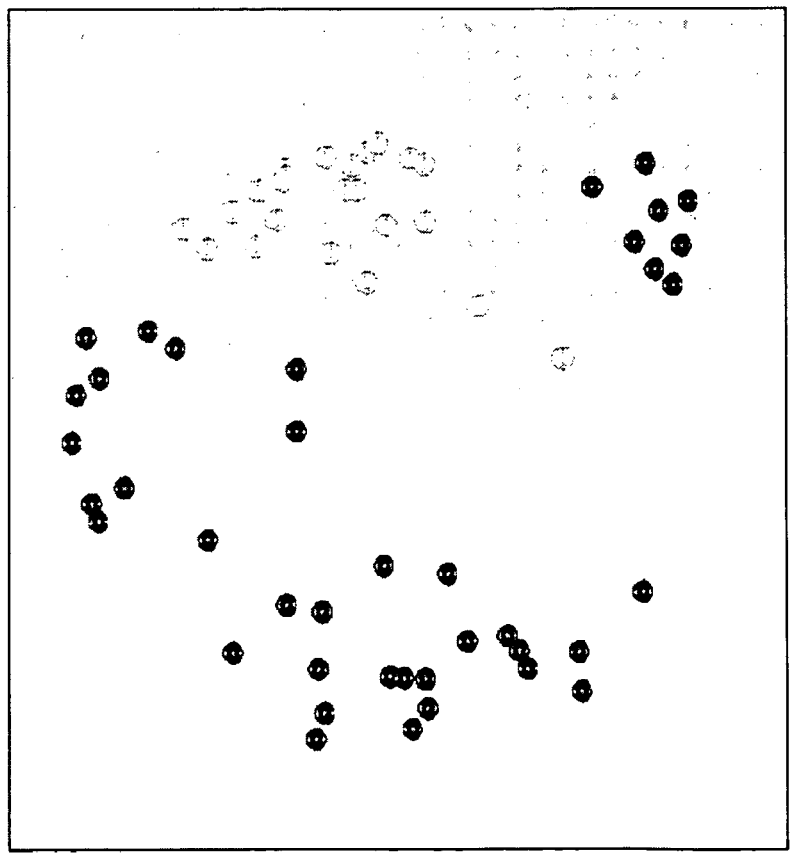
FIG. 7

SEQUENCE LISTING

```
<160> NUMBER OF SEQ ID NOS: 99

<210> SEQ ID NO 1
<211> LENGTH: 2318
<212> TYPE: DNA
<213> ORGANISM: Homo sapiens

<400> SEQUENCE: 1
cgcagggacc gtgctccgcc gtctccgccg catcttccac cctcgccgcc gccgcagctc      60
cccgcgctcg tgccaccgcc gccgcgtcca ccctcagcgc caccgccatg cgggagatcg     120
tgcacctgca ggccggccag tgcggcaacc agatcggggc caagttttgg gaggttatca    180
```

-continued

| | |
|---|---|
| gtgacgaaca tggcatcgac cccacaggca cataccatgg ggacagtgac ctgcaactgg | 240 |
| agaggatcaa cgtgtactac aacgaggcca caggaggaaa ttatgtcccc agagcggtgc | 300 |
| tggtggacct ggaacccggc accatggact ctgtccgttc tggccccttc ggtcagatct | 360 |
| ttcggccgga caacttcgtg tttggccaat ccggagccgg caacaactgg caaaggggc | 420 |
| actacacgga gggcgcagag ctggtggacg ctgtcctgga cgtagtccgg aaggaggccg | 480 |
| agagctgcga ctgccttcag ggcttccagc tgacccactc gctgggggt ggcacggggt | 540 |
| ccggaatggg cacgctgctc atcagtaaga tcccgaggag gttcccagac cgcatcatga | 600 |
| acaccttcag cgtggtgccc tcgcccaaag tgtcagacac ggtggtggag ccctacaacg | 660 |
| ccacgctgtc tgtgcaccag ctggtggaga atacggatga gacctactgc atcgacaacg | 720 |
| aggcactcta cgacatctgt ttccgcaccc tcaagctgac caccccccac cacgggggacc | 780 |
| tcaaccacct ggtgtcggcc accatgagcg gggtcaccac ctgcctgcgc ttcccggggcc | 840 |
| agctgaacgc cgacctgcgc aagctggccg tcaacatggt tccctttcct cgcctgcact | 900 |
| tcttcatgcc cggcttcgca ccctgacca gccggggcag ccagcagtac cgggccctga | 960 |
| cggtgcccga gctcacccag cagatgttcg atgccaagaa catgatggcg gcgtgcgacc | 1020 |
| cgcgccacgg ccgctacctg accgtggccg ccgtgttccg gggccgcatg tccatgaagg | 1080 |
| aggtggacga gcagatgctg agcgtgcaga gcaagaacag cagctacttc gtggagtgga | 1140 |
| tccccaacaa cgtgaagacg gccgtgtgcg acatcccgcc ccgcggcctg aagatggccg | 1200 |
| cgaccttcat cggcaacagc acggccatcc aggagctgtt caagcgcatc tccgagcagt | 1260 |
| tcacggccat gttccggcgc aaggccttct gcactggta cacgggcgag ggcatggacg | 1320 |
| agatggagtt caccgaggcc gagagcaaca tgaatgacct ggtatctgag taccagcagt | 1380 |
| accaggacgc cacggccgag gagggcgagt cgaggagga ggcggaggag gaggtggcct | 1440 |
| aggctgctcc catcgcttcc cacctgtccc ctcgaggctt ctgacctttg atccgctagg | 1500 |
| cccccccatct ctgaaccctta gagccccgct ttccctccaa ggctgactcc ccgctgaccc | 1560 |
| taacaatacc tttggagctc gcttttacctc tggctacttc atctccgacc ctggctcccc | 1620 |
| tttgagccct aatttatctt taaccccctt gagctcttcc aaccttgaca ttcccaggag | 1680 |
| gagccccgct tcaccccttc tgactctgga aaccgcacct ttaactttgc agaccttcct | 1740 |
| tcacccctga cttctgcttc acctttgacc tctgcccccc atgaatccca ttttacctct | 1800 |
| agacctataa gttctggttt atgtttgacc cctccctctg agctgcactt caccgctgac | 1860 |
| cttgcctcac ctttaacccc ccacctgagc cccagctcct acctctgacc ccaacttctc | 1920 |
| tttgatctct gaatcccctc tgactccaac ttctctttca ccctctatga gtcccatttt | 1980 |
| acttctacac ctgcaagtcc tggtttatat ggaccccctc cctccgagct gcagttcacc | 2040 |
| tttgaccttg cctcaccttt caccccccac ccccacagc gtcagctcct acctctgacc | 2100 |
| ccagcttctc tctgattccc acaggcccca tgcatcctcc ctgcctcact cccctcagcc | 2160 |
| cctgccgacc ttagcttatc tgggagagaa acaaggcctg gtgcctgtga ggaagagagg | 2220 |
| tcacccctac cctccctccc cgcttccctg cctcaccctc aataaataaa ttaattgttg | 2280 |
| tcatggaaaa aaaaaaaaa aaaaaaaaaa aaaaaaaa | 2318 |

<210> SEQ ID NO 2
<211> LENGTH: 1399
<212> TYPE: DNA
<213> ORGANISM: Homo sapiens

<400> SEQUENCE: 2

```
agtgtgaaat cttcagagaa gaatttctct ttagttcttt gcaagaaggt agagataaag        60
acacttttc aaaaatggca atggtatcag aattcctcaa gcaggcctgg tttattgaaa        120
atgaagagca ggaatatgtt caaactgtga agtcatccaa aggtggtccc ggatcagcgg        180
tgagcccta tcctaccttc aatccatcct cggatgtcgc tgccttgcat aaggccataa        240
tggttaaagg tgtggatgaa gcaaccatca ttgacattct aactaagcga aacaatgcac        300
agcgtcaaca gatcaaagca gcatatctcc aggaaacagg aaagcccctg gatgaaacac        360
ttaagaaagc ccttacaggt caccttgagg aggttgtttt agctctgcta aaaactccag        420
cgcaatttga tgctgatgaa cttcgtgctg ccatgaaggg ccttggaact gatgaagata        480
ctctaattga gattttggca tcaagaacta acaaagaaat cagagacatt aacagggtct        540
acagagagga actgaagaga gatctggcca agacataac ctcagacaca tctggagatt        600
ttcggaacgc tttgctttct cttgctaagg gtgaccgatc tgaggacttt ggtgtgaatg        660
aagacttggc tgattcagat gccagggcct tgtatgaagc aggagaaagg agaaagggga        720
cagacgtaaa cgtgttcaat accatcctta ccaccagaag ctatccacaa cttcgcagag        780
tgtttcagaa atacaccaag tacagtaagc atgacatgaa caaagttctg gacctggagt        840
tgaaaggtga cattgagaaa tgcctcacag ctatcgtgaa gtgcgccaca agcaaaccag        900
cttcttgc agagaagctt catcaagcca tgaaggtgt tggaactcgc cataaggcat        960
tgatcaggat tatggtttcc cgttctgaaa ttgacatgaa tgatatcaaa gcattctatc       1020
agaagatgta tggtatctcc ctttgccaag ccatcctgga tgaaaccaaa ggagattatg       1080
agaaaatcct ggtggctctt tgtggaggaa actaaacatt cccttgatgg tctcaagcta       1140
tgatcagaag actttaatta tatattttca tcctataagc ttaaatagga agtttcttc       1200
aacaggatta cagtgtagct acctacatgc tgaaaaatat agcctttaaa tcatttttat       1260
attataactc tgtataatag agataagtcc attttttaaa aatgttttcc ccaaaccata       1320
aaaccctata caagttgttc tagtaacaat acatgagaaa gatgtctatg tagctgaaaa       1380
taaaatgacg tcacaagac                                                    1399
```

<210> SEQ ID NO 3
<211> LENGTH: 1432
<212> TYPE: DNA
<213> ORGANISM: Homo sapiens

<400> SEQUENCE: 3

```
gctgttcggc ctgcgtcgct ccgggagctg ccgacggacg gagcgccccc gccccgccc         60
ggccgcccgc ccgccgccgc catgcccttc tccaacagcc acaacgcact gaagctgcgc       120
ttcccggccg aggacgagtt ccccgacctg agcgcccaca caaccacat ggccaaggtg       180
ctgacccccg agctgtacgc ggagctgcgc gccaagagca cgccgagcgg cttcacgctg       240
gacgacgtca tccagacagg cgtggacaac ccgggccacc cgtacatcat gaccgtgggc       300
tgcgtggcgg gcgacgagga gtcctacgaa gtgttcaagg atctcttcga ccccatcatc       360
gaggaccggc acggcggcta caagcccagc gatgagcaca gaccgacct caaccccgac       420
aacctgcagg gcgcgacga cctggacccc aactacgtgc tgagctcgcg ggtgcgcacg       480
ggccgcagca tccgtggctt ctgcctcccc cgcactgca gccgcgggga gcgccgcgcc       540
atcgagaagc tcgcggtgga agccctgtcc agcctggacg gcgacctggc gggccgatac       600
tacgcgctca gagagcatga cggaggcgga g cagcagcagc tcatcgacga ccacttcctc       660
```

```
ttcgacaagc cgtgtcgcc cctgctgctg gcctcgggca tggcccgcga ctggcccgac      720
gcccgcggta tctggcacaa tgacaataag accttcctgg tgtgggtcaa cgaggaggac      780
cacctgcggg tcatctccat gcagaagggg ggcaacatga aggaggtgtt cacccgcttc      840
tgcaccggcc tcacccagat tgaaactctc ttcaagtcta aggactatga gttcatgtgg      900
aaccctcacc tgggctacat cctcacctgc ccatccaacc tgggcaccgg gctgcgggca      960
ggtgtgcata tcaagctgcc caacctgggc aagcatgaga agttctcgga ggtgcttaag     1020
cggctgcgac ttcagaagcg aggcacaggc ggtgtggaca cggctgcggt gggcggggtc     1080
ttcgacgtct ccaacgctga ccgcctgggc ttctcagagg tggagctggt gcagatggtg     1140
gtggacggag tgaagctgct catcgagatg gagcagcggc tggagcaggg ccaggccatc     1200
gacgacctca tgcctgccca gaaatgaagc ccggcccaca cccgacacca gccctgctgc     1260
ttcctaactt attgcctggg cagtgcccac catgcacccc tgatgttcgc cgtctggcga     1320
gcccttagcc ttgctgtaga gacttccgtc acccttggta gagtttattt ttttgatggc     1380
taagatactg ctgatgctga aataaactag gttttggcc tgcctgcgtc tg              1432
```

<210> SEQ ID NO 4  
<211> LENGTH: 2384  
<212> TYPE: DNA  
<213> ORGANISM: Homo sapiens

<400> SEQUENCE: 4

```
gagctcctgt caccgctggg gccgggccgg gcgggagtgc aggggacgtg agggcgcaag       60
ggccgggaca tggggcccgc cagccccgct gctcgcggtc taagtcgccg cccgggccag      120
ccgccgctgc cgctgctgct gccactattg ctgctgcttc tgcgcgcgca gcccgccatc      180
gggagcctgg ccggtgggag ccccggcgcg gccgaggccc cggggtcggc ccaggtggct      240
ggactatgcg ggcgcctaac ccttcaccgg gacctgcgca ccggccgctg ggaaccagac      300
ccacagcgct ctcgacgctg tctccgggac ccgcagcgcg tgctggagta ctgcagacag      360
atgtacccgg agctgcagat tgcacgtgtg agcaggcta cgcaggccat ccccatggag      420
cgctggtgcg ggggttcccg gagcggcagc tgcgcccacc cccaccacca ggttgtgccc      480
ttccgctgcc tgcctggtga atttgtgagt gaggccctgc tggtgcctga aggctgccgg      540
ttcttgcacc aggagcgcat ggaccaatgt gagagttcaa cccggaggca tcaggaggca      600
caggaggcct gcagctccca gggcctcatc ctgcacggct cgggcatgct cttaccctgt      660
ggctcggatc ggttccgtgg tgtggagtat gtgtgctgtc cccctccagg accccccgac      720
ccatctggga cagcagttgg tgaccctcc accggtcct ggccccgggg gagcagagta      780 gaggggggctg aggacgagga agaggaggaa tccttcccac agccagtaga tgattacttc      840
gtggagcctc gcaggctga agaggaagag gaaacggtcc caccccaag ctcccataca      900 cttgcagtgg tcggcaaagt cactcccacc ccgaggccca cagacggtgt ggatattac      960 tttggcatgc ctgggggaaat cagtgagcac gaggggttcc tgagggccaa gatggacctg     1020
gaggagcgta ggatgcgcca gattaatgag gtgatgcgtg aatgggccat ggcagacaac     1080
cagtccaaga aacctgcctaa agccgacaga caggccctga tgagcactt ccagtccatt     1140 ctgcagactc tggaggagca ggtgtctggt gagcgacagc gcctggtgga aacccacgcc     1200
acccgcgtca tcgcccttat caacgaccag cgccggctg ccttggaggg cttcctggca     1260
gccctgcagg cagatccgcc tcaggcggag cgtgtcctgt tggccctgcg gcgctacctg     1320
```

```
cgtgcggagc agaaggaaca gaggcacacg ctgcgccact accagcatgt ggccgccgtg    1380
gatcccgaga aggcacagca gatgcgcttc caggtgcata cccaccttca agtgattgag    1440
gagagggtga atcagagcct gggcctgctt gaccagaacc cccacctggc tcaggagctg    1500
cggccccaaa tccaggaact cctccactct gaacacctgg gtcccagtga attggaagcc    1560
cctgcccctg ggggcagcag cgaggacaag ggtgggctgc agcctccaga ttccaaggat    1620 gacacccca tgacccttcc aaaagggtcc acagaacaag atgctgcatc ccctgagaaa     1680
gagaagatga acccgctgga acagtatgag cgaaaggtga atgcgtctgt tccaaggggt    1740 ttcccttcc actcatcgga gattcagagg gatgagctgg caccagctgg acagggtg       1800 tcccgtgagg ctgtgtcggg tctgctgatc atgggagcgg cggaggctc cctcatcgtc     1860 ctctccatgc tgctcctgcg caggaagaag ccctacgggg ctatcagcca tggcgtggtg    1920
gaggtggacc ccatgctgac cctggaggag cagcagctcc gcgaactgca gcggcacggc    1980
tatgagaacc ccacttaccg cttcctggag gaacgaccct gacccggccc ccttcacccc    2040
ttcagccgag cccagacctc ccctcttcct ggagcccag aaccccaact cccagcctag     2100
ggcagcaggg agtcttgaag tgatcattc acacccttt gtgagacggc tggaaattct      2160
tattccccct ttccaattcc aaaattccat ccctaagaat tcccagatag tcccagcagc    2220
ctccccacgt ggcacctcct caccttaatt tattttttaa gtttatttat ggctctttaa    2280
ggtgaccgcc accttggtcc tagtgtctat tccctggaat tcaccctctc atgtttccct    2340
actaacatcc caataaagtc ctcttcccta aaaaaaaaaa aaaa                     2384
```

<210> SEQ ID NO 5
<211> LENGTH: 1325
<212> TYPE: DNA
<213> ORGANISM: Homo sapiens

<400> SEQUENCE: 5

```
gcagtagcag cgagcagcag agtccgcacg ctccggcgag gggcagaaga gcgcgaggga     60
gcgcggggca gcagaagcga gagccgagcg cggacccagc caggacccac agccctcccc    120
agctgcccag gaagagcccc agccatggaa caccagctcc tgtgctgcga agtggaaacc    180
atccgccgcg cgtaccccga tgccaacctc ctcaacgacc gggtgctgcg ggccatgctg    240
aaggcggagg agacctgcgc gccctcggtg tcctacttca aatgtgtgca gaaggaggtc    300
ctgccgtcca tgcggaagat cgtcgccacc tggatgctgg aggtctgcga ggaacagaag    360
tgcgaggagg aggtcttccc gctggccatg aactacctgg accgcttcct gtcgctggag    420
cccgtgaaaa agagccgcct gcagctgctg ggggccactt gcatgttcgt ggcctctaag    480
atgaaggaga ccatccccct gacggccgag aagctgtgca tctacaccga cggctccatc    540
cggcccgagg agctgctgca aatggagctg ctcctggtga acaagctcaa gtggaacctg    600
gccgcaatga ccccgcacga tttcattgaa cacttcctct ccaaaatgcc agaggcggag    660
gagaacaaac agatcatccg caaacacgcg cagaccttcg ttgcctcttg tgccacagat    720
gtgaagttca tttccaatcc gcctccatg gtggcagcgg ggagcgtggt ggccgcagtg    780
caaggcctga acctgaggag ccccaacaac ttcctgtcct actaccgcct cacacgcttc    840
ctctccagag tgatcaagtg tgacccgac tgcctccggg cctgccagga gcagatcgaa    900
gccctgctgg agtcaagcct cgccaggcc cagcagaaca tggaccccaa ggccgccgag    960
gaggaggaag aggaggagga ggaggtggac ctggcttgca cacccaccga cgtgcggac    1020 gtggacatct gaggggccca ggcaggcggg cgccaccgcc acccgcagcg agggcggagc    1080
```

| | |
|---|---:|
| cggccccagg tgctccacat gacagtccct cctctccgga gcattttgat accagaaggg | 1140 |
| aaagcttcat tctccttgtt gttggttgtt ttttcctttg ctctttcccc cttccatctc | 1200 |
| tgacttaagc aaaagaaaaa gattacccaa aaactgtctt taaagagag agagagaaaa | 1260 |
| aaaaaaaaaa aaaaaaaaaa aaaaaaaaaa aaaaaaaaaa aaaaaaaaaa aaaaaaaaaa | 1320 |
| aaaaa | 1325 |

<210> SEQ ID NO 6
<211> LENGTH: 2254
<212> TYPE: DNA
<213> ORGANISM: Homo sapiens

<400> SEQUENCE: 6

| | |
|---|---:|
| aatcgaaagt agactctttt ctgaagcatt tcctgggatc agcctgacca cgctccatac | 60 |
| tgggagaggc ttctgggtca aaggaccagt ctgcagaggg atcctgtggc tggaagcgag | 120 |
| gaggctccac acggccgttg cagctaccgc agccaggatc tgggcatcca ggcacggcca | 180 |
| tgacccctcc gaggctcttc tgggtgtggc tgctggttgc aggaacccaa ggcgtgaacg | 240 |
| atggtgacat gcggctggcc gatggggggcg ccaccaacca gggccgcgtg gagatcttct | 300 |
| acagaggcca gtggggcact gtgtgtgaca acctgtggga cctgactgat gccagcgtcg | 360 |
| tctgccgggc cctgggcttc gagaacgcca cccaggctct gggcagagct gccttcgggc | 420 |
| aaggatcagg ccccatcatg ctggacgagg tccagtgcac gggaaccgag gcctcactgg | 480 |
| ccgactgcaa gtccctgggc tggctgaaga gcaactgcag gcacgagaga gacgctggtg | 540 |
| tggtctgcac caatgaaacc aggagcaccc acccctggga cctctccagg gagctctcgg | 600 |
| aggcccttgg ccagatcttt gacagccagc ggggctgcga cctgtccatc agcgtgaatg | 660 |
| tgcagggcga ggacgccctg ggcttctgtg ccacacggt catcctgact gccaacctgg | 720 |
| aggcccaggc cctgtggaag gagccgggca gcaatgtcac catgagtgtg gatgctgagt | 780 |
| gtgtgcccat ggtcagggac cttctcaggt acttctactc cgaaggatt gacatcaccc | 840 |
| tgtcgtcagt caagtgcttc cacaagctgg cctctgccta ggggccagg cagctgcagg | 900 |
| gctactgcgc aagcctcttt gccatcctcc tcccccagga cccctcgttc cagatgcccc | 960 |
| tggacctgta tgcctatgca gtggccacag gggacgccct gctggagaag ctctgcctac | 1020 |
| agttcctggc ctggaacttc gaggccttga cgcaggccga ggcctggccc agtgtcccca | 1080 |
| cagacctgct ccaactgctg ctgcccagga gcgacctggc ggtgcccagc gagctggccc | 1140 |
| tactgaaggc cgtggacacc tggagctggg gggagcgtgc ctcccatgag gaggtggagg | 1200 |
| gcttggtgga aagatccgc ttccccatga tgctccctga ggagctcttt gagctgcagt | 1260 |
| tcaacctgtc cctgtactgg agccacgagg ccctgttcca aagaagact ctgcaggccc | 1320 |
| tggaattcca cactgtgccc ttccagttgc tggcccggta caaaggcctg aacctcaccg | 1380 |
| aggataccta caagcccgg atttacacct cgcccacctg gagtgccttt gtgacagaca | 1440 |
| gttcctggag tgcacggaag tcacaactgg tctatcagtc cagacggggg ctttggtca | 1500 |
| aatattcttc tgattacttc caagccccct ctgactacag atactacccc taccagtcct | 1560 |
| tccagactcc acaacacccc agcttcctct tccaggacaa gagggtgtcc tggtccctgg | 1620 |
| tctacctccc caccatccag agctgctgga actacggctt ctcctgctcc tcggacgagc | 1680 |
| tccctgtcct gggcctcacc aagtctggcg gctcagatcg caccattgcc tacgaaaaca | 1740 |
| aagccctgat gctctgcgaa gggctcttcg tggcagacgt caccgatttc gagggctgga | 1800 |

```
aggctgcgat tcccagtgcc ctggacacca acagctcgaa gagcacctcc tccttcccct    1860
gcccggcagg gcacttcaac ggcttccgca cggtcatccg cccccttctac ctgaccaact   1920 cctcaggtgt ggactagacg cgtggccaag ggtggtgaga accggagaac cccaggacgc    1980
cctcactgca ggctcccctc ctcggcttcc ttcctctctg caatgacctt caacaaccgg    2040
ccaccagatg tcgccctact cacctgaggc tcagcttcaa gaaattactg gaaggcttcc    2100
actagggtcc accaggagtt ctcccaccac ctcaccagtt tccaggtggt aagcaccagg    2160
aggccctcga ggttgctctg gatcccccca cagcccctgg tcagtctgcc cttgtcactg    2220
gtctgaggtc attaaaatta cattgaggtt ccta                                2254

<210> SEQ ID NO 7
<211> LENGTH: 4213
<212> TYPE: DNA
<213> ORGANISM: Homo sapiens

<400> SEQUENCE: 7
tccactcctg gagcccgcgg accccgagca cgcgcctgac agcccctgct ggcccggcgc      60
gcggcgtcgc caggccagct atggcccccg accggtggc cgccgagacc gcggctcagg     120
gacctacccc gcgctacttc acctgggacg aggtggccca gcgctcaggg tgcgaggagc    180
ggtggctagt gatcgaccgt aaggtgtaca acatcagcga gttcacccgc cggcatccag    240
ggggctcccg ggtcatcagc cactacgccg ggcaggatgc cacggatccc tttgtggcct    300
tccacatcaa caagggcctt gtgaagaagt atatgaactc tctcctgatt ggagaactgt    360
ctccagagca gcccagcttt gagcccacca agaataaaga gctgacagat gagttccggg    420
agctgcgggc cacagtggag cggatgggc tcatgaaggc caaccatgtc ttcttcctgc     480
tgtacctgct gcacatcttg ctgctggatg gtgcagcctg gctcacccett tgggtctttg    540 ggacgtcctt tttgcccttc ctcctctgtg cggtgctgct cagtgcagtt caggcccagg    600
ctggctggct gcagcatgac tttgggcacc tgtcggtctt cagcacctca aagtggaacc    660
atctgctaca tcattttgtg attggccacc tgaagggggc ccccgccagt tggtggaacc    720
acatgcactt ccagcaccat gccaagccca actgcttccg caaagaccca gacatcaaca    780
tgcatcccct tcttctttgcc ttggggaaga tcctctctgt ggagcttggg aaacagaaga    840
aaaaatatat gccgtacaac caccagcaca atatacttctt cctaattggg cccccagcct   900
tgctgcctct ctacttccag tggtatattt tctatttgt tatccagcga agaagtggg      960 tggacttggc ctggatgatt accttctacg tccgcttctt cctcacttat gtgccactat    1020
tggggctgaa agccttcctg ggcctttctt tcatagtcag gttcctggaa agcaactggt    1080
ttgtgtgggt gacacagatg aaccatattc ccatgcacat tgatcatgac cggaacatgg    1140
actgggtttc cacccagctc caggccacat gcaatgtcca caagtctgcc ttcaatgact   1200
ggttcagtgg acacctcaac ttccagattg agcaccatct tttcccacg atgcctcgac    1260 acaattacca caagtggct ccctggtgc agtccttgtg tgccaagcat ggcatagagt      1320
accagtccaa gccctgctg tcagccttcg ccgacatcat ccactcacta aaggagtcag     1380
ggcagctctg gctagatgcc tatcttcacc aataacaaca gccaccctgc ccagtctgga    1440
agaagaggag gaagactctg gagccaaggc agaggggagc ttgagggaca atgccactat    1500
agtttaatac tcagagggg ttgggttggg ggacataaag cctctgactc aaactcctcc     1560
cttttatctt ctagccacag ttctaagacc caaagtggg ggtggacaca gaagtcccta     1620
ggagggaagg agctgttggg gcagggtgt aaattattttc cttttctag tttggcacat     1680
```

```
gcaggtagtt ggtgaacaga gagaaccagg agggtaacag aagaggaggg acctactgaa      1740
cccagagtca ggaagagatt taacactaaa attccactca tgccgggcgt ggtggcacgc      1800
gcctgtaatc ccagctaccc aggaggctga ggcaggagaa tcgcttgaac cggggaggtg      1860
gaggttgcag tgagctgaga tcacgccatt gtactccagc ctgggcgaca gagcaagact      1920
ccatttcaaa aaaaaaaaaa aaatccactc atataaaagg tgagctcagc tcactggtcc      1980
atttctcagt ggcttctcca tcctcatttg caaacctcag agggataagg cagttgaacc      2040
tgatgagcaa gaattataac agcaaggaaa cattaatgct tagaattctg agatccagca      2100
caactcagtc tgtgggagct cagctcgctg cccagggata ggtatgacct atgtctgcct      2160
taggctgctg ggagatgcca ttctccagtt tcagaagcag gcagggcaaa ggtcaagact      2220
gtggtattgg ggtcttttgg ctctgaagga tcctggaacc actgattttg gtttattccc      2280
tccagggtct aaagagaaca agaggtgcta gctcttacca aaacagatgg tagagagagt      2340
tgctggctat ttaaaaagct cttcatctt ttaattcacc tcttcttttc acctctttaa       2400
ccactcctca ggaacagaac acttctagga ctgggggtct tttagctcca taagcaagtg      2460
agcagatggg acaagttagt cttttctccc tagaaacaaa ggggatgccc agtggtttcc      2520
ctttgcttcc caacctaaaa tttcaagttt aataaaatag caattagcag aagtgaccaa      2580
attgggagat aattatcagt catgaggaaa gacacagatt tcggtcataa agaatgtaag      2640
ggctataagt agaaactttc tataacctaa atgatgttat agaattattt ttgagcagga      2700
gcagaaagat taaatatgat cacttcatac ttctaaatca gaaataggaa gattaaaacc      2760
acagaacagt ttgtgatttc tattgctgta gctaggtatc ttactctgtc cactcttgtt      2820
caagtatcta actcttctgg aaaccaaata ggctttagaa gagattatcc tatattccta      2880
tcagtataat actaaaatgt aacttttttaa tcatctggtt tttaaaagat aaacagttta     2940
gcccatctct ccagagagca aacataggaa tatgactcag gagcctccta gggcttatca      3000
tcagccctca cacccgcttc cccctccaac ccacagcctt tgcttccagg tggcaggatt      3060
actactttgc ctcttcagca gcatctactc taggcatatt gatcatttta gacactggga      3120
gaagagaacc tcaaactagg aggaaaagac agagcctcca cttagttttg ggaggggatg      3180
gcagacagtc aaggagatga gcgtcctaag gcatgttggg atagggtcag atgcaccacc      3240
catggagagg tttgtcaaca caaagacatg gaaggttaga ggtttgtcaa caaaagaca       3300 tggaaggtta ggtttgtcaa cacaaagaca tggaagatta gggtttgtc aacacaaaga       3360 cacaggaaga atgggctgca gaagatttag atgttttcca tttgggcaca ttttacttag      3420
ctggagaact aggtttaaaa cagcctgggt aggaaaatta gaagcaagct ggatgcagtg      3480
gctcatgcct gtaatcccaa cttttgggg aggtccaggc aggaggatca cttgggccca       3540
ggaggtcaag cctgcagcga gctgagatca caccactgca ctccagcctg ggtgataga      3600 acaagaccct gtctcaaaaa aaaaaaaaaa caacaaaaac ttagaattga ggagttgtac      3660
ctccattggc ttcctcactc caaaataggt gctgatcctt cctattccta ttctttgcca      3720
ccttttgggt gtggtgtcac cagcctgttt agccaagtag ctttgggcat aggctgccca      3780
atctgagcaa acaccagtga ggctctattg agccaagacc aagtcctcaa agcacctgaa      3840
ccactgtggc cttctcagcc tacagcagtg tggtctctta catggccaca aagggacaca      3900
cagtgacaaa aggctcggaa tgttacaatg gtaaaatgag tgatctcaaa tccactgaca      3960
gatataaaat aggcttagag aggaaaagct gcctctggtc aagtagatca tggcagcatg      4020
```

-continued

| | |
|---|---|
| aattccaact cacttttta caactccaac ttctatgttt atctttgtta ctttcactt | 4080 |
| tttacaacct ggccagaggc attttttaaa tcaggcccaa tatcagtatt cttttgtgt | 4140 |
| gtgccaattt tgttatcaca tccctatgaa gttgaaaaat aaagttaatt ttgaccaaaa | 4200 |
| aaaaaaaaaa aag | 4213 |

<210> SEQ ID NO 8
<211> LENGTH: 4459
<212> TYPE: DNA
<213> ORGANISM: Homo sapiens

<400> SEQUENCE: 8

| | |
|---|---|
| gtttctctct ctccttctct ctctctctct ctctctcttt tttttccgcc ctagctgggg | 60 |
| ctgtgttgga ggagaggaag aaagagagac agaggattgc attcatccgt tacgttcttg | 120 |
| aaatttccta atagcaagac cagcgaagcg gttgcaccct tttcaatctt gcaaaggaaa | 180 |
| aaaacaaaac aaaacaaaaa aacccaagt cccttcccg gcagttttg ccttaaagct | 240 |
| gccctcttga aattaatttt ttcccaggag agagatgtct tatcagggga agaaaaatat | 300 |
| tccacgcatc acgagcgatc gtcttctgat caaaggaggg aaaattgtta atgatgacca | 360 |
| gtcgttctat gcagacatat acatggaaga tgggttgatc aagcaaatag gagaaaatct | 420 |
| gattgtgcca ggaggagtga agaccatcga ggcccactcc cggatggtga tccccggagg | 480 |
| aattgacgtc cacactcgtt tccagatgcc tgatcaggga atgacgtctg ctgatgattt | 540 |
| cttccaagga accaaggcgg ccctggctgg ggaaccact atgatcattg accacgttgt | 600 |
| tcctgagcct gggacaagcc tgctcgctgc ctttgaccag tggagggaat gggccgacag | 660 |
| caagtcctgc tgtgactact ctctgcatgt ggacatcagc gagtggcata agggcatcca | 720 |
| ggaggagatg gaagcgcttg tgaaggatca cggggtaaat tccttcctcg tgtacatggc | 780 |
| tttcaaagat cgcttccagc taacggattg ccagatttat gaagtactga gtgtgatccg | 840 |
| ggatattggc gccatagccc aagtccacgc agaaaatggc gacatcattg cagaggagca | 900 |
| gcagaggatc ctggatctgg gcatcacggg ccccgaggga catgtgctga gccgacctga | 960 |
| ggaggtcgag gccgaagccg tgaatcgtgc catcaccatc gccaaccaga ccaactgccc | 1020 |
| gctgtatatc accaaggtga tgagcaaaag ctctgctgag gtcatcgccc aggcacggaa | 1080 |
| gaagggaact gtggtgtatg gcgagcccat cactgccagc ttgggaacgg acggctccca | 1140 |
| ttactggagc aagaactggg ccaaggctgc tgccttgtc acctccccac ccttgagccc | 1200 |
| tgatccaacc actccagact ttctcaactc cttgctgtcc tgtggagacc tccaggtcac | 1260 |
| gggcagtgcc cattgcacgt ttaacactgc ccagaaggct gtaggaaagg acaacttcac | 1320 |
| cctgattccg gagggcacca atggcactga ggagcggatg tccgtcatct gggacaaggc | 1380 |
| tgtggtcact gggaagatgg atgagaacca gtttgtggct gtgaccagca ccaatgcagc | 1440 |
| caaagtcttc aacctttacc cccggaaagg ccgcattgct gtgggatccg atgccgacct | 1500 |
| ggtcatctgg gaccccgaca gcgttaaaac catctctgcc aagacacaca acagctctct | 1560 |
| cgagtacaac atctttgaag gcatggagtg ccgcggctcc ccactggtgg tcatcagcca | 1620 |
| ggggaagatt gtcctggagg acggcaccct gcatgtcacc gaaggctctg gacgctacat | 1680 |
| tcccccggaag cccttccctg attttgttta caagcgtatc aaggcaagga gcaggctggc | 1740 |
| tgagctgaga ggggttcctc gtggcctgta tgacggacct gtgtgtgaag tgtctgtgac | 1800 |
| gcccaagaca gtcactccag cctcctcggc caagacgtct cctgccaagc agcaggcccc | 1860 |
| acctgtccgg aacctgcacc agtctggatt cagtttgtct ggtgctcaga ttgatgacaa | 1920 |

-continued

```
cattccccgc cgcaccaccc agcgtatcgt ggcgcccccc ggtggccgtg ccaacatcac    1980
cagcctgggc tagagctcct gggctgtgcg tccactgggg actggggatg ggacacctga    2040
ggacattctg agacttcttt cttccttcct ttttttttt ttgttttttt ttttaagagc     2100
ctgtgatagt tactgtggag cagccagttc atggggtccc ccttggggcc ccacaccccg    2160
tctctcacca agagttactg attttgctca tccacttccc tacacatcta tgggtatcac    2220
acccaagact acccaccaag ctcatacagg aaccacacc caacacttag acatgcgaac     2280
aagcagcccc cagcgagggt ctccttcgcc ttcaacctcc tagtgtctgt tagcatcttc    2340
cttttcatgg ggggagggaa gataaagtga attgcccaga gctgcctttt tcttttcttt    2400
ttaaaaattt taagaagttt tccttgtggg gctggggagg ggccggggtc agggagagtc    2460
tttttttttt tttttttaaa tactaaattg gaacatttaa ttccatatta atacaagggg    2520
tttgaactgg acatcctaat gatgcaatta cgtcatcacc cagctgattc cgggtggttg    2580
gcaaactcat cgtgtctgtc ctgagaggct ccacaatgcc cacccgcatc gccattctgt    2640
agtcttcagg gtcagctgtt gataaagggg caggcttgcg ttattggcct agattttgct    2700
gcagattaaa tcctttgagg attctcttct cttttaccat ttttctgcgt gctctcactc    2760
tctctttctc tctctagctt tttaattcat gaatattttc gtgtctgtct ctctctctct    2820
ctgtgtttcc tccagcccct gtctcggaga cggtgttttc ctcccttgcc ccattatctt    2880
ttcacctccc aggtctacca tttcatggtg gtcgttgggt ccgcctaaag gatttgagcg    2940
tttgccattg caagcatagt gctgtgtcat cctggtccat gtaggactgg tgctaaccac    3000
ctgccatcat gaggatgtgt gctagagtgt gggaccctgg ccaagtgcag gaatgggcca    3060
tgccgtctca cccacagtat cacacgtgga accgcagaca gggcccagaa gctttagagg    3120
tatgaggctg cagaaccgga gagattttcc tctgtgcagt gctctctggc taaagtcacg    3180
gtcaaaccta acaccgagc ctcattaacc caagtgaacc aaccaaagtc accagttcag     3240
aagtgctaag ctaataggag tctgacccga gggcctgctg cttcctggtt aagtatcttt    3300
tgagattcta aacacatgg gagctttta ttttcgggga aaaaccgtat ttttttcttg      3360
tccaattatt tctaaagaca cactacatag aaagaggccc tataaactca aaaagtcatt    3420
gggaaactta aagtctattc tactttgcaa gaggagaaat gtgttttatg aacgatagat    3480
cacatcagaa ctcctgtggg gaggaaacct tataaattaa acacatggcc cccttagaga    3540
ccacaggtga tgtctgtctc catccttccc tctccttttc tgtcaccttt ccccctagct    3600
ggctcctttg gacctacccc tgtccttgct gacttgtgtt gcattgtatt ccaaacgtgt    3660
ttacaggttc tcttaagcaa tgttgtattt gcaggctttt ctgaatacca aatctgcttt    3720
ttgtaaagcg taaaaacatc acaaagtagg tcattccatc accaccttg tctctctaca     3780
cattttgcct ttggggatct ggttggggtt ttgggttttt tgttgttgtt gtttatttgt    3840
tatttttaaag gtaaattgca cttttaaaaa aataattggt tgacttaata tatttgcttt   3900
ttttctcacc tgcacttaga ggaaatttga acaagttgga aaaaacaat ttttgtttca     3960
attctaagaa acacttgcag ctctagtatt cacttgagtc ttcctgtttt tcctgtaccg    4020
ggtcatggta atttttggtt gttttggttg ttttcttaaa aaacaagtta aaacctgacg    4080
atttctgcag gctgtgtaag catgtttacc tgttggcttg ctttgtgtgt ctgttaaatg    4140
aatgtcatat gtaaatgcta aaataaatcg acagtgtctc agaactgaat aactgcagtg    4200
acttgatgct ctaaaacagt gtaggattta agaatagatg gttttaatc ctggaaattg     4260
```

-continued

| | | | |
|---|---|---|---|
| tgattgtgac | ccatgagtgg | aggaactttc | agttctaaag ctgataaagt gtgtagccag | 4320 |
| aagagtactt | ttttttttgt | aaccactgtc | ttgatggcaa ataattatg gtaaaaaaca | 4380 |
| agtctcgtgt | ttattattcc | ttaagaactc | tgtgttatat taccatggaa cgcctaataa | 4440 |
| agcaaaatgt | ggttgtttc | | | 4459 |

<210> SEQ ID NO 9
<211> LENGTH: 7718
<212> TYPE: DNA
<213> ORGANISM: Homo sapiens

<400> SEQUENCE: 9

| | | | | |
|---|---|---|---|---|
| cgggagcggc | gggagcggtg | gcggcggcag | aggcggcggc tccagcttcg gctccggctc | 60 |
| gggctcgggc | tccggctccg | gctccggctc | cggctccagc tcgggtggcg gtggcgggag | 120 |
| cgggaccagg | tggaggcggc | ggcggcagag | gagtgggagc agcggcccta gcggcttgcg | 180 |
| ggggacatg | cggaccgacg | gcccctggat | aggcggaagg agtggaggcc ctggtgcccg | 240 |
| gcccttggtg | ctgagtatcc | agcaagagtg | accggggtga agaagcaaag actcggttga | 300 |
| ttgtcctggg | ctgtggctgg | ctgtggagct | agagccctgg atggcccctg agccagcccc | 360 |
| agggaggacg | atggtgcccc | ttgtgcctgc | actggtgatg cttggtttgg tggcaggcgc | 420 |
| ccatggtgac | agcaaacctg | tcttcattaa | agtccctgag gaccagactg gctgtcagg | 480 |
| aggggtagcc | tccttcgtgt | gccaagctac | aggagaaccc aagccgcgca tcacatggat | 540 |
| gaagaagggg | aagaaagtca | gctcccagcg | cttcgaggtc attgagtttg atgatggggc | 600 |
| agggtcagtg | cttcggatcc | agccattgcg | ggtgcagcga gatgaagcca tctatgagtg | 660 |
| tacagctact | aacagcctgg | gtgagatcaa | cactagtgcc aagctctcag tgctcgaaga | 720 |
| ggaacagctg | ccccctgggt | tcccttccat | cgacatgggg cctcagctga aggtggtgga | 780 |
| gaaggcacgc | acagccacca | tgctatgtgc | cgcaggcgga aatccagacc ctgagatttc | 840 |
| ttggttcaag | gacttccttc | tgtagaccc | tgccacgagc aacggccgca tcaagcagct | 900 |
| gcgttcaggt | gccttgcaga | tagagagcag | tgaggaatcc gaccaaggca agtacgagtg | 960 |
| tgtggcgacc | aactcggcag | gcacacgtta | ctcagcccct gcgaacctgt atgtgcgagt | 1020 |
| gcgccgcgtg | gctcctcgtt | tctccatccc | tcccagcagc caggaggtga tgccaggcgg | 1080 |
| cagcgtgaac | ctgacatgcg | tggcagtggg | tgcacccatg ccctacgtga agtggatgat | 1140 |
| gggggccgag | gagctcacca | aggaggatga | gatgccagtt ggccgcaacg tcctggagct | 1200 |
| cagcaatgtc | gtacgctctg | ccaactacac | ctgtgtggcc atctcctcgc tgggcatgat | 1260 |
| cgaggccaca | gcccaggtca | cagtgaaagc | tcttccaaag cctccgattg atcttgtggt | 1320 |
| gacagagaca | actgccacca | gtgtcaccct | cacctggac tctgggaact cggagcctgt | 1380 |
| aacctactat | ggcatccagt | accgcgcagc | gggcacggag ggccccttc aggaggtgga | 1440 |
| tggtgtggcc | accaccgct | acagcattgg | cggcctcagc cctttctcgg aatatgcctt | 1500 |
| ccgcgtgctg | gcggtgaaca | gcatcgggcg | agggccgccc agcgaggcag tgcgggcacg | 1560 |
| cacgggagaa | caggcgccct | ccagcccacc | gcgccgcgtg caggcacgca tgctgagcgc | 1620 |
| cagcaccatg | ctggtgcagt | gggagcctcc | cgaggagccc aacggcctgg tgcggggata | 1680 |
| ccgcgtctac | tatactccgg | actccgccg | ccccccgaac gcctggcaca gcacaacac | 1740 |
| cgacgcgggg | ctcctcacga | ccgtgggcag | cctgctgcct ggcatcacct acagcctgcg | 1800 |
| cgtgcttgcc | ttcaccgccg | tgggcgatgg | ccctcccagc cccaccatcc aggtcaagac | 1860 |
| gcagcaggga | gtgcctgccc | agcccgcgga | cttccaggcc gaggtggagt cggacaccag | 1920 |

-continued

```
gatccagctc tcgtggctgc tgcccccctca ggagcggatc atcatgtatg aactggtgta    1980
ctgggcggca gaggacgaag accaacagca caaggtcacc ttcgacccaa cctcctccta    2040
cacactagag gacctgaagc ctgacacact ctaccgcttc cagctggctg cacgctcgga    2100
tatgggggtg ggcgtcttca cccccaccat tgaggcccgc acagcccagt ccaccccctc    2160
cgcccctccc cagaaggtga tgtgtgtgag catgggctcc accacggtcc gggtaagttg    2220
ggtcccgccg cctgccgaca gccgcaacgg cgttatcacc cagtactccg tggcccacga    2280
ggcggtggac ggcgaggacc gcgggcggca tgtggtggat ggcatcagcc gtgagcactc    2340
cagctgggac ctggtgggcc tggagaagtg gacggagtac cgggtgtggg tgcgggcaca    2400
cacagacgtg ggccccggcc ccgagagcag cccggtgctg gtgcgcaccg atgaggacgt    2460
gcccagcggg cctccgcgga aggtggaggt ggagccactg aactccactg ctgtgcatgt    2520
ctactggaag ctgcctgtcc ccagcaagca gcatggccag atccgcggct accaggtcac    2580
ctacgtgcgg ctggagaatg cgagcccccg tggactcccc atcatccaag acgtcatgct    2640
agccgaggcc cagtggcggc cagaggagtc cgaggactat gaaaccacta tcagcggcct    2700
gaccccggag accacctact ccgttactgt tgctgcctat accaccaagg gggatggtgc    2760
ccgcagcaag cccaaaattg tcactacaac aggtgcagtc ccaggccggc ccaccatgat    2820
gatcagcacc acggccatga acactgcgct gctccagtgg cacccaccca aggaactgcc    2880
tggcgagctg ctgggctacc ggctgcagta ctgccgggcc gacgaggcgc ggcccaacac    2940
catagatttc ggcaaggatg accagcactt cacagtcacc ggcctgcaca aggggaccac    3000
ctacatcttc cggcttgctg ccaagaaccg ggctggcttg ggtgaggagt tcgagaagga    3060
gatcaggacc cccgaggacc tgcccagcgg cttcccccaa aacctgcatg tgacaggact    3120
gaccacgtct accacagaac tggcctggga cccgccagtg ctggcggaga ggaacgggcg    3180
catcatcagc tacaccgtgg tgttccgaga catcaacagc caacaggagc tgcagaacat    3240
cacgacagac acccgcttta cccttactgg cctcaagcca gacaccactt acgacatcaa    3300
ggtccgcgca tggaccagca aaggctctgg cccactcagc cccagcatcc agtcccggac    3360
catgccggtg gagcaagtgt ttgccaagaa cttccgggtg gcggctgcaa tgaagacgtc    3420
tgtgctgctc agctgggagg ttcccgactc ctataagtca gctgtgccct ttaagattct    3480
gtacaatggg cagagtgtgg aggtggacgg gcactcgatg cggaagctga tcgcagacct    3540
gcagcccaac acagagtact cgtttgtgct gatgaaccgt ggcagcagcg caggggcct    3600
gcagcacctg gtgtccatcc gcacagcccc cgacctcctg cctcacaagc cgctgcctgc    3660
ctctgcctac atagaggacg gccgcttcga tctctccatg ccccatgtgc aagacccctc    3720
gcttgtcagg tggttctaca ttgttgtggt acccattgac cgtgtgggcg ggagcatgct    3780
gacgccaagg tggagcacac ccgaggaact ggagctggac gagcttctag aagccatcga    3840
gcaaggcgga gaggagcagc ggcggcggcg gcggcaggca gaacgtctga agccatatgt    3900
ggctgctcaa ctggatgtgc tcccgggagac ctttaccttg ggggacaaga agaactaccg    3960
gggcttctac aaccggcccc tgtctccgga cttgagctac cagtgctttg tgcttgcctc    4020
cttgaaggaa cccatggacc agaagcgcta tgcctccagc ccctactcgg atgagatcgt    4080
ggtccaggtg acaccagccc agcagcagga ggagccggag atgctgtggg tgacgggtcc    4140
cgtgctggca gtcatcctca tcatcctcat tgtcatcgcc atcctcttgt tcaaaaggaa    4200
aaggacccac tctccgtcct ctaaggatga gcagtcgatc ggactgaagg actccttgct    4260
```

```
ggcccactcc tctgaccctg tggagatgcg gaggctcaac taccagaccc caggtatgcg    4320
agaccaccca cccatcccca tcaccgacct ggcggacaac atcgagcgcc tcaaagccaa    4380
cgatggcctc aagttctccc aggagtatga gtccatcgac cctggacagc agttcacgtg    4440
ggagaattca aacctggagg tgaacaagcc caagaaccgc tatgcgaatg tcatcgccta    4500
cgaccactct cgagtcatcc ttacctctat cgatggcgtc cccggagtg actacatcaa    4560
tgccaactac atcgatggct accgcaagca gaatgcctac atcgccacgc agggccccct    4620
gcccgagacc atgggcgatt tctggagaat ggtgtgggaa cagcgcacgg ccactgtggt    4680
catgatgaca cggctggagg agaagtcccg ggtaaaatgt gatcagtact ggccagcccg    4740
tggcaccgag acctgtggcc ttattcaggt gaccctgttg gacacagtgg agctggccac    4800
atacactgtg cgcaccttcg cactccacaa gagtggctcc agtgagaagc gtgagctgcg    4860
tcagtttcag ttcatggcct ggccagacca tggagttcct gagtacccaa ctcccatcct    4920
ggccttccta cgacgggtca aggcctgcaa cccccctaga gcaggcccca tggtggtgca    4980
ctgcagcgcg ggcgtgggcc gcaccggctg cttcatcgtg attgatgcca tgttggagcg    5040
gatgaagcac gagaagacgg tggacatcta tggccacgtg acctgcatgc gatcacagag    5100
gaactacatg gtgcagacgg aggaccagta cgtgttcatc catgaggcgc tgctggaggc    5160
tgccacgtgc ggccacacag aggtgcctgc ccgcaacctg tatgcccaca tccagaagct    5220
gggccaagtg cctccagggg agagtgtgac cgccatggag ctcgagttca agttgctggc    5280
cagctccaag gcccacacgt cccgcttcat cagcgccaac ctgccctgca acaagttcaa    5340
gaaccggctg gtgaacatca tgccctacga attgaccgt gtgtgtctgc agcccatccg    5400
tggtgtggag ggctctgact acatcaatgc cagcttcctg gatggttata cacagcagaa    5460
ggcctacata gctacacagg ggcctctggc agagagcacc gaggacttct ggcgcatgct    5520
atgggagcac aattccacca tcatcgtcat gctgaccaag cttcgggaga tgggcaggga    5580
gaaatgccac cagtactggc cagcagagcg ctctgctcgc taccagtact ttgttgttga    5640
cccgatggct gagtacaaca tgccccagta tatcctgcgt gagttcaagg tcacggatgc    5700
ccgggatggg cagtcaagga caatccggca gttccagttc acagactggc cagagcaggg    5760
cgtgcccaag acaggcgagg gattcattga cttcatcggg caggtgcata agaccaagga    5820
gcagtttgga caggatgggc ctatcacggt gcactgcagt gctggcgtgg gccgcaccgg    5880
ggtgttcatc actctgagca tcgtcctgga gcgcatgcgc tatgagggcg tggtcgacat    5940
gtttcagacc gtgaagaccc tgcgtacaca gcgtcctgcc atggtgcaga cagaggacca    6000
gtatcagctg tgctaccgtg cggccctgga gtacctcggc agctttgacc actatgcaac    6060
gtaactaccg ctcccctctc ctccgccacc ccgccgtgg ggctccggag ggacccagc     6120
tcctctgagc cataccgacc atcgtccagc cctcctacgc agatgctgtc actggcagag    6180
cacagcccac gggatcaca gcgtttcagg aacgttgcca caccaatcag agagcctaga    6240
acatccctgg gcaagtggat ggcccagcag gcaggcactg tggcccttct gtccaccaga    6300
cccacctgga gcccgcttca agctctctgt tgcgctcccg catttctcat gcttcttctc    6360
atggggtggg gttggggcaa agcctccttt ttaatacatt aagtggggta gactgaggga    6420
ttttagcctc ttccctctga tttttccttt cgcgaatccg tatctgcaga atgggccact    6480
gtaggggttg gggtttattt tgttttgttt ttttttttt tttgtatgac ttctgctgaa    6540
ggacagaaca ttgccttcct cgtgcagagc tgggctgcc agcctgagcg gaggctcggc    6600
cgtgggccgg gaggcagtgc tgatccggct gctcctccag cccttcagac gagatcctgt    6660
```

| | |
|---|---|
| ttcagctaaa tgcagggaaa ctcaatgttt ttttaagttt tgttttccct ttaaagcctt | 6720 |
| tttttaggcc acattgacag tggtgggcgg ggagaagata gggaacactc atccctggtc | 6780 |
| gtctatccca gtgtgtgttt aacattcaca gcccagaacc acagatgtgt ctgggagagc | 6840 |
| ctggcaaggc attcctcatc accatcgtgt tgcaaaggt taaaacaaaa acaaaaaacc | 6900 |
| acaaaaataa aaacaaaaa aacaaaaaa cccaaaaaaa aaaaaaaaaa gagtcagccc | 6960 |
| ttggcttctg cttcaaaccc tcaagagggg aagcaactcc gtgtgcctgg ggttcccgag | 7020 |
| ggagctgctg gctgacctgg gcccacagag cctggctttg gtccccagca ttgcagtatg | 7080 |
| gtgtggtgtt tgtaggctgt ggggtctggc tgtgtggcca aggtgaatag cacaggttag | 7140 |
| ggtgtgtgcc acaccccatg cacctcaggg ccaagcgggg gcgtggctgg cctttcaggt | 7200 |
| ccaggccagt gggcctggta gcacatgtct gtcctcagag caggggccag atgattttcc | 7260 |
| tccctggttt gcagctgttt tcaaagcccc cgataatcgc tcttttccac tccaagatgc | 7320 |
| cctcataaac caatgtggca agactactgg acttctatca atggtactct aatcagtcct | 7380 |
| tattatccca gcttgctgag gggcaggag agcgcctctt cctctgggca gcgctatcta | 7440 |
| gataggtaag tgggggcggg gaagggtgca tagctgtttt agctgaggga cgtggtgccg | 7500 |
| acgtccccaa acctagctag gctaagtcaa gatcaacatt ccagggttgg taatgttgga | 7560 |
| tgatgaaaca ttcatttta cctgtggat gctagtgctg tagagttcac tgttgtacac | 7620 |
| agtctgtttt ctatttgtta agaaaaacta cagcatcatt gcataattct tgatggtaat | 7680 |
| aaatttgaat aatcagattt cttacaaaaa aaaaaaaa | 7718 |

<210> SEQ ID NO 10
<211> LENGTH: 1809
<212> TYPE: DNA
<213> ORGANISM: Homo sapiens

<400> SEQUENCE: 10

| | |
|---|---|
| cctgctccaa ggtccagaga gctttctggt ctttgcagca ggcctgccgc cttcatgtcc | 60 |
| actctcctca tcaatcagcc ccagtatgcg tggctgaaag agctggggct ccgcgaggaa | 120 |
| aacgagggcg tgtataatgg aagctgggga ggccggggag aggttattac gacctattgc | 180 |
| cccgctaaca acgagccaat agcaagagtc cgacaggcca gtgtggcaga ctatgaagaa | 240 |
| actgtaaaga aagcaagaga agcatggaaa atctgggcag atattcctgc tccaaaacga | 300 |
| ggagaaatag taagacagat tggcgatgcc ttgcgggaga agatccaagt actaggaagc | 360 |
| ttggtgtctt tggagatggg gaaaatctta gtggaaggtg tgggtgaagt tcaggagtat | 420 |
| gtggatatct gtgactatgc tgttggttta tcaaggatga ttggaggacc tatcttgcct | 480 |
| tctgaaagat ctggccatgc actgattgag cagtggaatc ccgtaggcct ggttggaatc | 540 |
| atcacggcat tcaatttccc tgtggcagtg tatggttgga acaacgccat cgccatgatc | 600 |
| tgtggaaatg tctgcctctg gaaggagct ccaaccactt ccctcattag tgtggctgtc | 660 |
| acaaagataa tagccaaggt tctggaggac aacaagctgc ctggtgcaat tgttccttg | 720 |
| acttgtggtg gagcagatat tggcacagca atggccaaag atgaacgagt gaacctgctg | 780 |
| tccttcactg ggagcactca ggtgggaaaa caggtgggcc tgatggtgca ggagaggttt | 840 |
| gggagaagtc tgttggaact tggaggaaac aatgccatta ttgcctttga agatgcagac | 900 |
| ctcagcttag ttgttccatc agctctcttc gctgctgtgg aacagctgg ccagaggtgt | 960 |
| accactgcga ggcgactgtt tatacatgaa agcatccatg atgaggttgt aaacagactt | 1020 |

```
aaaaaggcct atgcacagat ccgagttggg aacccatggg accctaatgt tctctatggg    1080
ccactccaca ccaagcaggc agtgagcatg tttcttggag cagtggaaga agcaaagaaa    1140
gaaggtggca cagtggtcta tgggggcaag gttatggatc gccctggaaa ttatgtagaa    1200
ccgacaattg tgacaggtct tggccacgat gcgtccattg cacacacaga gactttcgct    1260
ccgattctct atgtctttaa attcaagaat gaagaagagg tctttgcatg gaataatgaa    1320
gtaaaacagg gactttcaag tagcatcttt accaaagatc tgggcagaat ctttcgctgg    1380
cttggaccta aaggatcaga ctgtggcatt gtaaatgtca acattccaac aagtggggct    1440
gagattggag gtgcctttgg aggagaaaag cacactggtg gtggcaggga gtctggcagt    1500
gatgcctgga aacagtacat gagaaggtct acttgtacta tcaactacag taaagacctt    1560
cctctggccc aaggaatcaa gtttcagtaa aggtgtttta gatgaacatc ccttaatttg    1620
aggtgttcca gcagctgttt ttggagaaga caaagaagat taaagttttc cctgaataaa    1680
tgcattatta tgactgtgac agtgactaat cccctatga ccccaaagcc ctgattaaat    1740
caagagattc cttttttaaa aatcaaaata aaattgttac aacatagcca tagttactaa    1800
aaaaaaaaa                                                           1809

<210> SEQ ID NO 11
<211> LENGTH: 1317
<212> TYPE: DNA
<213> ORGANISM: Homo sapiens

<400> SEQUENCE: 11
agctcccgcg cgctagagcc gcctgctggt ctcacccagc cgggaccgct gacctggcgc      60
tttgtgcggc tccaggcctc cgagtggact ccagaaaagcc tgaaaagcta tcatggcagc    120
aaggcccaag ctccactatc ccaacggaag aggccggatg gagtccgtga gatgggtttt    180
agctgccgcc ggagtcgagt ttgatgaaga atttctggaa acaaaagaac agttgtacaa    240
gttgcaggat ggtaaccacc tgctgttcca acaagtgccc atggttgaaa ttgacgggat    300
gaagttggta cagaccccgaa gcattctcca ctacatagca gacaagcaca atctctttgg    360
caagaacctc aaggagagaa ccctgattga catgtacgtg gaggggacac tggatctgct    420
ggaactgctt atcatgcatc ctttcttaaa accagatgat cagcaaaagg aagtggttaa    480
catggcccag aaggctataa ttagatactt tcctgtgttt gaaaagattt taagggtca    540 cggacaaagc tttcttgttg gtaatcagct gagccttgca gatgtgattt tactccaaac    600
cattttagct ctagaagaga aaattcctaa tatcctgtct gcatttcctt tcctccagga    660
atacacagtg aaactaagta atatccctac aattaagaga ttccttgaac ctggcagcaa    720
gaagaagcct ccccctgatg aaatttatgt gagaaccgtc tacaacatct ttaggccata    780
aaacaacaca tccatgtgtg agtgacagtg tgttcctaga gatggtattg tctacagtca    840
tgtcttaatg gatcccagct ctgtcatggt gctatctatg tattaagttg ggtcctaagt    900
tgggtctttt gtgtcaacga gatcatctct tctagaaata tcaacctttt ttgtccagta    960
aataattgtt aggggatctt tattggaaaa cttttttgga gaggctggta tttaagttag   1020
atctgattgg gctactcatg tcctgtagcc agttcatcct cataataaga atgggcagga   1080
tctcttgttc tctcctgagt gtctttctac tctcctgagc gtctttctgc tctccttatc   1140
ctgttctctt atccttatcc cctccagtct ctgcctaatt tttagtgttt aataacaacc   1200
gaatgtctag taaatgactc tcctctgagc tgtaataaat aaaatggtag taatgaatgc   1260
aatcagtatt agccaaaata aagaatttat gagtcattaa aaaaaaaaa aaaaaaa      1317
```

<210> SEQ ID NO 12
<211> LENGTH: 5910
<212> TYPE: DNA
<213> ORGANISM: Homo sapiens

<400> SEQUENCE: 12

| | | | | | |
|---|---|---|---|---|---|
| cggaggacag | ccggaccgag | ccaacgccgg | ggactttgtt | ccctccacgg | aggggactcg | 60 |
| gcaactcgca | gcggcagggt | ctggggccgg | cgcctgggag | ggatctgcgc | ccccactca | 120 |
| ctccctagct | gtgttcccgc | cgccgccccg | gctagtctcc | ggcgctggcg | cctatggtcg | 180 |
| gcctccgaca | gcgctccgga | gggaccgggg | gagctcccag | gcgcccggga | ctggagactg | 240 |
| atgcatgagg | ggcctacgga | ggcgcaggag | cggtggtgat | ggtctgggaa | gcggagctga | 300 |
| agtcccctgg | gctttggtga | ggcgtgacag | tttatcatga | ccgtgttcag | gcaggaaaac | 360 |
| gtggatgatt | actacgacac | cggcgaggaa | cttggcagtg | gacagtttgc | ggttgtgaag | 420 |
| aaatgccgtg | agaaaagtac | cggcctccag | tatgccgcca | aattcatcaa | gaaaaggagg | 480 |
| actaagtcca | gccggcgggg | tgtgagccgc | gaggacatcg | agcgggaggt | cagcatcctg | 540 |
| aaggagatcc | agcaccccaa | tgtcatcacc | ctgcacgagg | tctatgagaa | caagacggac | 600 |
| gtcatcctga | tcttggaact | cgttgcaggt | ggcgagctgt | ttgacttctt | agctgaaaag | 660 |
| gaatctttaa | ctgaagagga | agcaactgaa | tttctcaaac | aaattcttaa | tggtgtttac | 720 |
| tacctgcact | cccttcaaat | cgcccacttt | gatcttaagc | ctgagaacat | aatgcttttg | 780 |
| gatagaaatg | tccccaaacc | tcggatcaag | atcattgact | ttgggttggc | cataaaaatt | 840 |
| gactttggaa | atgaatttaa | aaacatattt | gggactccag | agtttgtcgc | tcctgagata | 900 |
| gtcaactatg | aacctcttgg | tcttgaggca | gatatgtgga | gtatcggggt | aataacctat | 960 |
| atcctcctaa | gtggggcctc | cccatttctt | ggagacacta | gcaagaaaac | gttagcaaat | 1020 |
| gtatccgctg | tcaactacga | atttgaggat | gaatacttca | gtaataccag | tgccctagcc | 1080 |
| aaagatttca | taagaagact | tctggtcaag | gatccaaaga | gagaatgac | aattcaagat | 1140 |
| agtttgcagc | atccctggat | caagcctaaa | gatacacaac | aggcacttag | tagaaaagca | 1200 |
| tcagcagtaa | acatggagaa | attcaagaag | tttgcagccc | ggaaaaaatg | gaaacaatcc | 1260 |
| gttcgcttga | tatcactgtg | ccaaagatta | tccaggtcat | tcctgtccag | aagtaacatg | 1320 |
| agtgttgcca | gaagcgatga | tactctggat | gaggaagact | cctttgtgat | gaaagccatc | 1380 |
| atccatgcca | tcaacgatga | caatgtccca | ggcctgcagc | accttctggg | ctcattatcc | 1440 |
| aactatgatg | ttaaccaacc | caacaagcac | gggacacctc | cattactcat | tgctgctggc | 1500 |
| tgtgggaata | ttcaaatact | acagttgctc | attaaaagag | gctcgagaat | cgatgtccag | 1560 |
| gataagggcg | ggtccaatgc | cgtctactgg | gctgctcggc | atggccacgt | cgataccttg | 1620 |
| aaatttctca | gtgagaacaa | atgcccttg | gatgtgaaag | acaagtctgg | agagatggcc | 1680 |
| ctccacgtgg | cagctcgcta | tggccatgct | gacgtggctc | aagttacttg | tgcagcttcg | 1740 |
| gctcaaatcc | caatatccag | gacaaaggaa | gaagaaaccc | cctgcactg | tgctgcttgg | 1800 |
| cacggctatt | actctgtggc | caaagccctt | tgtgaagccg | gctgtaacgt | gaacatcaag | 1860 |
| aaccgagaag | gagagacgcc | cctcctgaca | gcctctgcca | ggggctacca | cgacatcgtg | 1920 |
| gagtgtctgg | ccgaacatgg | agccgacctt | aatgcttgcg | acaaggacgg | acacattgcc | 1980 |
| cttcatctgg | ctgtaagacg | gtgtcagatg | gaggtaatca | agactctcct | cagccaaggg | 2040 |
| tgtttcgtcg | attatcaaga | caggcacggc | aatactcccc | tccatgtggc | atgtaaagat | 2100 |

```
ggcaacatgc ctatcgtggt ggccctctgt gaagcaaact gcaatttgga catctccaac    2160
aagtatgggc gaacgcctct gcaccttgcg gccaacaacg gaatcctaga cgtggtccgg    2220
tatctctgtc tgatgggagc cagcgttgag gcgctgacca cggacggaaa gacggcagaa    2280
gatcttgcta gatcggaaca gcacgagcac gtagcaggtc tccttgcaag acttcgaaag    2340
gatacgcacc gaggactctt catccagcag ctccgaccca cacagaacct gcagccaaga    2400
attaagctca agctgtttgg ccactcggga tccgggaaaa ccaccettgt agaatctctc    2460
aagtgtgggc tgctgaggag cttttcaga aggcgtcggc ccagactgtc ttccaccaac    2520
tccagcaggt tcccacctte accectggct tctaagccca cagtctcagt gagcatcaac    2580
aacctgtacc caggctgcga gaacgtgagt gtgaggagcc gcagcatgat gttcgagccg    2640
ggtcttacca aagggatgct ggaggtgttt gtggccccga cccaccaccc gcactgctcg    2700
gccgatgacc agtccaccaa ggccatcgac atccagaacg cttatttgaa tggagttggc    2760
gatttcagcg tgtgggagtt ctctggaaat cctgtgtatt tctgctgtta tgactatttt    2820
gctgcaaatg atcccacgtc aatccatgtt gttgtcttta gtctagaaga gccctatgag    2880
atccagctga cccagtgat tttctggctc agtttcctga agtcccttgt cccagttgaa    2940
gaacccatag ccttcggtgg caagctgaag aacccactcc aagttgtcct ggtggccacc    3000
cacgctgaca tcatgaatgt tcctcgaccg gctggaggcg agtttggata tgacaaagac    3060
acatcgttgc tgaaagagat taggaacagg tttggaaatg atcttcacat ttcaaataag    3120
ctgtttgttc tggatgctgg ggcttctggg tcaaaggaca tgaaggtact tcgaaatcat    3180
ctgcaagaaa tacgaagcca gattgtttcg gtctgtcctc ccatgactca cctgtgtgag    3240
aaaatcatct ccacgctgcc ttcctggagg aagctcaatg gacccaacca gctgatgtcg    3300
ctgcagcagt ttgtgtacga cgtgcaggac cagctgaacc cctggccag cgaggaggac    3360
ctcaggcgca ttgctcagca gctccacagc acaggcgaga tcaacatcat gcaaagtgaa    3420
acagttcagg acgtgctgct cctggacccc cgctggctct gcacaaacgt cctggggaag    3480
ttgctgtccg tggagacccc cacgggcgctg caccactacc ggggccgcta caccgtggag    3540
gacatccagc gcctggtgcc cgacagcgac gtggaggagc tgctgcagat cctcgatgcc    3600
atggacatct gcgcccggga cctgagcagc gggaccatgg tggacgtccc agccctgatc    3660
aagacagaca acctgcaccg ctcctgggct gatgaggagg acgaggtgat ggtgtatggt    3720
ggcgtgcgca tcgtgcccgt ggaacacctc accccttcc catgtggcat ctttcacaag    3780
gtccaggtga acctgtgccg gtggatccac cagcaaagca cagagggcga cgcggacatc    3840
cgcctgtggg tgaatggctg caagctggcc aaccgtgggg ccgagctgct ggtgctgctg    3900
gtcaaccacg gccagggcat tgaggtccag gtccgtggcc tggagacgga gaagatcaag    3960
tgctgcctgc tgctggactc ggtgtgcagc accattgaga acgtcatggc caccacgctg    4020
ccagggctcc tgaccgtgaa gcattacctg agccccagc agctgcggga gcaccatgag    4080
cccgtcatga tctaccagcc acgggacttc ttccgggcac agactctgaa ggaaacctca    4140
ctgaccaaca ccatgggggg gtacaaggaa agcttcagca gcatcatgtg cttcgggtgt    4200
cacgacgtct actcacaggc cagcctcggc atggacatcc atgcatcaga cctgaacctc    4260
ctcactcgga ggaaactgag tcgctgctg gaccgccgg accccctggg gaaggactgg    4320
tgccttctcg ccatgaactt aggcctccct gacctcgtgg caaagtacaa caccaataac    4380
ggggctccca aggatttcct ccccagcccc ctccacgccc tgctgcggga atggaccacc    4440
taccctgaga gcacagtggg caccctcatg tccaaactga gggagctggg tcgccgggat    4500
```

```
gccgcagacc tttgctgaa ggcatcctct gtgttcaaaa tcaacctgga tggcaatggc      4560
caggaggcct atgcctcgag ctgcaacagc ggcacctctt acaattccat tagctctgtt      4620
gtatcccggt gagggcagcc tctggcttgg acagggtctg tttggactgc agaaccaagg      4680
gggtgatgta gcccatcctt cccctttggag atgctgaggg tgtttcttcc tgcacccaca      4740
gccaggggga tgccactcct ccctccggct gacctgtttt ctctgccgct acctccctcc      4800
ccgtctcatt ccgttgtctg tggatggtca ttgcagttta agagcagaac agatctttta      4860
ctttggccgc ttgaaaagct agtgtacctc ctctcagtgt tttggactcc atctctcatc      4920
ctccagtacc ttgcttctta ctgataattt tgctggaatt cctaactttt caatgacatt      4980
ttttttaact atcatattga ttgtcccttta aaaagaaaaa gtgcatattt atccaaaatg      5040
tgtatttctt atacgctttt ctgtgttata ccatttcctc agcttatctc ttttatattt      5100
gtaggagaaa ctcccatgta tggaatccca ctgtatgatt tataaacaga caatatgtga      5160
gtgccttttg cagaagaggg tgtgtttgaa atcatcggag tcagccagga gctgtcacca      5220
aggaaacgct acctctctgt cccttgctgt atgctgatca tcgccagagg tgcttcaccc      5280
tgagttttgt tttgtattgt tttctgacag tttttctgtt ttgtttggca aggaaagggg      5340
agaagggaat cctcctccag ggtgatttta tgatcagtgt tgttgctcta ggaagacatt      5400
tttccgtttg cttttgttcc aatgtcaatg tgaacgtcca catgaaacct acacactgtc      5460
atgcttcatc attccctctc atctcaggta aaggttgac acagttgtag ggttacagag      5520
acctatgtaa gaattcagaa gaccccctgac tcatcatttg tggcagtccc ttataattgg      5580
tgcatagcag atggttttcca catttagatc ctggtttcat aacttcctgt acttgaagtc      5640
taaaagcaga aaataaagga agcaagtttt cttccatgat tttaaattgt gatcgagttt      5700
taaattgata ggagggaaca tgtcctaatt cttctgtcct gagaagcatg taatgttaat      5760
gttatatcat atgtatatat atatatgcac tatgtatata catatatatt aatactggta      5820
tttttactta atctataaaa tgtcgttaaa aagttgtttg ttttttttctt tttttataaa      5880 taaactgttg ctcgttaaaa aaaaaaaaaa                                       5910

<210> SEQ ID NO 13
<211> LENGTH: 980
<212> TYPE: DNA
<213> ORGANISM: Homo sapiens

<400> SEQUENCE: 13
gcgcggggga gccattagga ggcgaggaga gaggagggcg cagctcccgc ccagcccagc        60
cctgcccagc cctgcccgga ggcagacgcg ccggaaccgg gacgcgataa atatgcagag       120
cggaggcttc gcgcagcaga gcccgcgcgc cgcccgctcc gggtgctgaa tccaggcgtg       180
gggacacgag ccaggcgccg ccgccggagc cagcggagcc ggggcagag ccggagcgcg       240 tccgcgtcca cgcagccgcc ggccggccag cacccagggc cctgcatgcc aggtcgttgg       300
aggtggcagc gagacatgca cccggcccgg aagctcctca gcctcctctt cctcatcctg       360
atgggcactg aactcactca aaataaaaga gaaacaaag cagagaagat gggagggcca       420
gagagcgaga ggaagaccac aggagagaag acactgaacg agcttccctt gttttgcctg       480
gaagcccacg ctggctccct ggctctgccc aggatgtgca gtccaaatcc caatccagca       540
gtggggttat gtcgtcccgc ttaccctcag agcccttctc ctggtgctgc ccagacgatc       600
agccagtccc tcctggagag gttctgcatg gcctctagga gagaagtttt cttggcccca       660
```

```
ggaaggcctg gtggagggtg gtggttgtgc actgttgctg gacagatgca ttcattcatg    720
tgcacacaca cacacacaca tgcacacaca ggggagcaga tacctgcaga gaagagccaa    780
ccaggtcctg attagtggca agctgcccca caaagggcta tgcctgtgtc ttattgagac    840
accttggcaa agagatggct gattctgggt ggtcctggac atggccgcac ccaagggccc    900
tccaagcctt aatggcaccc tgaagcctcc atgcccaggc caaagatgc ttttcctccc    960 taaaaaaaaa aaaaaaaaa                                                 980

<210> SEQ ID NO 14
<211> LENGTH: 1721
<212> TYPE: DNA
<213> ORGANISM: Homo sapiens

<400> SEQUENCE: 14
caccagcaca gcaaacccgc cgggatcaaa gtgtaccagt cggcagcatg gctacgaaat     60
gtgggaattg tggaccccggc tactccaccc ctctggaggc catgaaagga cccagggaag    120
agatcgtcta cctgccctgc atttaccgaa acacaggcac tgaggcccca gattatctgg    180
ccactgtgga tgttgacccc aagtctcccc agtattgcca ggtcatccac cggctgccca    240
tgcccaacct gaaggacgag ctgcatcact caggatggaa cacctgcagc agctgcttcg    300
gtgatagcac caagtcgcgc accaagctgg tgctgcccag tctcatctcc tctcgcatct    360
atgtggtgga cgtgggctct gagccccggg ccccaaagct gcacaaggtc attgagccca    420
aggacatcca tgccaagtgc gaactggcct ttctccacac cagccactgc ctggccagcg    480
gggaagtgat gatcagctcc ctgggagacg tcaagggcaa tggcaaaggg ggttttgtgc    540
tgctggatgg ggagacgttc gaggtgaagg ggacatggga gagacctggg ggtgctgcac    600
cgttgggcta tgacttctgg taccagcctc gacacaatgt catgatcagc actgagtggg    660
cagctcccaa tgtcttacga gatggcttca accccgctga tgtggaggct ggactgtacg    720
ggagccactt atatgtatgg gactggcagc gccatgagat tgtgcagacc ctgtctctaa    780
aagatgggct tattcccttg gagatccgct tcctgcacaa cccagacgct gcccaaggct    840 tgtgggctg cgcactcagc tccaccatcc agcgcttcta caagaacgag ggaggtacat    900
ggtcagtgga gaaggtgatc caggtgcccc ccaagaaagt gaagggctgg ctgctgcccg    960
aaatgccagg cctgatcacc gacatcctgc tctccctgga cgaccgcttc ctctacttca   1020
gcaactggct gcatggggac ctgaggcagt atgacatctc tgacccacag agaccccgcc   1080
tcacaggaca gctcttcctc ggaggcagca ttgttaaggg aggccctgtg caagtgctgg   1140
aggacgagga actaaagtcc cagccagagc ccctagtggt caaggaaaaa cgggtggctg   1200
gaggccctca gatgatccag ctcagcctgg atgggaagcg cctctacatc accacgtcgc   1260
tgtacagtgc ctgggacaag cagttttacc ctgatctcat cagggaaggc tctgtgatgc   1320
tgcaggttga tgtagacaca gtaaaaggag ggctgaagtt gaaccccaac ttcctggtgg   1380
acttcgggaa ggagcccctt ggccagccc ttgcccatga gctccgctac cctgggggcg   1440
attgtagctc tgcatctgg atttgaactc caccctcatc acccacactc ctatttttgg   1500
gccctcactt ccttggggac ctggcttcat tctgctctct cttggcaccc gaccccttgc   1560
agcatgtacc acacagccaa gctgagactg tggcaatgtg ttgagtcata tacatttact   1620
gaccactgtt gcttgttgct cactgtgctg ctttttccatg agctcttgga ggcaccaaga   1680
aataaactcg taaccctgtc cttcaaaaaa aaaaaaaaaa a                        1721
```

<210> SEQ ID NO 15
<211> LENGTH: 2588
<212> TYPE: DNA
<213> ORGANISM: Homo sapiens

<400> SEQUENCE: 15

```
ggcacgaggc tctctcctcc ctctttcttc gggcagcctc cccaccaccc cacttcagcc      60
tcccccactc ttgccgcctc catatcatca agctctggtg gcgcctgggg ggcttttcgg     120
atcggcagga tgtaccccca gggaaggcac ccgaccccgc tccagtccgg ccagcccttc     180
aagttctcga tcttggagat ctgcgaccgc atcaaagaag aattccagtt tcttcaggct     240
caataccaca gcctcaagct agaatgtgag aagctggcca gcgagaagac ggaaatgcag     300
cgacattatg tcatgtatta tgagatgtcg tacgggctca acattgaaat gcataagcag     360
gcggagattg tgaagcgtct gagcggtatc tgcgctcaga ttatcccctt cctgacccag     420
gagcatcagc agcaggtgct ccaggccgta gaacgcgcca gcaggtcac cgtgggggag     480
ctgaacagcc tcatcgggca gcagctccag ccgctgtccc accacgcacc ccctgtgccc     540
ctcaccccc gcccagccgg gctggtgggc ggcagtgcta cggggctgct tgctctgtct     600
ggagccctgg ctgcccaggc tcagctggcg gcggctgtca aggaggaccg tgcgggcgtg     660
gaggccgagg ggtccagagt ggagagagcc ccgagcagga gtgcatctcc ctcgcccct     720
gagagtctcg tggaggagga gcgaccgagt ggccctggtg gtggcgggaa gcagagagca     780
gatgagaagg agccatcagg accttatgaa agcgacgaag acaagagtga ttacaatctg     840
gtggtggacg aggaccaacc ctcagagccc ccagcccgg ctaccacccc ctgcggaaag     900
gtacccatct gcattcctgc ccgtcgggac ctggtggaca gtccagcctc cttggcctct    960
agccttggct caccgctgcc tagagccaag gagctcatcc tgaatgacct tcccgccagc   1020
actcctgcct ccaaatcctg tgactcctcc ccgccccagg acgcttccac ccccgggccc   1080
agctcggcca gtcacctctg ccagcttgct gccaagccag caccttccac ggacagcgtc   1140
gccctgagga gccccctgac tctgtccagt cccttcacca gtccttcag cctgggctcc   1200
cacagcactc tcaacggaga cctctccgtg cccagctcct acgtcagcct ccacctgtcc   1260
ccccaggtca gcagctctgt ggtgtacgga cgctcccccg tgatggcatt tgagtctcat   1320
ccccatctcc gagggtcatc cgtctcttcc tccctaccca gcatccctgg gggaaagccg   1380
gcctactcct ccacgtgtc tgcggacggg cagatgcagc cggttccctt cccctcggat   1440
gcactggtag gcgcgggcat cccgcggcac gcccggcagc tgcacacgct ggcccatggc   1500
gaggtggtct gcgcggtcac catcagcggc tccacacagc atgtgtacac gggcggcaag   1560
ggctgtgtga aggtgtggga cgtgggccag cctggggcca agacgcccgt ggcccagctc   1620
gactgcctga accgagacaa ctacattcgt tcctgcaagt tgctgccgga tggccggagt   1680
ctgatcgtgg gcggtgaggc cagcaccttg tccatttggg acctggcggc gcccacccc   1740
cgtatcaagg ccgagctgac ttcctcagcc ccagcctgct acgccctggc cgtcagcccc   1800
gacgccaagt tttgcttctc ctgctgcagc gatggcaaca ttgtggtctg ggacctgcag   1860
aatcagacta tggtcaggca gttccagggc cacacggacg gcgccagctg cattgatatt   1920
tccgattacg gcactcggct ctggacaggg gcctggacac acggtgcg ctgctgggac   1980
ctgcgggagg gccgccagct gcagcagcat gacttcagct cccagatttt ctccctgggc   2040
cactgcccta accaggactg gctggcggtc ggaatggaga gtagcaacgt ggagatcctg   2100
cacgtccgca agccggagaa ataccagctg cacctccacg agagctgcgt gctgtccctg   2160
```

-continued

| | |
|---|---|
| aagtttgcct cctgcggacg gtggtttgtg agcaccggga aggacaacct gctcaacgcc | 2220 |
| tggaggacgc cgtacggggc cagcattttc cagtccaagg agtcgtcctc agtcctgagt | 2280 |
| tgtgacatct ccagaaataa caaatacatc gtgacaggct cggggggacaa gaaggccacc | 2340 |
| gtgtatgagg tggtctactg agacatgacc ccccttcctg tacccgaagt ccagactccc | 2400 |
| agggaatca gcagccagga cagacatcct agcagccgcc tcccagccct gcctaggaac | 2460 |
| cgtacatccc atctgctctc tggccaacgg cttcacacct tccctgctg catgtggggg | 2520 |
| ccgatgggca ggggacctcg gtggaaataa aatgtatcta tcacatccgc aaaaaaaaaa | 2580 |
| aaaaaaaa | 2588 |

<210> SEQ ID NO 16
<211> LENGTH: 8133
<212> TYPE: DNA
<213> ORGANISM: Homo sapiens

<400> SEQUENCE: 16

| | |
|---|---|
| cgtccctgca gccctcgccc ggcgctccag tagcaggacc cggtctcggg accagccggt | 60 |
| aatatgcacg tgtcactagc tgaggccctg gaggttcggg gtggaccact tcaggaggaa | 120 |
| gaaatatggg ctgtattaaa tcaaagtgct gaaagtctcc aagaattatt cagaaaagta | 180 |
| agcctagctg atcctgctgc ccttggcttc atcatttctc catggtctct gctgttgctg | 240 |
| ccatctggta gtgtgtcatt tacagatgaa atatttcca atcaggatct tcgagcattc | 300 |
| actgcaccag aggttcttca aaatcagtca ctaacttctc tctcagatgt tgaaaagatc | 360 |
| cacatttatt ctcttggaat gacactgtat tgggggggctg attatgaagt gcctcagagc | 420 |
| caacctatta agcttggaga tcatctcaac agcatactgc ttggaatgtg tgaggatgtt | 480 |
| atttacgctc gagtttctgt tcggactgtg ctggatgctt gcagtgccca cattaggaat | 540 |
| agcaattgtg caccctcatt ttcctacgtg aaacacttgg taaaactggt tctgggaaat | 600 |
| cttttctggga cagatcagct ttcctgtaac agtgaacaaa agcctgatcg aagccaggct | 660 |
| attcgagatc gattgcgagg aaaaggatta ccaacaggaa gaagctctac ttctgatgta | 720 |
| ctagacatac aaaagcctcc actctctcat cagacctttc ttaacaaagg cttagtaaa | 780 |
| tctatgggat ttctgtccat caaagataca caagatgaga attatttcaa ggacatttta | 840 |
| tcagataatt ctggacgtga agattctgaa atacattct ccccttacca gttcaaaact | 900 |
| agtggcccag aaaaaaaacc catccctggc attgatgtgc tttctaagaa gaagatctgg | 960 |
| gcttcatcca tggacttgct ttgtacagct gacagagact tctcttcagg agagactgcc | 1020 |
| acatatcgtc gttgtcaccc tgaggcagta acagtgcgga cttcaactac tcctagaaaa | 1080 |
| aaggaggcaa gatactcaga tggaagtata gccttggata tctttggccc tcagaaaatg | 1140 |
| gatccaatat atcacactcg agaattgccc acctcctcag caatatcaag tgctttggac | 1200 |
| cgaatccgag agagacaaaa gaaacttcag gttctgaggg aagccatgaa tgtagaagaa | 1260 |
| ccagttcgaa gatacaaaac ttatcatggt gatgtcttta gtacctccag tgaaagtcca | 1320 |
| tctattattt cctctgaatc agatttcaga caagtgagaa gaagtgaagc ctcaaagagg | 1380 |
| tttgaatcca gcagtggtct cccagggggta gatgaaacct taagtcaagg ccagtcacag | 1440 |
| agaccgagca gacaatatga aacacccttt gaaggcaact taattaatca agagatcatg | 1500 |
| ctaaaacggc aagaggaaga actgatgcag ctacaagcca aatggccct tagacagtct | 1560 |
| cggttgagcc tatatccagg agacacaatc aaagcgtcca tgcttgacat caccaggggat | 1620 |
| ccgttaagag aaaattgccct agaaacagcc atgactcaaa gaaaactgag gaatttcttt | 1680 |

-continued

```
ggccctgagt tgtgaaaat gacaattgaa ccatttatat ctttggattt gccacggtct    1740
attcttacta agaaagggaa gaatgaggat aaccgaagga aagtaaacat aatgcttctg    1800
aacgggcaaa gactggaact gacctgtgat accaaaacta tatgtaaaga tgtgtttgat    1860
atggttgtgg cacatattgg cttagtagag catcatttgt ttgctttagc taccctcaaa    1920
gataatgaat atttctttgt tgatcctgac ttaaaattaa ccaaagtggc cccagaggga    1980
tggaagaag aaccaaagaa aaagaccaaa gccactgtta attttacttt gttttttcaga    2040
attaaatttt ttatggatga tgttagtcta atacaacata ctctgacgtg tcatcagtat    2100
taccttcagc ttcgaaaaga tattttggag gaaaggatgc actgtgatga tgagacttcc    2160
ttattgctgg catccttggc tctccaggct gagtatggag attatcaacc agaggttcat    2220
ggtgtgtctt actttagaat ggagcactat ttgcccgcca gagtgatgga gaaacttgat    2280
ttatcctata tcaaagaaga gttacccaaa ttgcataata cctatgtggg agcttctgaa    2340
aaagagacag agttagaatt tttaaaggtc tgccaaagac tgacagaata tggagttcat    2400
tttcaccgag tgcaccctga gaagaagtca caaacaggaa tattgcttgg agtctgttct    2460
aaaggtgtcc ttgtgtttga agttcacaat ggagtgcgca cattggtcct tcgctttcca    2520
tggagggaaa ccaagaaaat atcttttttct aaaaagaaaa tcacattgca aaatacatca    2580
gatggaataa aacatggctt ccagacagac aacagtaaga tatgccagta cctgctgcac    2640
ctctgctctt accagcataa gttccagcta cagatgagag caagacagag caaccaagat    2700
gcccaagata ttgagagagc ttcgtttagg agcctgaatc tccaagcaga gtctgttaga    2760
ggatttaata tgggacgagc aatcagcact ggcagtctgg ccagcagcac cctcaacaaa    2820
cttgctgttc gacctttatc agttcaagct gagattctga agaggctatc ctgctcagag    2880
ctgtcgcttt accagccatt gcaaaacagt tcaaaagaga agaatgacaa agcttcatgg    2940
gaggaaaagc ctagagagat gagtaaatca taccatgatc tcagtcaggc ctctctctat    3000
ccacatcgga aaaatgtcat tgttaacatg aaccccccac cacaaaccgt gcagagttg    3060
gtgggaaaac cttctcacca gatgtcaaga tctgatgcag aatctttggc aggagtgaca    3120
aaacttaata attcaaagtc tgttgcgagt ttaaatagaa gtcctgaaag gaggaaacat    3180
gaatcagact cctcatccat tgaagaccct gggcaagcat atgttctagg aatgactatg    3240
catagttctg gaaactcttc atcccaagta cccttaaaag aaaatgatgt gctacacaaa    3300
agatggagca tagtatcttc accagaaagg gagatcacct tagtgaacct gaaaaaagat    3360
gcaaagtatg gcttgggatt tcaaattatt ggtggggaga agatgggaag actggaccta    3420
ggcatattta tcagttcagt tgcccctgga ggaccagctg acttggatgg atgcttgaag    3480
ccaggagacc gtttgatatc tgtgaatagt gtgagtctgg agggagtcag ccaccatgct    3540
gcaattgaaa ttttgcaaaa tgcacctgaa gatgtgacac ttgttatctc tcagccaaaa    3600
gaaaagatat ccaaagtgcc ttctactcct gtgcatctca ccaatgagat gaaaaactac    3660
atgaagaaat cttcctacat gcaagacagt gctatagatt cttcttccaa ggatcaccac    3720
tggtcacgtg gtaccctgag gcacatctcg gagaactcct ttgggccgtc tggggggcctg  3780
cgggaaggaa gcctgagttc tcaagattcc aggactgaga gtgccagctt gtctcaaagc    3840
caggtcaatg gtttctttgc cagccattta ggtgaccaaa cctggcagga atcacagcat    3900
ggcagccctt ccccatctgt aatatccaaa gccaccgaga agagactttt cactgatagt    3960
aaccaaagca aaactaaaaa gccaggcatt tctgatgtaa ctgattactc agaccgtgga    4020
```

```
gattcagaca tggatgaagc cacttactcc agcagtcagg atcatcaaac accaaaacag    4080
gaatcttcct cttcagtgaa tacatccaac aagatgaatt ttaaaacttt ttcttcatca    4140
cctcctaagc ctggagatat ctttgaggtt gaactggcta aaaatgataa cagcttgggg    4200
ataagtgtca cggtactgtt tgacaaggga ggtgtgaata cgagtgtcag acatggtggc    4260
atttatgtga aagctgttat tccccaggga gcagcagagt ctgatggtag aattcacaaa    4320
ggtgatcgcg tcctagctgt caatggagtt agtctagaag gagccaccca taagcaagct    4380
gtggaaacac tgagaaatac aggacaggtg gttcatctgt tattagaaaa gggacaatct    4440
ccaacatcta aagaacatgt cccggtaacc ccacagtgta ccctttcaga tcagaatgcc    4500
caaggtcaag gcccagaaaa agtgaagaaa acaactcagg tcaaagacta cagctttgtc    4560
actgaagaaa tacatttga ggtaaaatta tttaaaaata gctcaggtct aggattcagt    4620 tttctcgag aagataatct tataccggag caaattaatg ccagcatagt aagggttaaa    4680
aagctctttc ctggacagcc agcagcagaa agtggaaaaa ttgatgtagg agatgttatc    4740
ttgaaagtga atggagcctc tttgaaagga ctatctcagc aggaagtcat atctgctctc    4800
aggggaactg ctccagaagt attcttgctt ctctgcagac ctccacctgg tgtgctaccg    4860
gaaattgata ctgcgctttt gaccccactt cagtctccag cacaagtact tccaaacagc    4920
agtaaagact cttctcagcc atcatgtgtg gagcaaagca ccagctcaga tgaaaatgaa    4980
atgtcagaca aaagcaaaaa acagtgcaag tccccatcca agagacag ttacagtgac    5040 agcagtggga gtgagaaga tgacttagtg acagctccag caaacatatc aaattcgacc    5100
tggagttcag ctttgcatca gactctaagc aacatggtat cacaggcaca gagtcatcat    5160
gaagcaccca agagtcaaga agataccatt tgtaccatgt tttactatcc tcagaaaatt    5220
cccaataaac cagagtttga ggacagtaat ccttcccctc taccaccgga tatggctcct    5280
gggcagagtt atcaaccca atcagaatct gcttcctcta gttcgatgga taagtatcat    5340
atacatcaca tttctgaacc aactagacaa gaaaactgga caccttttgaa aaatgacttg    5400 gaaaatcacc ttgaagactt tgaactggaa gtagaactcc tcattaccct aattaaatca    5460
gaaaaaggaa gcctgggttt tacagtaacc aaaggcaatc agagaattgg ttgttatgtt    5520
catgatgtca tacaggatcc agccaaaagt gatggaaggc taaaacctgg ggaccggctc    5580
ataaaggtta atgatacaga tgttactaat atgactcata cagatgcagt taatctgctc    5640
cgggctgcat ccaaaaacagt cagattagtt attggacgag ttctagaatt acccagaata    5700
ccaatgttgc ctcatttgct accggacata acactaacgt gcaacaaaga ggagttgggt    5760
ttttccttat gtggaggtca tgacagcctt tatcaagtgg tatatattag tgatattaat    5820
ccaaggtccg tcgcagccat tgagggtaat ctccagctat tagatgtcat ccattatgtg    5880
aacggagtca gcacacaagg aatgaccttg gaggaagtta acagagcatt agacatgtca    5940
cttccttcat tggtattgaa agcaacaaga aatgatcttc cagtggtccc cagctcaaag    6000
aggtctgctg tttcagctcc aaagtcaacc aaaggcaatg gttcctacag tgtgggtct    6060 tgcagccagc ctgccctcac tcctaatgat tcattctcca cggttgctgg ggaagaaata    6120
aatgaaatat cgtaccccaa aggaaaatgt ctacttatc agataaaggg atcaccaaac    6180
ttgactctgc ccaaagaatc ttatatacaa gaagatgaca tttatgatga ttcccaagaa    6240
gctgaagtta ccagtctcct gctggatgtt gtggatgagg aagcccagaa tctttttaaaac    6300 gaaaataatg cagcaggata ctcctgtggt ccaggtacat taaagatgaa tgggaagtta    6360
tcagaagaga gaacagaaga tacagactgc gatggttcac ctttacctga gtattttact    6420
```

```
gaggccacca aaatgaatgg ctgtgaagaa tattgtgaag aaaaagtaaa aagtgaaagc   6480
ttaattcaga agccacaaga aaagaagact gatgatgatg aaataacatg gggaaatgat   6540
gagttgccaa tagagagaac aaaccatgaa gattctgata aagatcattc ctttctgaca   6600
aacgatgagc tcgctgtact ccctgtcgtc aaagtgcttc cctctggtaa atacacgggt   6660
gccaacttaa aatcagtcat tcgagtcctg cggggtttgc tagatcaagg aattccttct   6720
aaggagctgg agaatcttca agaattaaaa cctttggatc agtgtctaat tgggcaaact   6780
aaggaaaaca gaaggaagaa cagatataaa aatatacttc cctatgatgc tacaagagtg   6840
cctcttggag atgaaggtgg ctatatcaat gccagcttca ttaagatacc agttgggaaa   6900
gaagagttcg tttacattgc ctgccaagga ccactgccta caactgttgg agacttctgg   6960
cagatgattt gggagcaaaa atccacagtg atagccatga tgactcaaga agtagaagga   7020
gaaaaaatca aatgccagcg ctattggccc aacatcctag gcaaaacaac aatggtcagc   7080
aacagacttc gactggctct tgtgagaatg cagcagctga agggctttgt ggtgagggca   7140
atgacccttg aagatattca gaccagagag gtgcgccata tttctcatct gaatttcact   7200
gcctggccag accatgatac accttctcaa ccagatgatc tgcttacttt tatctcctac   7260
atgagacaca tccacagatc aggcccaatc attacgcact gcagtgctgg cattggacgt   7320
tcagggaccc tgatttgcat agatgtggtt ctgggattaa tcagtcagga tcttgatttt   7380
gacatctctg atttggtgcg ctgcatgaga ctacaaagac acggaatggt tcagacagag   7440
gatcaatata ttttctgcta tcaagtcatc ctttatgtcc tgacacgtct tcaagcagaa   7500
gaagagcaaa aacagcagcc tcagcttctg aagtgacatg aaaagagcct ctggatgcat   7560
ttccatttct ctccttaacc tccagcagac tcctgctctc tatccaaaat aagatcacag   7620
agcagcaagt tcatacaaca tgcatgttct cctctatctt agaggggtat tcttcttgaa   7680
aataaaaaat attgaaatgc tgtattttta cagctacttt aacctatgat aattatttac   7740
aaaattttaa cactaaccaa acaatgcaga tcttagggat gattaaaggc agcatttgat   7800
gatagcagac attgttacaa ggacatggtg agtctatttt taatgcacca atcttgttta   7860
tagcaaaaat gttttccaat attttaataa agtagttatt ttataggga tacttgaaac   7920 cagtatttaa gctttaaatg acagtaatat tggcatagaa aaaagtagca aatgtttact   7980
gtatcaattt ctaatgttta ctatatagaa tttcctgtaa tatatttata acttttttca   8040
tgaaaatgga gttatcagtt atctgtttgt tactgcatca tctgtttgta atcattatct   8100
cactttgtaa ataaaaacac accttaaaac atg                                8133

<210> SEQ ID NO 17
<211> LENGTH: 2272
<212> TYPE: DNA
<213> ORGANISM: Homo sapiens

<400> SEQUENCE: 17
aggcgcccgc cgccgcgcg tgattctcgc ctcgccgcag cccagccctg cgcgccttgc     60
ccggcggccc ccgcccggcc gctccgggcc cctggccccg cggagcgatg ctgctgctgg    120
ctgccgcctt cctcgtggcc ttcgtgctgc tgctgtacat ggtgtctccg ctcatcagcc    180
ccaagcccct cgccctgccc ggggcgcatg tggtggttac aggaggttcc agtggcatcg    240
ggaagtgcat tgctatcgag tgctataaac aaggagcttt tataactctg gttgcacgaa    300
atgaggataa gctgctgcag gcaaagaaag aaattgaaat gcactctatt aatgacaaac    360
```

```
aggtggtgct tgcatatca gttgatgtat ctcaagacta taaccaagta gagaatgtca    420
taaaacaagc acaggagaaa ctgggtccag tggacatgct ggtaaattgt gcaggaatgg    480
cagtgtcagg aaaatttgaa gatcttgaag ttagtacctt tgaaaggtta atgagcatca    540
attacctggg cagcgtgtac cccagccggg ccgtgatcac caccatgaag gagcgccggg    600
tgggcaggat cgtgtttgtg tcctcccagg caggacagtt gggattattc ggtttcacag    660
cctactctgc atccaagttt gccataaggg gattggcaga agctttgcag atggaggtga    720
agccatataa tgtctacatc acagttgctt acccaccaga cacagacaca cctggctttg    780
ccgaagaaaa cagaacaaag cctttggaga ctcgacttat ttcagagacc acatctgtgt    840
gcaaaccaga acaggtggcc aaacaaattg ttaaagatgc catacaagga aatttcaaca    900
gttcccttgg ctcagatggg tacatgctct cggccctgac ctgtgggatg gctccagtaa    960
cttctattac tgaggggctc cagcaggtgg tcaccatggg ccttttccgc actattgctt   1020
tgttttacct tggaagtttt gacagcatag ttcgtcgctg catgatgcag agagaaaaat   1080
ctgaaaatgc agacaaaact gcctaatctt cttacccctt ggaagaagac tgtttccaaa   1140
taatttgaac agcttgctgc taaatgggac ccaattttg gcctatagac acttatgtat    1200
tgttttcgaa tacgtcagat tggaccagtg ctcttcagga atgtggctgc aagcaagggg   1260
ctagaagttc acctcctgac agtattatta atactatgca aatatggaat aggagaccat   1320
ttgattttct aggctttgtg gtagagaggt gaaggtatga gaattaatag cgtgtgaaca   1380
aagtaaagaa caggattcca gaatgatcat taaatttgtt tctatttatt cttttttgcc   1440
cccctagaga ttaagtccag aaatgtactt tctggcacat aaagaaatct tgaggacttt   1500
gtttaaacct tccataaaaa aacaattttc ggtttctcgg gttctctctc tctgtctctc   1560
tgtctctctg tctctctgtc tctctgtctc tctctctctc tctcttctt tctttgtgta    1620 ttttattcaa gatgagttgg acccattgcc agtgagtctg aatgtcactg acagccctgt   1680
gttgtgctca ggactcactc tgctgctggt ggaaactcat ggcttctctc tctctttgat   1740
cccataaagc tacgaggggg acgggagagg gcagtgcaat gggaagtaaa gagatatttt   1800
ccagtaggaa aagcaatgct ttcttgtctt tagactcaaa tgcttaggga acgtttcatt   1860
tctcattcat ggggaaaggc agcctcctta aatgttttct gaagagcggt aaaatctaga   1920
agcttaagaa tttacagttc cttcaataac catgatgacc tgaagttcac ctatcccatt   1980
ttagcatcta cttgttttc ccatctcttc ctttccaatt ttgcttatac tgctgtaata    2040
tttttgtaaa aaaaaaaaa aaggaaaaaa aagaccagct aaaattttcg acttgacttt    2100
ttaacttaac tcatgaatta attaaagcaa atgaaaaaat taaaagtgt gactttttct    2160 cggagcatat atgtagcttt taggaaaggc tgatgatggt ataagttttg ctcattaaga   2220
aaaaaagaca aggctgattt tgaagagagt tgcttttgaa ataaatgat ca            2272
```

<210> SEQ ID NO 18
<211> LENGTH: 1414
<212> TYPE: DNA
<213> ORGANISM: Homo sapiens

<400> SEQUENCE: 18

```
gaattcgcac tgctctgaga atttgtgagc agcccctaac aggctgttac ttcactacaa     60
ctgacgatat gatcatctta atttacttat ttctcttgct atgggaagac actcaaggat    120
ggggattcaa ggatggaatt tttcataact ccatatggct tgaacgagca gccggtgtgt    180
accacagaga agcacggtct ggcaaataca agctcaccta cgcagaagct aaggcggtgt    240
```

| | |
|---|---|
| gtgaatttga aggcggccat ctcgcaactt acaagcagct agaggcagcc agaaaaattg | 300 |
| gatttcatgt ctgtgctgct ggatggatgg ctaagggcag agttggatac cccattgtga | 360 |
| agccagggcc caactgatga tttgaaaaaa ctggcattat tgattatgga atccgtctca | 420 |
| ataggagtga agatgggat gcctattgct acaacccaca cgcaaaggag tgtggtggcg | 480 |
| tctttacaga tccaaagcga attttttaaat ctccaggctt cccaaatgag tacgaagata | 540 |
| accaaatctg ctactggcac attagactca agtatggtca gcgtattcac ctgagttttt | 600 |
| tagattttga ccttgaagat gacccaggtt gcttggctga ttatgttgaa atatatgaca | 660 |
| gttacgatga tgtccatggc tttgtgggaa gatactgtgg agatgagctt ccagatgaca | 720 |
| tcatcagtac aggaaatgtc atgaccttga agtttctaag tgatgcttca gtgacagctg | 780 |
| gaggtttcca aatcaaatat gttgcaatgg atcctgtatc caaatccagt caaggaaaaa | 840 |
| atacaagtac tacttctact ggaaataaaa acttttagc tggaagattt agccacttat | 900 |
| aaaaaaaaaa aaggatgatc aaaacacaca gtgtttatgt tggaatcttt tggaactcct | 960 |
| ttgatctcac tgttattatt aacatttatt tattatttt ctaaatgtga agaaatacaa | 1020 |
| taatttaggg aaaattggaa aatataggaa actttaaacg agaaaatgaa acctctcata | 1080 |
| atcccactgc atagaaataa caagcgttaa cattttcata tttttttctt tcagtcattt | 1140 |
| ttgtatttgt ggtatatgta tatatgtacc tatatgtatt tgcatttgaa attttggaat | 1200 |
| cctgctctat gtacagtttt gtattatact ttttaaatct tgaactttat gaacattttc | 1260 |
| tgaaatcatt gattattcta caaaaacatg attttaaaca gctgtaaaat attctatgat | 1320 |
| atgaatgttt tatgcattat ttaagcctgt ctctattgtt ggaatttcag gtcattttca | 1380 |
| taaatattgt tgcaataaat atccttcgga attc | 1414 |

<210> SEQ ID NO 19
<211> LENGTH: 2704
<212> TYPE: DNA
<213> ORGANISM: Homo sapiens

<400> SEQUENCE: 19

| | |
|---|---|
| gggagaaacg ttctcactcg ctctctgctc gctgcgggcg ctccccgccc tctgctgcca | 60 |
| gaaccttggg gatgtgccta gacccggcgc agcacacgtc cgggccaacc gcagcagaa | 120 |
| caaacctttg gcgggcggcc aggaggctcc ctcccagcca ccgcccccct ccagcgcctt | 180 |
| ttttccccc catacaatac aagatcttcc ttcctcagtt cccttaaagc acagcccagg | 240 |
| gaaacctcct cacagttttc atccagccac gggccagcat gtctggggc aaatacgtag | 300 |
| actcggaggg acatctctac accgttccca tccgggaaca gggcaacatc tacaagccca | 360 |
| acaacaaggc catggcagac gagctgagcg agaagcaagt gtacgacgcg cacaccaagg | 420 |
| agatcgacct ggtcaaccgc gaccctaaac acctcaacga tgacgtggtc aagattgact | 480 |
| tgaagatgt gattgcagaa ccagaaggga cacacagttt tgacggcatt tggaaggcca | 540 |
| gcttcaccac cttcactgtg acgaaatact ggttttaccg cttgctgtct gccctctttg | 600 |
| gcatcccgat ggcactcatc tggggcattt acttcgccat tctctctttc ctgcacatct | 660 |
| gggcagttgt accatgcatt aagagcttcc tgattgagat tcagtgcatc agccgtgtct | 720 |
| attccatcta cgtccacacc gtctgtgacc cactctttga agctgttggg aaaatattca | 780 |
| gcaatgtccg catcaacttg cagaaagaaa tataaatgac atttcaagga tagaagtata | 840 |
| cctgattttt tttcctttta attttcctgg tgccaatttc aagttccaag ttgctaatac | 900 |

-continued

```
agcaacaatt tatgaattga attatcttgg ttgaaaataa aaagatcact ttctcagttt      960
tcataagtat tatgtctctt ctgagctatt tcatctattt ttggcagtct gaatttttaa     1020
aacccattta aattttttc cttacctttt tatttgcatg tggatcaacc atcgctttat     1080
tggctgagat atgaacatat tgttgaaagg taatttgaga gaaatatgaa gaactgagga     1140
ggaaaaaaaa aaaaagaaa agaaccaaca acctcaactg cctactccaa aatgttggtc     1200
attttatgtt aagggaagaa ttccagggta tggccatgga gtgtacaagt atgtgggcag     1260
attttcagca aactctttc ccactgttta aggagttagt ggattactgc cattcacttc     1320
ataatccagt aggatccagt gatccttaca agttagaaaa cataatcttc tgccttctca     1380
tgatccaact aatgccttac tcttcttgaa attttaacct atgatatttt ctgtgcctga     1440
atatttgtta tgtagataac aagacctcag tgccttcctg tttttcacat tttccttttc     1500
aaatagggtc taactcagca actcgcttta ggtcagcagc ctccctgaag accaaaatta     1560
gaatatccat gacctagttt tccatgcgtg tttctgactc tgagctacag agtctggtga     1620
agctcacttc tgggcttcat ctggcaacat ctttatccgt agtgggtatg gttgacacta     1680
gcccaatgaa atgaattaaa gtggaccaat agggctgagc tctctgtggg ctggcagtcc     1740
tggaagccag cttccctgc ctctcatcaa ctgaatgagg tcagcatgtc tattcagctt     1800 cgtttattt caagaataat cacgctttcc tgaatccaaa ctaatccatc accgggtgg     1860 tttagtggct caacattgtg ttcccatttc agctgatcag tgggcctcca aggaggggct     1920
gtaaaatgga ggccattgtg tgagcctatc agagttgctg caaacctgac ccctgctcag     1980
taaagcactt gcaaccgtct gttatgctgt gacacatggc ccctccccct gccaggagct     2040
ttggacctaa tccaagcatc cctttgccca gaaagaagat gggggaggag gcagtaataa     2100
aaagattgaa gtattttgct ggaataagtt caaattcttc tgaactcaaa ctgaggaatt     2160
tcacctgtaa acctgagtcg tacagaaagc tgcctggtat atccaaaagc ttttattcc     2220 tcctgctcat attgtgattc tgcctttggg acttttctt aaaccttcag ttatgatttt     2280
tttttcatac acttattgga actctgcttg attttttgcct cttccagtct tcctgacact     2340
ttaattacca acctgttacc tactttgact ttttgcattt aaaacagaca ctggcatgga     2400
tatagtttta cttttaaact gtgtacataa ctgaaaatgt gctatactgc atacttttta     2460
aatgtaaaga tattttttatc tttatatgaa gaaaatcact taggaaatgg ctttgtgatt     2520
caatctgtaa actgtgtatt ccaagacatg tctgttctac atagatgctt agtccctcat     2580
gcaaatcaat tactggtcca aaagattgct gaaatttat atgcttactg atatattttta     2640 caatttttta tcatgcatgt cctgtaaagg ttacaagcct gcacaataaa aatgtttaac     2700
ggtt                                                                 2704
```

<210> SEQ ID NO 20
<211> LENGTH: 1440
<212> TYPE: DNA
<213> ORGANISM: Homo sapiens

<400> SEQUENCE: 20

```
cgggcgcaga agcccctcct cggcgtcctg gtcccggccg tgcccgcggt gtcccgggag       60
gaaggggcgg gccggggtc gggaggagtc acgtgccccc tcccgcccca ggtcgtcctc      120
tcagcatggg ggtcccgcgg cctcagccct gggcgctggg gctcctgctc tttctccttc      180
ctgggagcct gggcgcagaa agccaccctct ccctcctgta ccaccttacc gcggtgtcct     240
cgcctgcccc ggggactcct gccttctggg tgtccggctg gctgggcccg cagcagtacc      300
```

-continued

| | |
|---|---|
| tgagctacaa tagcctgcgg ggcgaggcgg agccctgtgg agcttgggtc tgggaaaacc | 360 |
| aggtgtcctg gtattgggag aaagagacca cagatctgag gatcaaggag aagctctttc | 420 |
| tggaagcttt caaagctttg gggggaaaag gtccctacac tctgcagggc ctgctgggct | 480 |
| gtgaactggg ccctgacaac acctcggtgc ccaccgccaa gttcgccctg aacggcgagg | 540 |
| agttcatgaa tttcgacctc aagcaggca cctggggtgg ggactggccc gaggccctgg | 600 |
| ctatcagtca gcggtggcag cagcaggaca aggcggccaa caaggagctc accttcctgc | 660 |
| tattctcctg cccgcaccgc ctgcgggagc acctggagag gggccgcgga aacctggagt | 720 |
| ggaaggagcc cccctccatg cgcctgaagg cccgacccag cagccctggc ttttccgtgc | 780 |
| ttacctgcag cgccttctcc ttctaccctc cggagctgca acttcggttc ctgcggaatg | 840 |
| ggctggccgc tggcaccggc cagggtgact tcggccccaa cagtgacgga tccttccacg | 900 |
| cctcgtcgtc actaacagtc aaaagtggcg atgagcacca ctactgctgc attgtgcagc | 960 |
| acgcggggct ggcgcagccc ctcagggtgg agctggaatc tccagccaag tcctccgtgc | 1020 |
| tcgtggtggg aatcgtcatc ggtgtcttgc tactcacggc agcggctgta ggaggagctc | 1080 |
| tgttgtggag aaggatgagg agtgggctgc cagccccttg gatctcccct cgtggagacg | 1140 |
| acaccggggt cctcctgccc accccagggg aggcccagga tgctgatttg aaggatgtaa | 1200 |
| atgtgattcc agccaccgcc tgaccatccg ccattccgac tgctaaaagc gaatgtagtc | 1260 |
| aggccccttt catgctgtga gacctcctgg aacactggca tctctgagcc tccagaaggg | 1320 |
| gttctgggcc tagttgtcct ccctctggag ccccgtcctg tggtctgcct cagtttcccc | 1380 |
| tcctaataca tatggctgtt ttccacctcg ataatataac acgagtttgg gcccgaaaaa | 1440 |

<210> SEQ ID NO 21
<211> LENGTH: 1634
<212> TYPE: DNA
<213> ORGANISM: Homo sapiens

<400> SEQUENCE: 21

| | |
|---|---|
| ccctaagtga gaggaccaac agttccgaca gcgagcgctc cccagatctg ggccacagca | 60 |
| cgcagattcc aagaaaggtg gtgtatgacc agctcaatca gatcctggtg tcagatgcag | 120 |
| ccctcccaga aaatgtcatt ctggtgaaca ccactgactg gcagggccag tatgtggctg | 180 |
| agctgctcca ggaccagcgg aagcctgtgg tgtgcacctg ctccaccgtg gaggtccagg | 240 |
| ccgtgctgtc cgcccctgctc acccggatcc agcgctactg caactgcaac tcttccatgc | 300 |
| cgaggccagt gaaggtggct gctgtgggag gccagagcta cctgagctcc atcctcaggt | 360 |
| tctttgtcaa gtccctggcc aacatgacct ccgactggct tggctacatg cgcttcctca | 420 |
| tcatcccccct cggttctcac cctgtggcca aatacttggg gtcagtcgac agtaaataca | 480 |
| gtagttcctt cctggattct ggttggagag atctgttcag tcgctcggag ccaccagtgt | 540 |
| cagagcaact ggacgtggca gggcgggtga tgcagtacgt caacggggca gccacgacac | 600 |
| accagcttcc cgtggccgaa gccatgctga cttgccggca taagttccct gatgaagact | 660 |
| cctatcagaa gtttattccc ttcattggcg tggtgaaggt gggtctggtt gaagactctc | 720 |
| cctccacagc aggcgatggg gacgattctc ctgtggtcag ccttactgtg ccctccacat | 780 |
| caccaccctc cagctcgggc ctgagccgag acgccacggc caccctccc tcctcccat | 840 |
| ctatgagcag cgccctggcc atcgtgggga gccctaatag cccatatggg gacgtgattg | 900 |
| gcctccaggt ggactactgg ctgggccacc ccggggagcg gaggagggaa ggcgacaaga | 960 |

| | |
|---|---|
| gggacgccag ctcgaagaac accctcaaga gtgtcttccg ctcagtgcag gtgtcccgcc | 1020 |
| tgccccatag tggggaggcc cagctttctg gcaccatggc catgactgtg gtcaccaaag | 1080 |
| aaaagaacaa gaaagttccc accatcttcc tgagcaagaa accccgagaa aaggaggtgg | 1140 |
| attctaagag ccaggtcatt gaaggcatca gccgcctcat ctgttcttcc ccctccttag | 1200 |
| gccccagcct gggcccagac ccatcctccc agccaggttt ccctccagca ggctccttcc | 1260 |
| ctccctgtca cctccctctc accaacccgg gtctgagcc cctcattcct gaccgtccgt | 1320 |
| gttctcagga gtggttgagg acacagggcc ccagcccagc cctctgcacc ccccagcccg | 1380 |
| gccatctgcg ccccacagcc cctttggagc ttttctcttg tcctctcact ccttcccaga | 1440 |
| agttttgca cagaacttca ttttgaaagt gttttctca ttctccatac ctcccccaag | 1500 |
| ctctcctcca gccttccca gggctcagcc ctgctgtcct gagcgtctcc tgggccagag | 1560 |
| agaggagatg ggggtgggag ggactgagtt gatgttgggt ttttcattca ataaattggt | 1620 |
| gatttcttac cgac | 1634 |

<210> SEQ ID NO 22
<211> LENGTH: 1264
<212> TYPE: DNA
<213> ORGANISM: Homo sapiens

<400> SEQUENCE: 22

| | |
|---|---|
| ggcacgaggg gaggccgggg cggggcgggc gcagccggcg ctgagcttgc agggccgctc | 60 |
| ccctcacccg cccccttcga gtccccgggc ttcgccccac ccggcccgtg ggggagtatc | 120 |
| tgtcctgccg ccttcgccca cgccctgcac tccgggaccg tccctgcgcg ctctgggcgc | 180 |
| accatggccc gcggggctgc gctggcgctg ctgctcttcg gctgctgggg tgttctggtc | 240 |
| gccgccccgg atggtggttt cgatttatcc gatgcccttc ctgacaatga aacaagaaa | 300 |
| cccactgcaa tccccaagaa acccagtgct ggggatgact ttgacttagg agatgctgtt | 360 |
| gttgatggag aaaatgacga cccacgacca ccgaacccac ccaaaccgat gccaaatcca | 420 |
| aaccccaacc accctagttc ctccggtagc ttttcagatg ctgaccttgc ggatggcgtt | 480 |
| tcaggtggag aaggaaaagg aggcagtgat ggtgaggca gccacaggaa agaagggaa | 540 |
| gaggccgacg ccccaggcgt gatccccggg attgtggggg ctgtcgtggt cgccgtggct | 600 |
| ggagccatct ctagcttcat tgcttaccag aaaaagaagc tatgcttcaa agaaaatgca | 660 |
| gaacaagggg aggtggacat ggagagccac cggaatgcca acgcagagcc agctgttcag | 720 |
| cgtactcttt tagagaaata gaagattgtc ggcagaaaca gcccaggcgt tggcagcagg | 780 |
| gttagaacag ctgcctgagg ctcctccctg aaggacacct gcctgagagc agagatggag | 840 |
| gccttctgtt cacggcggat tctttgtttt aatcttgcga tgtgctttgc ttgttgctgg | 900 |
| gcggatgatg tttactaacg atgaatttta catccaaagg gggataggca cttggacccc | 960 |
| cattctccaa ggcccggggg ggcggtttcc catgggatgt gaaaggctgg ccattattaa | 1020 |
| gtccctgtaa ctcaaatgtc aaccccaccg aggcaccccc ccgtccccca gaatcttggc | 1080 |
| tgtttacaaa tcacgtgtcc atcgagcacg tctgaaaccc ctggtagccc cgacttcttt | 1140 |
| ttaattaaaa taaggtaagc ccttcaattt gtttcttcaa tatttctttc atttgtaggg | 1200 |
| atatttgttt ttcatatcag actaataaaa agaaattaga aaccaaaaaa aaaaaaaaaa | 1260 |
| aaaa | 1264 |

<210> SEQ ID NO 23
<211> LENGTH: 1567

<212> TYPE: DNA
<213> ORGANISM: Homo sapiens

<400> SEQUENCE: 23

```
tcctgggcct ctcaaagtct gagccccgct ccgctgatgc ctgtctgcag aatccgcacc      60
aaccagcacc atgcccatga ctctggggta ctggacatcc cgtgggctgg cccacgccat     120
ccgcttgctc ctggaataca cagactcaag ctatgtggaa aagaagtaca cgctggggga    180
cgctcctgac tatgacagaa gccagtggct gaatgaaaaa ttcaagctgg gcctggactt    240
tcccaatctg ccctacttga ttgatggggc tcacaagatc acccagagca atgccatcct    300
gcgctacatt gcccgcaagc acaacctgtg tggggagaca aagaggagag agattcgtgt    360
ggacattttg gagaaccagg ttatggataa ccacatggag ctggtcagac tgtgctatga    420
cccagatttt gagaaactga agccaaaata cttggaggaa ctccctgaaa agctaaagct    480
ctactcagag tttctgggga gcggccatg gtttgcagga gacaagatca cctttgtgga    540
tttccttgcc tatgatgtcc ttgacatgaa gcgtatattt gagcccaagt gcttggacgc    600
cttcctaaac ttgaaggact tcatctcccg ctttgagggt ttgaagaaga tctctgccta    660
catgaagtcc agccaattcc tccgaggtct tttgtttgga aagtcagcta catggaacag    720
caaatagggc ccagtgatgc cagaagatgg gagggaggag ccaaccttgc tgcctgcgac    780
cctggaggac agcctgactc cctggacctg ccttcttcct ttttccttct ttctactctc    840
ttctcttccc caaggcctca ttggcttcct ttcttctaac atcatccctc cccgcatcga    900
ggctctttaa agcttcagct ccccactgtc ctccatcaaa gtcccccctcc taacgtcttc    960
cttcccttgc actaacgcca acctgactgc ttttcctgtc agtgcttttc tcttctttga   1020
gaagccagac tgatctctga gctccctagc actgtcctca aagaccatct gtatgccctg   1080
ctcccttttgc tgggtcccta ccccagctcc gtgtgatgcc cagtaaagcc tgaaccatgc   1140
ctgccatgtc ttgtcttatt ccctgaggct cccttgactc aggactgtgc tcgaattgtg   1200
ggtggttttt tgtcttctgt tgtccacagc cagagcttag tggatgggtg tgtgtgtgtg   1260
tgtgttgggg gtggtgatca ggcaggttca taaatttcct tggtcatttc tgccctctag   1320
ccacatccct ctgttcctca ctgtggggat tactacagaa aggtgctctg tgccaagttc   1380
ctcactcatt cgcgctcctg taggccgtct agaactggca tggttcaaag aggggctagg   1440
ctgatgggga aggggctga gcagctccca ggcagactgc cttctttcac cctgtcctga   1500
tagacttccc tgatctagat atccttcgtc atgacacttc tcaataaaac gtatcccacc   1560
gtattgt                                                            1567
```

<210> SEQ ID NO 24
<211> LENGTH: 900
<212> TYPE: DNA
<213> ORGANISM: Homo sapiens

<400> SEQUENCE: 24

```
ggcacgagcg tgcgtgctgg cgtgcgttca ctttcagcct ggtgtggggc ttgtaaacat      60
ataacataaa aatggcttcc aaaagagctc tggtcatcct ggctaaagga gcagaggaaa    120
tggagacggt catccctgta gatgtcatga ggcgagctgg gattaaggtc accgttgcag    180
gcctggctgg aaaagaccca gtacagtgta gccgtgatgt ggtcatttgt cctgatgcca    240
gccttgaaga tgcaaaaaaa gagggaccat atgatgtggt ggttctacca ggaggtaatc    300
tgggcgcaca gaatttatct gagtctgctg ctgtgaagga gatactgaag gagcaggaaa    360
```

```
accggaaggg cctgatagcc gccatctgtg caggtcctac tgctctgttg gctcatgaaa    420
taggttttgg aagtaaagtt acaacacacc ctcttgctaa agacaaaatg atgaatggag    480
gtcattacac ctactctgag aatcgtgtgg aaaaagacgg cctgattctt acaagccggg    540
ggcctgggac cagcttcgag tttgcgcttg caattgttga agcccgaat ggcaaggagg     600 tggcggctca agtgaaggct ccacttgttc ttaaagacta gagcagcgaa ctgcgacgat    660
cacttagaga acaggccgt taggaatcca ttctcactgt gttcgctcta aacaaaacag     720
tggtaggtta atgtgttcag aagtcgctgt ccttactact tttgcggaag tatggaagtc    780
acaactacac agagatttct cagcctacaa attgtgtcta tacatttcta agccttgttt    840
gcagaataaa cagggcattt agcaaaaaaa aaaaaaaaaa aaaaaaaaaa aaaaaaaaaa    900
```

<210> SEQ ID NO 25
<211> LENGTH: 647
<212> TYPE: DNA
<213> ORGANISM: Homo sapiens

<400> SEQUENCE: 25

```
gctcactgag caccgtccca gcatccggac accacagcgg cccttcgctc cacgcagaaa     60
accacacttc tcatacccttc actcaacact tccttcccca agccagaag atgcacaagg     120 aggaacatga ggtggctgtg ctgggggcac ccccagcac catccttcca aggtccaccg     180
tgattaacat ccacagcgag acctccgtgc ccgaccatgt cgtctggtcc ctgttcaaca    240
ccctcttctt gaactggtgc tgtctgggct tcatagcatt cgcctactcc gtaaagtcta    300
gggacaggaa gatggttggc gacgtgaccg gggcccaggc ctatgcctcc accgccaagt    360
gcctgaacat ctgggccctg attctgggca tcctcatgac cattggattc atcctgttac    420
tggtattcgg ctctgtaaca gtctaccata ttatgttaca gataatacag gaaaaacggg    480
gttactagta gccgcccata gcctgcaacc tttgcactcc actgtgcaat gctggccctg    540
cacgctgggg ctgttgcccc tgccccttg gtcctgcccc tagatacagc agtttatacc     600
cacacacctg tctacagtgt cattcaataa agtgcacgtg cttgtga                  647
```

<210> SEQ ID NO 26
<211> LENGTH: 2850
<212> TYPE: DNA
<213> ORGANISM: Homo sapiens

<400> SEQUENCE: 26

```
aaaagaccag gtaattttaa catttgtgga atcacaaatg taaattcata agaagctcta     60
attaaaaaaa aaaagtctga agtatatgag cataacaact taggagtgtg tctacatact    120 taactttga agttttttgg caactttata tactttttt aaatttacaa gtctacttaa      180
agacttctta taccccaaat gattaagtta attttagagg tcacctttct cacagcagtg    240
tcacttgaaa tttagtaggg aaggatattg cagtattttt cagtttcctt agcacagcac    300
cacagaaagc agcttattcc ttttgagtgg cagacactcg acggtgcctg cccaactttc    360
ctcctgagtg gcaagcagat gagtctcagt aattcatact gaaccaaaat gccacataca    420
ctaggggcag tcagaaactg gctgagaaat ccccgcctc attcgcccct ctgctcccag     480
gaactagagt ccagttaaag cccctatgcg aaaggccgaa ttccacccca gggtttgtta    540
taacagtggc cagtctgaac cccatttgct cgtgctcaaa acttgattcc cacttgaaag    600
ccttccgggc gcgctgcctc gttgcccgc ccctttggca ggagagaggc agtgggcgag    660
gccgggctgg ggccccgcct cccactcacc tgccggtgcc tgaaattatg tgcggccccg    720
```

```
cgggctgctt tccgaggtca gagtgccctg ctgctgtctc agaggcatct gttctgcaaa      780
tcttaggaag aaaaatgtcc ctagtagcaa acgggtgtct tctgtgcata aataagtaca      840
acacaattct ccgaaagttc gggtaaaaag agatgcggta gcagctgccc tgtgtgaagc      900
tgtctacccc gcatctctca ggcgctaagc tcagttttg ttttgttt tgttttttta        960
aagaaaagat gtataattgc aggaattttt ttttatttt ttattttcca tcattctata      1020
tatgtgatgg tgaaagatat gcctggaaaa gttttgtttt gaaaagttta ttttctgctt     1080
cgtcttcagt tggcaaaagc tctcaattct ttagcttcca gtttcttttc tctctttttc     1140
tttgttaggt aattaaaggt atgtaaacaa attatctcat gtagcagggg attttcatgt     1200
tgagaggaat cttccgtgtg agttgtttgg tcacacaaat aacccttct caatttagg       1260
agtttggatt gtcaaatgta ggttttctc aaggggca taactaca tattgactgc         1320
caagaactat gactgtagca ctaatcagca cacatagagc cacacaatta tttaatttct    1380
aactctctgt ggtccctaga aaaattccgt tgatgtgctt aggttaaagt tctgaagata    1440
cccgttgtac ccttacttga aagttttctaa tcttaagttt tatgaaatgc aataatatgt   1500
atcagctagc aatatttctg tgatcaccaa caactctcag tttgatctta aagtctgaat   1560
aataaaacaa atcccagcag taatacattt cttaaacctc acagtgcatg atatatcttt   1620
tcattctgat cctgtgtttg caaaaatata cacatgtata tcatagttcc tcactttta    1680
ttcatttgtt ttcctattac ctgtagtaaa tatattagtt agtacatgga atttatagca   1740
tcagctaccc ccaggaacag cacctgacag gcgggggatt ttttttcaag ttgttctaca   1800
tttgcataaa ttatttctat tattattcat gtatgttatt tatttctgaa tcacactagt   1860
cctgtgaaag tacaactgaa ggcagaaagt gttaggattt tgcatctaat gttcattatc   1920
atggtattga tggacctaag aaaataaaaa ttagactaag cccccaaata agctgcatgc   1980
atttgtaaca tgattagtag atttgaatat atagatgtag tattttgggt atctaggtgt   2040
tttatcatta tgtaaaggaa ttaaagtaaa ggactttgta gttgttttta ttaaatatgc   2100
atatagtaga gtgcaaaaat atagcaaaaa taaaaactaa aggtagaaaa gcattttaga   2160
tatgccttaa tttagaaact gtgccaggtg gccctcggaa tagatgccag gcagagacca   2220
gtgcctgggt ggtgcctcct cttgtctgcc ctcatgaaga agcttccctc acgtgatgta   2280
gtgccctcgt aggtgtcatg tggagtagtg ggaacaggca gtactgttga gaggagagca   2340
gtgtgagagt ttttctgtag aagcagaact gtcagcttgt gccttgaggc ttccagaacg   2400
tgtcagatgg agaagtccaa gtttccatgc ttcaggcaac ttagctgtgt acagaagcaa   2460
tccagtgtgg taataaaaag caaggattgc ctgtataatt tattataaaa taaaagggat   2520
tttaacaacc aacaattccc aacacctcaa aagcttgttg cattttttgg tatttgaggt   2580
ttttatctga aggttaaagg gcaagtgttt ggtatagaag agcagtatgt gttaagaaaa   2640
gaaaaatatt ggttcgcgta gagtgcaaat tagaactaga aagttttata cgattatcat   2700
tttgagatgt gttaaagtag gttttcactg taaaatgtat tagtgtttct gcattgccat   2760
agggcctggt taaaactttc tcttaggttt caggaagact gtcacataca gtaagctttt   2820
ttccttctga cttataatag aaaatgtttt                                      2850
```

<210> SEQ ID NO 27
<211> LENGTH: 3579
<212> TYPE: DNA
<213> ORGANISM: Homo sapiens

<400> SEQUENCE: 27

```
agtttcctcg gcagcggtag gcgagagcac gcggaggagc gtgcgcgggg gccccgggag    60
acggcggcgg tggcggcgcg ggcagagcaa ggacgcggcg gatcccactc gcacagcagc   120
gcactcggtg ccccgcgcag ggtcgcgatg ctgcccggtt tggcactgct cctgctggcc   180
gcctggacgg ctcgggcgct ggaggtaccc actgatggta atgctggcct gctggctgaa   240
ccccagattg ccatgttctg tggcagactg aacatgcaca tgaatgtcca gaatgggaag   300
tgggattcag atccatcagg gaccaaaacc tgcattgata ccaaggaagg catcctgcag   360
tattgccaag aagtctaccc tgaactgcag atcaccaatg tggtagaagc caaccaacca   420
gtgaccatcc agaactggtg caagcggggc cgcaagcagt gcaagaccca tccccacttt   480
gtgattccct accgctgctt agttggtgag tttgtaagtg atgcccttct cgttcctgac   540
aagtgcaaat tcttacacca ggagaggatg gatgtttgcg aaactcatct tcactggcac   600
accgtcgcca agagacatg cagtgagaag agtaccaact tgcatgacta cggcatgttg   660
ctgccctgcg gaattgacaa gttccgaggg gtagagtttg tgtgttgccc actggctgaa   720
gaaagtgaca atgtggattc tgctgatgcg gaggaggatg actcggatgt ctggtggggc   780
ggagcagaca cagactatgc agatgggagt gaagacaaag tagtagaagt agcagaggag   840
gaagaagtgg ctgaggtgga agaagaagaa gccgatgatg acgaggacga tgaggatggt   900
gatgaggtag aggaagaggc tgaggaaccc tacgaagaag ccacagagag aaccaccagc   960
attgccacca ccaccaccac caccacagag tctgtggaaa aggtggttcg agaggtgtgc  1020
tctgaacaag ccgagacggg gccgtgccga gcaatgatct cccgctggta ctttgatgtg  1080
actgaaggga agtgtgcccc attcttttac ggcggatgtg gcggcaaccg gaacaacttt  1140
gacacagaag agtactgcat ggccgtgtgt ggcagcgcca tgtcccaaag tttactcaag  1200
actacccagg aacctcttgc ccgagatcct gttaaacttc ctacaacagc agccagtacc  1260
cctgatgccg ttgacaagta tctcgagaca cctggggatg agaatgaaca tgcccatttc  1320
cagaaagcca agagaggct tgaggccaag caccgagaga aatgtcccga ggtcatgaga  1380
gaatgggaag aggcagaacg tcaagcaaag aacttgccta aagctgataa gaaggcagtt  1440
atccagcatt tccaggagaa agtggaatct ttggaacagg aagcagccaa cgagagacag  1500
cagctggtgg agacacacat ggccagagtg gaagccatgc tcaatgaccg ccgccgcctg  1560
gccctggaga actacatcac cgctctgcag gctgttcctc ctcggcctcg tcacgtgttc  1620
aatatgctaa agaagtatgt ccgcgcagaa cagaaggaca gacagcacac cctaaagcat  1680
ttcgagcatg tgcgcatggt ggatcccaag aaagccgctc agatccggtc ccaggttatg  1740
acacacctcc gtgtgattta tgagcgcatg aatcagtctc tctccctgct ctacaacgtg  1800
cctgcagtgg ccgaggagat tcaggatgaa gttgatgagc tgcttcagaa agagcaaaac  1860
tattcagatg acgtcttggc caacatgatt agtgaaccaa ggatcagtta cggaaacgat  1920
gctctcatgc catctttgac cgaaacgaaa accaccgtgg agctccttcc cgtgaatgga  1980
gagttcagcc tggacgatct ccagccgtgg cattcttttg gggctgactc tgtgccagcc  2040
aacacagaaa acgaagttga gcctgttgat gcccgccctg ctgccgaccg aggactgacc  2100
actcgaccag gttctgggtt gacaaatatc aagacggagg agatctctga agtgaagatg  2160
gatgcagaat tccgacatga ctcaggatat gaagttcatc atcaaaaatt ggtgttcttt  2220
gcagaagatg tgggttcaaa caaggtgca atcattggac tcatggtggg cggtgttgtc  2280
atagcgacag tgatcgtcat caccttggtg atgctgaaga agaaacagta cacatccatt  2340
```

```
catcatggtg tggtggaggt tgacgccgct gtcaccccag aggagcgcca cctgtccaag    2400
atgcagcaga acggctacga aaatccaacc tacaagttct ttgagcagat gcagaactag    2460 accccccgcca cagcagcctc tgaagttgga cagcaaaacc attgcttcac tacccatcgg    2520
tgtccattta tagaataatg tgggaagaaa caaacccgtt ttatgattta ctcattatcg    2580 cctttttgaca gctgtgctgt aacacaagta gatgcctgaa cttgaattaa tccacacatc    2640
agtaatgtat tctatctctc tttacatttt ggtctctata ctacattatt aatgggtttt    2700
gtgtactgta aagaatttag ctgtatcaaa ctagtgcatg aatagattct ctcctgatta    2760
tttatcacat agccccttag ccagttgtat attattcttg tggtttgtga cccaattaag    2820
tcctacttta catatgcttt aagaatcgat ggggatgct tcatgtgaac gtgggagttc    2880
agctgcttct cttgcctaag tattccttc ctgatcacta tgcattttaa agttaaacat    2940
ttttaagtat ttcagatgct ttagagagat tttttttcca tgactgcatt ttactgtaca    3000
gattgctgct tctgctatat ttgtgatata ggaattaaga ggatacacac gtttgtttct    3060
tcgtgcctgt tttatgtgca cacattaggc attgagactt caagcttttc ttttttttgtc    3120 cacgtatctt tgggtctttg ataaagaaaa gaatccctgt tcattgtaag cacttttacg    3180
gggcgggtgg ggagggtgc tctgctggtc ttcaattacc aagaattctc caaaacaatt    3240
ttctgcagga tgattgtaca gaatcattgc ttatgacatg atcgctttct acactgtatt    3300
acataaataa attaaataaa ataacccccgg gcaagacttt tctttgaagg atgactacag    3360
acattaaata atcgaagtaa ttttgggtgg ggagaagagg cagattcaat tttcttttaac    3420 cagtctgaag tttcatttat gatacaaaag aagatgaaaa tggaagtggc aatataaggg    3480
gatgaggaag gcatgcctgg acaaacccctt cttttaagat gtgtcttcaa tttgtataaa    3540
atggtgtttt catgtaaata aatacattct tggaggagc                          3579
```

<210> SEQ ID NO 28
<211> LENGTH: 1433
<212> TYPE: DNA
<213> ORGANISM: Homo sapiens

<400> SEQUENCE: 28

```
attcggggcg agggaggagg aagaagcgga ggaggcggct cccgctcgca gggccgtgca     60
cctgcccgcc cgcccgctcg ctcgctcgcc cgccgcgccg cgctgccgac cgccagcatg    120
ctgccgagag tgggctgccc cgcgctgccg ctgccgccgc cgccgctgct gccgctgctg    180
ccgctgctgc tgctgctact gggcgcgagt ggcggcggcg gcggggcgcg cgcggaggtg    240
ctgttccgct gccgcccctg cacacccgag cgcctggccg cctgcgggcc ccgccggtt    300 gcgccgcccg ccgcggtggc cgcagtggcc ggaggcgccc gcatgccatg cgcggagctc    360
gtccgggagc cgggctgcgg ctgctgctcg gtgtgcgccc ggctggaggg cgaggcgtgc    420
ggcgtctaca ccccgcgctg cggccagggg ctgcgctgct atccccaccc gggctccgag    480 ctgccccctgc aggcgctggt catgggcgag ggcacttgtg agaagcgccg ggacgccgag    540
tatggcgcca gcccggagca ggttgcagac aatggcgatg accactcaga aggaggcctg    600
gtggagaacc acgtggacag caccatgaac atgttgggcg gggaggcag tgctggccgg    660 aagcccctca agtcgggtat gaaggagctg gccgtgttcc gggagaaggt cactgagcag    720
caccggcaga tgggcaaggg tggcaagcat accttggcc tggaggagcc caagaagctg    780
cgaccacccc ctgccaggac tccctgccaa caggaactgg accaggtcct ggagcggatc    840
```

-continued

```
tccaccatgc gccttccgga tgagcggggc cctctggagc acctctactc cctgcacatc    900
cccaactgtg acaagcatgg cctgtacaac ctcaaacagt gcaagatgtc tctgaacggg    960
cagcgtgggg agtgctggtg tgtgaacccc aacaccggga agctgatcca gggagccccc   1020
accatccggg gggaccccga gtgtcatctc ttctacaatg agcagcagga ggcttgcggg   1080
gtgcacaccc agcggatgca gtagaccgca gccagccggt gcctggcgcc cctgcccccc   1140
gcccctctcc aaacaccggc agaaaacgga gagtgcttgg gtggtgggtg ctggaggatt   1200
ttccagttct gacacacgta tttatatttg gaaagagacc agcaccgagc tcggcacctc   1260
cccggcctct ctcttcccag ctgcagatgc cacacctgct ccttcttgct ttccccgggg   1320
gaggaagggg gttgtggtcg gggagctggg gtacaggttt ggggaggggg aagagaaatt   1380
tttatttttg aaccccctgtg tcccttttgc ataagattaa aggaaggaaa agt          1433
```

<210> SEQ ID NO 29
<211> LENGTH: 2370
<212> TYPE: DNA
<213> ORGANISM: Homo sapiens

<400> SEQUENCE: 29

```
cctggaactc tagcacgccg agtgaacttg aatctttggc tatttaagga ggactgggtt     60
tgttgtgaag ttgcggtgat ccagcgcaga gccccgtcct gattgatcgc atcgcgggc    120 tcagatgact gtaaaatgaa tagatgaaat tcttgcttct cgaagatttt cttgggcatc    180
tcccggaaag tgcgttttaa ggcgaagtca tgatgtattc tcccatctgt ctcactcagg    240
atgaatttca cccattcatg gaagcacttc ttccacatgt ccgtgcaatt gcctatactt    300
ggttcaacct gcaggctcga aaacgcaagt actttaaaaa gcatgagaag cgaatgtcaa    360
aggatgaaga aagagcagtc aaagatgagc ttctcagtga aaagcctgaa atcaaacaga    420
agtgggcatc caggctcctt gccaaactgc gcaaagatat tcgccaggag tatcgagagg    480
actttgtgct caccgtgact ggcaagaagc accgtgctg tgtcttatcc aatcccgacc    540
agaagggtaa gattaggaga atcgactgcc tgcgacaggc agacaaagtc tggcgtctgg    600
atctagtcat ggtgatcctg ttcaaaggca tccccttgga aagtaccgat ggagagcggc    660
tcatgaaatc cccacattgc acaaacccag cactttgtgt ccagccacat catatcacag    720
tatcagttaa ggagcttgat tgttttttgg catactacgt gcaggagcaa gattctggac    780
aatcaggaag tccaagccac aatgatcctg ccaagaatcc tccaggttac cttgaggata    840
gttttgtaaa atctggagtc ttcaatgtat cagaacttgt aagagtatcc agaacgccca    900
taacccaggg aactggagtc aacttcccaa ttggagaaat cccaagccaa ccatactatc    960
atgacatgaa ctcgggggtc aatcttcaga ggtctctgtc ttctccacca agcagcaaaa   1020
gacccaaaac tatatccata gaygaaaata tggaaccaag tcctacagga gacttttacc   1080
cctctccaag ttcaccagct gctggaagtc gaacatggca cgaaagagat caagatatgt   1140
cttctccgac tactatgaag aagcctgaaa agccattgtt cagctctgca tctccacagg   1200
attcttcccc aagactgagc actttccccc agcaccacca tcccggaata cctggagttg   1260
cacacagtgt catctcaact cgaactccac ctccaccttc accgttgcca tttccaacac   1320
aagctatcct tcctccagcc ccatcgagct acttttctca tccaacaatc agatatcctc   1380
cccacctgaa tcctcaggat actctgaaga actatgtacc ttcttatgac ccatccagtc   1440
cacaaaccag ccagtcctgg tacctgggct agcttggttc ctttccaagt gtcaaatagg   1500
acacccatct taccggccaa tgtccaaaat tacggtttga acataattgg agaacctttc   1560
```

| | |
|---|---|
| cttcaagcag aaacaagcaa ctgagggaaa aagaaacaca acaatagttt aagaaatttt | 1620 |
| ttttttaaat aaaaaaaagg aaaagaggaa gactggacaa acaacacaa aggcagaaag | 1680 |
| gaaagaaact gaagaaagaa gataatagac cagcaattgc agcacttaca atcactaatt | 1740 |
| cccttaaggt taaactgtaa tgacataaaa agggtcgatg atatttcact gatggtagat | 1800 |
| cgcagcccct gcaacgtagc ctttgttaca tgaagtccgc tgggaaatag atgttctgtc | 1860 |
| tctatgacaa tatattttaa ctgactttct agatgcctta atatttgcat gataagctag | 1920 |
| ttttattggt ttagtattct tgttgtttac gcatggaatc actattcctg gttatctcac | 1980 |
| caacgaaggc taggaggcgg cgtcagagat gctgggtgac agagccatga ccagccatt | 2040 |
| ttataagcac tctgatttct aaaagttaaa aaaatatat gaatctctg tagcctttag | 2100 |
| ttatcagtac agatttatta aatttcggcc cttaacccag cctttccag tgtgtaaccc | 2160 |
| agtttgaaat cttaaaaaaa gaaaaaatga aaaaaaagg aaaaaagaa aaaggaaaa | 2220 |
| aaacagtttg aacacaaagg ctctatggaa gaaatgcctc tatgtaggtg aagtgttctc | 2280 |
| tctgcatgca acagtaaaaa ttaatataat attttcccca caaaagaaac acttaacaga | 2340 |
| gggcaagtgc aatttattaa atttatattc | 2370 |

<210> SEQ ID NO 30
<211> LENGTH: 2699
<212> TYPE: DNA
<213> ORGANISM: Homo sapiens

<400> SEQUENCE: 30

| | |
|---|---|
| gcccagcggg ggcgggactg gaacggagcc gtgcggcccc gcgcgctcgc agtctgtctc | 60 |
| ccgccgtccc cacgcacgcg tcccggctca cgcgtccgcc cgcccgcccc cgcttgtgcc | 120 |
| gccctacca gagacccca ggagcaggat gtccttccag ggcaagaaaa gcatccccg | 180 |
| gatcacgagt gaccgccttc tgatcagagg tgggaggatc gtgaatgacg accagtcctt | 240 |
| ttacgctgat gtgcacgtgg aagatggctt gataaaacaa atcggagaaa acctcatcgt | 300 |
| ccctgggggc atcaagacca ttgacgccca cggcctgatg gtccttcctg gtggcgttga | 360 |
| cgtccacaca aggctgcaga tgcctgtcct gggcatgaca ccggctgacg acttctgtca | 420 |
| gggcaccaag gcagcgctag caggaggaac caccatgatc ttggaccacg tcttccccga | 480 |
| cacgggtgtg agcctgctgg cggcctacga gcggtggcgg gagcgggcgg acagcgcggc | 540 |
| ctgctgcgac tactccctgc acgtggacat cacccgatgg catgagagca tcaaggagga | 600 |
| gctggaggcc ctggtcaagg agaagggtgt gaactccttc ctggtcttca tggcatacaa | 660 |
| ggaccggtgc cagtgcagcg acagccagat gtacgagatc ttcagcatca tccgggacct | 720 |
| gggggccttg gcccaggtgc acgctgagaa cggggacatc gtggaggagg agcagaagcg | 780 |
| gttgctggag ctcggcatca ctggcccga gggccacgtg tcagccacc cgaggaggt | 840 |
| ggaggctgag gcggtgtacc gagctgtcac catcgccaag caggcaaact gcccgctgta | 900 |
| cgtcaccaag gtgatgagca aggggcggc cgacgccatc gctcaggcca agcgcagagg | 960 |
| ggtggtcgtg tttggggagc ccatcaccgc cagcctgggc accgacggtt cacactactg | 1020 |
| gagcaagaac tgggccaagg ccgcagcctt cgtcacatca cccctgtca acccagaccc | 1080 |
| caccacggca gaccacctca cctgcttgct gtccagcggg gacctccagg tgacaggcag | 1140 |
| cgcccactgc acccttcacca ctgcccagaa ggctgtgggc aaggacaact cgcgctgat | 1200 |
| ccccgagggc accaacggca ttgaggagcg catgtcgatg gtctgggaga aatgtgtggc | 1260 |

```
ctctgggaag atggacgaga atgagttcgt cgcggtgacc agtacaaatg ctgccaaaat   1320
cttcaattt tacccaagga aggggcgagt ggctgtgggc tctgacgctg acctggtcat    1380
atggaacccc aaggccacca agatcatctc tgccaagacc cacaatctga acgtggagta   1440
caacatcttc gagggagtgg agtgccgggg agcgcctgcc gtggtcataa gtcagggccg   1500
agtggcgctg gaggacggga agatgttgt caccccgggg gcgggccgct tcgtccctcg   1560
gaaaacattc ccggactttg tctacaagag gatcaaagct cgcaacaggc tggcggagat   1620
ccacggtgtg cccgtgggc tgtatgacgg gcccgtccac gaggtgatgg tgcctgccaa   1680
gccagggagt ggcgctccgg cccgcgcgtc ctgcccagge aagatctccg tgcctcctgt   1740
gcgcaaccta catcagtcgg ggttcagcct atctgggtct caggctgatg accacatcgc   1800
ccgacgcaca gcacagaaga tcatggcacc acctggcggc cgctccaaca tcacctctct   1860
ctcctagacg cccaggaccg gccctgtgag ccgtgctggc ccacccgag gccgcggggg    1920
ccccagggca ctcgcccccc tccttagcat tttcttttgt agaagtttct cgaaggtgct   1980
tggcggtctt gccttccccc tccccacagg ctctccttgt ggggtcccag gtcctgctgc   2040
caagagcccc tcaagagaag ggctgaacct ggggagatgt cactgccagg gtgaggtgga   2100
gccacatggc agggacaatg ccggcagcct gagcccaggc accccagtgc ccgctgggcc   2160
cagcctgggg acaggaacc tgccgggctc acagtgtggg agcagctgga caccaggctt    2220
cttggtgaac cggcgagggg ccgagtcccg cctggtgggc atttgctgcc gcctccccac   2280
caccagtcac tgcctcgcag agccctacac tcccgcagcc gctcctcaga ggcctgtgcc   2340
catcgcaggc ctgggaggaa agtgggcgca gagccctcct gctcacacag ctgctgagac   2400
ttcagggacc catcagaact tggtgcagca cagccccgcc cgtggagggt cccttttacg   2460
cacccccaagg cccacaccta agcttccatg tagccctcat ccagggaagt tttgcgatcc   2520
tttaggaaga cactgtcctc ttattacaga ttgtgtattt ccgtaggctt cttagtagca   2580
gctttgtaca ctgaggacac tgtagccagg aacctgtgca tgccacccac cgcctggaca   2640
ggcagtcatc ctgcctctga tgtgaatcag gcccattaaa gacgtctggg tttgaagcc   2699
```

<210> SEQ ID NO 31
<211> LENGTH: 4122
<212> TYPE: DNA
<213> ORGANISM: Homo sapiens

<400> SEQUENCE: 31

```
tttgtcatca gctcgctctc cattggcggg gagcggagag cagcgaagaa gggggtgggg     60
aggggagggg aagggaaggg ggtggaaact gcctggagcc gtttctccgc gccgctgttg    120
gtgctgccgc tgcctcctcc tcctccgccg ccgccgccgc cgccgccgcc tcctccggct    180
cttcgctcgg cccctctccg cctccatgtg ccggatagcg ggagcgctgc ggaccctgct    240
gccgctgctg gcggccctgc ttcaggcgtc tgtagaggct tctggtgaaa tcgcattatg    300
caagactgga tttcctgaag atgtttacag tgcagtctta tcgaaggatg tgcatgaagg    360
acagcctctt ctcaatgtga agtttagcaa ctgcaatgaa aaagaaaag tacaatatga     420
gagcagtgag cctgcagatt ttaaggtgga tgaagatggc atggtgtatg ccgtgagaag    480
ctttccactc tcttctgagc atgccaagtt cctgatatat gcccaagaca aagagaccca    540
ggaaaagtgg caagtggcag taaaattgag cctgaagcca accttaactg aggagtcagt    600
gaaggagtca gcagaagttg aagaaatagt gttcccaaga caattcagta agcacagtgg    660
ccacctacaa aggcagaaga gagactgggt catcccttcca atcaacttgc cagaaaactc    720
```

```
cagggggacct tttcctcaag agcttgtcag gatcaggtct gatagagata aaaacctttc    780
actgcggtac agtgtaactg ggccaggagc tgaccagcct ccaactggta tcttcattat    840 caacccccatc tcgggtcagc tgtcggtgac aaagccctg gatcgcgagc agatagcccg    900
gtttcatttg agggcacatg cagtagatat taatggaaat caagtggaga accccattga    960
cattgtcatc aatgttattg acatgaatga caacagacct gagttcttac accaggtttg   1020
gaatgggaca gttcctgagg gatcaaagcc tggaacatat gtgatgaccg taacagcaat   1080
tgatgctgac gatcccaatg ccctcaatgg gatgttgagg tacagaatcg tgtctcaggc   1140
tccaagcacc ccttcaccca acatgtttac aatcaacaat gagactggtg acatcatcac   1200
agtggcagct ggacttgatc gagaaaagt gcaacagtat acgttaataa ttcaagctac   1260
agacatggaa ggcaatccca catatggcct ttcaaacaca gccacggccg tcatcacagt   1320
gacagatgtc aatgacaatc ctccagagtt tactgccatg acgttttatg gtgaagttcc   1380
tgagaacagg gtagacatca tagtagctaa tctaactgtg accgataagg atcaacccca   1440
tacaccagcc tggaacgcag tgtacagaat cagtggcgga gatcctactg gacggttcgc   1500
catccagacc gacccaaaca gcaacgacgg gttagtcacc gtggtcaaac caatcgactt   1560
tgaaacaaat aggatgtttg tccttactgt tgctgcagaa aatcaagtgc cattagccaa   1620
gggaattcag cacccgcctc agtcaactgc aaccgtgtct gttacagtta ttgacgtaaa   1680
tgaaacccct tattttgccc ccaatcctaa gatcattcgc caagaagaag ggcttcatgc   1740
cggtaccatg ttgacaacat tcactgctca ggacccagat cgatatatgc agcaaaatat   1800
tagatacact aaaattatctg atcctgccaa ttggctaaaa atagatcctg tgaatggaca   1860
aataactaca attgctgttt tggaccgaga atcaccaaat gtgaaaaaca atatatataa   1920
tgctactttc cttgcttctg acaatggaat tcctcctatg agtggaacag gaacgctgca   1980
gatctattta cttgatatta atgacaatgc ccctcaagtg ttacctcaag aggcagagac   2040
ttgcgaaact ccagaccca attcaattaa tattacagca cttgattatg acattgatcc   2100
aaatgctgga ccatttgctt ttgatcttcc tttatctcca gtgactatta agagaaattg   2160
gaccatcact cggcttaatg gtgattttgc tcagcttaat ttaaagataa aatttcttga   2220
agctggtatc tatgaagttc ccatcataat cacagattcg ggtaatcctc ccaaatcaaa   2280
tatttccatc ctgcgcgtga aggtttgcca gtgtgactcc aacggggact gcacagatgt   2340
ggacaggatt gtgggtgcgg ggcttggcac cggtgccatc attgccatcc tgctctgcat   2400
catcatcctg cttatccttg tgctgatgtt tgtggtatgg atgaaacgcc gggataaaga   2460
acgccaggcc aaacaacttt taattgatcc agaagatgat gtaagagata atatttttaaa   2520 atatgatgaa gaaggtggag gagaagaaga ccaggactat gacttgagcc agctgcagca   2580
gcctgacact gtggagcctg atgccatcaa gcctgtggga atccgacgaa tggatgaaag   2640
acccatccac gctgagcccc agtatccggt ccgatctgca gccccacacc ctggagacat   2700
tggggacttc attaatgagg ccttaaagc ggctgacaat gaccccacag ctccaccata   2760
tgactccctg ttagtgtttg actatgaagg cagtggctcc actgctgggt ccttgagctc   2820
ccttaattcc tcaagtagtg gtggtgagca ggactatgat tacctgaacg actgggggcc   2880
acggttcaag aaacttgctg acatgtatgg tggaggtgat gactgaactt cagggtgaac   2940 ttggttttg gacaagtaca aacaatttca actgatattc ccaaaaagca ttcagaagct   3000
aggctttaac tttgtagtct actagcacag tgcttgctgg aggctttggc ataggctgca   3060
```

-continued

```
aaccaatttg ggctcagagg gaatatcagt gatccatact gtttggaaaa acactgagct      3120
cagttacact tgaattttac agtacagaag cactgggatt ttatgtgcct ttttgtacct      3180
ttttcagatt ggaattagtt ttctgtttaa ggctttaatg gtactgattt ctgaaacgat      3240
aagtaaaaga caaatatttt tgtggtggga gcagtaagtt aaaccatgat atgcttcaac      3300
acgcttttgt tacattgcat ttgcttttat taaaatacaa aattaaacaa acaaaaaaac      3360
tcatggagcg attttattat cttggggggat gagaccatga gattggaaaa tgtacattac      3420
ttctagtttt agactttagt ttgtttttt tttttcacta aaatcttaaa acttactcag       3480
ctggttgcaa ataagggag ttttcatatc accaatttgt agcaaaattg aattttttca      3540
taaactagaa tgttagacac attttggtct taatccatgt acactttttt atttctgtat      3600
ttttccactt cactgtaaaa atagtatgtg tacataatgt tttattggca tagtctatgg      3660
agaagtgcag aaacttcaga acatgtgtat gtattatttg gactatggat tcaggttttt      3720
tgcatgttta tatcttcgt tatggataaa gtatttacaa aacagtgaca tttgattcaa      3780
ttgttgagct gtagttagaa tactcaattt ttaattttt taatttttt attttttatt       3840 ttcttttgg tttggggagg gagaaaagtt cttagcacaa atgttttaca taatttgtac      3900 caaaaaaaa aaaaggaaa ggaaagaaag gggtggcctg acactggtgg cactactaag      3960
tgtgtgtttt ttaaaaaaa aaatggaaaa aaaaagctt ttaaactgga gagacttctg       4020
acaacagctt tgcctctgta ttgtgtacca gaatataaat gatacacctc tgacccagc      4080 gttctgaata aatgctaat tttggaaaaa aaaaaaaaa aa                          4122
```

<210> SEQ ID NO 32
<211> LENGTH: 1653
<212> TYPE: DNA
<213> ORGANISM: Homo sapiens

<400> SEQUENCE: 32

```
agtcagcacg ggggtgctgg aagagatcgg gaataatagc gcagaccaat gagcctaggg        60
agatgctttc atcgtctctc cttccctcaa gtgttctgga acctatcatt tgaattagcc       120
gagtcaggca ggagggggcg gggaatcctt ccgcccttct taggaggggc tgcattgcag       180
ggggagagtg aactgacaga ctcagtcact gaagagggaa aaggagtgag aagacaaagc       240
cgtcaaagcc ccaacagctt tgtatttctc cagcccggcg cagaccccgg agctcccgag       300
gcactccctc catctttgga acacgccagt aattgattga taacaggaag ctatgaggga       360
ccctgtgagt agccagtaca gttcctttct tttctggagg atgcccatcc cagaactgga       420
tctgtcggag ctggaaggcc tgggtctgtc agatacagcc acctacaagg tcaaagacag       480
cagcgttggc aaaatgatcg ggcaagcaac tgcagcagac caggagaaaa accctgaagg       540
tgatggcctc cttgagtaca gcaccttcaa cttctggaga gctcccattg ccagcatcca       600
ctccttcgaa ctggacttgc tctaaggcca agacttctct ctcccatcac cttgccctca      660
ttgtcttccc tctcaagccc cttcctttcc actcctttcc catttaatc ttgttctctc       720 cctactgtgt tggtggtgct gatgaatctg ccagagttga gttctatgta tttatttatc      780
tatctgtcta ctccatttct ctcaaaagcc ctcaagtcac aaagtaaatg gttcaagcaa      840
tggagtactg gtcacaggg attcctcctt tccccccaa atattaactc cagaaactag       900
gcctgactgg ggacacctga gagtagtata gtagtgcaaa atggaagact gattttgac      960 tctattataa tcagcttcag agattcctta aaccttccta atttcctgct ccagggcagt     1020
aaacacaaat atttcttcaa ggggtgatga aaacctcgga agttttaatt tgaggttatc     1080
```

```
tgctacgaaa cagtatttct aaaaggctaa agtgataagt ctcttgcttt ttttgatcc    1140 tgctcttata ttcttttttt tcctcagaga aatcaggagg gtagttagag gtataaaaca   1200
ggaggaaata ttatggaaaa tgaaaatagg gaaaataatt gaatcatttt agaagtagct   1260 aatttcttt  ctcaaaagag tgtcccttct tcacacctac tcactttaca actttgctcc   1320
taactgtggg ttgaaaactc tagctaaaga aagttatcaa atcttaacat gcattcctac   1380
tattatgata gttttaagg  tttcaattca atcttctgaa cggcataagt cctatttag    1440 ccttacctcc tgcatttgca atacgtaata ctgatcagtg gcacagttc ttcagctaca    1500 ttgagaccct gaaatgaaca attatattct gactcgacat cttgtcccca atccttccaa   1560
aaatattgat ggtgatttgt gctaccattt actcgtttat ttaataaaga cattcaatcc   1620
cagaaaaaaa aaaaaaaaa aaaaaaaaaa aaa                                 1653

<210> SEQ ID NO 33
<211> LENGTH: 2928
<212> TYPE: DNA
<213> ORGANISM: Homo sapiens

<400> SEQUENCE: 33
ccgatccggg cggtgctggc agccggagcg gcggcgggcg ggccgagcag ccggggcagc     60
cgcgcgtggg catccacggg cgccgagcct ccgtccgtgt ctctatccct cccgggcctt    120
tgtcagcgcg cccgctggga gcgggccga  gagcgccggt tccagtcaga cagccccgca    180
ggtcagcggc cgggccgagg gcgccagagg gggccatgtc gtaccagggc aagaagagca    240
tcccgcacat cacgagtgac cgactcctca tcaaaggtgg acggatcatc aacgatgacc    300
aatcccttta tgctgacgtc tacctggagg atggacttat caaacaaata ggagagaact    360
taatcgttcc tggtggagtg aagaccattg aagccaacgg gcggatggtt attcccggag    420
gtattgatgt caacacgtac ctgcagaagc cctcccaggg gatgactgcg gctgatgact    480
tcttccaagg gaccagggcg gcactggtgg gcgggaccac gatgatcatt gaccatgttg    540
ttcctgaacc tgggtccagc ctactgacct ctttcgagaa gtggcacgaa gcagctgaca    600
ccaaatcctg ctgtgattac tccctccacg tggacatcac aagctggtac gatggcgttc    660
gggaggagct ggaggtgctg gtgcaggaca aaggcgtcaa ttccttccaa gtctacatgg    720
cctataagga tgtctaccaa atgtccgaca gccagctcta tgaagccttt accttcctta    780
agggcctggg agctgtgatc ttggtccatg cagaaaatgg agatttgata gctcaggaac    840
aaaagcggat cctggagatg ggcatcacgg gtcccgaggg ccatgccctg agcagacctg    900
aagagctgga ggccgaggcg gtgttccggg ccatcaccat tgcgggccgg atcaactgcc    960
ctgtgtacat caccaaggtc atgagcaaga gtgcagccga catcatcgct ctggccagga   1020
agaaagggcc cctagttttt ggagagccca ttgccgccag cctggggacc gatggcaccc   1080
attactggag caagaactgg gccaaggctg cggcgttcgt gacttcccct cccctgagcc   1140
cggaccctac cacgcccgac tacttgacct ccctactggc ctgtgtggga cttgcaggtca  1200 caggcagcgg ccactgtccc tacagcactg cccagaaggc ggtgggcaag gacaacttta   1260
ccctgatccc cgagggtgtc aacgggatag aggagcggat gacggtcgtc tgggacaagg   1320
cggtggctac tggcaaaatg gatgagaacc agtttgtcgc tgtcaccagc accaatgcag   1380
ccaagatctt taacctgtac ccaaggaaag ggcggattgc cgtgggctcg gatgccgacg   1440
tggtcatctg ggaccccgac aagttgaaga ccataacagc caaaagtcac aagtcggcgg   1500
```

```
tggagtacaa catcttcgag ggtatggagt gccacggctc cccactagtg gtcatcagcc      1560
agggcaagat cgtctttgaa gacggaaaca tcaacgtcaa caagggcatg ggccgcttca      1620
ttccgcggaa ggcgttcccg gagcacctgt accagcgcgt caaaatcagg aataaggttt      1680
ttggattgca agggggtttcc aggggcatgt atgacgtcc tgtgtacgag gtaccagcta      1740
cacccaaata tgcaactccc gctccttcag ccaaatcttc gccttctaaa caccagcccc      1800
cacccatcag aaacctccac cagtccaact tcagcttatc aggtgcccag atagatgaca      1860
acaatcccag gcgcaccggc caccgcatcg tggcgccccc tggtggccgc tccaacatca      1920
ccagcctcgg ttgaacgtgg atgcgcgag gagctagcct gaaggattct gggaatcatg      1980
tccatccctt ttcctgtcag tgttttgaa acccacagtt ttagttggtg ctgatggagg      2040
gagggggaag tcgaaggatg ctctttccct tttctgttta ggaagaagtg gtactagtgt      2100
ggtgtgtttg cttggaaatt ccttgcccca cagttgtgtt catgctgaat ccacctcgga      2160
gcatggtgtt tcattcccc cttcctagtg aaccacaggt tttagcattg tcttgttctg      2220
tcccttccac ttctaactcc actggctcca tgattctctg agtggtggtt cctttgcacc      2280
ctgtagatgt tctaggatag ttgatgcatg ttactaaatt acgtatgcaa gtctgtgagt      2340
gcgtctgagg ggacatcgcc aaggactgac tgagacacga tgccgagacc tcaagccctg      2400
aggggcagtc ccaaaaccct tacagtgaag atgtttactc attgccccca cctctggtcc      2460
acactagaaa gaagctcgcc ccacctccac ctgtgagatc cgtgaattct cggaatggca      2520
ggggaagcct tgcactaggt tgcagagaag catcctccac atcctgtgtc agaaaccctg      2580
gtctccgtgg cacttgtaac tcaccgtgct gtcttctggt ctgtgtgtgt tcttcaagcc      2640
agctctaggc ttcaggccga gccaggttca cactcagaaa gaggtctccc catcccatt      2700 cggggctgac gatgggggc tgatggctgc ccctgcgtgg cctgagtcct ggtccctctg      2760
aggcagttga cggggcagtc agatttttaa agttttgtac aaagttttcc tttgtaatca      2820
ctcccatttt tacttaacaa ccaacttgtt gtggctctta tttctgaatt caaagcttgt      2880
gaaaaaataa agaaaatgaa ctgcccactg aaaaaaaaaa aaaaaaaa                  2928
```

<210> SEQ ID NO 34
<211> LENGTH: 4913
<212> TYPE: DNA
<213> ORGANISM: Homo sapiens

<400> SEQUENCE: 34

```
cctcccagcg tccccaccct aggaggctgc atgcggattg aagacgtgcg cctgggggct        60
gggccggccc cgctgatccc gacctagcga gcaggatagc aggaccgccc aggctgcgga       120
ggggctcggg ggcaggaagg tcagagcagc aagatggcca gtaagaccaa ggccagcgag       180
gccctcaagg tggtgcccg gtgccgcccc ctcagcagga aggaggaggc tgctggtcac       240
gagcagatcc tgaccatgga cgtgaaactg gccaggtga ccctgcggaa ccccgcgcc        300 gccccggggg agctgcccaa gaccttcacc tttgacgccg tgtatgatgc cagctccaag       360
caggccgacc tgtatgacga aaccgtgagg cccctgatag actccgtgct ccagggtttc       420
aatggcacgg tgtttgccta tggccagacg ggcactggca agacctatac catgcagggg       480
acctgggtgg agcccgagct gcgcgggtc atcccgaatg cctttgagca catcttcacc       540
cacatctccc gctcccagaa ccaacagtac ctggtccggg cctcctattt ggagatctac       600
caggaagaga ttcgagacct gctctccaag gagccgggca gaggctaga gctgaaagag       660 aaccccgaga ctggcgtcta catcaaggac ctctcctcct tcgtcaccaa gaatgtcaag       720
```

```
gagattgagc atgtgatgaa cctggggaac cagacccggg ctgtgggcag cacccacatg      780
aatgaggtca gctcccgctc ccatgccatc ttcatcatca ctgtggagtg cagcgaacgt      840
ggctctgatg ccaggacca catccgagtg ggcaagctca acctcgtgga cctggctggc      900
agcgagaggc agaacaaggc aggccccaac acagcgggag gggcagccac accatcctcg      960
ggtggcggtg gtggcggtgg aggcagtggt ggtggtgctg gtggagagag gcctaaggaa     1020
gcctccaaaa tcaacctctc attatctgcc ctgggcaacg tgattgctgc cctggcgggc     1080
aacaggagca cccacattcc ctaccgggac tccaagctga cccggctgct ccaggactcc     1140 ctgggggga atgcgaagac catcatggta gccacactgg ggccagcttc tcacagctac      1200
gatgagagcc tctccacctt gcgctttgcc aaccgagcca agaacatcaa gaacaagccc     1260
cgggtgaacg aggaccccaa ggacacactg ctgcgggaat ccaagagga gattgcccgc      1320 ctgaaggccc agctggagaa gagggggatg ctggggaagc ggccccggag gaagagcagc     1380
cgcaggaaga aggccgtgtc cgccccgcct gggtaccctg agggcccagt gattgaggct     1440
tgggtggcag aagaggagga tgacaacaac aacaaccacc gcccgcccca gcccatcctg     1500
gagtcagcct tggagaagaa catggagaat tacctgcagg aacagaagga gcggctggag     1560
gaggagaagg cagccatcca ggatgaccgc agcctggtga gcgaggagaa gcagaagctg     1620
ctggaggaga aggagaagat gctggaggac ctgcggcggg aacagcaggc cacagagctg     1680
cttgcggcca gtacaaggc catggagagc aagctcctca tcggggcag gaacatcatg       1740 gatcacacca acgaacagca aagatgttg aactgaaga ggcaggagat tgccgagcag       1800
aaacgtcgtg agcgggagat gcagcaggag atgatgctcc gggacgagga gactatggag     1860 ctccgggca cctacacatc cctgcagcag gaggtggagg tcaaaaccaa gaaactcaag      1920
aagctctacg ccaagctgca ggcggtgaag gcggagatcc aggaccagca tgatgagtat     1980
atccgcgtgc ggcaggacct ggaggaggcg cagaacgagc agacccgcga actcaagctc     2040
aagtacctaa tcatcgagaa cttcatcccg ccggaggaga agaacaagat catgaaccgg     2100
cttttcctgg actgtgagga ggagcagtgg aagttccagc cactggtgcc agccggcgtc     2160
agtagcagcc agatgaagaa gcggccaaca tctgcagtgg gctacaagag gcctatcagc     2220
cagtatgctc gggttgccat ggcaatgggg tcccacccca ggtacagggc tgaaaacata     2280
atgtttctgg agttggatgt gtcccctcca gctgtctttg agatggaatt ctctcacgac     2340
caagaacaag accctcgtgc gctacacatg gagaggctca tgcgattgga cagctttctg     2400
gaaagacctt ccacgtctaa agtccgaaag tccagatcct ggtgccagag tcctcagcgg     2460
cctccacctt ccaccacaca tgcctccctg gcctctgctt ctctgcgccc tgcaacagtg     2520
gcggaccatg agtgacaacc atcacgtcag gctgcccatc caatagactc ctgggatggg     2580
gcagccaacc ctggctcatc tcatctgccg cttggtgcgt gtgcgtgtgc gtgcatgtgc     2640
gtgtgcgtgt gtgcagggt gagaatctgg cagatggtgc ctctgcctgc tcttcttcgc      2700
ctcctttatt taattcatgt tatttattcg cggacgtctg ttcgtgttgg ggagatgccc     2760
tcgcctgagc cgtctgggcc taccgtggtc actgcgtacg ctctttttct tctgacttga     2820
gagctccccc agtcagatct caggcttgtc ccctgtcag ctgcctccag aagggaaggt      2880
agccagtgcc tgagaagaca gtcccttttc tacccaccgc actccataac ctccatcttc     2940
tcccacactg atggcgagca gcccctgagc actttctggg actgggagac tgcttggtgt     3000
tccctgagga caagagacat cctgacagtg ttgggcatct gctccccgtg gacacagccc     3060
```

```
cactctccac tttctgagcc tcagacaacc tcattcagcc tcttgggctc cttttcaagg    3120
acattaataa cctcaccaac atagctcatg cccttcagct ttgacaagaa ctcacggctt    3180
cccaaactct gctttctgcc caccttggat gggaactgtg gaccaagcaa ttaccatcgc    3240
cttggaacct gcaggaaatg aacagcaat tgagacaact gaacagtca tcaacggaag      3300 tccctccact ggattccttt gtttctgtcc cctccgagga gtcatttgg tcgacaggct     3360 ctcaaggcaa ctcccattt tcaagaggct gctcctgcct gcttcgatca tttctccctg     3420
cagctgccta gaccccgttc acagtgggag gagtcaatgt cattctaccc ctcgctaaac    3480
gaagatatta acatctattg cttttccct tcatctgtca caggaaacag aagcccaggc     3540
acaatctttt ccagctttgc ctgttacccc tgtttctgaa ttgcatcttt aaggtattat    3600
tttgttgaca atagatcctt tattcactag ttacgcaaat tggttcctag ggggatactc    3660
cttaccttcc tttgtgatgg cccaaaatgt ctctaggtat ctcaagtgat aagtaaattt    3720
ctacaaaaaa aaaatggtta atgttcattg actggctttt taagtgtata ttttggagga    3780
cgggtgaaga ggtcataacg aaagcaagcg agtgaattag gatttcaaag tgccctaata    3840
gtgtgagtct ccagttccta gaatatgaag agtgctgtcg ttggggtgaa accatgagac    3900
tgacagatct gcctgaaatg gggggtgtgg gaggtggtgg cggggttat tctctttcct    3960 tcaggaaatg aaccttctt acatcattca agttctgctc tgaggatcaa gcttgggtct    4020
gatttaactc agcgacactg tcatttctgc ttcattactg gactagaggg ttgagccacc    4080
cacttgccat ttgctcctgt ccttccagga aatcacaatt ttcatcagag cccaagagat    4140
tatttgagac tcaggattca gatcagaggt tcgactgtgg ctgggacagg agttgtgtgt    4200
agaaattcac caggtggcct gagcgcaggg ggacctccag gctgcgttga gcagcctctc    4260
ccactgacct cttttctcgtt tgtggacaaa gcagcacgta tcacctcatt catcacttgg    4320
acacatcgcc tttgcattgt cttgtcacac ctccctcaca gtcttatagc acaatatacc    4380
caaatcagcc cccccagtcc gaggctgggc ccaaggtatg gtcggaggag gagctcctgc    4440
ctgcggtttt gtgtatgtgt gtatgtgtgt gcgtgtttgt gtgcgtgttt acctccacag    4500
gggacactct acactcagtg taagatctgc tgggaacagg gccaccagga gtgcgtggat    4560
ctcagtctct ctgtctctct ttctctcctt ttaattttgg tgtatcaaat atttgattga    4620
caaagtaagg gccttgatta ggaccaaatt ctcgtgtgtt gctatggtct ttatttagga    4680
caacaattaa caatgcagtg gcccattctt gtcactctac acatatgact atacgggaca    4740
tatgtaatat ataaatatat atataaaaca ttccctctg tccccttggc ttcggatgga    4800
ggaatttctg ttgagctgaa atgcacctgc agctgggtgc tgccagcagc ttgcaggccc    4860
cagccctgtt ccaatcaatg cagttgacaa taaaggaatg agtatcgtca cgg          4913
```

<210> SEQ ID NO 35
<211> LENGTH: 1231
<212> TYPE: DNA
<213> ORGANISM: Homo sapiens

<400> SEQUENCE: 35

```
gaattccaga aaagaggtgg agaggggggg aataagaaag agagagaagg aaaggagaga     60
aggcaggaag aaggcaaggg acgagacaac catgctgtgc tgtatgagaa gaaccaaaca    120
ggttgaaaaa aatgatgacg accaaaagat tgaacaagat ggtatcaaac cagaagataa    180
agctcataag gccgcaacca aaattcaggc tagcttccgt ggacacataa caaggaaaaa    240
gctcaaagga gagaagaagg atgatgtcca agctgctgag gctgaagcta ataagaagga    300
```

```
tgaagcccct gttgccgatg gggtggagaa gaagggagaa ggcaccacta ctgccgaagc    360
agccccagcc actggctcca agcctgatga gcccggcaaa gcaggagaaa ctccttccga    420
ggagaagaag gggagggtg atgctgccac agagcaggca gccccccagg ctcctgcatc     480
ctcagaggag aaggccggct cagctgagac agaaagtgcc actaaagctt ccactgataa    540
ctcgccgtcc tccaaggctg aagatgcccc agccaaggag gagcctaaac aagccgatgt    600
gcctgctgct gtcactgctg ctgctgccac caccctgcc gcagaggatg ctgctgccaa     660
ggcaacagcc cagcctccaa cggagactgg ggagagcagc caagctgaag agaacataga    720
agctgtagat gaaaccaaac ctaaggaaag tgcccggcag gacgagggta agaagagga    780 acctgaggct gaccaagaac atgcctgaac tctaagaaat ggcttttccac atccccaccc   840 tccctctcc tgagcctgtc tctccctacc ctcttctcag ctccactctg aagtcccttc     900
ctgtcctgct cacgtctgtg agtctgtcct tcccaccca ctagccctct ttctctctgt     960
gtggcaaaca tttaaaaaaa aaaaaaaaaa gcaggaaaga tcccaagtca aacagtgtgg    1020
cttaaacatt ttttgtttct tggtgttgtt atggcaagtt tttggtaatg atgattcaat   1080
cattttggga aattcttgca ctgtatccaa gttatttgat ctggtgcgtg tggccctgtg    1140
ggagtccact ttcctctctc tctctctctc tgttccaagt gtgtgtgcaa tgttccgttc    1200
atctgaggag tccaaaatat tgagtgaatt c                                  1231

<210> SEQ ID NO 36
<211> LENGTH: 1587
<212> TYPE: DNA
<213> ORGANISM: Homo sapiens

<400> SEQUENCE: 36
ccacgcgtcc gcgttcttgc tacaattgta ccatctggta attcctgaaa atgtcaattt     60
ttttgtgtta atatttttgg tttcaaacaa taacaaatgt ctctagaaag aaattttaag   120
aaagcttaat taatagtaaa aatgcctttc ctgaaataat cttggaaaat ttttaaatg    180 tcaaaatgat gagtcatgct aatacattga gggtttgttt ttttgtttgt ttgtttgttt   240
ttgagacaga gtttcgctct tgttgcccag gctggagtgc aatggcccga tctcagctca   300
ccgcaacctc cacctcccgg attccagcga ttctcctgcc tcagcctaca ttaagggttt   360
tgtcagacaa ttgtcacacg aagaatagtg tcacttatct gctcttgaca cacagaactg   420
gcctggcata tagcttttcca gatttttactc aaacttggta ctccagtttg aaaatttaaa  480
ttttgactgc tgattagctg gaaagcctag ttttaatgga aagaaagttt gcttttaaaa   540
ctgaaagtag tttctttttg ctaacaaatc taacttcata cataattggc catattagta   600
aaacacctca tgatagcagt gtatatatag tcttgtttgt agttggaagt catcttttag   660
gagttattct caaatatata taatagctac ccatgcatca ttattaaaat ccccaaattc   720
aaaaaacctc tgatatatat ataaatttt tttttttttt tttttttggc caactgagat    780
tgaaatccaa gtgctggttt ctagttctga acatcaacta aagagttttg gaaatgacag    840
caatttataa caagttcata ttgacttcct ctctatggca ggaagacatt ctgtgctgtt    900
ttgaacagat taaagatttg tgtagtttgt gggaaattga cgttttgtt taaattccac     960 ccgcgtttgt cttttcctac cacctgtggc caggtgctcg ctggccatca cagttgcgat   1020
tccatgagta gctgctttat gactgctttt tgtactatct ggatgtgccc agagttactt   1080
ctgtacaagc tctgtatctg tgtccgttga gaacattatt ttaacaagaa gaacaccaac   1140
```

-continued

| | |
|---|---|
| agtagcatga aatataatac tgttttataa ttctaaagct gctgttaatt tatgaagtac | 1200 |
| ataataatct aatgtaaact gcagaagtca gagcaagtgc ctacatttg ttattttgg | 1260 |
| cattactaca gagccatgta caatagaaag caatgcaaga cttgtaaact ctcaccactt | 1320 |
| cttgtaatat caaatgttcc ccctcaggtt attttgctta tggtacccat gagttgcctc | 1380 |
| tctctgtaca tagataaatt gttccaatat tttcctttga tgtttggaac tacagatagt | 1440 |
| caagggctgg aaattttagt tttcaatata agcttccagc ttagcaatta cctctagtcc | 1500 |
| aagacaatat tgattccta gttctgtttg gggcaaattt tcatttatct aaataaaatg | 1560 |
| caatctaatt aaaaaaaaaa aaaaaaa | 1587 |

<210> SEQ ID NO 37
<211> LENGTH: 9161
<212> TYPE: DNA
<213> ORGANISM: Homo sapiens

<400> SEQUENCE: 37

| | |
|---|---|
| ctgaaaactg gagagtgtga gagcgggagg agccccgac cacacaaacc cagcctgggg | 60 |
| aggaacctac tagtggctgc accctctttt ttaatagcac caattgtgtt tcccaagatg | 120 |
| atgtagagaa tttcagtgct gtgtaccacg tcggaggcag aaattcctct gctgtcccag | 180 |
| gagcaggcag ggcagttttt atctggaaaa gctaaaggtc tcctcttttg tttgtgtttt | 240 |
| tgtgcctgca caggacaaaa gatccttcat caccgaagtg acgttttaga aacagtggtc | 300 |
| ctgatcaacc cttctgatga agcagtcagc accgaggtgc gcttaatgat cactgatgct | 360 |
| gcccgacaca agctgctcgt gctgaccggg cagtgctttg aaaataccgg agagctcatt | 420 |
| ctccagtccg gctcttttctc cttccagaac ttcatagaga ttttcaccga tcaagagatc | 480 |
| ggggagttac taagcaccac ccatcctgcc aacaaagcca gcttaaccct gttctgtcct | 540 |
| gaagaagggg actggaagaa ctccaatctt gacagacaca atctccaaga cttcatcaat | 600 |
| attaaactca attcagcttc tatcttgcca gaaatggaag actttctga gtttaccgag | 660 |
| tatctctcag aatcagtgga agtcccatct ccctttgaca tcttggaacc tcccacatcg | 720 |
| ggtggatttc tgaagctctc caagccctgc tgttatattt ttccaggagg gaggggcgat | 780 |
| tctgccttgt ttgcagtgaa tggtttcaat atgctcatca atggcggatc agagagaaaa | 840 |
| tcctgcttct ggaagctcat ccgacactta gaccgagtgg actccatcct gctcacccac | 900 |
| attggggatg acaatttgcc tggaataaaa agcatgttac agcggaaaat tgcagagctc | 960 |
| gaggaagaac agtcccaggg ctccaccaca aatagtgact ggatgaaaaa cctcatctcc | 1020 |
| cctgacttag gagttgtatt tctcaatgta cctgaaaatc tcaaaaatcc agagccaaac | 1080 |
| atcaagatga agagaagcat agaagaagcc tgcttcactc tccagtacct aaacaaattg | 1140 |
| tccatgaaac cagaacctct gtttagaagt gtaggcaata ctattgatcc tgtcattctt | 1200 |
| ttccaaaaaa tgggagtagg taaacttgag atgtatgtgc ttaatccagt caagagcagc | 1260 |
| aaggaaatgc agtatttat gcagcagtgg actggtacca caaagacaa ggctgaattc | 1320 |
| attctgccta atggtcaaga agtagatctc ccgatttcct acttaacttc agtctcatct | 1380 |
| ttgattgtgt ggcatccagc aaaccctgcg gagaaaatca tccgagtcct gtttcctggg | 1440 |
| aacagcaccc agtacaacat cctggaaggg ttggaaaagc tcaaacatct agactttctg | 1500 |
| aagcagccac tggccacca aaaggatctc actggccagg tgcccactcc tgtggtgaaa | 1560 |
| caaacaaaac tgaaacagag ggctgatagc cgagaaagtc tgaagccagc cgcaaaacca | 1620 |
| cttcctagca aatccgtgcg caaggagtca aaagaagaaa cccctgaggt cacaaaagtg | 1680 |

```
aatcacgtgg aaaagccacc caaagttgaa agcaaagaaa aggtaatggt gaaaaaagac    1740
aagccagtaa aaacagagac caaaccttca gtgactgaaa aggaggttcc cagcaaagaa    1800
gagccatctc cagtgaaagc cgaggtggct gagaagcaag ccacagatgt caaacccaaa    1860
gctgccaagg agaagacggt gaaaaaggaa acaaaggtaa agcctgaaga caagaaagag    1920
gagaaagaaa agccaaagaa agaagtggct aaaaaggagg acaaaacacc tatcaagaag    1980
gaggaaaaac caaaaaagga gaggtgaaa aaagaagtca aaaagagat caagaaagaa      2040
gagaaaaaag aacccaagaa agaggttaag aagaaacac cgccaaagga agtcaagaag     2100
gaagttaaga aggaagagaa gaaggaagtg aaaaaggaag aaaaggaacc caaaaaagaa    2160
attaagaagc tccctaaaga cgcaaagaaa tcatctactc ctctgtctga agcaaaaaaa    2220
ccagctgctt taaaaccaaa agtacccaag aaggaagagt ctgtcaagaa agattctgtt    2280
gctgccggaa agccaaagga gaaggggaaa ataaaagtca ttaagaagga aggcaaggcc    2340
gcagaggctg tcgctgcagc tgtcggcact ggagccacca cagcagctgt catggcggca    2400
gctggaatag cagccattgg ccctgccaaa gaactcgaag ctgagaggtc ccttatgtca    2460
tctcctgagg atctaaccaa ggactttgaa gagttaaagg ctgaagaggt cgatgtaaca    2520
aaggacatca agcctcagct ggagctaatc gaagacgaag agaaactgaa ggaaactgag    2580
ccagtcgaag cctacgtcat ccagaaggag agagaagtca ccaaaggtcc tgccgagtcc    2640
cctgatgagg gaatcactac cactgaaggg gagggcgaat gtgaacagac acctgaggag    2700
ctggagcccg tcgagaagca gggagtagac gacattgaaa aatttgaaga tgaaggagcc    2760
ggttttgaag aatcttcaga gactggagac tatgaagaga aggcagaaac tgaggaggct    2820
gaggagccaa aagaggatgg ggaggaacac gtatgtgtga gcgcctccaa gcacagcccc    2880
actgaggatg aggaaagtgc caaggcggag gctgatgcat acatcaggga gaagagggag    2940
tctgtggcca gtgggatga ccgagccgaa gaagacatgg atgaggccat tgagaaagga    3000
gaggctgaac aatctgaaga ggaggctgat gaggaggaca agctgaaga tgccagagag    3060
gaggaatatg agccggaaaa aatggaagct gaagactatg tgatggctgt ggtcgacaag    3120
gctgcagagg ctggtggtgc cgaggagcag tatggattcc tcaccacacc aaccaagcaa    3180
ctaggagccc agtctcctgg ccgagaacct gcatcttcaa ttcatgatga ctttacct     3240
ggaggctcag agagcgaggc caccgcttct gatgaggaga atcgagaaga ccagcctgag    3300
gaattcactg ccacctctgg ctacactcag tctactattg agatatccag tgagcccacc    3360
cccatggatg agatgtctac ccctcgagac gtgatgagtg atgagaccaa caatgaagag    3420
acggagtccc cttctcagga attcgtaaat atcaccaaat atgaatcttc attgtattct    3480
caggaatact ctaaacctgc tgatgttaca ccgctcaacg gattttctga aggatcaaaa    3540
acagatgcca ctgatggcaa ggattacaat gcttcagcct ctaccatatc accaccctct    3600
tccatggagg aagacaaatt cagcagatct gctttacgtg atgcttactg ctctgaagtg    3660
aaagccagca ccactttgga catcaaagat agcatctcag ctgtttcaag tgaaaaggtc    3720
agcccatcga agagcccgtc cctgagtcca tctccaccat caccattaga aaagacccc    3780
ctgggtgaac gtagtgtgaa cttctctctg acgcccaatg agattaaagt ctctgcagag    3840
gcagaagtag ccccggtgtc tcctgaggtg acccaagaag tagttgaaga acattgtgct    3900
agtcctgagg acaagactct ggaagtggt tcaccatctc agtccgtgac tggcagtgct    3960
ggtcacacac cttactatca atctcctact gacgagaaat ccagtcatct ccctacagaa    4020
```

```
gtcattgaaa aaccaccagc agttccagtg agtttttgaat tcagtgatgc caaagatgag    4080
aatgaaaggg cttcagtaag ccccatggat gagcccgtgc ctgactcaga gtctcctatt    4140
gaaaaagttt tgtctccttt acgcagcccg cccctcattg gatccgagtc tgcttatgaa    4200
agttttctaa gtgctgatga caaggcttct ggcagaggtg ccgaaagtcc ttttgaagaa    4260
aagagtggaa acaaggctc tccagaccaa gtaagtccag tttctgaaat gacttctact    4320
agtctttacc aagacaaaca ggaagggaaa agcacagact ttgcaccaat aaaagaagac    4380
tttggccaag aaaagaaaac tgatgatgtt gaagccatga gttctcaacc agcactggct    4440
ctggatgaaa ggaaattagg agatgtttct cccacacaaa tagatgtcag tcagtttgga    4500
tcttttaaag aagacactaa gatgtccatt tctgaaggta ctgtctcaga caagtcagct    4560
actcctgttg atgagggcgt agcagaagac acgtactctc atatggaggg tgtggcctca    4620
gtgtccacag cctcagtggc tacgagctca tttccagagc caacaacaga tgatgtgtct    4680
ccatctctgc atgctgaggt tggctcccca cattccacag aagtagatga ctcccttttca    4740
gtgtctgttg tgcaaacacc taccacattc caggaaacag aaatgtctcc atctaaagaa    4800
gaatgcccaa gaccgatgtc aatttctcca ccagatttct cccctaaaac tgcaaagtcc    4860
aggacacccg ttcaagatca cagatctgaa cagtcctcaa tgtctattga atttggccaa    4920
gaatctcctg agcaatccct tgctatggac ttcagtcgac agtctccaga tcacccctaca    4980
gtgggtgcag gcgtgcttca catcactgaa aatgggccaa ctgaagtgga ctacagtcct    5040
tctgacatgc aggactccag tttatcacat aagataccac ctatggagga gccgtcctac    5100
acccaagata atgatctttc tgagctcatc tcagtatctc aggtagaggc ctccccgtcc    5160
acctcttctg ctcataccccc ttctcagatc gcttctcctc tccaagaaga tactctatcc    5220
gatgttgctc ctcccagaga tatgtcctta tatgcctcac tcacctctga aaaagtgcaa    5280
agtctggaag gagagaagct ctctccaaaa tctgatatct ctccactcac cccacgagag    5340
tcctctcctt tatattcacc tacttttttca gattctacct ctgcagtcaa agagaaaaca    5400
gcaacttgcc acagttcctc ttctccacca atagatgcag catccgcaga gcccatggc    5460
ttccgtgcct cagtgttatt cgatacaatg caacaccatc tagccttgaa tagagatttg    5520
tccacacctg gcctggagaa ggacagtgga gggaagacac ctggtgactt tagctatgcc    5580
tatcaaaagc ctgaggaaac aaccaggtcc ccagatgaag aagattatga ctatgagtct    5640
tatgagaaga ccacccggac ctcagatgtg ggtggctatt actatgagaa gatagagaga    5700
accacaaaat ctccaagtga cagtggctac tcctatgaga ccattgggaa aactaccaag    5760
accccctgaag atggtgacta ttcctatgaa attattgaga agaccacacg gacccctgaa    5820
gagggtgggt actcatatga cataagtgaa aagaccacca gccccccgga agtgagtggt    5880
tacagctatg aaaagactga gaggtctaga aggcttctgg atgacatcag caatggctat    5940
gatgactctg aggatggtgg ccacacactt ggggacccca gctactctta tgaaaccact    6000
gagaaaatta ccagtttccc tgagtctgaa ggttattcct atgagacatc tacaaagaca    6060
acacgaaccc ctgatacttc cacatactgt tacgagactg cagagaaaat cactagaacc    6120
cctcaggcat ccacatattc ctacgagact tcagacctat gctacactgc agaaaagaag    6180
tcccccctcag aagcccgtca ggatgtcgat ttatgcctcg tgtcctcttg tgaatacaag    6240
cacccccaaga cagagctttc accctctttc attaatccca atcctcttga gtggtttgcc    6300
agtgaagaac ccactgaaga atctgaaaag cccctcactc aatcagggg agccccaccg    6360
cctccaggag gaaagcaaca gggccgacag tgtgatgaaa cccctcccac ctcagtcagc    6420
```

```
gagtcagccc catcccagac cgactctgat gttccccegg agactgaaga gtgccccctcc    6480
atcacggccg atgccaatat cgactctgaa gacgagtcgg aaaccatccc cacagacaaa    6540
actgtcacgt acaaacacat ggacccacct ccagctcccg tgcaagaccg cagcccttcg    6600
ccacgccacc ctgatgtgtc catggtggac ccagaggcct tggccattga gcagaacctg    6660
ggcaaagctc taagaaaaga tctgaaagag aagaccaaaa ccaaaaagcc aggtacaaag    6720
accaagtcat cttcacctgt caaaaagagt gatgggaagt ctaagccctt ggcagcttca    6780
ccaaaaccag cgggcttgaa agaatcctcg gataaagtgt ccagggtggc ttctcctaag    6840
aagaaagaat ctgtggaaaa ggcagcaaaa cccaccacca ctcctgaggt caaagctgca    6900
cgtggggaag agaaagacaa ggagaccaag aatgctgcca atgcctctgc atccaagtcg    6960
gccaagaccg ccactgcagg accaggaact accaagacga ccaagtcatc tgctgtgccc    7020
ccaggcctcc ctgtgtattt ggacctgtgc tacattccta accacagcaa tagtaagaat    7080
gttgatgtgg aattttttcaa gagagtgcgg tcttcctact acgtggtgag tgggaatgac    7140
cctgctgctg aggagcccag ccgggctgtc ctggacgctt tgttggaagg aaaggctcag    7200
tggggcagca acatgcaggt gacactgatc ccaactcatg actcagaagt gatgagggaa    7260
tggtaccagg agacccatga gaaacagcaa gatctcaaca tcatggtttt agcaagcagc    7320
agcacagtgg ttatgcaaga tgaatccttc cctgcatgca agattgaact gtaaaaacca    7380
aggccagcca caccacagga tctgaacttt gttttccagaa attcttcaat ttgaaatcac    7440
cttttctaaa aagtcaattc atctagttaa gtcgctgaac aattacctgc caaatgctat    7500
actgtgtcat ggtgatgcaa gtcactaaat ttctcagttt ttgctgattg ctaagggaaa    7560
taacagtatt tccacaatag ggttcaaatt cctgcaaaat tacctacccc agttcatctc    7620
tgctgaacat ttggaaacca tgcactagcc aacccaactg acttctgcta ggtagaggca    7680
tttgtcttag agagagagag agcgcgggag agagtgagag agagtgagag cacaaagata    7740
acgcaggaga gagagagaga aagaatgaga aagaaaagga atgcaagaga aggagatgta    7800
atgacagaga gttctggtga gatacccaga gagaaaagaa gagagcaggg tggggtaagg    7860
aggagaaaat aaaccaacaa ttaggtctgc attttctcag gcagtaggca ttctttagtc    7920
tacataggca aagttttcca tttttgtcag tctgagtcat caaaaagagt cttaattttc    7980
taaaacaagt tggctagaag aaagtaaaaa gaacaacact tgttatgagg gcatgtgata    8040
ttttcacatc ttaattaagc tccttcagtt tgaaggctgc acactgacat aatgtagtga    8100
gtgtagactg gccatgcaag tggtttgggc cccattcaga actctcagac tctaaacaca    8160
caagtagatt gatctaaggc atgctcccag catttgtcca cccacttagt ccactctgag    8220
tcgattaacc tgcatgcagc aacacccaag tccacccccaa ttaactgaag caaataccaa    8280
agcagttggg agtacatatg gtagacaatt gccttaggga agtgacttga atgtacaaag    8340
atacttgatg cacttatttt ttaatgtgag acagcaagtt tataaaacat ccatataggga    8400
ttatagatac ttaaaggaac acgtgggtga gcgtgtgtgg gggtactaga agctgatctg    8460
attggtccaa cagtttgatg ctgagtcatg cgtgttgaat cccacttcag tgcacctgtg    8520
gcctctcagt caaacaagtt gtgccttcca cagcttcttt actactgcaa gttcaagact    8580
gaaatggctt ctatgatcag aactgggaaa acagtgaatc ttatggtgga agaggttctc    8640
agcaagtgta cagtatttac cttcctttgt cttacattgg cttttttaaat tttccattaa    8700
tttcaacata attatgggaa caagtgtaca gaagaatttt ttttttaaga tatgtgagaa    8760
```

| | | |
|---|---|---|
| cttttcatag atgaactttt taacaaatgt tttcatttac aggaaattgc aagaaaatt | 8820 | |
| ctcaagtgat agtctttttt tttaagtgtt tcgtaagaca aaaattgaat aatgtttttt | 8880 | |
| gaagttctgg caagattgaa gtctgatatt gcagtaatga tatttattaa aaacccataa | 8940 | |
| ctaccaggaa taatgatacc tcccaccct tgattcccat aacataaaag tgctacttga | 9000 | |
| gagtgggga gaatggcatg gtaggctact tttcagggcc ttgacaagta catcacccag | 9060 | |
| tggtatccta catacttctt tcaagatctt caaccatgag gtaaaagagc caagttcaaa | 9120 | |
| gaaccctagc acaaatttgc tttgggattt tcttttctgg a | 9161 | |

<210> SEQ ID NO 38
<211> LENGTH: 1190
<212> TYPE: DNA
<213> ORGANISM: Homo sapiens

<400> SEQUENCE: 38

| | | |
|---|---|---|
| gccctccaca aagctcctgg gcccctcctc ccttcaagga ttgcgaagaa ctggtcgcaa | 60 | |
| atcctcctaa gccaccagca tctcggtctt cagctcacac cagccttgag cccagcctgc | 120 | |
| ggccagggga ccacgcacgt cccacccacc cagcgactcc ccagccgctg cccactcttc | 180 | |
| ctcactcatg gggaacagca aaagtggggc cctgtccaag gagatcctgg aggagctgca | 240 | |
| gctgaacacc aagttctcgg aggaggagct gtgctcctgg taccagtcct tcctgaagga | 300 | |
| ctgtcccacc ggccgcatca cccagcagca gttccagagc atctacgcca gttcttccc | 360 | |
| cgacaccgac cccaaggcct acgcccagca tgtgttccgc agcttcgatt ccaacctcga | 420 | |
| cggcaccctg gacttcaagg agtacgtcat cgccctgcac atgaccaccg cgggcaagac | 480 | |
| caaccagaag ctggagtggg ccttctccct ctacgacgtg gacggtaacg ggaccatcag | 540 | |
| caagaatgaa gtgctggaga tcgtcatggc tattttcaaa atgatcactc ccgaggacgt | 600 | |
| gaagctcctt ccagacgatg aaaacacgcc ggaaaagcga gccgagaaga tctggaagta | 660 | |
| ctttggaaag aatgatgatg ataaacttac agagaaagaa ttcattgagg ggacactggc | 720 | |
| caataaggaa attctgcgac tgatccagtt tgagcctcaa aaagtgaagg aaaagatgaa | 780 | |
| gaacgcctga tgccaactgt tcagctgtcc tccctccacc taccactcac atgacacccg | 840 | |
| tgagcgcctg tgcacacaca cacacatgca cacacgcg cgcgcacaca cacacacaca | 900 | |
| catccaccc agggccaaga gaaaggcctg cacacaagcc cacagcacag ctccctgcca | 960 | |
| aactgaagca tctgtagtga cccactggtt ccttcttcct gggtcttcag cattccctcc | 1020 | |
| catcatgccc ggtcccaccc ctccctctgt ccaccagccc atgtccctgt gctaatccca | 1080 | |
| ggattaggcc ataggagtcc taagtgtcac cccgctgtaa gctcctttgt ggagtgctgg | 1140 | |
| gtaagcagtt tccaataaac gcaagctgag ctggaaaaaa aaaaaaaaa | 1190 | |

<210> SEQ ID NO 39
<211> LENGTH: 1880
<212> TYPE: DNA
<213> ORGANISM: Homo sapiens

<400> SEQUENCE: 39

| | | |
|---|---|---|
| aggatgcaag agtcagagtg agggatctgt ccctggatgg ggacaataag gggtcagttc | 60 | |
| agggggactt ccttgagctc tgaagtttca cctgagaatg ggagattcag aacttggtga | 120 | |
| cagagtttgt ggagctcact gtgtctttgc tgatccttca gcaaaggaag tgagattgtt | 180 | |
| tctagctttt ctgtttgggg tgcttctctg tcaactaaaa gtcttcatcc tttaaatatt | 240 | |
| gcatcatttg tgtatacttc attcattcac ttactcatga cccactcctc gagtgcctgc | 300 | |

-continued

```
aatgggcaag cgtctgtcct aggagccgtg tgctgggcca cagttaaatc tgagagatca    360
tgtgtggcat ttctcatgga ttgagatgtc tgagtgtcat tgttttgaga gagctagtgg    420
catggtttat aaagctgttt ttcattttct ccatacagga caacagcttt gagcagttca    480
ttattaatta ttgtaacgaa aagctgcaac aaatcttcat tgaacttact cttaaagaag    540
agcaggagga gtatatacgg gaggatatag aatggactca cattgactac ttcaataatg    600
ctatcatttg tgacctaata gaaaataaca caaatggaat cctggccatg ctggatgaag    660
agtgcctcag acctggcaca gtcactgatg agaccttctt agaaaagctg aaccaagtat    720
gtgccaccca ccagcatttt gaaagcagga tgagcaagtg ctctcggttc ctcaatgaca    780
cgtctctgcc tcacagctgc ttcaggatcc agcattatgc tggaaaggtg ctgtaccagg    840
tggaaggatt cgttgacaaa aacaatgacc ttctctatcg agacctgccc caagccatgt    900
ggaaggccag ccatgccctc atcaagtctt tgttccccga agggaatccc gccaagatca    960
acctgaaaag gcctcctaca gcaggctcac agttcaaggc atccgtggcc actctgatga   1020
aaaacctaca gaccaagaac ccaaactata ttaggtattt ttggcacatg aaactttcac   1080
agttcaaatg tgagagcacc ccgaaggaat atcatttttc cctttgcttc aatctgagtg   1140
tagcccaagc agagggtaac taaaatactt acagattaaa taatacctta tctgggattg   1200
gcttaaaaaa tgctccacta tcctttcccc taaaataaga aagtaaaaaa gtaaagtgtg   1260
gtggagaaga tagtagatat ttaatgaagc tcagtggttg agacctaggg gttttcaact   1320
ttctgtatgt ttattattat ttttttaacg gcaagttaaa aaacaaaatg caagtgtttt   1380
ttctggtcag tgttttgcag aaaactcttg ttggcttcat ttgggattct tgttctatta   1440
gcttagagca cagcattgaa gcaagtgctt tagttaactg ctctggcact tcttaggaga   1500
catgcacttt tttcttccct gtgagaggtg taggcctgga gaaagtaatg attcctaaag   1560
caatctgaat tttttccaag gcagtagaaa gaccttctta aaaagggctg ggcgtggtgg   1620
ctcacaccta taatcccaac acttagggag gcggaggcag gtggatcacc tcaggtcagg   1680
aattcgagac tagcctggcc aacatggcaa aaccctgtct ctactaaaaa tataaaaatt   1740
agctgggcgt ggtggcaggg acctataatc ccaactactt gggaggctga ggcaggagaa   1800
tcgcttggag gcagaggttg cagtgagccg aggtcacgcc actgcactcc agcccgggtg   1860
acaatacaag actccatctc                                               1880
```

<210> SEQ ID NO 40
<211> LENGTH: 1880
<212> TYPE: DNA
<213> ORGANISM: Homo sapiens

<400> SEQUENCE: 40

```
aggatgcaag agtcagagtg agggatctgt ccctggatgg ggacaataag gggtcagttc     60
agggggactt ccttgagctc tgaagtttca cctgagaatg ggagattcag aacttggtga    120
cagagtttgt ggagctcact gtgtctttgc tgatccttca gcaaaggaag tgagattgtt    180
tctagctttt ctgtttgggg tgcttctctg tcaactaaaa gtcttcatcc tttaaatatt    240
gcatcatttg tgtatacttc attcattcac ttactcatga cccactcctc gagtgcctgc    300
aatgggcaag cgtctgtcct aggagccgtg tgctgggcca cagttaaatc tgagagatca    360
tgtgtggcat ttctcatgga ttgagatgtc tgagtgtcat tgttttgaga gagctagtgg    420
catggtttat aaagctgttt ttcattttct ccatacagga caacagcttt gagcagttca    480
```

```
ttattaatta ttgtaacgaa aagctgcaac aaatcttcat tgaacttact cttaaagaag    540
agcaggagga gtatatacgg gaggatatag aatggactca cattgactac ttcaataatg    600
ctatcatttg tgacctaata gaaaataaca caaatggaat cctggccatg ctggatgaag    660
agtgcctcag acctggcaca gtcactgatg agaccttctt agaaaagctg aaccaagtat    720
gtgccaccca ccagcatttt gaaagcagga tgagcaagtg ctctcggttc tcaatgaca    780 cgtctctgcc tcacagctgc ttcaggatcc agcattatgc tggaaaggtg ctgtaccagg    840
tggaaggatt cgttgacaaa aacaatgacc ttctctatcg agacctgccc caagccatgt    900
ggaaggccag ccatgccctc atcaagtctt tgttccccga agggaatccc gccaagatca    960
acctgaaaag gcctcctaca gcaggctcac agttcaaggc atccgtggcc actctgatga   1020
aaaacctaca gaccaagaac ccaaactata ttaggtattt ttggcacatg aaactttcac   1080
agttcaaatg tgagagcacc ccgaaggaat atcattttc cctttgcttc aatctgagtg    1140
tagcccaagc agagggtaac taaaatactt acagattaaa taatacctta tctgggattg   1200
gcttaaaaaa tgctccacta tcctttcccc taaaataaga agtaaaaaa gtaaagtgtg    1260 gtggagaaga tagtagatat ttaatgaagc tcagtggttg agacctaggg gttttcaact    1320
ttctgtatgt ttattattat tttttaacg gcaagttaaa aaacaaaatg caagtgtttt    1380
ttctggtcag tgttttgcag aaaactcttg ttggcttcat ttgggattct tgttctatta    1440
gcttagagca cagcattgaa gcaagtgctt tagttaactg ctctggcact tcttaggaga    1500
catgcacttt tttcttccct gtgagaggtg taggcctgga gaaagtaatg attcctaaag    1560
caatctgaat tttttccaag gcagtagaaa gaccttctta aaagggctg ggcgtggtgg     1620 ctcacaccta taatcccaac acttaggag gcggaggcag gtggatcacc tcaggtcagg    1680
aattcgagac tagcctggcc aacatggcaa aaccctgtct ctactaaaaa tataaaaatt    1740
agctgggcgt ggtggcaggg acctataatc ccaactactt gggaggctga ggcaggagaa    1800
tcgcttggag gcagaggttg cagtgagccg aggtcacgcc actgcactcc agcccgggtg    1860
acaatacaag actccatctc                                                1880
```

<210> SEQ ID NO 41
<211> LENGTH: 2685
<212> TYPE: DNA
<213> ORGANISM: Homo sapiens

<400> SEQUENCE: 41

```
ggacttggga ggcgcggtga ggagtcaggc ttaaaacttg ttggaggga gtaaccagcc       60 tgctcctctc gctctcctcc tcgtctgcgc cgcgtttcag agagaaaatt cctgttccaa    120
gagaaaataa ggcaacatca atgaaggaga gaagagccag ccagaaatta tccagcaaat    180
ctatcatgga tcctaatcag aacgtgaaat gcaagatagt tgtggtggga gacagtcagt    240
gtggaaaaac tgcgctgctc catgtcttcg ccaaggactt cttccccgag aattacgttc    300
ctacagtgtt tgagaattac acggccagtt ttgaaatcga cacacaaaga atagagttga    360
gcctgtggga cacttcgggt tctccttact atgacaatgt ccgccccctc tcttaccctg    420
attcggatgc tgtgctgatt tgctttgaca tcagtagacc agagaccctg acagtgtcc    480 tcaaaaagtg gaaggtgaa atccaggaat ttgtccaaa taccaaaatg ctcttggtcg    540
gctgcaagtc tgatctgcgg acagatgtta gtacattagt agagctctcc aatcacaggc    600
agacgccagt gtcctatgac caggggggcaa atatggccaa acagattgga gcagctactt    660
atatcgaatg ctcagcttta cagtcggaaa atagcgtcag agacatttt cacgttgcca    720
```

| | |
|---|---|
| ccttggcatg tgtaaataag acaaataaaa acgttaagcg gaacaaatca cagagagcca | 780 |
| caaagcggat ttcacacatg cctagcagac cagaactctc ggcagttgct acggacttac | 840 |
| gaaaggacaa agcgaagagc tgcactgtga tgtgaatctt tcattatctt taatgaagac | 900 |
| aaaggaatct agtgtaaaaa acaacagcaa acaaaaaggt gaagtctaaa tgaagtgcac | 960 |
| agccaaagtc atgtatacca gaggcttagg aggcgtttga gaggatactc atcttttttgg | 1020 |
| aatcctgacc ttaggttcgg catgtagacc aagtgatgag aagtgaatac atggaagagt | 1080 |
| ttttaagtgt gacttgaaaa atatgccaaa aaatgagaga tacaaatgag ctagaggaag | 1140 |
| atgaggggg atgcgagtac ctccaagaag aaaaatcaca ctctgaatgg tgcttgcatt | 1200 |
| tttgggtttt ttttttttttt gttataatct attcatggat ctccactttg atttaattttt | 1260 |
| taaatgtttt aatctccttt acaaaaagta tacgttaata taccgtcctc aagggggaac | 1320 |
| tggcactgtg accttagcat ttagtttctt agaggatgtg atctaatttc tttctagctc | 1380 |
| atcattaaaa aggaaattgt atcaggaccc atgggatata tccagaggca aactttatga | 1440 |
| ggctttgaaa tcttgccttc ctgaagatag ctgagtagga tggttctaag gaaagccttt | 1500 |
| gcaatcttgc aagatttgta gaccagcact acaaagatcg catagatcaa ataggaaaaa | 1560 |
| aaatgtcgat tttattcag tctgatggtt ctgttcttca ttgtgattgt cattaaaaag | 1620 |
| tggtaaattg ctcaatgtaa tattttttgtg cgctgtttag aagttgtgtg atttttttgcc | 1680 |
| atcgttgata aaaatgcaaa gtcaaataaa aggtgtcttg gtttgatgtc atagaatgat | 1740 |
| ccaaggagag aaaaaaggta gttactgttt tcaccagaaa aggtaatgag tgaaggaaag | 1800 |
| aatagtagca gaaagcacag tttgtgagta aagctgtctg gaattaagtt accaaaaata | 1860 |
| caaagcaaaa ggactattat tttgggttga agctccaaaa ctgacagcat ctgataatct | 1920 |
| gttggtttat ttcactttttc attaaatgaa cattgatgag agaagatgcc acttacccaa | 1980 |
| gctttagaga atccctagtg gaagattata tgataaactt tcagtcctga cataacacta | 2040 |
| gggcatttct agagtgtcat tgctaaaacc tcactgaaca gacgcagcca aggtctgtgt | 2100 |
| tcagcacttg gtctctgttg ttacgtaaaa taataagcat ttaaaatagt ttacagatat | 2160 |
| ttttgaccag ttccttttag agattctttc agagaagaaa ccagatctga cctgtttatt | 2220 |
| gttggcgctt gttgaaaacg agctttctt cccatgatag tgcttcgttt ttgaagtgtt | 2280 |
| gaagctgtgc tccccttaaa tcgtggcagg agagattaag gtaattacaa cactcagttc | 2340 |
| tatgtcttac aagcactttg tcttgtctct gcaagaaaat tcgattccag tcatttccca | 2400 |
| taaaatacag acatttttacc aacataatat gctttgattg atgcagcatt atgctttggg | 2460 |
| cagtattaca aaatagctgg cgagtgcttt ctgtatttaa atattgtaaa aagaaaataa | 2520 |
| gttataactg ttataaagca gaacttttgt tgcatttttt aaactgttga agtcactgtg | 2580 |
| tatgtttgtt tggtcaatgt ttccgcagta tttattaaaa catactttttt tttttcttca | 2640 |
| aataaaaaag taaccatgtc tttgtctaaa aaaaaaaaaa aaaaa | 2685 |

<210> SEQ ID NO 42
<211> LENGTH: 4469
<212> TYPE: DNA
<213> ORGANISM: Homo sapiens

<400> SEQUENCE: 42

| | |
|---|---|
| cctgcagcct ccggagtcag tgccgcgcgc ccgccgcccc gcgccttcct gctcgccgca | 60 |
| cctccgggag ccggggcgca cccagcccgc agcgccgcct ccccgcccgc gccgcctccg | 120 |

-continued

```
accgcaggcc gagggccgcc actggccggg gggaccgggc agcagcttgc ggccgcggag    180
ccgggcaacg ctggggactg cgccttttgt ccccggaggt ccctggaagt ttgcggcagg    240
acgcgcgcgg ggaggcggcg gaggcagccc cgacgtcgcg gagaacaggg cgcagagccg    300
gcatgggcat cgggcgcagc gagggggggcc gccgcgggge cctgggcgtg ctgctggcgc    360
tgggcgcggc gcttctggcc gtgggctcgg ccagcgagta cgactacgtg agcttccagt    420
cggacatcgg cccgtaccag agcgggcgct tctacaccaa gccacctcag tgcgtggaca    480
tccccgcgga cctgcggctg tgccacaacg tgggctacaa gaagatggtg ctgcccaacc    540
tgctggagca cgagaccatg gcggaggtga agcagcaggc cagcagctgg gtgcccctgc    600
tcaacaagaa ctgccacgcc gggacccagg tcttcctctg ctcgctcttc gcgcccgtct    660
gcctggaccg gcccatctac ccgtgtcgct ggctctgcga ggccgtgcgc gactcgtgcg    720
agccggtcat gcagttcttc ggcttctact ggcccgagat gcttaagtgt gacaagttcc    780
cggaggggga cgtctgcatc gccatgacgc cgcccaatgc caccgaagcc tccaagcccc    840
aaggcacaac ggtgtgtcct ccctgtgaca acgagttgaa atctgaggcc atcattgaac    900
atctctgtgc cagcgagttt gcactgagga tgaaaataaa agaagtgaaa aagaaaatg    960
gcgacaagaa gattgtcccc aagaagaaga agcccctgaa gttggggccc atcaagaaga   1020
aggacctgaa gaagcttgtg ctgtacctga agaatgggGc tgactgtccc tgccaccagc   1080
tggacaacct cagccaccac ttcctcatca tgggccgcaa ggtgaagagc cagtacttgc   1140
tgacggccat ccacaagtgg gacaagaaaa acaaggagtt caaaaacttc atgaagaaaa   1200
tgaaaaacca tgagtgcccc acctttcagt ccgtgtttaa gtgattctcc cggggcagg   1260
gtggggaggg agcctcgggt ggggtgggag cgggggggac agtgcccggg aacccgtggt   1320
cacacacacg cactgccctg tcagtagtgg acattgtaat ccagtcggct tgttcttgca   1380
gcattcccgc tcccttttccc tccatagcca cgctccaaac cccagggtag ccatggccgg   1440
gtaaagcaag ggccatttag attaggaagg ttttaagat ccgcaatgtg gagcagcagc   1500
cactgcacag gaggaggtga caaaccattt ccaacagcaa cacagccact aaaacacaaa   1560
aaggggggatt gggcggaaag tgagagccag cagcaaaaac tacattttgc aacttgttgg   1620
tgtggatcta ttggctgatc tatgcctttc aactagaaaa ttctaatgat tggcaagtca   1680
cgttgttttc aggtccagag tagtttcttt ctgtctgctt taaatggaaa cagactcata   1740
ccacacttac aattaaggtc aagcccagaa agtgataagt gcaggagga aaagtgcaag   1800
tccattatct aatagtgaca gcaaagggac caggggagag gcattgcctt ctctgcccac   1860
agtcttccg tgtgattgtc tttgaatctg aatcagccag tctcagatgc cccaaagttt   1920
cggttcctat gagcccgggg catgatctga tccccaagac atgtggaggg gcagcctgtg   1980
cctgcctttg tgtcagaaaa aggaaaccac agtgagcctg agagagacgg cgattttcgg   2040
gctgagaagg cagtagtttt caaaacacat agttaaaaaa gaaacaaatg aaaaaaattt   2100
tagaacagtc cagcaaattg ctagtcaggg tgaattgtga aattgggtga agagcttagg   2160
attctaatct catgtttttt ccttttcaca tttttaaaag aacaatgaca acacccact    2220
tattttcaa ggttttaaaa cagtctacat tgagcatttg aaaggtgtgc tagaacaagg   2280
tctcctgatc cgtccgaggc tgcttccag aggagcagct ctccccaggc atttgccaag   2340
ggaggcggat tccctggta gtgtagctgt gtggcttcc ttcctgaaga gtccgtggtt   2400
gccctagaac ctaacacccc ctagcaaaac tcacagagct ttcgttttt ttctttcctg   2460
taaagaaaca tttcctttga acttgattgc ctatggatca aagaaattca gaacagcctg   2520
```

```
cctgttcccc cgcactttt  acatatattt gtttcatttc tgcagatgga aagttgacat    2580
gggtggggtg tccccatcca gcgagagagt ttcaaaagca aaacatctct gcagtttttc    2640
ccaagtaccc tgagatactt cccaaagccc ttatgtttaa tcagcgatgt atataagcca    2700
gttcacttag acaactttac ccttcttgtc caatgtacag gaagtagttc taaaaaaaat    2760
gcatattaat ttcttccccc aaagccggat tcttaattct ctgcaacact ttgaggacat    2820
ttatgattgt ccctctgggc caatgcttat acccagtgag gatgctgcag tgaggctgta    2880
aagtggcccc ctgcggccct agcctgaccc ggagaaagga tggtagattc tgttaactct    2940
tgaagactcc agtatgaaaa tcagcatgcc cgcctagtta cctaccggag agttatcctg    3000
ataaattaac ctctcacagt tagtgatcct gtccttttaa caccttttt  gtggggttct    3060
ctctgacctt tcatcgtaaa gtgctgggga ccttaagtga tttgcctgta attttggatg    3120
attaaaaaat gtgtatatat attagctaat tagaaatatt ctacttctct gttgtcaaac    3180
tgaaattcag agcaagttcc tgagtgcgtg gatctgggtc ttagttctgg ttgattcact    3240
caagagttca gtgctcatac gtatctgctc attttgacaa agtgcctcat gcaaccgggc    3300
cctctctctg cggcagagtc cttagtggag gggtttacct ggaacataag tagttaccac    3360
agaatacgga agagcaggtg actgtgctgt gcagctctct aaatgggaat tctcaggtag    3420
gaagcaacag cttcagaaag agctcaaaat aaattggaaa tgtgaatcgc agctgtgggt    3480
tttaccaccg tctgtctcag agtcccagga ccttgagtgt cattagttac tttattgaag    3540
gttttagacc catagcagct ttgtctctgt cacatcagca atttcagaac caaaagggag    3600
gctctctgta ggcacagagc tgcactatca cgagcctttg ttttctcca  caaagtatct    3660
aacaaaacca atgtgcagac tgattggcct ggtcattggt ctccgagaga ggaggtttgc    3720
ctgtgatttg cctgtgattt cctaattatc gctagggcca aggtgggatt tgtaaagctt    3780
tacaataatc attctggata gagtcctggg aggtccttgg cagaactcag ttaaatcttt    3840
gaagaatatt tgtagttatc ttagaagata gcatgggagg tgaggattcc aaaaacattt    3900
tatttttaaa atatcctgtg taacacttgg ctccttggtac ctgtgggtta gcatcaagtt    3960
ctccccaggg tagaattcaa tcagagctcc agtttgcatt tggatgtgta aattacagta    4020
atcccatttc ccaaacctaa aatctgtttt tctcatcaga ctctgagtaa ctggttgctg    4080
tgtcataact tcatagatgc aggaggctca ggtgatctgt ttgaggagag caccctaggc    4140
agcctgcagg gaataacata ctggccgttc tgacctgttg ccagcagata cacaggacat    4200
ggatgaaatt cccgtttcct ctagtttctt cctgtagtac tcctcttta  gatcctaagt    4260
ctcttacaaa agctttgaat actgtgaaaa tgttttacat tccatttcat ttgtgttgtt    4320
tttttaactg cattttacca gatgttttga tgttatcgct tatgttaata gtaattcccg    4380
tacgtgttca ttttatttc atgcttttc  agccatgtat caatattcac ttgactaaaa    4440
tcactcaatt aatcaatgaa aaaaaaaaa                                      4469
```

<210> SEQ ID NO 43
<211> LENGTH: 1607
<212> TYPE: DNA
<213> ORGANISM: Homo sapiens

<400> SEQUENCE: 43

```
gctctgtagc acccaggagc ggggaagcga agtgcgagag accccggacc ccagcgctgt      60
ctcttcccgc cgcccgaacc accatgaccc acttcaacaa gggcccttcc tatgggctct     120
```

```
cggcccgaagt caagaacaag attgcttcca agtatgatca tcaggcagaa gaagatcttc    180
gcaattggat agaagaggtg acaggcatga gcattggccc caacttccag ctgggcttaa    240
aggatggcat catcctctgc gaacttataa acaagctaca gccaggctca gtgaagaagg    300
tcaacgagtc ctcactgaac tggcctcagt tggagaatat tggcaacttt attaaagcta    360
ttcaggctta tggtatgaag ccacatgaca tattcgaagc aaatgatctt tttgagaatg    420
gaaacatgac ccaggttcag actactctgg tggctctagc aggtctggct aaaacaaaag    480
gattccatac aaccattgac attggagtta gtatgcaga aaaacaaaca agacgttttg    540
atgaaggaaa attaaaagct ggccaaagtg taattggtct gcagatggga accaacaaat    600
gtgccagcca ggcaggtatg acagcttacg ggactaggag gcatctttat gatcccaaaa    660
tgcaaactga caaacctttt gaccagacca caattagtct gcagatgggc actaataaag    720
gagccagcca ggcagggatg ttagcaccag gtaccagaag agacatctat gatcagaagc    780
taacattaca gccggtggac aactcgacaa tttccctaca gatgggtacc aacaaagttg    840
cttcccagaa aggaatgagt gtgtatgggc ttgggcggca agtatatgat cccaaatact    900
gtgctgctcc tacagaacct gtcattcaca acggaagcca aggaacagga acaaatggtt    960
cggaaatcag tgatagtgat tatcaggcag aatacccctga tgagtatcat ggcgagtacc   1020
aggatgacta ccccagagat taccaatata gcgaccaagg cattgattat tagatccaca   1080
cagaaggagc tcagtattta gtcctttgtt tttattcagt gagaaccaag ctagccttga   1140
gtaattttta tcttgtcttc ctaaaacact attaagctta ttgtactttt aagaaaaatt   1200
gccttacgta cattccttt tcctttttct gcctcttccc tcaatagttg ccttttagtg   1260
ctgtaatagg ttaaatccta cagcataatc aataactcgc atatgaagta aaaaggaata   1320
ctgtgaaagg ggagtactct tgtacagcca gttcttttat gcaaaaatct atgcattttt   1380
acaatcttat attaaactgg tatttttcaaa caataggaaa cttttttttt tttttttttac   1440 agtttagtgt atctggtttc tacatggaag actaaactca tgcttattgc taaatgtggt   1500
ctttgccaac taaatttaag atgcagcatt ttagaaattt acatatcaat gtttctacag   1560
tattgtttgc taatttttaa ataaagtcat gatcagtgtg aaaaaaa                 1607
```

<210> SEQ ID NO 44
<211> LENGTH: 3144
<212> TYPE: DNA
<213> ORGANISM: Homo sapiens

<400> SEQUENCE: 44

```
ggcacgaggg tccgcccggg ggcgccgccc accgcgcctc gctcgggccg ttgccgtctg     60
cacccagacc ctgagccgcc gccgccggcc atggaggtgg cgccggagca gccgcgctgg    120
atggcgcacc cggccgtgct gaatgcgcag caccccgact cacaccaccc gggcctggcg    180
cacaactaca tggaacccgc gcagctgctg cctccagacg aggtggacgt cttcttcaat    240
cacctcgact cgcagggcaa ccctactat gccaacccccg ctcacgcgcg ggcgcgcgtc    300
tcctacagcc ccgcgcacgc ccgcctgacc ggaggccaga tgtgccgccc acacttgttg    360
cacagcccgg gtttgccctg gctggacggg ggcaaagcag ccctctctgc cgctgcggcc    420
caccaccaca cccctggac cgtgagcccc ttctccaaga cgccactgca cccctcagct    480
gctggaggcc ctggaggccc actctctgtg tacccagggg ctgggggtgg gagcggggga    540
ggcagcggga gctcagtggc ctccctcacc cctacagcag cccactctgg ctcccacctt    600
ttcggcttcc cacccacgcc acccaaagaa gtgtctcctg accctagcac cacggggct    660
```

```
gcgtctccag cctcatcttc cgcggggggt agtgcagccc gaggagagga caaggacggc    720
gtcaagtacc aggtgtcact gacggagagc atgaagatgg aaagtggcag tccctgcgc     780 ccaggcctag ctactatggg cacccagcct gctacacacc ccccatccc cacctacccc     840 tcctatgtgc cggcggctgc ccacgactac agcagcggac tcttccaccc cggaggcttc    900 ctgggggac cggcctccag cttcaccct aagcagcgca gcaaggctcg ttcctgttca       960
gaaggccggg agtgtgtcaa ctgtggggcc acagccaccc ctctctggcg gcgggacggc   1020
accggccact acctgtgcaa tgcctgtggc ctctaccaca agatgaatgg gcagaaccga   1080
ccactcatca agcccaagcg aagactgtcg gccgccagaa gagccggcac ctgttgtgca   1140
aattgtcaga cgacaaccac caccttatgg cgccgaaacg ccaacgggga ccctgtctgc   1200
aacgcctgtg gcctctacta caagctgcac aatgttaaca ggccactgac catgaagaag   1260
gaagggatcc agactcggaa ccggaagatg tccaacaagt ccaagaagag caagaaaggg   1320
gcggagtgct tcgaggagct gtcaaagtgc atgcaggaga agtcatcccc cttcagtgca   1380
gctgccctgg ctggacacat ggcacctgtg ggccacctcc cgcccttcag ccactccgga   1440
cacatcctgc ccactccgac gcccatccac ccctcctcca gcctctcctt cggccacccc   1500
cacccgtcca gcatggtgac cgccatgggc tagggaacag atggacgtcg aggaccgggc   1560
actcccggga tgggtggacc aaaccctag cagcccagca tttcccgaag ccgacacca     1620 ctcctgccag cccggctcgg cccagcaccc cctctcctgg agggcgccca gcagcctgcc   1680
agcagttact gtgaatgttc cccaccgctg agaggctgcc tccgcacctg actgctgccc   1740
aggtggggtt cctgcatgg acagttgttt ggagaacaac aaggacaact ttatgtagag    1800
aaaaggaggg gacgggacag acgaaggcaa ccattttag aaggaaaaag gattaggcaa    1860
aaataattta ttttgctctt gtttctaaca aggacttgga gacttggtgg tctgagctgt   1920
cccaagtcct ccggttcttc ctcgggattg gcggtccac ttgccagggc tctggggca     1980 gatttgtggg gacctcagcc tgcaccctct tctcttctgg cttccctctc tgaaatagcc   2040
gaactccagc tgggctgag ccaaagccag agtggccacg gccagggag ggtgagctgg     2100 tgcctgcttt gacgggccag gccctggagg gcagagacaa tcacgggcgg tcctgcacag   2160
attcccaggc cagggctggg tcacaggaag gaaacaacat tttcttgaaa ggggaaacgt   2220
ctcccagatc gctcccttgg ctttgaggcc gaagctgctg tgactgtgtc cccttactga   2280
gcgcaagcca cagcctgtct tgtcaggtgg accctgtaaa tacatccttt ttctgctaac   2340
ccttcaaccc cctcgcctcc tactctgaga caaaagaaaa aatattaaaa aaatgcatag   2400
gcttaactcg ctgatgagtt aattgtttta tttttaaact cttttgggt ccagttgatt    2460 gtacgtagcc acaggagccc tgctatgaaa ggaataaaac ctacacacaa ggttggagct   2520
ttgcaattct ttttggaaaa gagctgggat cccacagccc tagtatgaaa gctggggtg    2580 gggaggggcc tttgctgccc ttggtttctg ggggctggtt ggcatttgct ggcctggcag   2640
ggggtgaagg caggagttgg gggcaggtca ggaccaggac ccaggagag gctgtgtccc    2700 tgctggggtc tcaggtccag ctttactgtg gctgtctgga tccttcccaa ggtacagctg   2760
tatataaacg tgtcccgagc ttagattctg tatgcggtga cggcggggtg tggtggcctg   2820 tgagggccc ctggcccagg aggaggattg tgctgatgta gtgaccaagt gcaatatggg    2880
cgggcagtcg ctgcagggag caccacggcc agaagtaact tatttgtac tagtgtccgc    2940 ataagaaaaa gaatcggcag tatttctgt ttttatgttt tatttggctt gttttatttt    3000
```

-continued

```
ggattagtga actaagttat tgttaattat gtacaacatt tatatattgt ctgtaaaaaa      3060
tgtatgctat cctcttattc ctttaaagtg agtactgtta agaataataa aatactttt       3120 gtgaaaaaaa aaaaaaaaaa aaaa                                              3144
```

<210> SEQ ID NO 45
<211> LENGTH: 2038
<212> TYPE: DNA
<213> ORGANISM: Homo sapiens

<400> SEQUENCE: 45

```
cgaagggctc gaagatggcc ggttggcaga gctacgtgga taacctgatg tgcgatggct        60
gctgccagga ggccgccatt gtcggctact gcgacgccaa atacgtctgg gcagccacgg       120
ccgggggcgt ctttcagagc attacgccaa tagaaataga tatgattgta ggaaaagacc       180
gggaaggttt ctttaccaac ggtttgactc ttggcgcgaa gaaatgctca gtgatcagag       240
atagtctata cgtcgatggt gactgcacaa tggacatccg gacaaagagt caaggtgggg       300
agccaacata caatgtggct gtcggcagag ctggtagagt cttggtcttt gtaatgggaa       360
aagaaggggt ccatggaggc ggattgaata agaaggcata ctcaatggca aaatacttga       420
gagactctgg gttctagctg ctaggcagac tgttaagtat tagggaaaaa ttgctcttaa       480
actttcctag ctataagctt aagtcttaat tctggaaatt ttattagcaa tgcagggtga       540
tggggtatga acctgtgtct cctttgtatc cctctgttgg tggggaaagg tgtctttctt       600
tctgccctcc cccccaaaa taattctgtt cacttttgtt ttgtttcctt gtgtactcca       660
gcattggtta tagtcatggg aaaggaaggt gtccacggag gcacacttaa caagaaagca       720
tatgaactcg ctttatacct gaggaggtct gatgtgtaag cagcctctcc ccatctacct       780
agcaactgtc ttcatcaaca accctaatta tggtcacaat gctaccaaac tgtagatggt       840
agctaatttt tctttaccta ttttctaatg tcatgattcc tgtttgccca atggatcatt       900
tgtatgttaa ccactgtatg taaccaaccc ttatctggca acataattgc agcacaataa       960
tgatttgcat gataccttga aattgggggg aggggcatg ccaagttggg catcactttg       1020
tcttagcaat taatgggata ttgattacta aaataagtta atattaagca aggtgccggt       1080
tgtacaatct ctgatcagtg tctttttcagc actttgagca tttacttggc tcatttagtc       1140
ttccttttgt agcgcatggt tgggaggaaa aagtgcatgc atcattcctt cactcttctc       1200
tttttcccgc ccccccctcc cttcgcacat aggcatttgg tttgcttcca tctttttta       1260 tgcagtgcct gtttttttt aaccaattaa atcccttttt gttgatgagc tattgagagc       1320
tgcagtagtt tgcttttagt attgttgttg cacttgagca gagacaaacc tttattcata       1380
gtgtctacag gacatatgaa gagtgcaatg gcaaaacaag agcaaaaagc acttcctccc       1440
atgaccttac agtaaccata ctgattgaat ccccagggac attccatcat gcaatagct        1500 cagattttc ttccttttc tttgcacacc agctctactc tttagtaaaa ttgtaaaagg        1560
ctgccattat ggacattagg tatcccaaca taaccatctg gagtgtgtcc agtttgttct       1620
tcataggacc aatttttatt tgcagcttga gttttatat gaagttgcat tatttgtggac       1680 ttggctgtct tgtgatgaat ttttttcata tgtattctgt gccatactat tgttaaaatg       1740
aactgttgct attgtgagat ggattttaac tgacctatta agggtttctt tcgaatggca       1800
ctactttagg gacattctag tatttgcttc tattgtttgg gccttgtgga taatgtacag       1860
atttaaaaac aaatcttgtt gctgattgt ccatttcttt ccctgcactt tgttacatct       1920
gggatacagt ctaactcatc tgatttaata tgcatttaaa aaaatgccat aactattaaa       1980
```
caccttgttt acagacagat gaaataaatt tattccaacc aaaaaaaaaa aaaaaaaa    2038

<210> SEQ ID NO 46
<211> LENGTH: 5487
<212> TYPE: DNA
<213> ORGANISM: Homo sapiens

<400> SEQUENCE: 46
tctgtcgact tgccccagag ctgatccttg tctttgtcca cttctcagcg aggatggcac      60
ttcagggagc ccttcccttaa ctatcgcaga gagagcaggc cctccccagt catgtccaac    120
ccagaactct gttttgtttt cttcatagcc ctagcatcac agaaaatcac cctgtgcatt    180
catggatgtc cacgggggca agggctttgt gttgcttaac ccagcatcct gaaccgtgtt    240
tgttgaatga atacagaacc ccgtttgctc tgggagagca cagaaaacag tcttctatca    300
tatatcatag ccagctgcaa acagcagatg gcttcccata tcccagagag taagaaccag    360
agagagagag aaagagagag agtttgggtc tttctcctct gtgcctgctc tctccagaga    420
aactggaggg gtagcagtta gcattccccc gctggttcca ccaagcacag tcaaggtctc    480
taggacatgg ccaccccctca cctgtggaag cggtcctgct ggggtgggtg ggtgttagtt    540
ggttctggtt tgggtcagag acaccccagtg gcccaggtgg gcgtggggcc agggcgcaga    600
cgagaagggg cacgagggct ccgctccgag gacccagcgg caagcaccgg tcccgggcgc    660
gccccagccc acccactcgc gtgcccacgg cggcattatt ccctataagg atctgaacga    720
tccggggggcg gccccgcccc gttacccctt gccccggcc ccgccccctt tttggagggc    780
cgatgaggta atgcggctct gccattggtc tgaggggggcg ggcccaaca gcccgaggcg    840
gggtccccgg gggcccagcg ctatatcact cggccgccca ggcagcggcg cagagcgggc    900
agcaggcagg cggcgggcgc tcagacggct tctcctcctc ctcttgctcc tccagctcct    960
gctccttcgc cgggaggccg cccgccgagt cctgcgccag cgccgaggca gcctcgctgc   1020
gccccatccc gtcccgccgg gcactcggag ggcagcgcgc cggaggccaa ggttgccccg   1080
cacggcccgg cgggcgagcg agctcgggct gcagcagccc cgccggcggc gcgcacggca   1140
actttggaga ggcgagcagc agccccggca gcggcggcag cagcggcaat gaccccttgg   1200
ctcgggctca tcgtgctcct gggcagctgg agcctggggg actggggcgc cgaggcgtgc   1260
acatgctcgc ccagccaccc ccaggacgcc ttctgcaact ccgacatcgt gatccgggcc   1320
aaggtggtgg ggaagaagct ggtaaaggag gggcccttcg gcacgctggt ctacaccatc   1380
aagcagatga agatgtaccg aggcttcacc aagatgcccc atgtgcagta catccacacg   1440
gaagcttccg agagtctctg tggccttaag ctggaggtca acaagtacca gtacctgctg   1500
acaggtcgcg tctatgatgg caagatgtac acggggctgt gcaacttcgt ggagaggtgg   1560
gaccagctca ccctctccca gcgcaagggg ctgaactatc ggtatcacct gggttgtaac   1620
tgcaagatca agtcctgcta ctacctgcct tgctttgtga cttccaagaa cgagtgtctc   1680
tggaccgaca tgctctccaa tttcggttac cctggctacc agtccaaaca ctacgcctgc   1740
atccggcaga agggcggcta ctgcagctgg taccgaggat gggccccccc ggataaaagc   1800
atcatcaatg ccacagaccc ctgagcgcca gaccctgccc cacctcactt ccctcccttc   1860
ccgctgagct tcccttggac actaactctt cccagatgat gacaatgaaa ttagtgcctg   1920
ttttcttgca aatttagcac ttggaacatt taaagaaagg tctatgctgt catatgggt    1980
ttattgggaa ctatcctcct ggccccaccc tgcccttct ttttggtttt gacatcattc    2040

```
atttccacct gggaatttct ggtgccatgc cagaaagaat gaggaacctg tattcctctt    2100
cttcgtgata atataatctc tattttttta ggaaaacaaa aatgaaaaac tactccattt    2160
gaggattgta attcccaccc ctcttgcttc ttccccacct caccatctcc cagaccctct    2220 tcccttttgcc cttctcctcc aatacataaa ggacacagac aaggaacttg ctgaaaggcc    2280
aaccatttca ggatcagtca aaggcagcaa gcagatagac tcaaggtgtg tgaaagatgt    2340
tatacaccag gagctgccac tgcatgtccc aaccagactg tgtctgtctg tgtctgcatg    2400
taagagtgag ggagggaagg aaggaactac aagagagtcg gagatgatgc agcacacaca    2460
caattcccca gcccagtgat gcttgtgttg accagatgtt cctgagtctg gagcaagcac    2520
ccaggccaga ataacagagc tttcttagtt ggtgaagact taaacatctg cctgaggtca    2580
ggaggcaatt tgcctgcctt gtacaaaagc tcaggtgaaa gactgagatg aatgtctttc    2640
ctctccctgc ctcccaccag acttcctcct ggaaaacgct ttggtagatt tggccaggag    2700
cttctcttta tgtaaattgg ataaatacac acaccataca ctatccacag atatagccaa    2760
gtagatttgg gtagaggata ctatttccag aatagtgttt agctcaccta gggggatatg    2820
tttgtataca catttgcata tacccacatg gggacataag ctaattttt tacaggacac    2880 agaattctgt tcaatgctgt taaatatgcc aatagtttaa tctcttctat tttgttgtcg    2940
ttgcttgttt gaagaaaatc atgacattcc aagttgacat ttttttttca ttttaattaa    3000
aatttgaaat tctgaacacc gtcagcaccc tctcttccct atcatgggtc atctgacccc    3060
tgtccgtctc cttgtccctg cttcatgttt gggggccttt cttaactgc cttcctggct    3120 tagctcagat ggcagatgag agtgtagtca agggcctggg cacaggaggg agagctgcag    3180
agtgtcctgc ctgccttggc tggagggaca cctctcctgg gtgtggagac agcttggttc    3240
cctttcccta gctccctggt gggtgaatgc cacctcctga gatcctcacc tcttggaatt    3300
aaaattgttg gtcactgggg aaagcctgag tttgcaacca gttgtagggt ttctgttgtg    3360
tttttttttt tttttttgaa ataaaactat aatataaatt ctcctattaa ataaaattat    3420
tttaagtttt agtgtcaaaa gtgagatgct gagagtaggt gataatgtat attttacaga    3480
gtgggggttg gcaggatggt gacattgaac atgattgctc tctgtctctt ttttcagctt    3540
atgggtattt atcttctatt agtatttgta tcttcagttc attccacttt aggaaacaga    3600
gctgccaatt gaaacagaag aagaaaaaaa aaaaaagcag cagacaacac actgtagagt    3660
cttgcacaca cacaagtgcc caggcaaggt gcttggcaga accgcagagt gggaagagag    3720
taccggcatc gggtttcctt gggatcaatt tcattaccgt gtacctttcc cattgtggtc    3780
atgccatttg gcaggggag aatgggaggc ttggccttct ttgtgaggca gtgtgagcag    3840
aagctgatgc cagcatgtca ctggttttga agggatgagc ccagacttga tgttttggga    3900
ttgtccttat tttaacctca aggtctcgca tggtggggcc cctgaccaac ctacacaagt    3960
tccctcccac aagtggacat cagtgtcttc tctgtgaggc atctggccat cgcactccc    4020 tggtgtggtc agcctctctc acacaaggag gaacttgggt gaaggctgag tgtgaggcac    4080
ctgaagtttc cctgcggagt cgataaatta gcagaaccac atccccatct gttaggcctt    4140
ggtgaggagg ccctgggcaa agaagggtct ttcgcaaagc gatgtcagag ggcggttttg    4200
agctttctat aagctatagc tttgtttatt cacccgttc acttactgta taatttaaaa    4260
tcatttatgt agctgagaca cttctgtatt tcaatcatat catgaacatt ttatttgct    4320 aaatcttgtg tcatgtgtag gctgtaatat gtgtacattg tgtttaagag aaaaatgaaa    4380
cccacatgcc gccatttttcc tgaatcaaat tctgcagtgg aatggagagg aaaatacttc    4440
```

| | |
|---|---|
| taggcaagca gctagactgg tgaattgggg gaaatagaag gaactagtaa ctgagactcc | 4500 |
| tccagcctcc tccctattgg aatcccaatg gctcctggag taggaaaaaa gtttaaacta | 4560 |
| cattcatgtt cttgttctgt gtcactcggc cctgggtagt ctaccattta cttcacccca | 4620 |
| agtcctgctg cccatccagt tgggaagcca tgattttcct aagaatccag ggccatggga | 4680 |
| gatacaattc caagttctcg cttcctcctt tgggcatctc ttctgcctcc caatcaagga | 4740 |
| agctccatgc tcaggctctc agctctcggg ccagtgctct gctctgtcca gggtaggtaa | 4800 |
| tactgggaga ctcctgtctt ttaccctccc ctcgttccag acctgcctca tggtggcaac | 4860 |
| atggttcttg aacaattaaa gaaacaaatg acttttttgga atagccctgt ctagggcaaa | 4920 |
| ctgtggcccc caggagacac tacccttcca tgccccagac ctctgtcttg catgtgacaa | 4980 |
| ttgacaatct ggactacccc aagatggcac ccaagtgttt ggcttctggc tacctaaggt | 5040 |
| taacatgtca ctagagtatt tttatgagag acaaacatta taaaaatctg atggcaaaag | 5100 |
| caaaacaaaa tggaaagtag gggaggtgga tgtgacaaca acttccaaat tggctctttg | 5160 |
| gaggcgagag gaaggggaga acttggagaa tagttttttgc tttgggggta gaggcttctt | 5220 |
| agattctccc agcatccgcc tttcccttta gccagtctgc tgtcctgaaa cccagaagtg | 5280 |
| atggagagaa accaacaaga gatctcgaac cctgtctaga aggaatgtat ttgttgctaa | 5340 |
| atttcgtagc actgtttaca gttttcctcc atgttattta tgaattttat attccgtgaa | 5400 |
| tgtatattgt cttgtaatgt tgcataatgt tcactttttta tagtgtgtcc tttattctaa | 5460 |
| acagtaaagt ggttttattt ctatcac | 5487 |

<210> SEQ ID NO 47
<211> LENGTH: 2407
<212> TYPE: DNA
<213> ORGANISM: Homo sapiens

<400> SEQUENCE: 47

| | |
|---|---|
| ggcacgaggc ggaggggggct cagtccgcag ccgccgccgc caccgccgcg cctcggcctc | 60 |
| ggtgcaggca gcgccgccg ccgccgagac agctgcgcgg gcgagcatcc ccacgcagca | 120 |
| ccttggaagt tgttttcaac catatccagc cttttgccgaa tacatcctat ctgccacaca | 180 |
| tccagcgtga ggtccctcca gctacaaggt gggcaccatg gcggagaagt ttgactgcca | 240 |
| ctactgcagg gatcccttgc aggggaagaa gtatgtgcaa aaggatggcc accactgctg | 300 |
| cctgaaatgc tttgacaagt tctgtgccaa cacctgtgtg gaatgccgca agcccatcgg | 360 |
| tgcggactcc aaggaggtgc actataagaa ccgcttctgg catgacacct gcttccgctg | 420 |
| tgccaagtgc cttcaccect tggccaatga gacctttgtg gccaaggaca caagatcct | 480 |
| gtgcaacaag tgcaccactc gggaggactc ccccaagtgc aagggtgct tcaaggccat | 540 |
| tgtggcagga gatcaaaacg tggagtacaa ggggaccgtc tggcacaaag actgcttcac | 600 |
| ctgtagtaac tgcaagcaag tcatcgggac tggaagcttc ttccctaaag gggaggactt | 660 |
| ctactgcgtg acttgccatg agaccaagtt tgccaagcat tgcgtgaagt gcaacaaggc | 720 |
| catcacatct ggaggaatca cttaccagga tcagccctgg catgccgatt gctttgtgtg | 780 |
| tgttacctgc tctaagaagc tggctgggca gcgtttcacc gctgtggagg accagtatta | 840 |
| ctgcgtggat tgctacaaga acttttgtggc caagaagtgt gctggatgca agaacccat | 900 |
| cactgggttt ggtaaaggct ccagtgtggt ggcctatgaa ggacaatcct ggcacgacta | 960 |
| ctgcttccac tgcaaaaaat gctccgtgaa tctggccaac aagcgctttg ttttccacca | 1020 |

```
ggagcaagtg tattgtcccg actgtgccaa aaagctgtaa actgacaggg gctcctgtcc    1080
tgtaaaatgg catttgaatc tcgttctttg tgtccttact ttctgcccta taccatcaat    1140
aggggaagag tggtccttcc cttctttaaa gttctccttc cgtcttttct cccattttac    1200
agtattactc aaataagggc acacagtgat catattagca tttagcaaaa agcaaccctg    1260
cagcaaagtg aatttctgtc cggctgcaat ttaaaaatga aaacttaggt agattgactc    1320
ttctgcatgt ttctcataga gcagaaaagt gctaatcatt tagccactta gtgatgtaag    1380
caagaagcat aggagataaa accccactg agatgcctct catgcctcag ctgggaccca     1440
ccgtgtagac acacgacatg caagagttgc agcggctgct ccaactcact gctcaccctc    1500
ttctgtgagc aggaaaagaa ccctactgac atgcatggtt taacttcctc atcagaactc    1560
tgcccttcct tctgttcttt tgtgctttca ataactaac acgaacttcc agaaaattaa     1620
catttgaact tagctgtaat tctaaactga ccttttcccg tactaacgtt tggtttcccc    1680
gtgtggcatg ttttctgagc gttcctactt taaagcatgg aacatgcagg tgatttggga    1740
agtgtagaaa gacctgagaa aacgagcctg tttcagagga acatcgtcac aacgaatact    1800
tctggaagct taacaaaact aaccctgctg tcctttttat tgttttttaat taatattttt   1860 gttttaattg atagcaaaat agtttatggg tttggaaact tgcatgaaaa tattttagcc    1920
ccctcagatg ttcctgcagt gctgaaattc atcctacgga agtaaccgca aaactctaga    1980
gggggagttg agcaggcgcc agggctgtca tcaacatgga tatgacattt cacaacagtg    2040
actagttgaa tcccttgtaa cgtagtagtt gtctgctctt tgtccatgtg ttaatgagga    2100
ctgcaaagtc ccttctgttg tgattcctag gacttttcct caagaggaaa tctggatttc    2160
cacctaccgc ttacctgaaa tgcaggatca cctacttact gtattctaca ttattatatg    2220
acatagtata atgagacaat atcaaaagta aacatgtaat gacaatacat actaacattc    2280
ttgtaggagt ggttagagaa gctgatgcct catttctaca ttctgtcatt agctattatc    2340
atctaacgtt tcagtgtatc cttacagaaa taaagcagca tatgaaaaaa aaaaaaaaa    2400 aaaaaaa                                                             2407
```

<210> SEQ ID NO 48
<211> LENGTH: 2649
<212> TYPE: DNA
<213> ORGANISM: Homo sapiens

<400> SEQUENCE: 48

```
tccgaattaa ttggatttca ttcactgggg aggaacaaaa actatctggg cagcttcatt     60
gagagagatt cattgacact aagagccagc ggctgcagct gggtgcagag agaacctccg    120
gctttacttc tgtctcgtct gccccaaccg ctagcctcgg cttgggtaag gcgaggcgga    180
attaaacccc gctccgagag cggcagcttc gcgcgcggtg cgctcggcct atgcctgccc    240 cgagggggcgt ctggtaggca ccccgccctc tcccgcagct cgaccccat gatagatacg     300 ctcagacccg tgcccttcgc gtcggaaatg gcgatcagca agacggtggc gtggctcaac    360
gagcagctgg agctgggcaa cgagcggctg ctgctgatgg actgccggcc gcaggagcta    420
tacgagtcgt cgcacatcga gtcggccatc aacgtggcca tcccgggcat catgctgcgg    480
cgcctgcaga agggtaacct gccggtgcgc gcgctcttca cgcgcggcga ggaccgggac    540
cgcttcaccc ggcgctgtgg caccgacaca gtggtgctct acgacgagag cagcagcgac    600
tggaacgaga atacgggcgg cgagtcgttg ctcgggctgc tgctcaagaa gctcaaggac    660
gagggctgcc gggcgttcta cctggaaggt ggcttcagta agttccaagc cgagttctcc    720
```

-continued

```
ctgcattgcg agaccaatct agacggctcg tgtagcagca gctcgccgcc gttgccagtg    780
ctggggctcg ggggcctgcg gatcagctct gactcttcct cggacatcga gtctgacctt    840
gaccgagacc ccaatagtgc aacagactcg gatggtagtc cgctgtccaa cagccagcct    900
tccttcccag tggagatctt gcccttcctc tacttgggct gtgccaaaga ctccaccaac    960
ttggacgtgt tggaggaatt cggcatcaag tacatcttga acgtcacccc caatttgccg   1020
aatctctttg agaacgcagg agagtttaaa tacaagcaaa tccccatctc ggatcactgg   1080
agccaaaacc tgtcccagtt tttccctgag gccatttctt tcatagatga agcccggggc   1140
aagaactgtg gtgtcttggt acattgcttg gctggcatta gccgctcagt cactgtgact   1200
gtggcttacc ttatgcagaa gctcaatctg tcgatgaacg atgcctatga cattgtcaaa   1260
atgaaaaaat ccaacatatc ccctaacttc aacttcatgg gtcagctgct ggacttcgag   1320
aggacgctgg gactcagcag cccatgtgac aacagggttc cagcacagca gctgtatttt   1380
accaccccct tccaaccagaa tgtataccag gtggactctc tgcaatctac gtgaaagacc   1440
ccacatccct ccttgctgga atgtgtctgg cccttcagca gtttctcttg gcagcatcag   1500
ctgggctgct ttcttgtgt gtggccccag gtgtcaaaat gacaccagct gtctgtacta   1560
gacaaggtta ccaagtgcgg aattggttaa tactaacaga gagatttgct ccattctctt   1620
tggaataaca ggacatgctg tatagataca ggcagtaggt ttgctctgta cccatgtgta   1680
cagcctaccc atgcagggac tgggattcga ggacttccag gcgcataggg tagaaccaaa   1740
tgatagggta ggagcatgtg ttctttaggg ccttgtaagg ctgtttcctt ttgcatctgg   1800
aactgactat ataattgtct tcaatgaaga ctaattcaat tttgcatata gaggagccaa   1860
agagagattt cagctctgta tttgtggtat cagtttggaa aaaaaaatct gatactccat   1920
ttgattattg taaatatttg atcttgaatc acttgacagt gtttgtttga attgtgtttg   1980 tttttttcctt tgatgggctt aaaagaaatt atccaagggg agaaagagca gtatgccact   2040
tcttaaaaca gaacaaaaca aaaaagaaa attgtgctct tttctaatcc aaagggtata   2100
tttgcagcat gcttgacttt accaattctg atgacatctt tacggacact attatcacta   2160
agaccttgtt atggcgaagt ctttagtctt tttcatgtat tttcctcatg attttttctc   2220
tttatgtagt ttgactatgc cttacctttg taaatatttt tgcttgtgtt gtcgcaaagg   2280
ggataatctg ggaaagacac caaatcatgg gctcacttta aaaaagaaa gaataaaaaa   2340 accttcagct gtgctaaaca gtatattacc tctgtataaa attcttcagg gagtgtcacc   2400
tcaaatgcaa tactttgggt tggtttcttt cctttaaaaa aatttgtata aaactggaag   2460
tgtgtgtgtg tgagcatggg tacccatttg ataagagaaa tgcatttgat tgtgaagaag   2520
ggagagttaa attctccatt atgttcgtgg tgtaaagttt agagctggaa tttattataa   2580
gaatgtaaaa ccttaaatta ttaataaata actattttgg ctattgaaaa aaaaaaaaa   2640 aaaaaaaaa                                                          2649
```

<210> SEQ ID NO 49
<211> LENGTH: 670
<212> TYPE: DNA
<213> ORGANISM: Homo sapiens

<400> SEQUENCE: 49

```
cggccacgag gcggaatccc ttctgctctc ccagcgcagc gccgccgccc ggcccctcca     60
gcttcccgga ccatggccaa cctggagcgc accttcatcg ccatcaagcc ggacggcgtg    120
```

```
cagcgcggcc tggtgggcga gatcatcaag cgcttcgagc agaagggatt ccgcctcgtg      180
gccatgaagt tcctccgggc ctctgaagaa cacctgaagc agcactacat tgacctgaaa      240
gaccgaccat tcttccctgg gctggtgaag tacatgaact cagggccggt tgtggccatg      300
gtctgggagg ggctgaacgt ggtgaagaca ggccgagtga tgcttgggga gaccaatcca      360
gcagattcaa agccaggcac cattcgtggg gacttctgca ttcaggttgg caggaacatc      420
attcatggca gtgattcagt aaaaagtgct gaaaagaaa tcagcctatg gtttaagcct       480
gaagaactgg ttgactacaa gtcttgtgct catgactggg tctatgaata agaggtggac      540
acaacagcag tctccttcag cacggcgtgg tgtgtccctg acacagctc ttcattccat       600 tgacttagag gcaacaggat tgatcattct tttatagagc atatttgcca ataaagcttt      660
tggaagccgg                                                             670

<210> SEQ ID NO 50
<211> LENGTH: 1675
<212> TYPE: DNA
<213> ORGANISM: Homo sapiens

<400> SEQUENCE: 50
ccagccgtcc attccggtgg aggcagaggc agtcctgggg ctctggggct cgggctttgt       60
caccgggacc cgcaggagcc agaaccactc ggcgccgcct ggtgcatggg aggggagccg      120
ggccaggagt aagtaactca tacgggcgcc ggggacccgg gtcgggctgg gggcttccaa      180
ctcagaggga gtgtgatttg cctgatcctc ttcggcgttg tcctgctctg ccgcatccag      240
ccctgtaccg ccatcccact tcccgccgtt cccatctgtg ttccgggtgg gatcggtctg      300
gaggcggccg aggacttccc aggcaggagc tcggggcgga ggccgggtcc gcggcagacc      360
agggcagcga ggcgctggcc ggcaggggc gctgcggtgc cagcctgagg ctgggctgct      420
ccgcgaggat acagcggccc ctgccctgtc ctgtcctgcc ctgccctgtc ctgtcctgcc      480
ctgccctgcc ctgtcctgtc ctgccctgcc ctgccctgtg tcctcagaca atatgttagc      540
cgtgcacttt gacaagccgg gaggaccgga aaacctctac gtgaaggagg tggccaagcc      600
gagcccgggg gagggtgaag tcctcctgaa ggtggcggcc agcgccctga accgggcgga      660
cttaatgcag agacaaggcc agtatgaccc acctccagga gccagcaaca ttttgggact      720
tgaggcatct ggacatgtgg cagagctggg gcctggctgc cagggacact ggaagatcgg      780
ggacacagcc atggctctgc tccccggtgg gggccaggct cagtacgtca ctgtccccga      840
agggctcctc atgcctatcc cagagggatt gaccctgacc caggctgcag ccatcccaga      900
ggcctggctc accgccttcc agctgttaca tcttgtggga aatgttcagg ctggagacta      960
tgtgctaatc catgcaggac tgagtggtgt gggcacagct gctatccaac tcacccggat      1020
ggctggagct attcctctgg tcacagctgg ctcccagaag aagcttcaaa tggcagaaaa      1080
gcttggagca gctgctggat tcaattacaa aaagaggatt ttctctgaag caacgctgaa      1140
attcaccaaa ggtgctggag ttaatcttat tctagactgc ataggcggat cctactggga      1200
gaagaacgtc aactgcctgg ctcttgatgg tcgatgggtt ctctatggtc tgatgggagg      1260
aggtgacatc aatgggcccc tgttttcaaa gctactttt aagcgaggaa gtctgatcac      1320
cagtttgctg aggtctaggg acaataagta caagcaaatg ctggtgaatg cttttcacgga      1380 gcaaattctg cctcacttct ccacggaggg cccccaacgt ctgctgccgg ttctggacag      1440
aatctaccca gtgaccgaaa tccaggaggc ccataagtac atgaggccca acaagaacat      1500
aggcaagatc gtcctggaac tgccccagtg aaggaggatg gggcaggaca ggacgcggcc      1560
```

```
accccaggcc tttccagagc aaacctggag aagattcaca atagacaggc caagaaaccc    1620
ggtgcttcct ccagagccgt ttaaagctga tatgaggaaa taaagagtga actgg         1675

<210> SEQ ID NO 51
<211> LENGTH: 4099
<212> TYPE: DNA
<213> ORGANISM: Homo sapiens

<400> SEQUENCE: 51
cagctgccag ccgaggaggc gcggcggaga ggggactgcg gtcagctgcg tccacttggg      60
gctgtgcggc ggtcccgcgc ccggcgatgt tcccgggcac tccctgagta gcggcagctt    120 atccccccgcc cgctagcccg ccctggtccc cggctcgctc gctggctggc gcggccccgg   180
ccccgctctg cgtcggcccc gccgcggtgg aggcgcgcga gggggacgcg gccggggatg    240
agcggattgc gggtgaactc gccgcccggg ggccccgcga agccgtgagc cgctgctttt    300
ctccgagtcg ccgccctgcc cttggatttg agatcatgtc catccacatc gtggcgctgg    360
ggaacgaggg ggacacattc caccaggaca accggccgtc ggggcttatc cgcacttacc    420
tggggagaag ccctctggtc tccggggacg agagcagctt gttgctgaac gcggccagca    480
cggtcgcgcg tccggtgttc accgagtatc aggccagtgc gtttgggaat gtcaagctgg    540
tggtccacga ctgtcccgtc tgggacatat ttgacagtga ttggtacact tctcgaaatc    600
taattggggg cgctgacatc attgtgatca aatacaacgt taatgacaag tttttcattcc   660 atgaagtaaa ggataattat attccagtga taaaaagagc attaaattca gttccagtaa    720
ttattgctgc tgttggtacc agacaaaatg aagagttacc ttgtacatgc ccactatgta    780
cctcagacag agggagctgt gttagtacaa ctgaagggat ccaacttgca aaagaactag    840
gagcaaccta tcttgaactc cacagccttg atgacttcta cataggaaag tattttggag    900
gagtgttgga gtattttatg attcaagcct taaatcagaa gacaagtgaa aaaatgaaga    960
aaagaaaaat gagcaactcc tttcatggaa ttagaccacc tcaacttgaa caaccagaaa   1020
aaatgcctgt cttaaaggct gaagcgtcac attataactc tgacttaaat aacttgctgt   1080
tctgctgcca gtgtgtggac gtggtatttt ataaccccga tttaaagaaa gttgtagagg   1140
cccacaagat cgttctctgc gctgtaagcc atgttttcat gctgcttttc aatgtgaaga   1200
gtcccactga cattcaggat tccagtatca tccgaactac ccaggatctt tttgctataa   1260
acagagatac tgcatttcca ggtgctagcc atgaatcttc aggcaaccca ccattacgag   1320
tcattgttaa agacgccctc ttctgttctt gtttatcaga catccttcgc ttcatttatt   1380
caggtgcttt tcagtgggaa gaattggaag aagatatcag gaagaagttg aaagattctg   1440
gggatgtttc aaatgtaatc gagaaagtta aatgcatttt aaaaacacca ggaaagatta   1500
attgcctaag gaattgcaaa acctatcaag ccagaaaacc tttgtggttt tataacactt   1560
ccctcaagtt tttccttaat aagccgatgc ttgccgatgt tgtcttcgaa attcaaggta   1620
cgacagtgcc agcccacagg gccatcctgg tgcccgttg tgaagtgatg gcagccatgt    1680
ttaatggtaa ttacatggaa gcaaagagtg tcctgattcc cgtttatggt gtttccaaag   1740
agactttctt gtcattttta gaatacctgt acacagactc ctgctgccca gctggcatat   1800
tccaggccat gtgtctcctg atctgtgccg agatgtacca agtgtccaga ctgcagcaca   1860
tctgtgagct gttcatcatt acccagctgc agagcatgcc aagcagggaa ctggcatcca   1920
tgaaccttga tatagttgac ctgcttaaaa aggccaagtt tcaccactct gattgccttt   1980
```

```
caacctggct acttcatttc attgctacta actacctcat cttcagtcaa aagcctgaat    2040
ttcaggatct ttcagtggaa gaacgcagtt ttgttgaaaa gcacagatgg ccgtcgaata    2100
tgtacttgaa gcagcttgcg aatacagga agtatattca ctcccggaaa tgtcgttgct    2160
tagtaatgta acctggagct tttatacact acatttcttt tttattatta tgaagaatgg    2220
gatacctcca ggttccagta aaattcttct gaccgaaacc aatgtgggtg ttagaaaaat    2280
taccatatag cttaatatgt ttattagttc tctttggaaa aaaactacca ctgtggtctt    2340
aaaagggaac aaaatatacc ataggctaaa actaaggctt tcactctaga atgcaaagct    2400
gttttgcagc tgttttccct aaagatgtc ctgttgcttt agtgatattt agacccctct    2460
cagttaagaa atgcttagat taaaaaaaaa aaattacgta ggattaatac agaaatttaa    2520
tcatgtctga ttaattgctc tattaaaata aggggcattt aaagacccag cataaccatt    2580
tgtataatga gaaatctagg ggaaaaccaa tcagtccaac atgagatttt aggaatagaa    2640
atttgccggc catttggaaa gtgaaatgcc acttagttct caattgatga cagtgtttga    2700
atcatcataa aaaaaatacc tgcttttcat ctggacaacc caattgagcc actttatctc    2760
cttttggcaa tctgagtagg cggggaacct aggcagggct ggctttctta gcgtgtaact    2820
tgtgtagcag cacagggccc acacttagaa ggaccccaca cttggttcaa ggctctgcta    2880
tagcggaaat tcttaataat gtttgaagaa gggcccatg atttcatttt gtgctgagcc     2940
ctcaaaatta tgtctgtttc gtggtgggaa atatcctatg ttttcttgct caaacacctt    3000
tctctctgaa agcagaaaaa ggcactgata taaagggaag agaaggaggc tcaccggagg    3060
gaagagaaca tagtgaagat tcccgccttt ggggaggtct ggaccaccca gggcctccac    3120
tgccaccttg gctggcaagg gagaaatgtg ttgtgttgtc ttagctttaa aacagtcaca    3180
gttcttgctc tatcatagat gaacaaatac tttcttgatc attctgtaag accaggaggt    3240
tggtaagagt gactaaccag cctaacttta atacacatgt ataaagatgt tcacagagaa    3300
agatgctctg tagagaattt gctaccgaag ttggctcaag aatttgtttt tagtgttatt    3360
taccaagatt aggacgtcag tggcttaaat tctttgaatt cttttcaagg actgcaagat    3420
tatttgataa agagtagcat gaatcttgtg ctctaatatt acacagtaag ttcaaagaaa    3480
ggatgtaagt caaagacttg ttacatagag ggaaaatgga ctgggataga ggacagactg    3540
atagtttctt tctttcatat cacatgtata gagaaataat tatatcagaa actcacaaac    3600
ctagacatgg aaaaacagat tactgtctat tgtcagcatc attttcatct gtaagtcact    3660
actggaatat attttctttt taatttccag tgactttaga atacacacag tttttccgac    3720
ttttcaaaaa tttgattaaa tggttttata gtataatatt gggaccccat accgttagcc    3780
cttgtatgta taccaacact gccaaagtaa aacattaggt caggcatggt ggctcaggcc    3840
tgtaatccca gcattttggg aggctgaggc aagtggataa cttgaggtca tgagttcgaa    3900
accagcctgg ccaaaacagt gaaacccccgt ctctactaaa aatacaaaat tagccagatg    3960
tggtggcgca cacctgtaat cccagctact caggaagctg aggcaggaaa atcgcttgaa    4020
cctgggaggt ggaagttgca gtgagccgag atcgcaccac tgcactccag cctgggtgac    4080
aagagcgaaa ctccatctc                                                  4099
```

<210> SEQ ID NO 52
<211> LENGTH: 2508
<212> TYPE: DNA
<213> ORGANISM: Homo sapiens

<400> SEQUENCE: 52

```
cgcgcccctc cctcctcgcg gacctggcgg tgccggcgcc cggagtggcc ctttaaaagg    60
cagcttattg tccggagggg gcgggcgggg ggcgccgacc gcggcctgag gcccggcccc   120
tccccctctcc ctccctctgt ccccgcgtcg ctcgctggct agctcgctgg ctcgctcgcc   180
cgtccggcgc acgctccgcc tccgtcagtt ggctccgctg tcgggtgcgc ggcgtggagc   240
ggcagccggt ctggacgcgc ggccggggct ggggctggg agcgcggcgc gcaagatctc    300
cccgcgcgag agcggcccct gccaccgggc gaggcctgcg ccgcgatggc agagatgggc   360
agtaaagggg tgacggcggg aaagatcgcc agcaacgtgc agaagaagct cacccgcgcg   420
caggagaagg ttctccagaa gctggggaag gcagatgaga ccaaggatga gcagtttgag   480
cagtgcgtcc agaatttcaa caagcagctg acggagggca cccggctgca gaaggatctc   540
cggacctacc tggcctccgt caaagccatg cacgaggctt ccaagaagct gaatgagtgt   600
ctgcaggagg tgtatgagcc cgattggccc ggcaggatg aggcaaacaa gatcgcagag    660
aacaacgacc tgctgtggat ggattaccac cagaagctgg tggaccaggc gctgctgacc   720
atggacacgt acctgggcca gttccccgac atcaagtcac gcattgccaa gcggggcgc    780
aagctggtgg actacgacag tgcccggcac cactacgagt cccttcaaac tgccaaaaag   840
aaggatgaag ccaaaattgc caagcctgtc tcgctgcttg agaaagccgc ccccagtgg    900
tgccaaggca aactgcaggc tcatctcgta gctcaaacta acctgctccg aaatcaggcc   960
gaggaggagc tcatcaaagc ccagaaggtg tttgaggaga tgaatgtgga tctgcaggag  1020
gagctgccgt ccctgtggaa cagccgcgta ggtttctacg tcaacacgtt ccagagcatc  1080
gcgggcctgg aggaaaactt ccacaaggag atgagcaagc tcaaccagaa cctcaatgat  1140
gtgctggtcg gcctggagaa gcaacacggg agcaacacct tcacggtcaa ggcccagccc  1200
agtgacaacg cgcctgcaaa agggaacaag agcccttcgc ctccagatgg ctcccctgcc  1260
gccacccccg agatcagagt caaccacgag ccagagccgg ccggcggggc cacgcccggg  1320
gccaccctcc ccaagtcccc atctcagttt gaggccccgg ggccttctctc ggagcaggcc  1380
agtctgctgg acctggactt tgaccccctc ccgcccgtga cgagccctgt gaaggcaccc  1440
acgccctctg gtcagtcaat tccatgggac ctctgggagc ccacagagag tccagccggc  1500
agcctgcctt ccggggagcc cagcgctgcc gagggcacct ttgctgtgtc ctggcccagc  1560
cagacggccg agccggggcc tgcccaacca gcagaggcct cggaggtggc gggtgggacc  1620
caacctgcgg ctggagccca ggagccaggg agacggcgg caagtgaagc agcctccagc  1680
tctcttcctg ctgtcgtggt ggagaccttc ccagcaactg tgaatggcac cgtggagggc  1740
ggcagtgggg ccggcgcctt ggacctgccc ccaggtttca tgttcaaggt acaggcccag  1800
cacgactaca cggccactga cacagacgag ctgcagctca aggctggtga tgtggtgctg  1860
gtgatcccct tccagaaccc tgaagagcag gatgaaggct ggctcatggg cgtgaaggag  1920
agcgactgga accagcacaa ggagctggag aagtgccgtg gcgtcttccc cgagaacttc  1980
actgagaggg tccatgacg gcggggccca ggcagcctcc gggcgtgtga agaacacctc  2040
ctcccgaaaa atgtgtggtt cttttttttg ttttgttttc gttttcatc tttttgaagag  2100
caaagggaaa tcaagaggag accccaggc agaggggcgt tctcccaaag attaggtcgt  2160
tttccaaaga gccgcgtccc ggcaagtccg gcggaattca ccagtgttcc tgaagctgct  2220
gtgtcctcta gttgagtttc tggcgcccct gcctgtgccc gcatgtgtgc ctggccgcag  2280
ggcggggctg ggggctgccg agccaccatg cttgcctgaa gcttcggccg cgccacccgg  2340
```

| | |
|---|---|
| gcaagggtcc tctttcctg gcagctgctg tgggtgggc ccagacacca gcctagcctg | 2400 |
| gctctgcccc gcagacggtc tgtgtgctgt ttgaaaataa atcttagtgt tcaaaacaaa | 2460 |
| atgaaacaaa aaaaaaatga taaaaactct caaaaaaaaa aaaaaaa | 2508 |

<210> SEQ ID NO 53
<211> LENGTH: 2278
<212> TYPE: DNA
<213> ORGANISM: Homo sapiens

<400> SEQUENCE: 53

| | |
|---|---|
| ggggagtgct ccattttccc cgacagcgaa tttcccctga gaaacgatac tagaccctgg | 60 |
| gtttgcccac cttgtaactc ttccttatct cctccttttc atccctaatt catcctccct | 120 |
| ctggcatgga attgacgccc gtgcagtaca tttgccaagt ggcaccttct ttcaatttat | 180 |
| gttttatttt gctatggtgg tgattcttta tttgctggtt gtcttttctc acacatcttt | 240 |
| ctctctgtct ctctctttcc tgctctttgt ttttctgccc agaaaaacct gacttcgata | 300 |
| ccaaaaaaga tgaaactaca gaaactcaaa tttaaaaaaa actttaaaag aaacaaaaaa | 360 |
| atactcaacg attctttcag ctttattaac attttccatt gtttcttgcg acttgtgtct | 420 |
| cgttctttgt agtattgatg atgaacattt gataatgaat gttcttgtat attcagataa | 480 |
| agaaaaaaaa aaccaaaaaa gcggtctgaa tttaatagtg tttataataa aaattttaaa | 540 |
| aatgaccctc atagcacgca aaacaggatg gggaatttcc cctcttcttt ctgtgacaat | 600 |
| gcgcatcatt cctgcattag tttttaacac cagactacct acattcatca tttccctcat | 660 |
| ttttctttta ttttcttgca tttgtgaatt agttcaagaa tgctagaaaa gtgtcgagtt | 720 |
| gtgcacatcc atttcttgtt tcacaatgtt taaaagtgac agtaattcat tttgtaaact | 780 |
| aaaaaaaaaa aaaaaaaggt tggaatagtg agcataatag gtacaaccta acacattatt | 840 |
| atgttttatta actttgagac ccagaaataa attcttttct tttcttgatt cttgctctta | 900 |
| aaaatacaaa aaaaaaaatg ttttgttttg tgttattttt ggtttgttta ttgggggct | 960 |
| ttttttaatt gtcaggatta tgatcttgct gttttcttc aatatgtata caaggtgatg | 1020 |
| tgaaagatg acttgggcag aggagtaaga acaagtaggc ttgttcttct actttgcttc | 1080 |
| agaattcagt taatgccaaa agcgaagatc aagcccatgt tgatgtctcg ttgctcacct | 1140 |
| gcatttccag agagtgtgac actcatgcag tccctgagaa aaataaaatc agggacatac | 1200 |
| ttctcctttt agccttttaa aaattcaaaa acgttagtc caagggaact ttttatgcta | 1260 |
| tcaggaaagg ttttgctgt ttttgattct gattatcaca gccaagtact tgtttatt | 1320 |
| tctccctaat taataactac attccatgag gcctcttcca accaagagg cctttcttc | 1380 |
| caggagagtc ccgcaggaga tgctggtatg atgggcacca ttggttaagt aaactacatg | 1440 |
| caggaagaag tccttgggc cagtctgcca gctgagtcct ggttttggat gaagagttaa | 1500 |
| tgagatattg ggccaggctc aatgctgtag ttttaatgct aagaggttac gtttacttca | 1560 |
| cagagtacac ctcttagtaa cctctgactt aggcagctgc ttaaagcaaa ttgcaaaact | 1620 |
| ggcttgattt ggaatgtttt tattagagga aaaagaaag ccatattatc tggaaaaaaa | 1680 |
| ttcattttaa ataccatcat tcaacaaatt atgttcagaa agtggtcaga acttaagcaa | 1740 |
| gaaaagtaaa gaaagaatgc agaattgtgg agcaatgctt taggaaatat ttctacctga | 1800 |
| acacttgtac tcttgaagtc acaacaaaat aatgatgagc ttttcacatc acctttatgg | 1860 |
| tttcaatccc tagctcaaag cttcctggaa tcttttattt tttgtaaact ttttttcctt | 1920 |
| ttgttaaaat aaataaaaca ttcaatgttt ttctccttt ctctcttatt acttcttcc | 1980 |

```
tttggcattt tcaatttgaa atgctttcct ttggttgttg gttttattct cccctaccc      2040 ctccccttt  cttattattc agaatataaa cctgcaaagc tctgctctgt tttggttttg     2100
aaagtttaag cttttctgct tctgtgagag cacaggcttc tgtccctttt gattccaact     2160
gaacttttgt gttctctaat gatactaaca cggtgtaggt tttacagtct cctaatttgt     2220
actggtaatg catattccaa ataaatagtt tcttttgttg caaaaaaaaa aaaaaaa        2278

<210> SEQ ID NO 54
<211> LENGTH: 4322
<212> TYPE: DNA
<213> ORGANISM: Homo sapiens

<400> SEQUENCE: 54
cccccagagg cgccggagcc cggaatcccg ctcggagcca gccagccgtc ccgagctacc       60
agcaggtttc attgaaaaca gatcctgcaa aagttccagg tgcccacact ggaaacttgg      120
agatcctgct tcccagacca cagctgtggg gaacttgggg tggagcagag aagtttctgt      180
attcagctgc ccaggcagag gagaatgggg tctccacagc ctgaagaatg aagacacgac      240
agaataaaga ctcgatgtca atgaggagtg gacggaagaa agaggcccct gggccccggg      300
aagaactgag atcgagggc  cgggcctccc ctggaggggt cagcacgtcc agcagtgatg      360
gcaaagctga gaagtccagg cagacagcca agaaggcccg agtagaggaa gcctccaccc      420
caaaggtcaa caagcagggt cggagtgagg agatctcaga gagtgaaagt gaggagacca      480
atgcaccaaa aaagaccaaa actgaggaac tccctcggcc acagtctccc tccgatctgg      540
atagcttgga cgggcggagc cttaatgatg atggcagcag cgaccctagg gatatcgacc      600
aggacaaccg aagcacgtcc cccagtatct acagccctgg aagtgtggag aatgactctg      660
actcatcttc tggcctgtcc cagggcccag cccgccccta ccacccacct ccactctttc      720
ctccttcccc tcaaccgcca gacagcaccc ctcgacagcc agaggctagc tttgaacccc      780
atccttctgt gacacccact ggatatcatg ctcccatgga gccccccaca tctcgaatgt      840
tccaggctcc tcctgggggcc cctcccctc acccacagct ctatcccggg ggcactggtg      900
gagttttgtc tggacccca atgggtccca aggggggagg ggctgcctca tcagtggggg      960
gccctaatgg gggtaagcag cacccccac ccactactcc catttcagta tcaagctctg     1020
gggctagtgg tgctcccca acaaagccgc ctaccactcc agtgggtggt gggaacctac     1080
cttctgctcc accaccagcc aacttccccc atgtgacacc gaacctgcct ccccacctg     1140 ccctgagacc cctcaacaat gcatcagcct ctccccctgg cctggggcc caaccactac     1200 ctggtcatct gccctctccc cacgccatgg gacagggtat cggtggactt cctcctggcc     1260
cagagaaggg cccaactctg gctccttcac cccactctct gcctcctgct tcctcttctg     1320
ctccagcgcc cccatgagg tttccttatt catcctctag tagtagctct gcagcagcct     1380
cctcttccag ttcttcctcc tcttcctctg cctcccctt cccagcttcc caggcattgc     1440
ccagctaccc ccactctttc cctccccaa caagcctctc tgtctccaat cagcccccca     1500
agtatactca gccttctctc ccatcccagg ctgtgtggag ccagggtccc ccaccacctc     1560
ctccctatgg ccgcctctta gccaacagca atgcccatcc aggcccttc ctccctcta      1620 ctggggccca gtccaccgcc cacccaccag tctcaacaca tcaccatcac caccagcaac     1680
agcaacagca gcagcagcag cagcagcagc agcagcatca cggaaactct gggccccctc     1740
ctcctggagc atttccccac ccactggagg cggtagctc  ccaccacgca cacccttacg     1800
```

```
ccatgtctcc ctccctgggg tctctgaggc cctacccacc agggccagca cacctgcccc    1860
cacctcacag ccaggtgtcc tacagccaag caggccccaa tgggcctcca gtctcttcct    1920
cttccaactc ttcctcttcc acttctcaag ggtcctaccc atgttcacac ccctcccctt    1980
cccagggccc tcaaggggcg ccctacccdt tcccaccggt gcctacggtc accacctctt    2040
cggctaccct ttccacgtc attgccaccg tggcttcctc gccagcaggc tacaaaacgg    2100
cctccccacc tgggccccca ccgtacggaa agagagcccc gtccccgggg gcctacaaga    2160
cagccacccc acccggatac aaacccgggt cgcctccctc cttccgaacg gggaccccac    2220
cgggctatcg aggaacctcg ccacctgcag gcccagggac cttcaagccg ggctcgccca    2280
ccgtgggacc tgggcccctg ccacctgcgg ggccctcagg cctgccatcg ctgccaccac    2340
cacctgcggc ccctgcctca gggccgcccc tgagcgccac gcagatcaaa caggagccgg    2400
ctgaggagta tgagaccccc gagagcccgg tgccccagcc ccgcagcccc tcgccccctc    2460
ccaaggtggt agatgtaccc agccatgcca gtcagtctgc caggttcaac aaacacctgg    2520
atcgcggctt caactcgtgc gcgcgcagcg acctgtactt cgtgccactg gagggctcca    2580
agctggccaa gaagcgggcc gacctggtgg agaaggtgcg gcgcgaggcc gagcagcgcg    2640
cgcgcgaaga aaaggagcgc gagcgcgagc gggaacgcga gaaagagcgc gagcgcgaga    2700
aggagcgcga gcttgaacgc agcgtgaagt tggctcagga gggccgtgct ccggtggaat    2760
gcccatctct gggcccagtg ccccatcgcc ctccatttga accgggcagt gcggtggcta    2820
cagtgccccc ctacctgggt cctgacactc cagccttgcg cactctcagt gaatatgccc    2880
ggcctcatgt catgtctcct ggcaatcgca accatccatt ctacgtgccc ctgggggcag    2940
tggacccggg gctcctgggt tacaatgtcc cggccctgta cagcagtgat ccagctgccc    3000
gggagaggga acgggaagcc cgtgaacgag acctccgtga ccgcctcaag cctggctttg    3060
aggtgaagcc tagtgagctg gaaccccctac atggggtccc tgggccgggc ttggatccct    3120
ttccccgaca tgggggcctg gctctgcagc ctggcccacc tggcctgcac cctttcccct    3180
ttcatccgag cctggggccc ctggagcgag aacgtctagc gctggcagct gggccagccc    3240
tgcggcctga catgtcctat gctgagcggc tggcagctga gaggcagcac gcagaaaggg    3300
tggcggccct gggcaatgac ccactggccc ggctgcagat gctcaatgtg actccccatc    3360
accaccagca ctcccacatc cactcgcacc tgcacctgca ccagcaagat gctatccatg    3420
cagcctctgc ctcggtgcac cctctcattg acccctggc ctcagggtct caccttaccc    3480 ggatcccta cccagctgga actctccca accccctgct tcctcaccct ctgcacgaga    3540
acgaagttct tcgtcaccag ctcttgctg cccttaccg ggacctgccg gcctcccttt    3600 ctgcccgat gtcagcagct catcagctgc aggccatgca cgcacagtca gctgagctgc    3660
agcgcttggc gctggaacag cagcagtggc tgcatgccca tcaccgctg cacagtgtgc    3720 cgctgcctgc ccaggaggac tactacgtc acctgaagaa ggaaagcgac aagccactgt    3780
agaacctgcg atcaagagag caccatggct cctacattgg accttggagc accccccacc    3840
tccccccacc gtgcccttgg cctgccaccc agagccaaga gggtgctgct cagttgcagg    3900
gcctccgcag ctggacagag agtggggag ggagggacag acagaaggcc aaggcccgat    3960
gtggtgtgca gaggtgggga ggtggcgagg atggggacag aaagcgcaca gaatcttgga    4020
ccaggtctct cttccttgtc ccccctgctt ttctcctccc ccatgcccaa ccccctgtggc    4080 cgccgcccct cccctgcccc gttggtgtga ttatttcatc tgttagatgt ggctgttttg    4140
cgtagcatcg tgtgccaccc ctgcccctcc ccgatccctg tgtgcgcgcc ccctctgcaa    4200
```

| | |
|---|---|
| tgtatgcccc ttgccccttc cccacactaa taatttatat atataaatat ctatatgacg | 4260 |
| ctcttaaaaa aacatcccaa ccaaaaccaa ccaaacaaaa acatcctcac aactccccag | 4320 |
| ga | 4322 |

```
<210> SEQ ID NO 55
<211> LENGTH: 808
<212> TYPE: DNA
<213> ORGANISM: Homo sapiens

<400> SEQUENCE: 55
```

| | |
|---|---|
| tgctcccttg ggctctagag aggaggcccc tcttagccct cagcccctcc ttcctctcta | 60 |
| tcttaaagta atttgatcct caggaatttg ttccgccctc atctggcccg gccaaatccc | 120 |
| gatttgacaa atgccaggaa aaggaaactg ttgagaaacc gaaactactg gggaaaggga | 180 |
| gggctcactg agtaaccatc ccagtaaccc gaccgccgct ggtcttcgct ggacaccatg | 240 |
| agtcacactg tccaaacctt cttctctcct gtcaacagtg gccagccccc caactatgag | 300 |
| atgctcaagg aggagcacga ggtggctgtg ctggggggc cccacaaccc tgctcccccg | 360 |
| acgtccaccg tgatccacat ccgcagcgag acctccgtgc ccgaccatgt cgtctggtcc | 420 |
| ctgttcaaca ccctcttcat gaaccccctgc tgcctgggct tcatagcatt cgcctactcc | 480 |
| gtgaagtcta gggacaggaa gatggttggc gacgtgaccg ggcccaggc ctatgcctcc | 540 |
| accgccaagt gcctgaacat ctgggccctg attctgggca tcctcatgac cattctgctc | 600 |
| atcgtcatcc cagtgctgat cttccaggcc tatggataga tcaggaggca tcactgaggc | 660 |
| caggagctct gcccatgacc tgtatcccac gtactccaac ttccattcct cgccctgccc | 720 |
| ccggagccga gtcctgtatc agccctttat cctcacacgc ttttctacaa tggcattcaa | 780 |
| taaagtgcac gtgtttctgg tgctgctg | 808 |

```
<210> SEQ ID NO 56
<211> LENGTH: 3454
<212> TYPE: DNA
<213> ORGANISM: Homo sapiens

<400> SEQUENCE: 56
```

| | |
|---|---|
| ggaaatgact gctgtccatg caggcaacat aaacttcaag tgggatccta aaagtctaga | 60 |
| gatcaggact ctggcagttg agagactgtt ggagcctctt gttacacagg ttacaaccct | 120 |
| tgtaaacacc aatagtaaag ggccctctaa taagaagaga ggtcgttcta agaaggccca | 180 |
| tgttttggct gcatctgttg aacaagcaac tgagaatttc ttggagaagg gggataaaat | 240 |
| tgcaaaagag agccagtttc tcaaggagga gcttgtggtt gctgtagaag atgttcgaaa | 300 |
| acaaggtgat tgatgaagg ctgctgctgg agagttcgca gatgatccct gctcttctgt | 360 |
| gaagcgaggc aacatggttc gggcagctcg agctttgctc tctgctgtta cccggttgct | 420 |
| cattttggct gacatggcag atgtctacaa attacttgtt cagctgaaag ttgtggaaga | 480 |
| tggtatattg aaactgagga atgctggcaa tgaacaagac ttagggaatc agtataaagc | 540 |
| cctaaaacct gaagtggata agctgaacat tatggcagca aaaagacaac aggaattgaa | 600 |
| agatgttggg catcgtgatc agatggctgc ggctagagga atcctgcaga gcaacgttcc | 660 |
| gatcctctat actgcatccc aggcatggcc acagcaccct gatgtcgcag cctataaggc | 720 |
| caacagggac ctgatataca agcagctgca gcaggcggtc acagggattt ccaatgcagc | 780 |
| ccaggccact gcctcagacg atgcctcaca gcaccagggt ggaggaggag gagaactggc | 840 |

```
atatgcactc aataactttg acaaacaaat cattgtggac cccttgagct tcagcgagga    900
gcgctttagg ccttccctgg aggagcgtct ggaaagcatc attagtgggg ctgccttgat    960
ggccgactcg tcctgcacgc gtgatgaccg tcgtgagcga attgtggcag agtgtaatgc   1020
tgtccgccag gcctgcagga cctgcgtttc ggagtacatg ggcaatgctg gacgtaaaga   1080
aagaagtgat gcactcaatt ctgcaataga taaaatgacc aagaagacca gggacttgcg   1140
tagacagctt cgcaaagctg tcatggacca cgtttcagat tctttcctgg aaaccaatgt   1200
tccacttttg gtattgattg aagctgcaaa gaatggaaat gagaagaag ttaaggaata    1260
tgcccaagtt ttccgtgaac atgccaacaa attgattgag gttgccaact tggcctgttc   1320
catctcaaat aatgaagaag gtgtaaagct tgttcgaatg tctgcaagcc agttagaagc   1380
cggttgtcct caggttatta atgctgcaac ctgggcttta gcaccaaaac cacagagtaa   1440
actggcccaa gagaacatgg atcttttaa agaacaatgg gaaaaacaag tccgtgttct    1500
cacagatgct gtcgatgaca ttacttccat tgatgacttc ttggctgtct cagagaatca   1560
cattttggaa gatgtgaaca atgtgtcat tgctctccaa gagaaggatg tggatggcct    1620
ggaccgcaca gctggtgcaa ttcgaggccg ggcagcccgg gtcattcacg tagtcacctc   1680
agagatggac aactatgagc aggagtcta cacagagaag gttctggaag ccactaagct    1740
gctctccaac acagtcatgc cacgttttac tgagcaagta gaagcagccg tggaagccct   1800
cagctcggac cctgcccagc ccatggatga gaatgagttt atcgatgctt cccgcctggt   1860
atatgatggc atccgggaca tcaggaaagc agtgctgatg ataaggaccc ctgaggagtt   1920
ggatgactct gactttgaga cagaggattt tgatgtcaga agcgagacga gcgtccagac   1980
agaagacgat cagctgatag ctggccagag tgcccgggcg atcatggctc agcttcccca   2040
ggagcaaaaa gcgaagattc gggaacaggt ggccagcttc caggaagaaa agagcaagct   2100
ggatgctgaa gtgtccaaat gggacgacag tggcaatgac atcattgtgc tggccaagca   2160
gatgtgcatg attatgatgg agatgacaga ctttacccga ggtaaaggac cactcaaaaa   2220
tacatcggat gtcatcagtg ctgccaagaa aattgctgag gcaggatcca ggatggacaa   2280
gcttggccgg accattcgag accattgccc cgactcggct tgcaagcagg acctgctggc   2340
ctacctgcaa cgcatcgccc tctactgcca ccagctgaac atctgcagca aggtcaaggc   2400
cgaggtgcag aatctcggcg gggagcttgt tgtctctggg gtggacagcg ccatgtccct   2460
gatccaggca gccaagaact tgatgaatgc tgtggtgcag acagtgaagg catcctacgt   2520
cgcctctacc aaataccaaa agtcacaggg tatggcttcc ctcaaccttc ctgctgtgtc   2580
aatgaagatg aaggcaccag agaaaaagcc attggtgaag agagaaaac aggatgagac   2640
acagaccaag attaaacggg catctcagaa gaagcacgtg aacccagtgc aggccctcag   2700
cgagttcaaa gctatggaca gcatctaagt ctgcccaggc cggccgcccc caccctctg   2760
gctcctgaat atcagtcact gttcgtcact caaatgaatt tgctaaatac aacactgata   2820
ctagattcca cagggaaatg ggcagactga accagtccag gtggtgaatt ttccaagaac   2880
atagtttaag ttgattaaaa atgcttttag aatgcaggag cctacttcta gctgtattt    2940
ttgtatgctt aaataaaata aaattcataa ccaagagatc cacattagct tgttagtaat   3000
gctctgacca agccgagatg ccattctctt agtgatggcg gcgttaggtt tgagagaagg   3060
aattggctca acttcagttg agagggtgca gtccagacag cttgactgct tttaaatgac   3120
caaagatgac ctgtggtaag caacctggca tcttaggaag cagtccttga aaggcatgt    3180
tccagaaagg tctctgagga caaactcact cagtaaaaca taatgtatca tgaagaaaac   3240
```

```
tgattctcta tgacatgaaa tgaaaatttt aatgcattgt tataattact aatgtacgct    3300
gctgcaggac attaataaag ttgcttttt aggctacagt gtctcgatgc cataatcaga    3360
acacactttt tttcctcttt ctcccagctt caaatgcaca attcatcatt gggctcactt    3420
ctaataactg cagtgtttcc gccttgcgtt gcag                                3454

<210> SEQ ID NO 57
<211> LENGTH: 5128
<212> TYPE: DNA
<213> ORGANISM: Homo sapiens

<400> SEQUENCE: 57
ccgagtgcct cgcagcccct cccgaggcgc agccgccaga ccagtggagc cggggcgcag      60
ggcgggggcg gaggcgccgg ggcggggggat gcgggggccgc ggcgcagccc cccggccctg    120
agagcgagga cagcgccgcc cggcccgcag ccgtcgccgc ttctccacct cggcccgtgg     180
agccggggcg tccgggcgta gccctcgctc gctgggtca ggggtgcgc gtcggggag      240 gcagaagcca tggatcccgg gcagcagccg ccgcctcaac cggccccca gggccaaggg      300 cagccgcctt cgcagccccc gcaggggcag ggcccgccgt ccggacccgg gcaaccggca    360
cccgcggcga cccaggcggc gccgcaggca ccccccgccg ggcatcagat cgtgcacgtc    420
cgcggggact cggagaccga cctggaggcg ctcttcaacg ccgtcatgaa ccccaagacg    480
gccaacgtgc cccagaccgt gcccatgagg ctccggaagc tgcccgactc cttcttcaag    540
ccgccggagc ccaaatccca ctcccgacag gccagtactg atgcaggcac tgcaggagcc    600
ctgactccac agcatgttcg agctcattcc tctccagctt ctctgcagtt gggagctgtt    660
tctcctggga cactgacccc cactggagta gtctctggcc cagcagctac acccacagct    720
cagcatcttc gacagtcttc ttttgagata cctgatgatg tacctctgcc agcaggttgg    780
gagatggcaa agacatcttc tggtcagaga tacttcttaa atcacatcga tcagacaaca    840
acatggcagg accccaggaa ggccatgctg tcccagatga acgtcacagc ccccaccagt    900
ccaccagtgc agcagaatat gatgaactcg gcttcagcca tgaaccagag aatcagtcag    960
agtgctccag tgaaacagcc accacccctg gctccccaga gcccacaggg aggcgtcatg   1020
ggtggcagca actccaacca gcagcaacag atgcgactgc agcaactgca gatggagaag   1080
gagaggctgc ggctgaaaca gcaagaactg cttcggcagg tgaggccaca ggagttagcc   1140
ctgcgtagcc agttaccaac actggagcag gatggtggga ctcaaaatcc agtgtcttct   1200
cccgggatgt ctcaggaatt gagaacaatg acgaccaata gctcagatcc tttccttaac   1260
agtggcacct atcactctcg agatgagagt acagacagtg gactaagcat gagcagctac   1320
agtgtccctc gaacccccaga tgacttcctg aacagtgtgg atgagatgga tacaggtgat   1380
actatcaacc aaagcaccct gccctcacag cagaaccgtt cccagacta ccttgaagcc   1440 attcctggga caaatgtgga ccttggaaca ctggaaggag atggaatgaa catagaagga   1500
gaggagctga tgccaagtct gcaggaagct ttgagttctg acatccttaa tgacatggag   1560
tctgttttgg ctgccaccaa gctagataaa gaaagctttc ttacatggtt atagagccct   1620
caggcagact gaattctaaa tctgtgaagg atctaaggag acacatgcac cggaaatttc   1680
cataagccag ttgcagtttt caggctaata cagaaaaaga tgaacaaacg tccagcaaga   1740
tactttaatc ctctatttg ctcttccttg tccattgctg ctgttaatgt attgctgacc   1800
tctttcacag ttggctctaa agaatcaaaa gaaaaaaact tttatttct tttgctatta   1860
```

```
aaactactgt tcattttggg ggctgggggga agtgagcctg tttggatgat ggatgccatt    1920
ccttttgccc agttaaatgt tcaccaatca ttttaactaa atactcagac ttagaagtca    1980
gatgcttcat gtcacagcat ttagtttgtt caacagttgt ttcttcagct tcctttgtcc    2040
agtggaaaaa catgatttac tggtctgaca agccaaaaat gttatatctg atattaaata    2100
cttaatgctg atttgaagag atagctgaaa ccaaggctga agactgtttt actttcagta    2160
ttttcttttc ctcctagtgc tatcattagt cacataatga ccttgatttt attttaggag    2220
cttataaggc atgagacaat ttccatataa atatattaat tattgccaca tactctaata    2280
tagattttgg tggataattt tgtgggtgtg cattttgttc tgttttgttg ggttttttgt    2340 ttttttttgtt tttggcaggg tcggtggggg ggttggttgg ttggttggtt ttgtcggaac    2400
ctaggcaaat gaccatatta gtgaatctgt taatagttgt agcttgggat ggttattgta    2460
gttgttttgg taaaatcttc atttcctggt ttttttacc accttattta aatctcgatt    2520
atctgctctc tcttttatat acatacacac acccaaacat aacatttata atagtgtggt    2580
agtggaatgt atccttttttt aggtttccct gctttccagt taattttttaa aatggtagcg    2640 ctttgtatgc atttagaata catgactagt agtttatatt tcactggtag tttaaatctg    2700
gttggggcag tctgcagatg tttgaagtag tttagtgttc tagaaagagc tattactgtg    2760
gatagtgcct aggggagtgc tccacgccct ctgggcatac ggtagatatt atctgatgaa    2820
ttggaaagga gcaaaccaga aatggctttta ttttctcccct tggactaatt tttaagtctc    2880
gattggaatt cagtgagtag gttcataatg tgcatgacag aaataagctt tatagtggtt    2940
taccttcatt tagctttgga agttttcttt gccttagttt tggaagtaaa ttctagtttg    3000
tagttctcat ttgtaatgaa cacattaacg actagattaa aatattgcct tcaagattgt    3060
tcttacttac aagacttgct cctacttcta tgctgaaaat tgaccctgga tagaatacta    3120
taaggttttg agttagctgg aaaagtgatc agattaataa atgtatattg gtagttgaat    3180
ttagcaaaga aatagagata atcatgatta tacctttatt tttacaggaa gagatgatgt    3240
aactagagta tgtgtctaca ggagtaataa tggtttccaa agagtatttt ttaaaggaac    3300
aaaacgagca tgaattaact cttcaatata agctatgaag taatagttgg ttgtgaatta    3360
aagtggcacc agctagcacc tctgtgtttt aagggtcttt caatgtttct agaataagcc    3420
cttattttca agggttcata acaggcataa aatctcttct cctggcaaaa gctgctatga    3480
aaagcctcag cttgggaaga tagatttttt tccccccaat tacaaaatct aagtattttg    3540
gcccttcaat ttggaggagg gcaaaagttg gaagtaagaa gttttatttt aagtactttc    3600
agtgctcaaa aaaatgcaat cactgtgttg tatataatag ttcataggtt gatcactcat    3660
aataattgac tctaaggctt ttattaagaa aacagcagaa agattaaatc ttgaattaag    3720
tctgggggga aatggccact gcagatggag ttttagagta gtaatgaaat tctacctaga    3780
atgcaaaatt gggtatatga attacatagc atgttgttgg gatttttttt aatgtgcaga    3840
agatcaaagc tacttggaag gagtgcctat aatttgccag tagccacaga ttaagattat    3900
atcttatata tcagcagatt agctttagct tagggggagg gtgggaaagt ttggggggg    3960 ggttgtgaag atttagggggg accttgatag agaactttat aaacttcttt ctctttaata    4020
aagacttgtc ttacaccgtg ctgccattaa aggcagctgt tctagagttt cagtcaccta    4080
agtacaccca caaaacaata tgaatatgga gatcttcctt tacccctcaa cttttaatttg    4140 cccagttata cctcagtgtt gtagcagtac tgtgatacct ggcacagtgc tttgatctta    4200
cgatgccctc tgtactgacc tgaaggagac ctaagagtcc tttcccttttt tgagtttgaa    4260
```

| | |
|---|---|
| tcatagcctt gatgtggtct cttgttttat gtccttgttc ctaatgtaaa agtgcttaac | 4320 |
| tgcttcttgg ttgtattggg tagcattggg ataagatttt aactgggtat tcttgaattg | 4380 |
| cttttacaat aaaccaattt tataatcttt aaatttatca acttttttaca tttgtgttat | 4440 |
| tttcagtcag ggcttcttag atctacttat ggttgatgga gcacattgat ttggagtttc | 4500 |
| agatcttcca aagcactatt tgttgtaata acttttctaa atgtagtgcc tttaaaggaa | 4560 |
| aaatgaacac agggaagtga ctttgctaca ataatgttg ctgtgttaag tattcatatt | 4620 |
| aaatacatgc cttctatatg gaacatggca gaaagactga aaataacag taattaattg | 4680 |
| tgtaattcag aattcatacc aatcagtgtt gaaactcaaa cattgcaaaa gtgggtggca | 4740 |
| atattcagtg cttaacactt ttctagcgtt ggtacatctg agaaatgagt gctcaggtgg | 4800 |
| attttatcct cgcaagcatg ttgttataag aattgtgggt gtgcctatca taacaattgt | 4860 |
| tttctgtatc ttgaaaaagt attctccaca ttttaaatgt tttatattag agaattcttt | 4920 |
| aatgcacact tgtcaaatat atatatatag taccaatgtt acctttttat tttttgtttt | 4980 |
| agatgtaaga gcatgctcat atgttaggta cttacataaa ttgttacatt attttttctt | 5040 |
| atgtaatacc ttttttgtttg tttatgtggt tcaaatatat tctttcctta aaaaaaaaaa | 5100 |
| aaaaaaaaaa aaaaaaaaaa aaaaaaaa | 5128 |

<210> SEQ ID NO 58
<211> LENGTH: 1454
<212> TYPE: DNA
<213> ORGANISM: Homo sapiens

<400> SEQUENCE: 58

| | |
|---|---|
| aattgcttcc gggagttgc gagggagcga gggggaataa aggacccgcg aggaagggcc | 60 |
| cgcggatggc gcgtccctga gggtcgtggc gagttcgcgg agcgtgggaa ggagcggacc | 120 |
| ctgctctccc cgggctgcgg gccatggcca cggcggagcg gagagccctc ggcatcggct | 180 |
| tccagtggct ctctttggcc actctggtgc tcatctgcgc cgggcaaggg ggacgcaggg | 240 |
| aggatggggg tccagcctgc tacggcggat ttgacctgta cttcattttg gacaaatcag | 300 |
| gaagtgtgct gcaccactgg aatgaaatct attactttgt ggaacagttg gctcacaaat | 360 |
| tcatcagccc acagttgaga atgtccttta ttgttttctc cacccgagga acaaccttaa | 420 |
| tgaaactgac agaagacaga gaacaaatcc gtcaaggcct agaagaactc cagaaagttc | 480 |
| tgccaggagg agacacttac atgcatgaag gatttgaaag ggccagtgag cagatttatt | 540 |
| atgaaaacag acaagggtac aggacagcca gcgtcatcat tgctttgact gatggagaac | 600 |
| tccatgaaga tctctttttc tattcagaga gggaggctaa taggtctcga gatcttggtg | 660 |
| caattgttta ctgtgttggt gtgaaagatt tcaatgagac acagctggcc cggattgcgg | 720 |
| acagtaagga tcatgtgttt cccgtgaatg acgctttca ggctctgcaa ggcatcatcc | 780 |
| actcaatttt gaagaagtcc tgcatcgaaa ttctagcagc tgaaccatcc accatatgtg | 840 |
| caggagagtc atttcaagtt gtcgtgagag gaaacggctt ccgacatgcc cgcaacgtgg | 900 |
| acagggtcct ctgcagcttc aagatcaatg actcggtcac actcaatgag aagccctttt | 960 |
| ctgtggaaga cacttattta ctgtgtccag cgcctatctt aaaagaagtt ggcatgaaag | 1020 |
| ctgcactcca ggtcagcatg aacgatggcc tctcttttat ctccagttct gtcatcatca | 1080 |
| ccaccacaca ctgttctgac ggttccatcc tggccatcgc cctgctgatc ctgttcctgc | 1140 |
| tcctagccct ggctctcctc tggtggttct ggccctctg ctgcactgtg attatcaagg | 1200 |

-continued

| | |
|---|---|
| aggtccctcc accccctgcc gaggagagtg aggaaaataa aataaaataa caagaagaag | 1260 |
| aaagaaagaa atcccacaga aacagataac ctaacacagc ccgtgcaacg tattttatac | 1320 |
| aatgctctga aaatcatagt ctcaatctag acagtctttt cctctagttc cctgtattca | 1380 |
| aatcccagtg tctaacattc aataaatagc tatatgaaat caaaaaaaaa aaaaaaaaaa | 1440 |
| aaaaaaaaaa aaaa | 1454 |

<210> SEQ ID NO 59
<211> LENGTH: 2828
<212> TYPE: DNA
<213> ORGANISM: Homo sapiens

<400> SEQUENCE: 59

| | |
|---|---|
| agcagccggc acggggacag ccggccgcac aacggatctg caggcgcgga gcaaaatgca | 60 |
| cccgccgcgc cgcgcggtcc tgcagccccg ccacggcccc gcggcccgca ccccccgggg | 120 |
| gcgacagtga gcctctcccg ccaccaccgg gggccgagcg gagggctctc gggtgggaga | 180 |
| gcgggaccag atctcgacag ctgttcattt ccaggaagcc accgcagcca gagcgaaagg | 240 |
| ggaccttctg ccaccagcgg ggcatcagcc agcggcgcgc atggatttat gaagacactc | 300 |
| atgcaagaag tgggcaggac ttggacaaac ttttccaccg gctccgcgtc cgccgctccc | 360 |
| cgcgcctcgt ctcctttccc ctcctctccc ggcggccgcc gctgcccgcg atggtggccg | 420 |
| cgctgctggg cggcggcggc gaggcccgcg ggggacagt gccgggcgcc tggctgtgcc | 480 |
| tgatggcgct gctgcagctg ctgggctcgg cgccgcgggg atcggggctg gcgcacggcc | 540 |
| gccgcctcat ctgctggcag gcgctgctgc agtgccaggg ggagccggag tgcagctacg | 600 |
| cctacaacca gtacgccgag gcgtgcgcgc cggtgctggc gcagcacggc gggggcgacg | 660 |
| cgcccggggc cgccgccgcc gctttcccgg cctcggccgc ctctttctcg tcgcgctggc | 720 |
| gctgcccgag tcactgcatc tcggcccctca ttcagctcaa ccacgcgc cgcgggcccg | 780 |
| ccctggagga ctgtgactgc gcgcaggacg agaactgcaa gtccaccaag cgcgccattg | 840 |
| agccgtgcct gccccggacg agcggcggcg gcgcgggcgg ccccggcgcg gcggggtca | 900 |
| tgggctgcac cgaggcccgg cggcgctgcg accgcgacag ccgctgcaac ctggcgctga | 960 |
| gccgctacct gacctactgc ggcaaagtct tcaacgggct cgcgctgcacg gacgaatgcc | 1020 |
| gcaccgtcat tgaggacatg ctggctatgc ccaaggtggc gctgctcaac gactgcgtgt | 1080 |
| gcgacgcct cgagcggccc atctgcgagt cggtcaagga gaacatggcc cgcctgtgct | 1140 |
| tcggcgccga gctgggcaac ggccccgca gcagcggctc ggacggggc ctggacgact | 1200 |
| actacgatga ggactacgat gacgagcagc gcaccggggg cgcgggtggt gagcagccgc | 1260 |
| tggacgacga cgacggcgtc ccgcacccac gcgcccggg cagcggcgct gctgcatcgg | 1320 |
| gcggccgcgg ggacctgccc tatgggcctg ggcgcaggag cagcggcggc ggcggccgct | 1380 |
| tggcgccccg gggcgcctgg accccactcg cctccatctt gctgctgctg cttgggccgc | 1440 |
| tcttttagcc ctcgcgcccc ccgccgttgg ctgcgggaga gcccgcgtcc cactcccgtg | 1500 |
| ctcgcctcga ccccgcgccg ggcacctgtg gcttgggaca gatagaaggg atggttgggg | 1560 |
| atacttccca aaactttttc caagtcaact tggtgtagcc ggttccccgg ccacgactct | 1620 |
| gggcacttcc cctgaagctc ctctccggag cttgacttct tggacctcct ccccccgccc | 1680 |
| aattccaagc tccagaaact cccaactcgt ctgccgtcca gaaagctagc tgcagtgttc | 1740 |
| aggacgtccg ggaggaagca agcatgtggg ggacagaaca gtagtcctgg actcgaaagg | 1800 |
| gaaggtgctg accagtgggg ccttagcaat ttgaagggtt gggaaggagg aattatattt | 1860 |

```
gcaaaggggc tgtctattag catatttcct ttgaggggc aaaaaaaagt gccagtatcg    1920
acttttacag attgtggcca gtgaggatat tataatccta tgtaaacaga aaagtcccac    1980
ttaccgattc attctttcac tgtttgtatc tgcgcccaga attctcagtg acgtgggggt    2040
gagggtgggt ggcgattgcc ttagagggaa ccctaaatt ggttttggat aagtttgagc    2100
ccttgacctt aatttcattg ctaccactct gatctcttag cacatttctt aggattaagg    2160
gtccaaaaat gctgatctaa ggggttgcca tggtgttgaa caatgcaact tttatttaa     2220 aaaagctctg cactgccatg tatgaaagtc tctttatgat gtttgttttt ttgtcatttt    2280
tgttctttac atcaagaaat tttatgttta aatatgcgga gaatgtatat tgcctctgct    2340
cctatcaggg ttgctaaacc ctggtacatc gtatataaaa tgtattaaaa ctggggtttg    2400
ttaccagttg ctgtactttg tatatagaat ttttataaat tgtatgcttc agaaataatt    2460
tatttttaaa aagaaattaa aagttttaaa ctcacatcca tattcaccct ttccccctg     2520 aaatgtatag aatccatttg tcatcaggaa tcaaaaccca cagtccattg tgaagtgtgc    2580
tatatttaga acagtcttaa aatgtacagt gtattttata gaattgaagt taacattctt    2640
attttcaaga gaatttatgg acgttgtaga aatgtacaaa tgcatttcca aactgcctta    2700
aacgttgtat ttttatagac atgttttttt aaaaatccta agttttaaa taactatgga    2760 tttgtgtatt tttttggtt atttgtttta ttaaaacatg tacatcagta aagagtttta    2820
aacaatga                                                             2828

<210> SEQ ID NO 60
<211> LENGTH: 7568
<212> TYPE: DNA
<213> ORGANISM: Homo sapiens

<400> SEQUENCE: 60
gcgcggaggc agggaaccgg agccttggag cgacccaacc cctcgtctcg ctgccctccc      60
gcgcctgcaa cggtgcgcgg agactccggc gaactcagac acccaacggc ggagaacaga    120
agcggcaggc ggcggacgtg gcccggaagc tgcgcgccga acgcagcgca cccgctgccg    180
agcagaggag ccgcgccttt ccccgaccct cggctccagc ccccggcgcc tgccgcctcg    240
cagcccctct cgctcctcgg ctcggggggcc ggcaccggcg atgccgagcg acgctccag    300 tcctccgacc cgctgaagaa gcagcagccg ctcgcccgga gcctacgggg attgtgcgag    360
cggatcgtgc tcggtggagg ctcgggctg ggggcgcggg gactccgggg ggcggggga     420 gggaccgctc tgtcggtgcc cggcgccagc cgcggctttg aagggtctcc ctcccctgcc    480
cttagcagct ctgccacgga ctccggagg ctgcgggcgg cgtcctgagg ctccccagc      540 agacccaatc ggacttgaga aggtgatcgc tctgctctcc caaccccctt ccctccccat    600
tccccccact taactttttg tctccgttca tccgcggctt cgtcccctcc ccggcagacc    660
caccccgcgc tgtgacaacc gcccggggca tgggcccccc aacacggctc ctagaggccc    720
cgcggcctcg caagatgtga gaggcccctcc ccgggcagaa tcggagcttc aggagaggag    780 ctaataccc gcccccgtc cctcacatca ggcgggggtgg aggtgcgcgc tgagcccccg      840
cggtgctgag cgtcccggag cgcccaatcc tgggctggaa cgagtagctg gccgaggcg     900 cgccgcggag agccggctgt catgcctat tgatccccct ctgccccccg ccaagtatgt    960
ttgggctgga ccaattcgag ccccaggtca acagcaggaa cgctggccag ggcgagagga   1020
actttaacga gaccggactg agcatgaaca cccactttaa ggccccggct ttccacactg   1080
```

-continued

```
gggggccccc tggccctgtg gatcctgcta tgagcgcgct ggggcaaccc ccgatcttgg    1140
gcatgaacat ggagccctac ggcttccacg cgcgcggcca ctcggagttg cacgcagggg    1200
ggctgcaagc gcagcctgtg cacggcttct ttggcggcca gcagcctcac cacggccacc    1260
cgggaagtca tcatccccac cagcatcacc cccactttgg gggcaacttc ggtggcccgg    1320
accccggggc ctcgtgcctg cacggggtc gcctgctcgg ctacggcggc gcagccggag    1380
gcctgggcag ccagccgccc ttcgccgagg gctatgagca catggcggag agccaggggc    1440
ctgagagctt cggcccgcag cgaccgggga acctcccgga cttccacagt tcaggtgcct    1500
ccagccaccg cgtgccggcc ccatgcctgc cgctggacca gagccctaac cgagccgcct    1560
ccttccacgg cctgccgtcc tccagcggct ccgattccca cagtctggag ccacggaggg    1620
tgacgaacca aggagccgtc gactcgctgg aatacaatta ccgggcgagg cgccctcggg    1680
acattttgac atgttttcgc cctctgactc cgaagggcag ctgcctcatt atgcagcggg    1740
tcgccaggtt cctgggggc ggcttttccg gggcgccctc ggccatgccc agagctgcgg    1800
gcatggtggg cttgtccaaa atgcacgccc agccaccgca gcagcagccc cagcagcagc    1860
agcagcccca gcagcagcag cagcatggtg tgttctttga gaggttcagt gggggccagaa    1920
agatgcctgt gggtctggag ccctcagtgg gctccaggca cccgttaatg cagcctcccc    1980
agcaggcccc gccacccct cagcagcagc cccgcagca gccgccacag cagcagccgc    2040
cgccgccacc cgggcttcta gtccgacaaa attcgttgcc cgcctgcgct ccctcggccc    2100
cagcagggcg aggcgggcac gcccagcggc ggcctgcagg acggaggccc catgctgccc    2160
agccagcacg cgcaattcga gtatcccatc caccggctgg agaaccggag catgcaccct    2220
tattccgagc ctgttttcag catgcagcat cctcctccgc agcaggcgcc caaccagcgg    2280
ctgcagcatt tcgacgcgcc cccctacatg aacgtggcca agaggcgcgc ttcgactttc    2340
cgggcagcgc gggagtggac cgctgcgctt cgtggaacgg cagcatgcac aacggcgctc    2400
tggataatca cctctcccct tccgcctacc caggcctacc cggcgagttc acaccgcctg    2460
tgcccgacag cttcccttcg gggccgcccc tgcagcatcc ggccccggac caccagtccc    2520
tgcaacagca gcagcagcag cagcagcagc agcaacagca gcagcagcag cagcaacagc    2580
aacagcaaca gcagcagcag cagcagcgcc aaaacgcggc cctcatgatt aagcagatgg    2640
cgtcgcggaa tcagcagcag cggctgcgcc agcccaacct ggctcagcta ggccaccccg    2700
gggacgtggg ccaggcggc ctggtgcatg gcggcccggt gggcggcttg gcccagccga    2760
actttgagcg cgaaggcggc agcacgggcg ccgggcgtct gggcaccttc gagcagcagg    2820
cgccgcactt ggcgcaagag agcgcgtggt tctcaggtcc gcatccgccg cccggagacc    2880
tgctgccccg taggatgggc ggctcgggtc tgcccgctga ctgtggcccg cacgacccca    2940
gcctggcgcc ccctcctccg cctggtggct cgggggtgct gttccggggc cctctgcagg    3000
agccgatgag gatgcccgga gaggccacgt gccgcgctgc cttcaccggc ctgcagttcg    3060
ggggcagtct gggaggcctg ggtcagctgc agtcgcccgg ggcgggcgtg gggctcccca    3120
gcgctgcttc ggagcgccgg ccccgccgc cggactttgc tacgtctgcg ctcggggggcc    3180
agccgggctt tccgtttggt gcagccggcc ggcagtccac gccgcacagc ggtccaggcg    3240
tgaactcgcc ccccagcgcg ggaggggcg gtggcagctc tggtggcggc ggtggcgggg    3300
gtgcctaccc gccgcagcct gatttccagc ccagccagcg cacctcggcc agtaaattgg    3360
gcgcgctctc gctgggctcc ttcaacaagc ccagctccaa ggacaacctg ttcggccaga    3420
gctgcctggc tgcgctctcc accgcttgcc agaacatgat cgccagcctc ggggccccca    3480
```

```
acctcaacgt gaccttcaac aagaagaacc cgccagaggg caagaggaaa ctgagccaga    3540
acgagaccga cggcgcggca gtggccggca acccgggctc ggattacttc ccaggaggga    3600
ctgctcctgg ggggcccagg acccggaggc cgtccgggac cagtagcagc ggctccaaag    3660
cctcggggcc gcccaaccct ccagcccagg gggacggcac cagcctctcc cccaactaca    3720
ccctggaatc cacgtcgggg aatgacggca agccggtctc cggggcggc ggccggggac     3780
ggggtcgcag aaaaagggac agtggtcacg tgagccctgg caccttcttt gacaagtact    3840
cggcggctcc ggacagcggg ggcgcacctg gggtgagccc agggcagcag caagcgtcag    3900
gcgcagccgt cggggggaagc tccgcaggcg agacgcgcgg ggcaccgacg ccccacgaaa   3960
aggcgctcac gtcgccatcc tgggggaagg gggctgagtt gctcctgggg gatcagccgg    4020
acctcattgg gtccctggac ggcggggcca agtcggacag tagttcgcca aacgtgggtg    4080
agttcgcctc ggacgaggtg agcacgagct acgccaatga ggacgaggtg tcgtccagct    4140
ctgacaaccc ccaggcacta gttaaagcga gcaggagtcc cctggtgacc ggctcgccca    4200
aactccctcc ccgtgggata ggcgccgggg aacacggacc gaaggcgccc ccgcccgccc    4260
tcggcctggg catcatgtct aactctacct cgacccctga cagctacggc ggcggtgggg    4320
gcccgggcca tccgggcact ccgggcctgg agcaggtccg caccccgacg agcagcagcg    4380
gcgccccgcc acccgacgag atccaccccc tggagatcct tcaggcgcag atccagctac    4440
agaggcagca gttcagcatc tccgaggacc agcctctggg gctgaagggt ggcaagaagg    4500
gtgagtgcgc cgtcgggggcc tcaggggcgc agaatggcga cagcgagctg ggcagctgct    4560
gctccgaggc ggtcaagagc gccatgagca ccattgacct ggactcgctg atggcagagc    4620
acagcgctgc ctggtacatg cccgctgaca aggccctggt ggacagcgcg gacgacgaca    4680
agacgttggc gccctgggag aaggccaaac cccagaaccc caacagcaaa gaagcccacg    4740
acctccctgc aaacaaggcc tcagcatccc agcctggcag ccacttgcag tgcctgtctg    4800
tccactgcac agacgacgtg ggtgacgcca aggctcgagc ctccgtgccc acctggcggt    4860
ccctgcattc tgacatctcc aacagatttg ggacattcgt ggctgcccta acttgaatga    4920
caagaaagat cccctcctct accaggccct tcctctcccc ctgtctgttt ccttccccct    4980
caaccttacc ccacccctct gttaatttga aagggccact attgctgagt ggatgagttt    5040
ttttttttc ctctaggttg gtacctgctt agtggcatat ggaccggaaa gggttaattt     5100
aaaggggggg aacctcaaaa gttttttaa aaagaaact tgtctgccac agtatgttac       5160
cagtgttaac ccttctgcag ttagcaaact tttgcttaag cctttttcct ctagatactc    5220
cccatgtttc ggtaatcttg gcatacattt tttagatgac ctctttcctt gttttgtttt    5280
catgctgctg tatgtccaag tattgttatt tcataataag acaagagttg ctttctttt     5340
tattctttt cctttcttta ccccctcccc tttattttc ttttgcttt gttcactgct       5400
tattaaaatg gaaatcctgg agaatagtag ttctggaata ttgccgggtg aaagtccaat    5460
tgtcatcaca atgttatata ttgacacccc agtgtcatca gtcaggcagg agccaaacaa    5520
tgaatgcccc tcttaggtat tccgcctggg attttgtttt gtctgttccc taagaaaata    5580
tattttcatt cctgcaaaca cagtgctcag ccttcagttc ccttccactt gagttctctc    5640
ttctcctgct ggaagccgcc cctctctgcg atggacgtga ggacgtgtcc agctctgctc    5700
tgtgggaagg agttggaatg ttcgacagca gtgttttctc tccttttctg ggcctcctcg    5760
caaatgccca ggccctgcat tttcacgctg tgctaagcag cctttggtct gcatggggga    5820
```

| | | | | |
|---|---|---|---|---|
| tggtgtgctc | ccagcctgca | gtctttggag | caaggctgct | gcccgtgcct | tgggtgctgg | 5880 |
| agttggagga | ggctgttctc | agcccttttcc | cttttctgaa | agctgttcct | ggccgggcat | 5940 |
| cccagggaag | aaggagggga | ctgcgtgtat | ctcctccacc | tctcccattc | catccccagt | 6000 |
| ccagcctggg | caaccccacc | cctgggaggg | atgaggcacc | ctcttgctca | gcctgctcag | 6060 |
| ccttctctga | gcctttgcag | ggatctgcag | actcctgagg | gctagaggac | agagaaagag | 6120 |
| aatagaatga | aatgactttg | attcctgcgc | cttttagttt | tgaactctgg | aattcctctg | 6180 |
| cccccctcccc | aacattttt | tggaatctca | ccctgttgca | aaactagagc | catgtcccaa | 6240 |
| gcatctcaca | aaggaataac | tgctctgagc | agagatgagt | ggtggttggc | aggggcaggc | 6300 |
| aactttgggt | gctgctgatg | cctgcaaaag | ccatttatgg | cttgtggtgg | ggggcacata | 6360 |
| gattccccgg | tgggttagac | aggaagtaac | tgatatcact | tcacccaaat | atataaccgt | 6420 |
| gatggttatc | tatttaattt | cagttttgt | taacgagcgt | gtcttactaa | aacgctccac | 6480 |
| tttgagctcc | cccacccct | ccaggtcctc | agagtttgca | gatctgggct | ttctaaagca | 6540 |
| agtgacctga | aggctctggg | ctcaccatac | aacacccacg | ttgtttattt | caaagaactt | 6600 |
| ttcagcgaag | ggagaggagc | tttcagaaaa | acctcactct | ttcccctccc | ttctcccctc | 6660 |
| tttccttctg | ccggtccttt | tggctggggt | ctgagtctgc | ggttctcgcc | tgggcagtct | 6720 |
| tgacgaggag | caaccccgc | cttcagaggg | cagacaaagc | aggtggcatg | aattgatcag | 6780 |
| cgagaaaggt | gtgagccgag | gcagttcctg | cgttctgcta | caaaaggaat | ggaaagggaa | 6840 |
| gggaatttcc | ccccaccatg | ggctgtggga | gagttgaccg | tattctgggc | aagactccat | 6900 |
| gaccctctg | attctgcagt | gtacagctgt | ttgagagcct | catcatttta | cttttgaaac | 6960 |
| aggaatgatt | tctccttaat | tgcttaaggc | cggggagcaa | agtgtcttaa | cttctgtctt | 7020 |
| tgactttccc | agcgttgagt | catcaacact | ttgccaatta | gctcatggtc | ctggcaacct | 7080 |
| cagaaacccc | tgaagttta | aaactttct | cgctccccac | gacccagaa | tgaaacagct | 7140 |
| ttaaaaatag | ccttaagcaa | aaggatgtta | tttcattaaa | tttggtttaa | tggaaagaat | 7200 |
| aaaagtaaat | gaaaaacaca | ccctacacac | tagactccga | acactggtaa | tcagtactgc | 7260 |
| atagcaaact | ctttgggaaa | gaaaacgaaa | atgttattgc | acatgtaaaa | tatgaaaact | 7320 |
| taactctgct | gtgtgttagg | caatcctgta | atctttttg | actcttaaaa | gaaattcatt | 7380 |
| tctgaaatgc | ttggttggaa | gactgtgaca | atagctcatg | aaattgagtg | ttatttttt | 7440 |
| ctttctttt | taaaaaaata | tgtaaagtgc | agtcttctgt | attcctgcat | attgtatata | 7500 |
| cctgtatatg | ttttcctgag | cagttaaata | acaataaata | tgacgttaat | ggtgaaaaaa | 7560 |
| aaaaaaaa | | | | | 7568 |

<210> SEQ ID NO 61
<211> LENGTH: 691
<212> TYPE: DNA
<213> ORGANISM: Homo sapiens

<400> SEQUENCE: 61

| | | | | |
|---|---|---|---|---|
| gaccctcac | actcacctag | ccaccatgga | catcgccatc | caccacccct | ggatccgccg | 60 |
| cccttcttt | cctttccact | cccccagccg | cctctttgac | cagttcttcg | gagagcacct | 120 |
| gttggagtct | gatctttcc | cgacgtctac | ttccctgagt | cccttctacc | ttcggccacc | 180 |
| ctccttcctg | cgggcaccca | gctggtttga | cactggactc | tcagagatgc | gcctggagaa | 240 |
| ggacaggttc | tctgtcaacc | tggatgtgaa | gcacttctcc | ccagaggaac | tcaaagttaa | 300 |
| ggtgttggga | gatgtgattg | aggtgcatgg | aaaacatgaa | gagcgccagg | atgaacatgg | 360 |

```
tttcatctcc agggagttcc acaggaaata ccggatccca gctgatgtag accctctcac    420
cattacttca tccctgtcat ctgatggggt cctcactgtg aatggaccaa ggaaacaggt    480
ctctggccct gagcgcacca ttcccatcac ccgtgaagag aagcctgctg tcaccgcagc    540
ccccaagaaa tagatgccct tcttgaatt gcattttta aaacaagaaa gtttccccac      600
cagtgaatga aagtcttgtg actagtgctg aagcttatta atgctaaggg caggcccaaa    660
ttatcaagct aataaaatat cattcagcaa c                                   691

<210> SEQ ID NO 62
<211> LENGTH: 874
<212> TYPE: DNA
<213> ORGANISM: Homo sapiens

<400> SEQUENCE: 62
gcggccgcgt cgaccgctgc gcctgttggg gctgcacctc ggaccagggc ttctgctgca     60
tctgcagcca tgtcgggccg ctcagtgcca catgcccacc cggccaccgc cgagtacgaa    120
tttgccaacc cgagccgcct gggtgagcag cgcttcggag aaggcctcct gccagaagag    180
atcctgaccc ccacactcta ccatggctac tatgtccggc ctcgggccgc cccagctggg    240
gagggcagca gggcagggc ctccgagctt aggctcagtg agggcaagtt ccaggcattt     300
ctggatgtga gccactttac cccagacgag gtgactgtga ggactgtgga taacctgctg    360
gaggtgtctg cccggcaccc ccagcgcctg accgccacg gcttcgtgtc ccgagagttc     420
tgccgcacct atgtcctgcc tgctgatgtc gaccctggc gagtccgagc tgctctctcc    480
catgatggca tcttaaacct ggaagcacct cggggtggcc gacatttgga cacagaggtc    540
aatgaggtct acatctccct gctccctgcg cctcctgatc cagaggaaga ggaggaggca    600
gccatagttg agccctgatt gccacagacc cagcacccag caaatccctc tctacctccc    660
aaggtgatat gggcagctgc ccaccactcc agaggtagca gcatccttgg gggaagggaa    720
aggtgcatgg tccacaatgt atggtttggt cccatgggac atgtcatagc cttggtttag    780
ttttgggtgg agctgaataa acccaaattt cagggcaaaa aaaaaaaaaa aaagaaaaa     840 aaaaaaaaaa aaaaaaaaa gtcgacgcgg ccgc                                 874

<210> SEQ ID NO 63
<211> LENGTH: 2569
<212> TYPE: DNA
<213> ORGANISM: Homo sapiens

<400> SEQUENCE: 63
tccctcgtct ctctcgggca acatggcggg cgtggaggag gtagcggcct ccgggagcca     60
cctgaatggc gacctggatc agacgacag ggaagaagga gctgcctcta cggctgagga    120
agcagccaag aaaaaaagac gaaagaagaa gaagagcaaa gggcccttctg cagcagggga   180 acaggaacct gataaagaat caggagcctc agtggatgaa gtagcaagac agttggaaag    240
atcagcattg gaagataaag aaagagatga agatgatgaa gatggagatg gcgatggaga    300
tggagcaact ggaaagaaga agaaaagaa gaagaagaag agaggaccaa aagttcaaac     360
agaccctccc tcagttccaa tatgtgacct gtatcctaat ggtgtatttc ccaaaggaca    420
agaatgcgaa tacccaccca cacaagatgg gcgaacagct gcttggagaa ctacaagtga    480
agaaaagaaa gcattagatc aggcaagtga agagatttgg aatgattttc gagaagctgc    540
agaagcacat cgacaagtta gaaatacgt aatgagctgg atcaagcctg ggatgacaat    600
```

-continued

```
gatagaaatc tgtgaaaagt tggaagactg ttcacgcaag ttaataaaag agaatggatt      660
aaatgcaggc ctggcatttc ctactggatg ttctctcaat aattgtgctg cccattatac      720
tcccaatgcc ggtgacacaa cagtattaca gtatgatgac atctgtaaaa tagactttgg      780
aacacatata agtggtagga ttattgactg tgcttttact gtcacttta atcccaaata       840 tgatacgtta ttaaaagctg taaaagatgc tactaacact ggaataaagt gtgctggaat      900
tgatgttcgt ctgtgtgatg ttggtgaggc catccaagaa gttatggagt cctatgaagt      960
tgaaatagat gggaagacat atcaagtgaa accaatccgt aatctaaatg gacattcaat     1020
tgggcaatat agaatacatg ctggaaaaac agtgccgatt gtgaaggag gggaggcaac      1080 aagaatggag gaaggagaag tatatgcaat tgaaaccttt ggtagtacag gaaaaggtgt     1140
tgttcatgat gatatggaat gttcacatta catgaaaaat tttgatgttg acatgtgcc     1200 aataaggctt ccaagaacaa aacacttgtt aaatgtcatc aatgaaaact tggaaccct     1260 tgccttctgc cgcagatggc tggatcgctt gggagaaagt aaatacttga tggctctgaa    1320
gaatctgtgt gacttgggca ttgtagatcc atatccacca ttatgtgaca ttaaaggatc    1380
atatacagcg caatttgaac ataccatcct gttgcgtcca acatgtaaag aagttgtcag    1440
cagaggagat gactattaaa cttagtccaa agccacctca acacctttat tttctgagct    1500
ttgttggaaa acatgatacc agaattaatt tgccacatgt tgtctgtttt aacagtggac    1560
ccatgtaata cttttatcca tgtttaaaaa agaaggaatt tggacaaagg caaaccgtct    1620
aatgtaatta accaacgaaa aagctttccg gacttttaaa tgctaactgt ttttcccctt    1680
cctgtctagg aaaatgctat aaagctcaaa ttagttagga atgacttata cgttttgttt    1740
tgaataccta agagatactt tttggatatt tatattgcca tattcttact tgaatgcttt    1800
gaatgactac atccagttct gcacctatac cctctggtgt tgcttttaa ccttcctgga    1860 atccattttc taaaaaataa agacacattc ttctcagcac cacacaacac ctattccaaa    1920
atcgaccaca tatttggaag taaagctctc ctcagcaaat gtaaagaac agaaattata    1980 acaaactgtc tctcagacca cagtataacc aaactagaac tcaggattaa gaaactcact    2040
caaaaccaca caactacatg gaaactgaac aacctgctcc tgaatgacta ctggatacat    2100
aacaaaatga aggcagaaat aaagatgttc tttaaaacca atgagaacaa agacacaaca    2160
taccagaatc tctgggacac attcaaagca gtgtgtagag ggaaatttat agcactaaat    2220
gcccacaaga gaaagcagga atatctaaa attgacaccc taacatcaca attaaaagaa     2280
ctagagaagc aagagcaaac acattgaaaa gctaagagaa ggcaagaaat aactaagatc    2340
agagcagaac tgaaggaaat agagacacaa aaaactcttc aaaaaatcaa tgaatccagg    2400
agctggtttt tgaaacgat caacaaaatt gatagacact agcaagacta ataaagaaga    2460
aaggagagaa gaatcaaata gaagcaataa aaaatgataa aggggatatc accaccaatc    2520
ccacagaaat aaaccaccat cagagaatac tacaaacacc tctacgcaa                2569
```

<210> SEQ ID NO 64
<211> LENGTH: 3672
<212> TYPE: DNA
<213> ORGANISM: Homo sapiens

<400> SEQUENCE: 64

```
acatgtgcat atttcattcc ccaggcagac atttttaga aatcaataca tgccccaata       60
ttggaaagac ttgttcttcc acggtgacta cagtacatgc tgaagcgtgc cgtttcagcc      120
ctcatttaat tcaatttgta agtagcgcac gagcctctgt gggggaggat aggctgaaaa      180
```

```
aaaaaagtgg gctcgtattt atctacagga ctccatatag tcatatatag gcatataaat    240
ctatgctttt tctttgtttt tttctttctt cctttctttc aaaggtttgc attaacttt     300 caaagtagtt cctataggg cattgaggag cttcctcatt ctgggaaaac tgagaaaacc     360
catattctcc taatacaacc cgtaatagca tttttgcctg cctcgaggca gagtttccg     420 tgagcaataa actcagcttt tttgtggggc acagtactgg atttgacagt gattccccac    480
gtgtgttcat ctgcacccac cgagccaggc agaggccagc cctccgtggt gcacacagca    540
cgcgcctcag tccatcccat tttagtcttt aaaccctcag gaagtcacag tctccggaca    600
ccacaccaca ttgagcccaa caggtccacg atggatccac ctagtcccac cccagccttt    660
ttctttcatc tgaacagaat gtgcattttt ggaagcctcc ctcactctcc atgctggcag    720
agcaggaggg agactgaagt aagagatggc agagggagat ggtggcaaaa aggtttagat    780
gcaggagaac agtaagatgg atggttccgg ccagagtcga tgtggggagg aacagagggc    840
tgaagggaga gggggctgac tgttccattc tagctttggc acaaagcagc agaaaggggg    900
aaaagccaat agaaatttcc ttagcttccc caccatatgt attttcatgg atttgagagg    960
aaagagagga aaatggggga atgggttgca aaatagaaat gagcttaatc caggccgcag   1020
agccagggaa ggtgagtaac cttaggaggg tgctagactt tagaagccag ataggaagaa   1080
tcagtctaaa ctggccatgc tttggaaggg acaagactat gtgctccgct gcccaccttc   1140
agcctgcaat gagggactga ggcccacgag tctttccagc tcttcctcca ttctggccag   1200
tccctgcatc ctccctgggg tggaggatgg aaggaaagct gggacaagca gggaacgcat   1260
gattcaggga tgctgtcact cggcagccag attccgaaac tcccattctc caatgacttc   1320
ctcaaccaat gggtggcctt gtgactgttc tttaaggctg aagatatcca ggaaggggg    1380 cttggacact ggccaaggag acccccttcgt gctgtggaca cagctctctt cactctttgc   1440
tcatggcatg acacagcgga gaccgcctcc aacaacgaat tgggggctac gaagaggaat   1500
agcgaaaaag caaatctgtt tcaactgatg ggaaccctat agctatagaa cttgggggct   1560
atctcctatg cccctggaca ggacagttgg ctggggacag gagaagtgct caatcttcat   1620
gagacaaagg ggcccgatca aggcagccac aaggccttga cctgccgagt cagcatgccc   1680
catctctctc gacagctgtc ccctaaaccc aactcacgtt tctgtatgtc ttaggccagt   1740
atcccaaacc tcttccacgt cactgttctt tccacccatt ctcccttgc atcttgagca    1800 gttatccaac taggatctgc caagtggata ctggggtgcc actcccctga gaaaagactg   1860
agccaggaac tacaagctcc ccccacattc ctcccagcct ggacctaatt cttgagaggg   1920
gctctctctt cacggactgt gtctggactt tgagcaggct tctgccccttt gcgttggctc   1980 tttgctgcca gccatcaggt gggggattag agcctggtgt aagtgcgcca gactcttccg   2040
gtttccaaag ttcgtgcctg cgaacccaaa cctgtgagtc tcttctgcat gcaggagttt   2100
ctcctgggca gctggtcact ccccagagaa gctgggcctt catggacaca tggaactaag   2160
cctcccaaat gggagttctg gctgagccca ggtggggag atcctgggaa gggaggcact    2220
ggaggaagac ggcacctctt cccccatggc agggtgtgag ggaggcaggt ttggaatggt   2280
gcgagtatgg caatctaagc aggggtctgg tctctttgac tccaggctcg ctttggccga   2340
ctgtctgctc acccagagac cttggactcc ggactatcca tggctccgaa tctaagtgct   2400
gcccactccc atgctcacac ccacagaagg tcttcccatc ccctttagat tcgtgcctca   2460
ctccaccagt gaggaagatg cctctgtctt tcccacgact gccaggagat agggaagccc   2520
```

| | | | | |
|---|---|---|---|---|
| agccaggact | gaccctcctt | cctccagcct | gccctgaccc | acctggcaaa gcagggcaca | 2580 |
| tggggaggaa | gagactggaa | cctttctttg | acagccaggc | ctagacagac aggcctgggg | 2640 |
| acactggccc | atgaggggag | gaaggcaggc | gcacgaggtc | cagggaggcc cttttctgat | 2700 |
| catgcccctt | ctctcccacc | ccatctcccc | accaccacct | ctgtggcctc catggtaccc | 2760 |
| ccacagggct | ggcctcccct | agagggtggg | cctcaaccac | ctcgtcccgc cacgcaccgg | 2820 |
| ttagtgagac | agggctgcca | cgcaaccgcc | aagcccccct | caaggtggga cagtaccccg | 2880 |
| gacccatcca | ctcactcctg | agaggctccg | gcccagaatg | ggaacctcag agaagagctc | 2940 |
| taaggagaag | aaaccccata | gcgtcagaga | ggatatgtct | ggcttccaag agaaaggagg | 3000 |
| ctccgttttg | caaagtggag | gagggacgag | ggacaggggt | ttcaccagcc agcaacctgg | 3060 |
| gccttgtact | gtctgtgttt | ttaaaaccac | taaagtgcaa | gaattacatt gcactgtttc | 3120 |
| tccactttt | attttctctt | aggcttttgt | ttctatttca | aacatacttt cttggttttc | 3180 |
| taatggagta | tatagtttag | tcatttcaca | gactctggcc | tcctctcctg aaatcctttt | 3240 |
| ggatggggaa | agggaaggtg | gggagggtcc | gaggggaagg | ggaccccagc ttccctgtgc | 3300 |
| ccgctcaccc | cactccacca | gtccccggtc | gccagccgga | gtctcctctc taccgccact | 3360 |
| gtcacaccgt | agcccacatg | gatagcacag | ttgtcagaca | agattccttc agattccgag | 3420 |
| ttgctaccgg | ttgttttcgt | tgttgttgtt | gttgttttc | ttttcttttt ttttttgaa | 3480 |
| gacagcaata | accacagtac | atattactgt | agttctctat | agttttacat acattcatac | 3540 |
| cataactctg | ttctctcctc | ttttttgttt | tcaactttaa | aaacaaaaat aaacgatgat | 3600 |
| aatctttact | ggtgaaaagg | atggaaaaat | aaatcaacaa | atgcaaccag tttgtgagaa | 3660 |
| aaaaaaaaa | aa | | | | 3672 |

<210> SEQ ID NO 65
<211> LENGTH: 1826
<212> TYPE: DNA
<213> ORGANISM: Homo sapiens

<400> SEQUENCE: 65

| | | | | |
|---|---|---|---|---|
| agtctgcact | ggagctgcct | ggtgaccaga | agtttggagt | ccgctgacgt cgccgcccag | 60 |
| atggcctcca | ggctgaccct | gctgaccctc | ctgctgctgc | tgctggctgg ggatagagcc | 120 |
| tcctcaaatc | caaatgctac | cagctccagc | tcccaggatc | cagagagttt gcaagacaga | 180 |
| ggcgaaggga | aggtcgcaac | aacagttatc | tccaagatgc | tattcgttga acccatcctg | 240 |
| gaggtttcca | gcttgccgac | aaccaactca | caaccaatt | cagccaccaa ataacagct | 300 |
| aataccactg | atgaacccac | cacacaaccc | accacagagc | ccaccaccca acccaccatc | 360 |
| caacccaccc | aaccaactac | ccagctccca | acagattctc | ctacccagcc cactactggg | 420 |
| tccttctgcc | caggacctgt | tactctctgc | tctgacttgg | agagtcattc aacagaggcc | 480 |
| gtgttggggg | atgctttggt | agattttctcc | ctgaagctct | accacgcctt tcagcaatg | 540 |
| aagaaggtgg | agaccaacat | ggccttttcc | ccattcagca | tcgccagcct ccttacccag | 600 |
| gtcctgctcg | ggctgggca | gaacaccaaa | acaaacctgg | agagcatcct ctcttacccc | 660 |
| aaggacttca | cctgtgtcca | ccaggccctg | aagggcttca | cgaccaaagg tgtcacctca | 720 |
| gtctctcaga | tcttccacag | cccagacctg | gccataaggg | acacctttgt gaatgcctct | 780 |
| cggaccctgt | acagcagcag | ccccagagtc | ctaagcaaca | acagtgacgc caacttggag | 840 |
| ctcatcaaca | cctgggtggc | caagaacacc | aacaacaaga | tcagccggct gctagacagt | 900 |
| ctgccctccg | ataccccgcct | tgtcctcctc | aatgctatct | acctgagtgc caagtggaag | 960 |

|  |  |
|---|---|
| acaacatttg atcccaagaa aaccagaatg gaacccttc acttcaaaaa ctcagttata | 1020 |
| aaagtgccca tgatgaatag caagaagtac cctgtggccc atttcattga ccaaactttg | 1080 |
| aaagccaagg tggggcagct gcagctctcc cacaatctga gtttggtgat cctggtaccc | 1140 |
| cagaacctga acatcgtct tgaagacatg aacaggctc tcagcccttc tgttttcaag | 1200 |
| gccatcatga gaaactgga gatgtccaag ttccagccca ctctcctaac actaccccgc | 1260 |
| atcaaagtga cgaccagcca ggatatgctc tcaatcatgg agaaattgga attcttcgat | 1320 |
| ttttcttatg accttaacct gtgtgggctg acagaggacc cagatcttca ggtttctgcg | 1380 |
| atgcagcacc agacagtgct ggaactgaca gagactgggg tggaggcggc tgcagcctcc | 1440 |
| gccatctctg tgcccgcac cctgctggtc tttgaagtgc agcagccctt cctcttcgtg | 1500 |
| ctctgggacc agcagcacaa gttccctgtc ttcatggggc gagtatatga ccccagggcc | 1560 |
| tgagacctgc aggatcaggt tagggcgagc gctacctctc cagcctcagc tctcagttgc | 1620 |
| agccctgctg ctgcctgcct ggacttgccc ctgccacctc ctgcctcagg tgtccgctat | 1680 |
| ccaccaaaag ggctcctgag ggtctgggca agggacctgc ttctattagc ccttctccat | 1740 |
| ggccctgcca tgctctccaa accacttttt gcagctttct ctagttcaag ttcaccagac | 1800 |
| tctataaata aaacctgaca gaccat | 1826 |

<210> SEQ ID NO 66
<211> LENGTH: 5489
<212> TYPE: DNA
<213> ORGANISM: Homo sapiens

<400> SEQUENCE: 66

|  |  |
|---|---|
| ggctgagttt tatgacgggc ccggtgctga agggcaggga acaacttgat ggtgctactt | 60 |
| tgaactgctt ttcttttctc cttttgcac aaagagtctc atgtctgata tttagacatg | 120 |
| atgagctttg tgcaaaaggg gagctggcta cttctcgctc tgcttcatcc cactattatt | 180 |
| ttggcacaac aggaagctgt tgaaggagga tgttcccatc ttggtcagtc ctatgcggat | 240 |
| agagatgtct ggaagccaga accatgccaa atatgtgtct gtgactcagg atccgttctc | 300 |
| tgcgatgaca taatatgtga cgatcaagaa ttagactgcc ccaacccaga aattccattt | 360 |
| ggagaatgtt gtgcagtttg cccacagcct ccaactgctc ctactcgccc tcctaatggt | 420 |
| caaggacctc aaggccccaa gggagatcca ggccctcctg gtattcctgg agaaatggt | 480 |
| gaccctggta ttccaggaca accagggtcc cctggttctc ctggcccccc tggaatctgt | 540 |
| gaatcatgcc ctactggtcc tcagaactat tctccccagt atgattcata tgatgtcaag | 600 |
| tctggagtag cagtaggagg actcgcaggc tatcctggac cagctggccc cccaggccct | 660 |
| cccggtcccc ctggtacatc tggtcatcct ggttcccctg gatctccagg ataccaagga | 720 |
| cccctggtg aacctgggca agctggtcct tcaggccctc caggacctcc tggtgctata | 780 |
| ggtccatctg gtcctgctgg aaaagatgga gaatcaggta gacccggacg acctggagag | 840 |
| cgaggattgc ctggacctcc aggtatcaaa ggtccagctg gatacctgg attccctggt | 900 |
| atgaaaggac acagaggctt cgatggacga aatggagaaa agggtgaaac aggtgctcct | 960 |
| ggattaaagg gtgaaaatgg tcttccaggc gaaaatggag ctcctggacc catgggtcca | 1020 |
| agagggctc ctggtgagcg aggacggcca ggacttcctg gggctgcagg tgctcggggt | 1080 |
| aatgacggtg ctcgaggcag tgatggtcaa ccaggccctc ctggtcctcc tggaactgcc | 1140 |
| ggattccctg gatcccctgg tgctaagggt gaagttggac ctgcagggtc tcctggttca | 1200 |

```
aatggtgccc ctggacaaag aggagaacct ggacctcagg gacacgctgg tgctcaaggt    1260
cctcctggcc ctcctgggat taatggtagt cctggtggta aaggcgaaat gggtcccgct    1320
ggcattcctg gagctcctgg actgatggga gcccggggtc ctccaggacc agccggtgct    1380
aatggtgctc ctggactgcg aggtggtgca ggtgagcctg gtaagaatgg tgccaaagga    1440
gagcccggac cacgtggtga acgcggtgag gctggtattc caggtgttcc aggagctaaa    1500
ggcgaagatg gcaaggatgg atcacctgga gaacctggtg caaatgggct tccaggagct    1560
gcaggagaaa ggggtgcccc tgggttccga ggacctgctg gaccaaatgg catcccagga    1620
gaaaagggtc ctgctggaga gcgtggtgct ccaggccctg cagggcccag aggagctgct    1680
ggagaacctg gcagagatgg cgtccctgga ggtccaggaa tgaggggcat gcccggaagt    1740
ccaggaggac caggaagtga tgggaaacca gggcctcccg gaagtcaagg agaaagtggt    1800
cgaccaggtc ctcctgggcc atctggtccc cgaggtcagc tggtgtcat gggcttcccc    1860 ggtcctaaag gaaatgatgg tgctcctggt aagaatggag aacgaggtgg ccctggagga    1920
cctggccctc agggtcctcc tggaaagaat ggtgaaactg gacctcaagg accccaggg    1980 cctactgggc ctggtggtga caaaggagac acaggacccc ctggtccaca aggattacaa    2040
ggcttgcctg gtacaggtgg tcctccagga gaaaatggaa aacctgggga accaggtcca    2100
aagggtgatg ccggtgcacc tggagctcca ggaggcaagg gtgatgctgg tgcccctggt    2160
gaacgtggac ctcctggatt ggcaggggcc ccaggactta gaggtggagc tggtccccct    2220
ggtcccgaag gaggaaaggg tgctgctggt cctcctgggc cacctggtgc tgctggtact    2280
cctggtctgc aaggaatgcc tggagaaaga ggaggtcttg gaagtcctgg tccaaagggt    2340
gacaagggtg aaccaggcgg cccaggtgct gatggtgtcc cagggaaaga tgggcccaagg   2400 ggtcctactg gtcctattgg tcctcctggc ccagctggcc agcctggaga taagggtgaa    2460
ggtggtgccc ccggacttcc aggtatagct ggacctcgtg gtagccctgg tgagagaggt    2520
gaaactggcc ctccaggacc tgctggtttc cctggtgctc ctggacagaa tggtgaacct    2580
ggtggtaaag gagaagagg ggctccgggt gagaaaggtg aaggaggccc tcctggagtt    2640
gcaggacccc ctggaggttc tggacctgct ggtcctcctg gtccccaagg tgtcaaaggt    2700
gaacgtggca gtcctggtgg acctggtgct gctggcttcc ctggtgctcg tggtcttcct    2760
ggtcctcctg gtagtaatgg taacccagga ccccaggtc ccagcggttc tccaggcaag    2820
gatgggcccc aggtcctgc gggtaacact ggtgctcctg gcagccctgg agtgtctgga    2880
ccaaaaggtg atgctggcca accaggagag aagggatcgc ctggtgccca gggcccacca    2940
ggagctccag ccccacttgg gattgctggg atcactggag cacggggtct tgcaggacca    3000
ccaggcatgc caggtcctag gggaagccct ggccctcagg gtgtcaaggg tgaaagtggg    3060
aaaccaggag ctaacggtct cagtggagaa cgtggtcccc ctggacccca ggtcttcct    3120 ggtctgctct gtacagctgg tgaacctgga agagatggaa accctggatc agatggtctt    3180
ccaggccgag atggatctcc tggtggcaag ggtgatcgtg gtgaaaatgg ctctcctggt    3240
gcccctggcg ctcctggtca tccaggccca cctggtcctg tcggtccagc tggaaagagt    3300
ggtgacagag gagaaagtgg ccctgctggc cctgctggtg ctcccggtcc tgctggttcc    3360
cgaggtgctc ctggtcctca aggccacgt ggtgacaaag gtgaaacagg tgaacgtgga    3420
gctgctggca tcaaaggaca tcgaggattc cctggtaatc caggtgcccc aggttctcca    3480
ggccctgctg gtcagcaggg tgcaatcggc agtccaggac ctgcaggccc cagaggacct    3540
gttggaccca gtggacctcc tggcaaagat ggaaccagtg gacatccagg tcccattgga    3600
```

| | |
|---|---|
| ccaccagggc ctcgaggtaa cagaggtgaa agaggatctg agggctcccc aggccaccca | 3660 |
| gggcaaccag gccctcctgg acctcctggt gccctggtc cttgctgtgg tggtgttgga | 3720 |
| gccgctgcca ttgctgggat tggaggtgaa aaagctggcg gttttgcccc gtattatgga | 3780 |
| gatgaaccaa tggatttcaa atcaacacc gatgagatta tgacttcact caagtctgtt | 3840 |
| aatggacaaa tagaaagcct cattagtcct gatggttctc gtaaaaaccc cgctagaaac | 3900 |
| tgcagagacc tgaaattctg ccatcctgaa ctcaagagtg gagaatactg ggttgaccct | 3960 |
| aaccaaggat gcaaattgga tgctatcaag gtattctgta atatggaaac tggggaaaca | 4020 |
| tgcataagtg ccaatccttt gaatgttcca cggaaacact ggtggacaga ttctagtgct | 4080 |
| gagaagaaac acgtttggtt tggagagtcc atggatggtg gttttcagtt tagctacggc | 4140 |
| aatcctgaac ttcctgaaga tgtccttgat gtgcagctgg cattccttcg acttctctcc | 4200 |
| agccgagctt cccagaacat cacatatcac tgcaaaaata gcattgcata catggatcag | 4260 |
| gccagtggaa atgtaaagaa ggccctgaag ctgatggggt caaatgaagg tgaattcaag | 4320 |
| gctgaaggaa atagcaaatt cacctacaca gttctggagg atggttgcac gaaacacact | 4380 |
| ggggaatgga gcaaaacagt cttttgaatat cgaacacgca aggctgtgag actacctatt | 4440 |
| gtagatattg caccctatga cattggtggt cctgatcaag aatttggtgt ggacgttggc | 4500 |
| cctgtttgct ttttataaac caaactctat ctgaaatccc aacaaaaaaa atttaactcc | 4560 |
| atatgtgttc ctcttgttct aatcttgtca accagtgcaa gtgaccgaca aaattccagt | 4620 |
| tatttatttc caaaatgttt ggaaacagta taatttgaca agaaaaatg atacttctct | 4680 |
| tttttgctg ttccaccaaa tacaattcaa atgcttttg ttttattttt ttaccaattc | 4740 |
| caatttcaaa atgtctcaat ggtgctataa taaataaact tcaacactct ttatgataac | 4800 |
| aacactgtgt tatattcttt gaatcctagc ccatctgcag agcaatgact gtgctcacca | 4860 |
| gtaaaagata acctttcttt ctgaaatagt caaatacgaa attagaaaag ccctccctat | 4920 |
| tttaactacc tcaactggtc agaaacacag attgtattct atgagtccca gaagatgaaa | 4980 |
| aaaattttat acgttgataa aacttataaa tttcattgat taatctcctg gaagattggt | 5040 |
| ttaaaagaa aagtgtaatg caagaattta agaaatatt tttaaagcca caattatttt | 5100 |
| aatattggat atcaactgct tgtaaaggtg ctcctctttt ttcttgtcat tgctggtcaa | 5160 |
| gattactaat atttgggaag ctttaaaga cgcatgttat ggtgctaatg tactttcact | 5220 |
| tttaaactct agatcagaat tgttgacttg cattcagaac ataaatgcac aaaatctgta | 5280 |
| catgtctccc atcagaaaga ttcattggca tgccacaggg attctcctcc ttcatcctgt | 5340 |
| aaaggtcaac aataaaaacc aaattatggg gctgcttttg tcacactagc atagagaatg | 5400 |
| tgttgaaatt taactttgta agcttgtatg tggttgttga tcttttttt ccttacagac | 5460 |
| acccataata aaatatcata ttaaaattc | 5489 |

<210> SEQ ID NO 67
<211> LENGTH: 5222
<212> TYPE: DNA
<213> ORGANISM: Homo sapiens

<400> SEQUENCE: 67

| | |
|---|---|
| ttctgcccgc cgccgccgct gccgagcgcc gcctttgttc cctgcaggaa gggcgagcgc | 60 |
| gcgggccagc gctcagccag cgcctcacga cccttcgtcc tccgctaagc tccaacgctc | 120 |
| tgctcgacta gccgcgcgcc ttccggggct ccgcagaccc gcgagatggc accaaggagg | 180 |

```
aacaacgggc agtgctggtg tctgctgatg ctgctctcgg tctccacgcc cctccctgct    240
gtcacccaga cccgcggtgc gacagagact gcttcccagg gtcacctgga cctcacgcag    300
ctcatcggtg tcccgctgcc ctcgtccgta tcctttgtca caggctatgg tggcttcccg    360
gcctacagtt tcgggcctgg tgccaatgtt ggccgcccag ccaggactct catcccatcc    420
accttcttca gggacttcgc catcaggtc gtggtgaagc ccagcagcac ccgtggtggc     480
gtgctcttcg ccatcactga cgccttccag aaggtcatct acctgggcct gcggctctca    540
ggtgtggagg acggccacca gcggatcatc ctctactaca cggagccagg ctcccatgtg    600
tcccaagaag ctgctgcctt tcggtgcct gtgatgaccc acaggtggaa ccgcttcgcc     660
atgattgtcc agggtgagga agtgaccctc ctcgtgaact gtgaggagca cagccgcatc    720 ccttccagc ggtcctccca ggctttggct tttgagtcca cgctggaat cttcatgggc      780 aatgcaggag ctacagggct cgagagattc actggctccc tccagcagct caccgtgcac    840
cccgacccca ggactcccga ggagctgtgt gaccctgaag agtcctcggc atctggagag    900
accagtgggc tgcaggaggc agacggagta gctgagatct agaagccgt cacctacact     960 caagcctcgc ccaaagaagc aaaagttgaa cccataaaca cacctccaac tccatcctcc    1020 cccctttgaag acatggaact ttctggtgaa cctgtacccg aggggaccct ggaaaccacc   1080
aacatgagca tcatccagca cagcagcccc aaacaagggt ctggtgagat cctgaatgac    1140
acactggagg gggttcattc tgtggatggt gaccccatta ctgacagcgg ctcaggggct    1200
ggggccttcc ttgacattgc tgaagaaaag aatttagcag caacagcagc ggggctggcc    1260
gaggtgccca tcagcactgc tggagaagca gaggccagca gtgtgcccac cggggggacca   1320 accctctcta tgtccacgga gaacccagag gaaggggtca ctccaggtcc agataatgaa    1380
gagcgtttac gagcaacagc agcaggggag gccgaggcac tcgccagcat gcctggggaa    1440
gtggaggcca gtggtgtggc ccccggggag ctggacctct ccatgtccgc ccagagcctc    1500
ggggaagagg ccactgtggg tccaagcagt gaagacagtt taacaacagc tgcagctgca    1560
accgaagtgt ccctcagtac ttttgaggat gaggaagcca gtggggtccc cacagatggc    1620
ctggctcccc tcacagccac catggccct gagcgggcag tcacttctgg tcctggtgat     1680
gaagaagact tggcagcagc cacaacagag gagcccctca tcacagctgg gggtgaagag    1740
tccggcagcc ctccccctga tgggccaccg ctgcccctgc ccacagtggc tcctgaaaga    1800
tggatcactc cagctcaaag agaacatgtg ggaatgaaag acaggctgg gcccaaagga     1860 gaaaagggtg atgctgggga ggagcttcct ggccctcctg aaccttctgg gctgttgga    1920 cccacggcag gagcagaagc agagggctct ggcctaggct ggggctcgga cgtcggctct   1980
ggctctggtg acctggtggg cagtgagcag ctgctgagag gtcctccagg accccaggg    2040 ccacctggct tacctgggat tccaggaaaa ccaggaactg atgttttcat gggacccct    2100 ggatctcctg gagaggatgg aacctgctggt gaacctgggc cccgggccc tgaggacag    2160 cctggagttg atggagccac cggccttccc gggatgaaag gggagaaggg agcaagaggg   2220
cctaatggct cagttggtga aaagggtgac cctggcaaca gaggcttacc tggacccccg   2280
gggaaaaagg acaagctggg ccctcctggg gtcatgggac cccagggcc tcctggaccc   2340 cctgggcccc caggccctgg atgcacaatg ggacttggat tcgaggatac cgaaggctct   2400
ggaagcaccc agctattgaa tgaacccaaa ctctccagac caacggctgc aattggtctc    2460
aaaggagaga aaggagaccg ggacccaag ggagaaaggg ggatggatgg agccagtatt     2520
gtgggacccc ctgggccgag agggccacct gggcacatca aggtcttgtc taattccttg    2580
```

```
atcaatatca cccatggatt catgaatttc tcggacattc ctgagctggt ggggcctccg    2640
gggccggacg ggttgcctgg gctgccagga tttccaggtc ctagaggacc aaaaggtgac    2700
actggtttac ctggctttcc aggactaaaa ggagaacagg gcgagaaggg agagccgggt    2760
gccatcctga cagaggacat tcctctggaa aggctgatgg ggaaaaggg tgaacctgga     2820 atgcatggag ccccaggacc aatggggccc aaaggaccac caggacataa aggagaattt    2880
ggccttcccg ggcgacctgg tcgcccagga ctgaatggcc tcaagggtac caaggagat    2940 ccaggggtca ttatgcaggg cccacctggc ttacctggcc ctccaggccc cctgggcca    3000 cctggagctg tgattaacat caaaggagcc attttcccaa tacccgtccg accacactgc    3060
aaaatgccag ttgatactgc tcatcctggg agtccagagc tcatcacttt tcacggtgtt    3120
aaaggagaga aggatcctg gggtcttcct ggctcaaagg gagaaaaagg cgaccaggga    3180
gcccagggac caccaggtcc tccacttgat ctagcttacc tgagcacttt tctgaacaac    3240
ttgaaggggg agaatggaga caaggggttc aaaggtgaaa aggagaaaa aggagacatt     3300 aatggcagct tccttatgtc tgggcctcca ggcctgcccg gaaatccagg cccggctggc    3360
caaaaagggg agacagtcgt tgggccccaa ggaccccag gtgctcctgg tctgcctggg     3420
ccacctggct ttggaagacc tggtgatcct gggccaccgg ggcccccggg gccaccagga    3480
cctccagcta tcctgggagc agctgtggcc cttccaggtc ccctggccc tccaggacag    3540 ccagggcttc ccggatccag aaacctggtc acagcattca gcaacatgga tgacatgctg    3600
cagaaagcgc atttggttat agaaggaaca ttcatctacc tgagggacag cactgagttt    3660
ttcattcgtg ttagagatgg ctggaaaaaa ttacagctgg agaactgat ccccattcct     3720 gccgacagcc ctccacccc tgcgctttcc agcaacccac atcagcttct gcctccacca    3780
aaccctattt caagtgccaa ttatgagaag cctgctctgc atttggctgc tctgaacatg    3840
ccattttctg gggacattcg agctgatttt cagtgcttca gcaggccag agctgcagga    3900 ctgttgtcca cctaccgagc attcttatct cccatttgc aagatctgtc caccattgtg     3960
aggaaagcag agagatacag ccttcccata gtgaacctca agggccaagt acttttaat    4020 aattgggact caattttttc tggccacgga ggtcagttca atatgcatat tccaatatac    4080
tcctttgatg tcgagacat aatgacagat ccttcttggc cccagaaagt catttggcat    4140
ggctccagcc cccatggcgt ccgccttgtg ataactact gtgaagcatg gcgaaccgcg     4200
gacacagcgg tcacgggact tgcctcccg ctgagcacgg ggaagattct ggaccagaaa    4260
gcatacagct gtgctaatcg gctaattgtc ctatgtatcg aaaacagttt catgacagac    4320
gctaggaagt aatggcctc tgatgattct taaagagttt tcaatttttt cttatgtgaa     4380
gagttgacac tgaaatctaa aatgtttaat tgttgtaaat attacagttt ttttttttt     4440 actacatatt ctttacaaca gcaaccaaag aaaacatacc tcaatacact caaaactgaa    4500
gacatagagg actcagatca aagacaaaat ctgatccata tattggtgct agattctgca    4560 ggaaaccca gcagtgtgaa cgcatcccaa cataggttaa gagcaagttg aaaacaaagg     4620
ccagattctg ccactgcatc cttcagacag ttatatcctc cttttaaacc attgttgttg    4680
agtgtaagat gtccttcatg ttttcttata aagtcagtgt ttagaaatgt tacccttct    4740 aagttatata cagatcaaat gctttttct ttcacgtaca tccatcattt gcaactgctg     4800
ttcgtacaca gaaacaggac tgctcaaatg atcctatttg tattttctga tgctatcaga    4860
ctctaatgtt ttttccccta aaatattatt gccatcatgc tttaggaatt tttatatttt    4920
```

-continued

| | |
|---|---:|
| tacacaatca tattttagta tggtgtctgt ttatgtaact ctgacttgct ggaaaagttg | 4980 |
| aaactccaaa taatctgaaa ctagaaaaga aatagcacat aattactacc ttcccctkgg | 5040 |
| cggctctcct cccccaaccc ccaccccaca attttatgac ttccatttgg caattgttga | 5100 |
| attataactg cgactgaaac aaacaggttc atagagatga attttctgag aaacatatat | 5160 |
| ctacatgttg tataattgga ttttttttcc atgtaagtga acataaaaac atcttttccg | 5220 |
| gg | 5222 |

```
<210> SEQ ID NO 68
<211> LENGTH: 4079
<212> TYPE: DNA
<213> ORGANISM: Homo sapiens

<400> SEQUENCE: 68
```

| | |
|---|---:|
| ggagcggcgg gcgggcggga gggctggcgg ggcgaacgtc tgggagacgt ctgaaagacc | 60 |
| aacgagactt tggagaccag agacgcgcct gggggggacct ggggcttggg gcgtgcgaga | 120 |
| tttcccttgc attcgctggg agctcgcgca gggatcgtcc catggccggg gctcggagcc | 180 |
| gcgaccettg gggggcctcc gggatttgct acctttttgg ctcccctgctc gtcgaactgc | 240 |
| tcttctcacg ggctgtcgcc ttcaatctgg acgtgatggg tgccttgcgc aaggagggcg | 300 |
| agccaggcag cctcttcggc ttctctgtgg ccctgcaccg gcagttgcag ccccgacccc | 360 |
| agagctggct gctggtgggt gctccccagg ccctggctct tcctgggcag caggcgaatc | 420 |
| gcactggagg cctcttcgct gcccgttga gcctggagga gactgactgc tacagagtgg | 480 |
| acatcgacca gggagctgat atgcaaaagg aaagcaagga gaaccagtgg ttgggagtca | 540 |
| gtgttcggag ccagggggcct gggggcaaga ttgttacctg tgcacaccga tatgaggcaa | 600 |
| ggcagcgagt ggaccagatc ctggagacgc gggatatgat tggtcgctgc tttgtgctca | 660 |
| gccaggacct ggccatccgg gatgagttgg atggtgggga atggaagttc tgtgagggac | 720 |
| gcccccaagg ccatgaacaa tttgggttct gccagcaggg cacagctgcc gccttctccc | 780 |
| ctgatagcca ctacctcctc tttggggccc caggaaccta taattggaag gggttgcttt | 840 |
| ttgtgaccaa cattgatagc tcagaccccg accagctggt gtataaaact ttggaccctg | 900 |
| ctgaccggct cccaggacca gccggagact tggccctcaa tagctactta ggcttctcta | 960 |
| ttgactcggg gaaaggtctg gtgcgtgcag aagagctgag ctttgtggct ggagcccccc | 1020 |
| gcgccaacca caagggtgct gtggttatcc tgcgcaagga cagcgccagt cgcctggtgc | 1080 |
| ccgaggttat gctgtctggg gagcgcctga cctccggctt tggctactca ctggctgtgg | 1140 |
| ctgacctcaa cagtgatggc tggccagacc tgatagtggg tgcccctac ttctttgagc | 1200 |
| gccaagaaga gctggggggt gctgtgtatg tgtacttgaa ccaggggggt cactgggctg | 1260 |
| ggatctcccc tctccggctc tgcggctccc ctgactccat gttcgggatc agcctggctg | 1320 |
| tcctggggga cctcaaccaa gatggctttc cagatattgc agtgggtgcc cccttttgatg | 1380 |
| gtgatgggaa agtcttcatc taccatggga gcagcctggg ggttgtcgcc aaaccttcac | 1440 |
| aggtgctgga gggcgaggct gtgggcatca agagcttcgg ctactccctg tcaggcagct | 1500 |
| tggatatgga tgggaaccaa taccctgacc tgctggtggg ctccctggct gacaccgcag | 1560 |
| tgctcttcag ggccagaccc atcctccatg tctcccatga ggtctctatt gctccacgaa | 1620 |
| gcatcgacct ggagcagccc aactgtgctg gcggccactc ggtctgtgtg gacctaaggg | 1680 |
| tctgtttcag ctacattgca gtccccagca gctatagccc tactgtggcc ctggactatg | 1740 |
| tgttagatgc ggacacagac cggaggctcc ggggccaggt tcccgtgtg acgttcctga | 1800 |

```
gccgtaacct ggaagaaccc aagcaccagg cctcgggcac cgtgtggctg aagcaccagc    1860
atgaccgagt ctgtggagac gccatgttcc agctccagga aaatgtcaaa gacaagcttc    1920
gggccattgt agtgaccttg tcctacagtc tccagacccc tcggctccgg cgacaggctc    1980
ctggccaggg gctgcctcca gtggccccca tcctcaatgc ccaccagccc agcacccagc    2040
gggcagagat ccacttcctg aagcaaggct gtggtgaaga caagatctgc cagagcaatc    2100
tgcagctggt ccacgcccgc ttctgtaccc gggtcagcga cacggaattc caacctctgc    2160
ccatggatgt ggatggaaca cagcccctgt ttgcactgag tgggcagcca gtcattggcc    2220
tggagctgat ggtcaccaac ctgccatcgg acccagccca gccccaggct gatggggatg    2280
atgcccatga agcccagctc ctggtcatgc ttcctgactc actgcactac tcaggggtcc    2340
gggccctgga ccctgcggag aagccactct gcctgtccaa tgagaatgcc tcccatgttg    2400
agtgtgagct ggggaacccc atgaagagag gtgcccaggt caccttctac ctcatcctta    2460
gcacctccgg gatcagcatt gagaccacgg aactggaggt agagctgctg ttggccacga    2520
tcagtgagca ggagctgcat ccagtctctg cacgagcccg tgtcttcatt gagctgccac    2580
tgtccattgc aggaatggcc attccccagc aactcttctt ctctggtgtg gtgaggggcg    2640
agagagccat gcagtctgag cgggatgtgg gcagcaaggt caagtatgag gtcacggttt    2700
ccaaccaagg ccagtcgctc agaaccctgg gctctgcctt cctcaacatc atgtggcctc    2760
atgagattgc caatgggaag tggttgctgt acccaatgca ggttgagctg gagggcgggc    2820
aggggcctgg gcagaaaggg cttgtctctc caggcccaa catcctccac ctggatgtgg    2880
acagtaggga taggaggcgg cgggagctgg agccacctga gcagcaggag cctggtgagc    2940
ggcaggagcc cagcatgtcc tggtggccag tgtcctctgc tgagaagaag aaaaacatca    3000
ccctggactg cgcccggggc acggccaact gtgtggtgtt cagctgccca ctctacagct    3060
ttgaccgcgc ggctgtgctg catgtctggg gccgtctctg gaacagcacc tttctggagg    3120
agtactcagc tgtgaagtcc ctggaagtga ttgtccgggc caacatcaca gtgaagtcct    3180
ccataaagaa cttgatgctc cgagatgcct ccacagtgat cccagtgatg gtatacttgg    3240
accccatggc tgtggtggca aaggagtgcc ctggtgggt catcctcctg gctgtactgg    3300
ctgggctgct ggtgctagca ctgctggtgc tgctcctgtg gaagatggga ttcttcaaac    3360
gggcgaagca ccccgaggcc accgtgcccc agtaccatgc ggtgaagatt cctcgggaag    3420
accgacagca gttcaaggag gagaagacgg gcaccatcct gaggaacaac tggggcagcc    3480
cccggcggga gggcccggat gcacacccca tcctggctgc tgacgggcat cccgagctgg    3540
gccccgatgg gcatccaggg ccaggcaccg cctaggttcc catgtcccag cctgcctgt    3600 ggctgccctc catcccttcc ccagagatgg ctccttggga tgaagagggt agagtgggct    3660
gctggtgtcg catcaagatt tggcaggatc ggcttcctca ggggcacaga cctctcccac    3720
ccacaagaac tcctcccacc caacttcccc ttagagtgct gtgagatgag agtgggtaaa    3780
tcagggacag ggccatgggg tagggtgaga agggcagggg tgtcctgatg caaaggtggg    3840
gagaagggat cctaatccct tcctctccca ttcaccctgt gtaacaggac cccaaggacc    3900
tgcctccccg gaagtgcctt aacctagagg gtcggggagg aggttgtgtc actgactcag    3960
gctgctcctt ctctagtttc ccctctcatc tgaccttagt ttgctgccat cagtctagtg    4020
gtttcgtggt ttcgtctatt tattaaaaaa tatttgagaa caaaaaaaaa aaaaaaaa     4079

<210> SEQ ID NO 69
```

```
<211> LENGTH: 6276
<212> TYPE: DNA
<213> ORGANISM: Homo sapiens

<400> SEQUENCE: 69
gagtgtggct gcagtgcgcc gggacaccag ggctccgcgc tccgcactca agaggctccc      60
gcgtcccaac ccctcgcgcc cgcgcgttcg cggatccagg ccgaggaccg aaagggccg      120 cccgagcccc cggggccggc gcccagagag cccagcaagg ccggccgccc tgccggtgtg     180
ccgccggcgg gtgcttctgg aagggccaat gcgttcgggc agcagccctg aagccgagcc     240
cgaggctaag tgggactgac cggggcccag agtggacgaa ccgccagcat ggggagagac     300
cagcgcgcgg tggccggccc tgccctacgg cggtggctgc tgctggggac agtgaccgtg     360
gggttcctcg cccagagcgt cttggcgggt gtgaagaagt ttgatgtgcc gtgtggagga     420
agagattgca gtggggctg ccagtgctac cctgagaaag gtggacgtgg tcagcctggg      480
ccagtgggcc cccaggggta caatgggcca ccaggattac aaggattccc cgggctgcag     540
ggacgtaaag gagacaaggg tgaaagggga gcccccggag taacaggacc caagggcgac     600
gtgggagcaa gaggcgtttc tggattccct ggtgccgatg gaattcctgg cacccggg      660 caaggtgggc caggggaag gccgggctac gatggctgca acggaaccca gggagactca     720
ggtccacagg ggccccccgg ctctgagggg ttcaccgggc ctcccgggcc caaggacca     780 aaagggcaga aaggtgagcc ttatgcactg cctaaagagg agcgcgacag atatcggggt     840
gaacctggag agcctggatt ggtcggtttc cagggacctc ccggccgccc tgggcatgtg     900
ggacagatgg gtccagttgg agctccaggg agaccaggac cacctggacc ccctggacca     960
aaaggacagc aaggcaacag aggacttggt ttctacggag ttaagggtga aaagggtgac    1020
gtagggcagc cgggacccaa cggattcca tcagacaccc tccaccccat catcgcgccc    1080
acaggagtca ccttccaccc agatcagtac aagggtgaaa aaggcagtga ggggaacca    1140 ggaataagag gcatttcctt gaagggagaa gaaggaatca tgggctttcc tggacttagg    1200
ggttaccctg gcttgagtgg tgaaaaagga tcaccaggac agaagggaag ccgaggcctg    1260
gatggctatc aagggcctga tgaccccgg ggacctaagg gagaagccgg agacccaggg    1320 cccctgac tacctgccta ctcccctcac ccttccctag caaaaggtgc cagaggtgac     1380
ccaggattcc caggggccca aggggagcca ggaagcagg gtgagccagg agacccgggc    1440
ctcccaggtc ccctggcct ctccattgga gatggagatc agaggagagg cctgccgggt    1500
gagatgggac ccaagggctt catcggagac cccggcatcc ctgcgctcta cgggggccca    1560
cctggacctg atggaaagcg agggcctcca ggaccccccg gctccctgg accacctgga    1620 cctgatggct tcctgtttgg gctgaaagga gcaaaggaa gagcaggctt ccctgggctt    1680
cccggctccc ctgagccccc cggaccaaag gggtggaaag gtgacgctgg ggaatgcaga    1740
tgtacagaag gcgacgaagc tatcaaaggt cttccaggac tgccaggacc caagggcttc    1800
gcaggcatca cggggagcc gggggaaa gggacaaag gagacccgg ccaacacggc    1860 ctccctgggt tccagggct caaggagtg cctggcaaca ttggtgctcc cggacccaaa    1920
ggagcaaaag gagattccag aacaatcaca accaaggtg agcgggaca gccggcgtc    1980 ccaggtgtgc ccgggatgaa aggtgacgat ggcagcccag ccgcgatgg gctcgatgga    2040 ttccccggcc tccaggccc tccggtgat ggcatcaagg gcctccagg gacccaggt    2100 tatccaggaa tacctggaac gaagggtact ccaggagaaa tggccccccc aggactgggc    2160 cttccccggcc tcaaaggcca acgtggtttc cctggagacg ccggcttacc tggaccacca    2220
```

-continued

```
ggcttcctgg gccctcctgg ccccgcaggg accccaggac aaatagattg tgacacagat    2280
gtgaaaaggg ccgttggagg tgacagacag gaggccatcc agccaggttg cataggaggg    2340
cccaagggat tgccaggcct gccaggaccc ccaggcccca caggtgccaa aggcctccga    2400
ggaatcccag gcttcgcagg agctgatgga ggaccagggc caggggcttg ccaggagac     2460 gcaggtcgtg aagggttccc aggacccccca gggttcatag gaccccgagg atccaaaggt   2520
gcagtgggcc tccctggccc agatggatcc ccaggtccca tcggcctgcc agggccagat    2580 gggcccctg gggaaagggg cctccctgga gaagtcctgg gagctcagcc cgggccacgg     2640
ggagatgctg gtgtgcctgg acagcctggg cttaaaggcc ttcccggaga cagaggcccc    2700
cctggattca gaggaagcca agggatgcct gggatgccag ggctgaaggg ccagccaggc    2760
ctcccaggac cttccggcca gccaggcctg tatgggcctc caggactgca tggattccca    2820
ggagctcctg gccaagaggg gcccttgggg ctgccaggaa tcccaggccg tgaaggtctg    2880
cctggtgata gaggggaccc tggggacaca ggcgctcctg gccctgtggg catgaaaggt    2940
ctctctggtg acagaggaga tgctggcttc acaggggagc aaggccatcc aggaagccct    3000
ggatttaaag gaattgatgg aatgcctggg accccgggc taaaaggaga tagaggctca     3060
cctgggatgg atggttttcca aggcatgcct ggactcaaag ggagaccggg gtttccaggg   3120
agcaaaggcg aggctggatt tttcggaata cccggtctga agggtctggc tggtgagcca    3180
ggttttaaag gcagccgagg ggaccctggg ccccaggac cacctcctgt catcctgcca     3240
ggaatgaaag acattaaagg agagaaagga gatgaagggc ctatggggct gaaaggatac    3300
ctgggcgcaa aaggtatcca aggaatgcca ggcatcccag ggctgtcagg aatccctggg    3360
ctgcctggga ggcccggcca catcaaagga gtcaaggag acatcggagt ccccggcatc    3420
cccggtttgc caggattccc tgggtggct ggcccccctg gaattacggg attcccagga     3480
ttcataggaa gccggggtga caaaggtgcc ccagggagag caggcctgta tggcgagatt    3540
ggcgcgactg gtgatttcgg tgacatcggg gacactataa atttaccagg aagaccaggc    3600
ctgaaggggg agcggggcac cactggaata ccaggtctga agggattctt tggagagaag    3660
ggaacagaag gtgacatcgg cttccctggg ataacaggcg tgactggagt ccaaggccct    3720
cctggactta aaggacaaac aggctttcca gggctgactg gcctccagg gtcgcaggga    3780 gagctggggc ggattggact gcctggtggc aaaggagatg atggctggcc gggagctccg    3840
ggcttaccag gttttccggg actccgtggg atcgcggct tacacggctt gccaggcacc     3900
aagggctttc caggatcccc aggttctgac atccacggag acccaggctt cccaggccct    3960 cctgggaaa gaggtgaccc aggagaggcc aacaccctc caggccctgt gggagtccca     4020
ggacagaaag gagaccaagg agctccaggg gaacgaggcc cacctgggag cccaggactt    4080
caggggttcc caggcatcac accccttcc aacatctctg ggcacctgg tgacaaaggg      4140 gcgccaggga tatttggcct gaaaggttat cggggcccac caggccacc aggttctgct     4200 gctcttcctg gaagcaaagg tgacacaggg aacccaggag ctccaggaac cccagggacc    4260
aaaggatggg ccggggactc cgggcccag gcaggcctg gtgtgtttgg tctcccagga      4320 gaaaagggc ccagggtga acaaggcttc atggggaaca ctggacccac cggggcggtg     4380
ggcgacagag gccccaaggg acccaaggga gacccaggat tccctggtgc cccgggact    4440 gtgggagccc ccgggattgc aggaatcccc cagaagattg ccgtccaacc agggacagtg    4500
ggtccccagg ggaggcgagg cccccctggg gcaccggggg agatggggcc ccagggcccc    4560
```

-continued

```
cccggagaac caggttttcg tggggctcca gggaaagctg ggccccaagg aagaggtggt      4620
gtgtctgctg ttcccggctt ccggggagat gaaggaccca taggccacca ggggccgatt      4680
ggccaagaag gtgcaccagg ccgtccaggg agcccgggcc tgccgggtat gccaggccgc      4740
agcgtcagca tcggctacct cctggtgaag cacagccaga cggaccagga gcccatgtgc      4800
ccggtgggca tgaacaaact ctggagtgga tacagcctgc tgtacttcga gggccaggag      4860
aaggcgcaca accaggacct ggggctggcg ggctcctgcc tggcgcggtt cagcaccatg      4920
cccttcctgt actgcaaccc tggtgatgtc tgctactatg ccagccggaa cgacaagtcc      4980
tactggctct ctaccactgc gccgctgccc atgatgcccg tggccgagga cgagatcaag      5040
ccctacatca gccgctgttc tgtgtgtgag gccccggcca tcgccatcgc ggtccacagt      5100
caggatgtct ccatcccaca ctgcccagct gggtggcgga gtttgtggat cggatattcc      5160
ttcctcatgc acacggcggc gggagacgaa ggcggtggcc aatcactggt gtcaccgggc      5220
agctgtctag aggacttccg cgccacacca ttcatcgaat gcaatggagg ccgcggcacc      5280
tgccactact acgccaacaa gtacagcttc tggctgacca ccattcccga gcagagcttc      5340
cagggctcgc cctccgccga cacgctcaag gccggcctca tccgcacaca catcagccgc      5400
tgccaggtgt gcatgaagaa cctgtgagcc ggcgcgtgcc aggaagggcc attttggtgc      5460
ttattcttaa cttattacct caggtgccaa cccaaaaatt ggctttattt ttttcttaaa      5520
aaaaaaaaag tctaccaaag gaatttgcat ccagcagcag cacttagacc tgccagccac      5580
tgtcaccgag cgggtgcaag cactcggggt ccctggaggg caagccctgc ccacagaaag      5640
ccaggagcag ccctggcccc catcagccct gctagacgca ccgcctgaag gcacagctaa      5700
ccacttcgca cacacccatg taaccactgc actttccaat gccacagaca actcacattg      5760
ttcaactccc ttctcggggt gggacagacg agacaacagc acacaggcag ccagccgtgg      5820
ccagaggctc gaggggctca ggggctcagg cacccgtccc cacacgaggg ccccgtgggt      5880
gggcctggcc ctgctttcta cgccaatgtt atgccagctc catgttctcc caaataccgt      5940
tgatgtgaat tattttaaag gcaaaaccgt gctctttatt ttagaaaaca ctgataatca      6000
cactgcggta ggtcattctt ttgccacatc cctatagacc actgggtttg gcaaaactca      6060
ggcagaagtg gagacccttc tagacatcac tgtcagcctt gctacttgaa ggtacacccc      6120
atagggtcgg aggtgctgtc cccactgccc cacgttgtcc ctgagattta acccctccac      6180
tgctgggggt gagctgtact cttctgactg ccccctcctg tgtaacgact acaaaataaa      6240
acttggttct gaatattttt aaaaaaaaaa aaaaaa                                6276
```

<210> SEQ ID NO 70
<211> LENGTH: 1018
<212> TYPE: DNA
<213> ORGANISM: Homo sapiens

<400> SEQUENCE: 70

```
ggcacgaggc tcaagattca cagcatctca gacgcagcct aggttcccat ggacttgtca        60
taagacaaaa gaggacagct gtgctgaggg gcagggtct gcagcctcct ggctgtgcca       120
ggaccacacc taccaaggcc gcaccaggat gtcggacacc gaggagcagg aatatgagga       180
ggagcagccg gaagaggagg ctgcggagga ggaggaggaa gaagaggaac gccccaaacc       240
aagccgcccc gtggtgcctc ctttgatccc gccaaagatc ccagaagggg agcgcgttga       300
cttcgatgac atccaccgca agcgcatgga gaaagacctg ctggagctgc agacactcat       360
cgatgtacat ttcgagcagc ggaagaagga ggaagaggag ctggttgcct tgaaggagcg       420
```

```
cattgagcgg cgccggtcag agagagccga gcaacagcgc ttcagaactg agaaggaacg      480
cgaacgtcag gctaagctgg cggaggagaa gatgaggaag gaagaggaag aggccaagaa      540
gcgggcagag gatgatgcca agaaaaagaa ggtgctgtcc aacatggggg cccatttttgg    600 cggctacctg gtcaaggcag aacagaagcg tggtaagcgg cagacggggc gggagatgaa     660
ggtgcgcatc ctctccgagc gtaagaagcc tctggacatt gactacatgg gggaggaaca     720
gctccgggag aaagcccagg agctgtcgga ctggatccac cagctggagt ctgagaagtt     780
cgacctgatg gcgaagctga acagcagaaa atatgagatc aacgtgctgt acaaccgcat     840
cagccacgcc cagaagttcc ggaagggggc agggaagggc cgcgttggag gccgctggaa     900
gtgaggatgc cgccccggac agtggcacct gggaagcctg ggagtgtttg tcccatcggt     960
agcttgaaat aaacgctccc ctcagacact caaaaaaaaa aaaaaaaaa aaaaaaa        1018

<210> SEQ ID NO 71
<211> LENGTH: 2895
<212> TYPE: DNA
<213> ORGANISM: Homo sapiens

<400> SEQUENCE: 71
ccgaggagcg ctcgggctgt ctgcggaccc tgccgcgtgc aggggtcgcg gccggctgga      60
gctgggagtg aggcggcgga ggagccaggt gaggaggagc caggaaggca gttggtggga     120
agtccagctt gggtccctga gagctgtgag aaggagatgc ggctgctgct ggccctgttg     180
ggggtcctgc tgagtgtgcc tgggcctcca gtcttgtccc tggaggcctc tgaggaagtg     240
gagcttgagc cctgcctggc tcccagcctg gagcagcaag agcaggagct gacagtagcc     300
cttgggcagc ctgtgcggct gtgctgtggg cgggctgagc gtggtggcca ctggtacaag     360
gagggcagtc gcctggcacc tgctggccgt gtacgggct ggaggggccg cctagagatt      420
gccagcttcc tacctgagga tgctggccgc tacctctgcc tggcacgagg ctccatgatc     480
gtcctgcaga atctcacctt gattacaggt gactccttga cctccagcaa cgatgatgag     540
gaccccaagt cccatagggga cctctcgaat aggcacagtt accccagca agcaccctac    600 tggacacacc cccagcgcat ggagaagaaa ctgcatgcag tacctgcggg gaacaccgtc     660
aagttccgct gtccagctgc aggcaacccc acgcccacca tccgctggct taaggatgga     720
caggcctttc atggggagaa ccgcattgga ggcattcggc tgcgccatca gcactggagt     780
ctcgtgatgg agagcgtggt gccctcggac cgcggcacat acacctgcct ggtagagaac     840
gctgtgggca gcatccgcta taactacctg ctagatgtgc tggagcggtc cccgcaccgg     900
cccatcctgc aggccgggct cccggccaac accacagccg tggtgggcag cgacgtggag     960
ctgctgtgca aggtgtacag cgatgcccag ccccacatcc agtggctgaa gcacatcgtc    1020
atcaacggca gcagcttcgg agccgacggt ttccccctatg tgcaagtcct aaagactgca  1080
gacatcaata gctcagaggt ggaggtcctg tacctgcgga acgtgtcagc cgaggacgca   1140
ggcgagtaca cctgcctcgc aggcaattcc atcggcctct cctaccagtc tgcctggctc    1200
acggtgctgc caggtactgg gcgcatcccc cacctcacat gtgacagcct gactccagca   1260
ggcagaacca agtctcccac tttgcagttc tccctggagt caggctcttc cggcaagtca   1320
agctcatccc tggtacgagg cgtgcgtctc tcctccagcg gccccgcctt gctcgccggc   1380
ctcgtgagtc tagatctacc tctcgaccca ctatggggagt tccccgggga caggctggtg    1440
cttgggaagc cctaggcga gggctgcttt ggccaggtag tacgtgcaga ggcctttggc     1500
```

-continued

```
atggaccctg cccggcctga ccaagccagc actgtggccg tcaagatgct caaagacaac    1560
gcctctgaca aggacctggc cgacctggtc tcggagatgg aggtgatgaa gctgatcggc    1620
cgacacaaga acatcatcaa cctgcttggt gtctgcaccc aggaagggcc cctgtacgtg    1680
atcgtggagt gcgccgccaa gggaaacctg cgggagttcc tgcgggcccg cgcccccca    1740
ggccccgacc tcagcccga cggtcctcgg agcagtgagg ggccgctctc cttcccagtc    1800
ctggtctcct gcgcctacca ggtggcccga ggcatgcagt atctggagtc ccggaagtgt    1860
atccaccggg acctggctgc cgcaatgtg ctggtgactg aggacaatgt gatgaagatt    1920
gctgactttg gctggcccg cggcgtccac cacattgact actataagaa aaccagcaac    1980
ggccgcctgc ctgtgaagtg gatggcgccc gaggccttgt ttgaccgggt gtacacacac    2040
cagagtgacg tgtggtcttt tgggatcctg ctatgggaga tcttcaccct cggggggctcc    2100
ccgtatcctg gcatcccggt ggaggagctg ttctcgctgc tgcgggaggg acatcggatg    2160
gaccgaccc cacactgccc cccagagctg tacgggctga tgcgtgagtg ctggcacgca    2220
gcgccctccc agaggcctac cttcaagcag ctggtggagg cgctggacaa ggtcctgctg    2280
gccgtctctg aggagtacct cgacctccgc ctgaccttcg accctattc ccctctggt    2340
ggggacgcca gcagcacctg ctcctccagc gattctgtct cagccacga ccccctgcca    2400
ttgggatcca gctccttccc cttcgggtct ggggtgcaga catgagcaag gctcaaggct    2460
gtgcaggcac ataggctggt ggccttgggc cttggggctc agccacagcc tgacacagtg    2520
ctcgaccttg atagcatggg gccctgcc cagagttgct gtgccgtgtc caagggccgt    2580
gcccttgccc ttggagctgc cgtgcctgtg tcctgatggc ccaaatgtca gggttctgct    2640
cggcttcttg gaccatggcg cttagtcccc atcccgggtt tggctgagcc tggctggaga    2700
gctgctatgc taaacctcct gcctcccaat accagcagga ggttctgggc ctctgaaccc    2760
cctttcccca cacctccccc tgctgctgct gccccagcgt cttgacggga gcattggccc    2820
ctgagcccag agaagctgga agcctgccga aaacaggagc aaatggcgtt ttataaatta    2880
tttttttgaa ataaa                                                     2895
```

```
<210> SEQ ID NO 72
<211> LENGTH: 1356
<212> TYPE: DNA
<213> ORGANISM: Homo sapiens

<400> SEQUENCE: 72
```

```
ttctcccgca accttccctt cgctccctcc cgtccccccc agctcctagc ctccgactcc     60
ctccccccct cacgcccgcc ctctcgcctt cgccgaacca agtggatta attacacgct    120
ttctgtttct ctccgtgctg ttctctcccg ctgtgcgcct gcccgcctct cgctgtcctc    180
tctcccccctc gccctctctt cggccccccc ctttcacgtt cactctgtct ctcccactat    240
ctctgccccc ctctatcctt gatacaacag ctgacctcat ttcccgatac cttttccccc    300
ccgaaaagta caacatctgg cccgccccag cccgaagaca gcccgtcctc cctggacaat    360
cagacgaatt ctccccccc ccccaaaaaa aaaagccatc ccccgctct gccccgtcgc    420
acattcggcc cccgcgactc ggccagagcg gcgctggcag aggagtgtcc ggcaggaggg    480
ccaacgcccg ctgttcggtt tgcgacacgc agcaggagg tgggcggcag cgtcgccggc    540
ttccagacac caatgggaat cccaatgggg aagtcgatgc tggtgcttct caccttcttg    600
gccttcgcct cgtgctgcat tgctgcttac cgccccagtg agaccctgtg cggcggggag    660
ctggtggaca ccctccagtt cgtctgtggg gaccgcggct tctacttcag caggcccgca    720
```

| | | | | |
|---|---|---|---|---|
| agccgtgtga | gccgtcgcag | ccgtggcatc | gttgaggagt | gctgtttccg | cagctgtgac | 780 |
| ctggccctcc | tggagacgta | ctgtgctacc | cccgccaagt | ccgagaggga | cgtgtcgacc | 840 |
| cctccgaccg | tgcttccgga | caacttcccc | agatacccg | tgggcaagtt | cttccaatat | 900 |
| gacacctgga | agcagtccac | ccagcgcctg | cgcaggggcc | tgcctgccct | cctgcgtgcc | 960 |
| cgccggggtc | acgtgctcgc | caaggagctc | gaggcgttca | ggaggccaa | acgtcaccgt | 1020 |
| ccccctgattg | ctctacccac | ccaagacccc | gcccacgggg | gcgcccccc | agagatggcc | 1080 |
| agcaatcgga | agtgagcaaa | actgccgcaa | gtctgcagcc | cggcgccacc | atcctgcagc | 1140 |
| ctcctcctga | ccacggacgt | ttccatcagg | ttccatcccg | aaaatctctc | ggttccacgt | 1200 |
| cccctgggg | cttctcctga | cccagtcccc | gtgccccgcc | tccccgaaac | aggctactct | 1260 |
| cctcggcccc | ctccatcggg | ctgaggaagc | acagcagcat | cttcaaacat | gtacaaaatc | 1320 |
| gattggcttt | aaacacccctt | cacatacccct | cccccc | | | 1356 |

<210> SEQ ID NO 73
<211> LENGTH: 2281
<212> TYPE: DNA
<213> ORGANISM: Homo sapiens

<400> SEQUENCE: 73

| | | | | | | |
|---|---|---|---|---|---|---|
| aaacaataag | catatctaag | caactacgat | atctgtatgg | atcaggccaa | agtcccgcta | 60 |
| agattctcca | atgttttcat | ggtctgagcc | ccctcctgt | tcccatctcc | actgcccctc | 120 |
| ggccctgtct | gtgccctgcc | tctcagagga | gggggctcag | atggtgcggc | ctgagtgtgc | 180 |
| ggccggcggc | atttgggata | caccgtagg | gtgggcgggg | tgtgtcccag | gcctaattcc | 240 |
| atctttccac | catgacagag | atgcccttgt | gaggctggcc | tccttggcgc | ctgtccccac | 300 |
| ggcccccgca | gcgtgagcca | cgatgctccc | catacccccac | ccattcccga | tacaccttac | 360 |
| ttactgtgtg | ttggcccagc | cagagtgagg | aaggagtttg | ccacattgg | agatggcggt | 420 |
| agctgagcag | acatgccccc | acgagtagcc | tgactccctg | gtgtgctcct | ggaaggaaga | 480 |
| tcttggggac | ccccccaccg | gagcacacct | agggatcatc | tttgcccgtc | tcctggggac | 540 |
| ccccaagaa | atgtggagtc | ctcgggggcc | gtgcactgat | gcggggagtg | tgggaagtct | 600 |
| ggcggttgga | ggggtgggtg | ggggcagtg | ggggctgggc | gggggagtc | ctggggtagg | 660 |
| aagtggtccc | gggagatttt | ggatggaaaa | gtcaggagga | ttgacagcag | acttgcagaa | 720 |
| ttacatagag | aaattaggaa | ccccaaatt | tcatgtcaat | tgatctattc | ccctctttg | 780 |
| tttcttgggg | catttttcct | ttttttttt | tttgttttt | ttttaccccct | ccttagctttt | 840 |
| atgcgctcag | aaaccaaatt | aaaccccccc | cccatgtaac | aggggggcag | tgacaaaagc | 900 |
| aagaacgcac | gaagccagcc | tggagaccac | cacgtcctgc | cccccgccat | ttatcgccct | 960 |
| gattggattt | tgtttttcat | ctgtcccctgt | tgcttgggtt | gagttgaggg | tggagcctcc | 1020 |
| tgggggcac | tggccactga | gccccccttgg | agaagtcaga | ggggagtgga | gaaggccact | 1080 |
| gtccggcctg | gcttctgggg | acagtggctg | gtccccagaa | gtcctgaggg | cggagggggg | 1140 |
| ggttgggcag | ggtctcctca | ggtgtcagga | gggtgctcgg | aggccacagg | aggggctcc | 1200 |
| tggctggcct | gaggctggcc | ggaggggaag | gggctagcag | gtgtgtaaac | agagggttcc | 1260 |
| atcaggctgg | ggcagggtgg | ccgccttccg | cacacttgag | gaaccctccc | ctctccctcg | 1320 |
| gtgacatctt | gcccgcccct | cagcaccctg | ccttgtctcc | aggaggtccg | aagctctgtg | 1380 |
| ggacctcttg | ggggcaaggt | ggggtgaggc | cggggagtag | ggaggtcagg | cgggtctgag | 1440 |

```
cccacagagc aggagagctg ccaggtctgc ccatcgacca ggttgcttgg gccccggagc      1500
ccacgggtct ggtgatgcca tagcagccac caccgcggcg cctagggctg cggcagggac      1560
tcggcctctg ggaggtttac ctcgccccca cttgtgcccc cagctcagcc ccctgcacg       1620 cagcccgact agcagtctag aggcctgagg cttctgggtc ctggtgacgg ggctggcatg      1680
accccggggg tcgtccatgc cagtccgcct cagtcgcaga gggtccctcg gcaagcgccc      1740
tgtgagtggg ccattcggaa cattggacag aagcccaaag agccaaattg tcacaattgt      1800
ggaacccaca ttggcctgag atccaaaacg cttcgaggca ccccaaatta cctgcccatt      1860
cgtcaggaca cccaccccac cagtgttata ttctgcctcg ccggagtggg tgttcccggg      1920
ggcacttgcc gaccagcccc ttgcgtcccc aggtttgcag ctctcccctg gccactaac       1980 catcctggcc cgggctgcct gtctgacctc cgtgcctagt cgtggctctc catcttgtct      2040
cctccccgtg tccccaatgt cttcagtggg gggccccctc ttgggtcccc tcctctgcca      2100
tcacctgaag accccacgc caaacactga atgtcacctg tgcctgccgc ctcggtccac       2160
cttgcggccc gtgtttgact caactcagct cctttaacgc taatatttcc ggcaaaatcc      2220
catgcttggg ttttgtcttt aaccttgtaa cgcttgcaat cccaataaag cattaaaagt      2280
c                                                                      2281

<210> SEQ ID NO 74
<211> LENGTH: 1124
<212> TYPE: DNA
<213> ORGANISM: Homo sapiens

<400> SEQUENCE: 74
cgggaaacct gcactgactt ttttctcctt ttggagggag agcagagacc atgtctgaca        60
tagaagaggt ggtggaagag tacgaggagg aggagcagga agaagcagct gttgaagagc       120
aggaggaggc agcggaagag gatgctgaag cagaggctga gaccgaggag accagggcag       180
aagaagatga agaagaagag gaagcaaagg aggctgaaga tggcccaatg gaggagtcca       240
aaccaaagcc caggtcgttc atgcccaact tggtgcctcc caagatcccc gatggagaga       300
gagtggactt tgatgacatc caccggaagc gcatggaaa ggacctgaat gagttgcagg       360
cgctgattga ggctcacttt gagaacagga gaaagaggga ggaggagctc gtttctctca       420
aagacaggat cgagagacgt cgggcagagc gggccgagca gcagcgcatc cggaatgagc       480
gggagaagga gcggcagaac cgcctggctg aagagagggc tcgacgagag gaggaggaga       540
acaggaggaa ggctgaggat gaggcccgga agaagaaggc tttgtccaac atgatgcatt       600 ttggggtta catccagaag caggcccaga cagagcggaa aagtgggaag aggcagactg        660
agcgggaaaa gaagaagaag attctggctg agaggaggaa ggtgctggcc attgaccacc       720
tgaatgaaga tcagctgagg gagaaggcca aggagctgtg gcagagcatc tataacttgg       780 aggcagaaa gttcgacctg caggagaagt tcaagcagca gaaatatgag atcaatgttc        840
tccgaaacag gatcaacgat aaccagaaag tctccaagac ccgcgggaag gctaaagtca       900
ccgggcgctg gaaatagagc ctggcctcct tcaccaaaga tctgctcctc gctcgcacct       960
gcctccggcc tgcactcccc cagttcccgg ccctcctgg gcaccccagg cagctcctgt       1020
ttggaaatgg ggagctggcc taggtgggag ccaccactcc tgcctgcccc cacacccact      1080
ccacaccagt aataaaaagc caccacacac tgaaaaaaaa aaaa                       1124

<210> SEQ ID NO 75
<211> LENGTH: 855
```

<212> TYPE: DNA
<213> ORGANISM: Homo sapiens

<400> SEQUENCE: 75

```
atctcatctc ccagacgcca cgtctctcgg tttcttctta gatcactcct ctgccaaaga      60
tcccaacaag acaacatggc tcccaagaag cctgagccta agaaggaggc agccaagcca     120
gctccagctc cagctccagc ccctgcacca gcccctgccc cagctcctga ggctcccaag     180
gaacctgcct ttgaccccaa gagtgtaaag atagacttca ctgccgacca gattgaagag     240
ttcaaagagg cctttcatt gtttgaccgg accccgactg gagagatgaa gatcacctac     300
ggccagtgcg gggatgtact gcgggccctg gccagaaacc ctaccaatgc cgaggtgctg     360
cgtgtgctgg gcaagcccaa gcctgaagag atgaatgtca gatgctgga ctttgagacg     420
ttcttgccca tcctgcagca catttcccgc aacaaggagc agggcaccta tgaggacttc     480
gtggagggcc tgcgtgtctt tgacaaggag agcaatggca cggtcatggg tgctgagctt     540
cggcacgtcc ttgccaccct gggagagaag atgactgagg ctgaagtgga gcagctgtta     600
gctgggcaag aggatgccaa tggctgcatc aattatgaag cctttgtcaa gcacatcatg     660
tcagggtgaa gcagagtctt ccaggtgcct ggcccttggc tttagccata ccagggtgag     720
ttaaagagag gccccggctg ggtgagctga gatggagtcc tcgacttatc accacaccac     780
tgccccaagg accttacagg ccctccctgt aataaacag ctctaacacg gccaggctgg     840
gctctgggat tctga                                                      855
```

<210> SEQ ID NO 76
<211> LENGTH: 1404
<212> TYPE: DNA
<213> ORGANISM: Homo sapiens

<400> SEQUENCE: 76

```
gccgggcagc catggctgag acactcttct ggactcctct cctcgtggtt ctcctggcag      60
ggctggggga caccgaggcc cagcagacca cgctacaccc acttgtgggc cgtgtctttg     120
tgcacaccttt ggaccatgag acgtttctga gccttcctga gcatgtcgct gtcccacccg     180
ctgtccacat cacctaccac gcccacctcc agggacaccc agacctgccc cggtggctcc     240
gctacaccca cgcagccccc caccaccctg gcttcctcta cggctctgcc accccagaag     300
atcgtgggct ccaggtcatt gaggtcacag cctacaatcg ggacagcttt gataccactc     360
ggcagaggct ggtgctggag attggggacc cagaaggccc cctgctgcca taccaagccg     420
agttcctggt gcgcagccac gatgcggagg aggtgctgcc ctcaacacct gccagccgct     480
tcctctcagc cttgggggga ctctgggagc ccggagagct tcagctgctc aacgtcacct     540
ctgccttgga ccgtgggggc cgtgtccccc ttcccattga gggccgaaaa gaagggggtat     600
acattaaggt gggttctgcc tcaccttttt ctacttgcct gaagatggtg gcatcccccg     660
atagccacgc ccgctgtgcc cagggccagc ctccacttct gtcttgctac gacaccttgg     720
caccccactt ccgcgttgac tggtgcaatg tgacccctggt ggataagtca gtgccggagc     780
ctgcagatga ggtgcccacc ccaggtgatg ggatcctgga gcatgaccc ttcttctgcc     840
cacccactga ggccccagac cgtgacttct tggtggatgc tctggtcacc ctcctggtgc     900
ccctgctggt ggcctgcctt ctcaccttgc tgctggccta tgtcatgtgc tgccggcggg     960
agggaaggct gaagagagac ctggctacct ccgacatcca gatggtccac cactgcacca    1020
tccacgggaa cacagaggag ctgcggcaga tggcggccag ccgcgaggtg ccccggccac    1080
```

-continued

| | |
|---|---|
| tctccaccct gcccatgttc aatgtgcaca caggtgagcg gctgcctccc cgcgtggaca | 1140 |
| gcgcccaggt gccctcatt ctggaccagc actgacagcc cagccagtgg ttccaggtcc | 1200 |
| agccctgact tcatcctccc ttctctgtcc acaccacgag tggcacatcc cacctgctga | 1260 |
| ttccagctcc tggccctcct ggaacccagg ctctaaacaa gcagggagag ggggtgggt | 1320 |
| ggggtgagag tgtgtggagt aaggacattc agaataaata tctgctgctc tgctcaccaa | 1380 |
| ttgctgctgg cagcctctcc cgtc | 1404 |

<210> SEQ ID NO 77
<211> LENGTH: 1610
<212> TYPE: DNA
<213> ORGANISM: Homo sapiens

<400> SEQUENCE: 77

| | |
|---|---|
| gcatcagaaa ccagcacacc agagcaccag ggcgggggc ttctccgcag caagtttcca | 60 |
| aacaagccct cagtgaacat cattgaagcg tgactgcctg tctgcaggga gaaggattcc | 120 |
| attttcttc tcagctggtc cccaggccca cgggcacagg gagagggaca actgcagcag | 180 |
| tggggaggag gcacagctag ctgcacagtt ctctcttctc cttgtcctag tcagatgaag | 240 |
| gaggctgcac tacaaaccca aattctgcaa aaaaataaa aataagccac aaaactaaaa | 300 |
| ggcctggccc cattctggaa aaggcaaagc tgcatgagac acagccttct gcctcctcgc | 360 |
| ctctcctgga ctggcttcct cttgagaaa atgcacaaag ccctgggaga tgacaagcac | 420 |
| aaggactgac tcaagctgtg tctttcagac caaggaacat cagagaagct gtggggctgc | 480 |
| ctgccaggca ggatcatggc tgccatcaag ccttttctgg atccagccat caaggacatg | 540 |
| tttgtggtgt gatgcacact tttgcaagcg tgtaagatgt tacctggttt gtctcttttg | 600 |
| gaaaacaaaa atcagaaggc tgcattctag agggcagaga aattccccg aagactgagc | 660 |
| tggttgcctg catcctctat cttctttgac ccttatgact gaaagatcat cagtttggaa | 720 |
| ggtactggtc caatttattt aggaagtatc tcttggagtt tcagaaatgc tagcttggac | 780 |
| aactgaaaag tcacatcaca gctggcattc tgggggctac caaaacaccc cttctggagt | 840 |
| agaagctgct ggaaggcagg cctgagccat tcaccacgga caggaagagc agctctggct | 900 |
| atcaccactg gcctctgggg tcttcatatc ttgccatctc atccagggtt ccatgaaagt | 960 |
| tacccagggt cctcatgtcc ttccttagag cctgagtggt gtgaggtgac aggtctctct | 1020 |
| ctccactgcc cctttctggt ttaaaaaaat ggtgcttgat gagggaaggt agactcttcc | 1080 |
| ctaggactga cgagttacgg ctgccagatg cctgcatggg aagaggtgga catctgcatc | 1140 |
| ttccattggt ggtcaaggat gggtgtggga gaaccacacc tagtgcaagc ctggtactca | 1200 |
| gtaaatattt gttgaaatga atgataagag cattggtccc caagccagag agccagaagc | 1260 |
| catcacccaa tgaccgcccc ttccttccgg tctacaagag ctctcaaggc tgggtctgcc | 1320 |
| accactctgc tttgcccaag tgtgacagca ctggggagga gagacaggat aaagggcaga | 1380 |
| tgtcagcaat actaagggct tcctcatggg agggcatgag gctccactca ttgtcttgtg | 1440 |
| acttccatcc ctgctgaatg gggctgcaag gccaaggctc cttaggggag aggtccttac | 1500 |
| ctctgatcca cttagagcaa taaccacttt ttaaatgtaa aataaaaga caaatgaaaa | 1560 |
| ggcaaaaaaa aaaaaaaaaa aaaaaaaaa aaaaaaaaa aaaaaaaaa | 1610 |

<210> SEQ ID NO 78
<211> LENGTH: 1356
<212> TYPE: DNA
<213> ORGANISM: Homo sapiens

<400> SEQUENCE: 78

```
ttctcccgca accttccctt cgctccctcc cgtccccccc agctcctagc ctccgactcc       60
ctcccccct cacgcccgcc ctctcgcctt cgccgaacca aagtggatta attacacgct      120
ttctgtttct ctccgtgctg ttctctcccg ctgtgcgcct gcccgcctct cgctgtcctc      180
tctcccctc gccctctctt cggcccccc ctttcacgtt cactctgtct ctcccactat       240
ctctgccccc ctctatcctt gatacaacag ctgacctcat ttcccgatac cttttccccc      300
ccgaaaagta caacatctgg cccgcccag cccgaagaca gcccgtcctc cctggacaat      360
cagacgaatt ctccccccc cccaaaaaa aaaagccatc ccccgctct gcccgtcgc       420
acattcggcc cccgcgactc ggccagagcg gcgctggcag aggagtgtcc ggcaggaggg     480
ccaacgcccg ctgttcggtt tgcgacacgc agcagggagg tgggcggcag cgtcgccggc     540
ttccagacac caatgggaat cccaatgggg aagtcgatgc tggtgcttct caccttcttg     600
gccttcgcct cgtgctgcat tgctgcttac cgccccagtg agaccctgtg cggcggggag     660
ctggtggaca ccctccagtt cgtctgtggg gaccgcggct tctacttcag caggcccgca     720
agccgtgtga gccgtcgcag ccgtggcatc gttgaggagt gctgtttccg cagctgtgac     780
ctggccctcc tggagacgta ctgtgctacc cccgccaagt ccgagaggga cgtgtcgacc     840
cctccgaccg tgcttccgga caacttcccc agatacccccg tgggcaagtt cttccaatat     900
gacacctgga agcagtccac ccagcgcctg cgcaggggcc tgcctgccct cctgcgtgcc     960
cgccggggtc acgtgctcgc caaggagctc gaggcgttca gggaggccaa acgtcaccgt    1020
cccctgattg ctctacccac ccaagacccc gccacggggg cgcccccccc agagatggcc    1080
agcaatcgga agtgagcaaa actgccgcaa gtctgcagcc cggcgccacc atcctgcagc    1140
ctcctcctga ccacggacgt ttccatcagg ttccatcccg aaaatctctc ggttccacgt    1200
cccctgggg cttctcctga cccagtcccc gtgccccgcc tccccgaaac aggctactct    1260
cctcggcccc ctccatcggg ctgaggaagc acagcagcat cttcaaacat gtacaaaatc    1320
gattggcttt aaacaccctt cacataccct cccccc                              1356
```

<210> SEQ ID NO 79
<211> LENGTH: 2330
<212> TYPE: DNA
<213> ORGANISM: Homo sapiens

<400> SEQUENCE: 79

```
gaattcggca cgagcgacgc ggcccagagg ccaggaacat tccgcgcgtg gaccagccgg       60
gccagggcga tgctgcgggt gcggtgtctg cgcggcggga gccgcggcgc cgaggcggtg      120
cactacatcg gatctcggct tggacgaacc ttgacaggat gggtgcagcg aactttccag      180
agcacccagg cagctacggc ttcctcccgg aactcctgtg cagctgacga caaagccact      240
gagcctctgc ccaaggactg ccctgtctct tcttacaacg aatgggaccc cttagaggaa      300
gtgatagtgg gcagagcaga aaacgcctgt gttccaccgt tcaccatcga ggtgaaggcc      360
aacacatatg aaaagtactg gccattttac cagaagcaag gagggcatta ttttcccaaa      420
gatcatttga aaaaggctgt tgctgaaatt gaagaaatgt gcaatatttt aaaaacggaa      480
ggagtgacag taaggaggcc tgaccccatt gactggtcat gaagtataaa actcctgat      540
tttgagtcta cgggttata cagtgcaatg cctcgagaca tcctgatagt tgtgggcaat      600
gagattatcg aggctcccat ggcatggcgt tcacgcttct ttgagtaccg agcgtacagg      660
```

| | |
|---|---|
| tcaattatca aagactactt ccaccgtggc gccaagtgga caacagctcc taagcccaca | 720 |
| atggctgatg agctttataa ccaggattat cccatccact ctgtagaaga cagacacaaa | 780 |
| ttggctgctc agggaaaatt tgtgacaact gagtttgagc catgctttga tgctgctgac | 840 |
| ttcattcgag ctggaagaga tattttttgca cagagaagcc aggttacaaa ctacctaggc | 900 |
| attgaatgga tgcgtaggca tcttgctcca gactacagag tgcatatcat ctcctttaaa | 960 |
| gatcccaatc ccatgcatat tgatgctacc ttcaacatca ttggacctgg tattgtgctt | 1020 |
| tccaaccctg accgaccatg tcaccagatt gatcttttca gaaagcagg atggactatc | 1080 |
| attactcctc caacaccaat catcccagac gatcatccac tctggatgtc atccaaatgg | 1140 |
| ctttccatga atgtcttaat gctagatgaa aaacgtgtta tggtggatgc caatgaagtt | 1200 |
| ccaattcaaa agatgtttga aaagctgggt atcactacca ttaaagttaa cattcgtaat | 1260 |
| gccaattccc tgggaggagg cttccattgc tggacctgcg atgtccggcg ccgaggcacc | 1320 |
| ctacagtcct acttggactg aacaggcctg atggagcttg tggctggcct cagatacacc | 1380 |
| taagaagctt aggggcaagg ttcattctcc tgctttaaaa agtgcatgaa ctgtagtgct | 1440 |
| ttaaacaatc atctccttaa caggggtcgt aagcctggtt tgcttctatt acttttcttt | 1500 |
| gacataaaga aaataacttc tgctaggtat tactctctac tcctaaagtt atttactatt | 1560 |
| tggcttcaag tataaaattt tggtgaatgt gtaccaagaa aaaattagtc acctgagtaa | 1620 |
| cttggccact aataattaac catctacctc tgttttaat tttctttcca aaaggcagct | 1680 |
| tgaaatgttg gtcctaatct taatttttttt tcctcttcta tagacttgag aatgtttttc | 1740 |
| tctaaatgag agaaagactt agaatgtaca cagatccaaa atagaatcag attatctctt | 1800 |
| tttttctaaa ggagagaaag acttagaaca tacacagatc ctaagtagaa ccaggtaatt | 1860 |
| gtctcttttt ctaataagga atttgggtaa ttttttaattt tttgtttttt aaaaaataac | 1920 |
| ctagactatg caaaacatca aagtgaattt tccatgaatg ttttaatat tctcatctca | 1980 |
| acattgtgat atatgctact aaaaaccttt tcatatacat cttacctcat ttcaagtgaa | 2040 |
| ttattttaat cttttttctct ctttccaaaa atttacagga atgtttagtg taattggatt | 2100 |
| tcgctatcag ttcccatcct taagttttga tattcaatat ctgatagata cactgcatct | 2160 |
| ttggtcatct aagatttgtt tacaaatgtg caaattattt agagcataga ctttataagc | 2220 |
| attaaaaaaa actaatggag gtaaaaccta aatgcgatgt gaaataattt tagtgttgat | 2280 |
| actgtatgtg tatttttatt ctaataaact tttgtgttcc agattgaaaa | 2330 |

<210> SEQ ID NO 80
<211> LENGTH: 2436
<212> TYPE: DNA
<213> ORGANISM: Homo sapiens

<400> SEQUENCE: 80

| | |
|---|---|
| ggctcccaca gtgggtggcg gaaaacaact ttcagagctt tgtaaatgcc agttgtgccc | 60 |
| atcctcagct gctaaaagga agaagcattt ttgctgttag cccagatggc tttgtgtgtg | 120 |
| atgattttcc caaccccag atcacggttc agccagaaac acagtcggca ataaaaggtt | 180 |
| ccaatttgag tttcatctgc tcagctgcca gcagcagtga ttccccaatg acttttgctt | 240 |
| ggaaaaaaga caatgaacta ctgcatgatg ctgaaatgga aaattatgca cacctccggg | 300 |
| cccaaggtgg cgaggtgatg gagtatacca ccatccttcg gctgcgcgag gtggaatttg | 360 |
| ccagtgaggg gaaatatcag tgtgtcatct ccaatcactt tggttcatcc tactctgtca | 420 |
| aagccaagct tacagtaaat atgcttccct cattcaccaa gaccccatg gatctcacca | 480 |

```
tccgagctgg ggccatggca cgcttggagt gtgctgctgt ggggcaccca gccccccaga    540
tagcctggca gaaggatggg ggcacagact cccagctgc acgggagaga cgcatgcatg     600
tgatgcccga ggatgacgtg ttctttatcg tggatgtgaa gatagaggac attgggtat     660 acagctgcac agctcagaac agtgcaggaa gtatttcagc aaatgcaact ctgactgtcc    720
tagaaacacc atcattttg cggccactgt tggaccgaac tgtaaccaag ggagaaacag     780
ccgtcctaca gtgcattgct ggaggaagcc ctcccctaa actgaactgg accaaagatg     840
atagcccatt ggtggtaacc gagaggcact ttttgcagc aggcaatcag cttctgatta     900
ttgtggactc agatgtcagt gatgctggga atacacatg tgagatgtct aacacccttg     960
gcactgagag aggaaacgtg cgcctcagtg tgatccccac tccaacctgc gactcccctc    1020
agatgacagc cccatcgtta gacgatgacg gatgggccac tgtgggtgtc gtgatcatag    1080
ccgtggtttg ctgtgtggtg ggcacgtcac tcgtgtgggt ggtcatcata taccacacaa    1140
ggcggaggaa tgaagattgc agcattacca acacagatga gaccaacttg ccagcagata    1200
ttcctagtta tttgtcatct cagggaacgt tagctgacag gcaggatggg tacgtgtctt    1260
cagaaagtgg aagccaccac cagtttgtca catcttcagg tgctggattt ttcttaccac    1320
aacatgacag tagtgggacc tgccatattg acaatagcag tgaagctgat gtggaagctg    1380
ccacagatct gttcctttgt ccgttttgg gatccacagg ccctatgtat ttgaagggaa     1440
atgtgtatgg ctcagatcct tttgaaacat atcatacagg ttgcagtcct gacccaagaa    1500
cagttttaat ggaccactat gagcccagtt acataaagaa aaaggagtgc tacccatgtt    1560
ctcatccttc agaagaatcc tgcgaacgga gcttcagtaa tatatcgtgg ccttcacatg    1620
tgaggaagct acttaacact agttactctc acaatgaagg acctggaatg aaaaatctgt    1680
gtctaaacaa gtcctcttta gattttagtg caaatccaga gccagcgtcg gttgcctcga    1740
gtaattcttt catgggtacc tttggaaaag ctctcaggag acctcaccta gatgccatt    1800 caagctttgg acagccatca gattgtcagc caagagcctt ttatttgaaa gctcattctt    1860
ccccagactt ggactctggg tcagaggaag atgggaaaga aaggacagat ttcaggaag     1920 aaaatcacat ttgtaccttt aaacagactt tagaaaacta caggactcca aatttttcagt   1980 cttatgactt ggacacatag actgaatgag accaaaggaa aagcttaaca tactacctca    2040
agtgaacttt tatttaaaag agagagaatc ttatgttttt taaatggagt tatgaatttt    2100
aaaaggataa aaatgcttta tttatacaga tgaaccaaaa ttacaaaaag ttatgaaaat    2160
ttttatactg ggaatgatgc tcatataaga ataccttttt aaactatttt ttaactttgt    2220
tttatgcaaa aaagtatctt acgtaaatta atgatataaa tcatgattat tttatgtatt    2280
tttataatgc cagatttctt tttatggaaa atgagttact aaagcatttt aaataatacc    2340
tgccttgtac cattttttaa atagaagtta cttcattata ttttgcacat tatatttaat    2400
aaaatgtgtc aatttgaaaa aaaaaaaaa aaaaaa                              2436

<210> SEQ ID NO 81
<211> LENGTH: 2121
<212> TYPE: DNA
<213> ORGANISM: Homo sapiens

<400> SEQUENCE: 81
ctgctcgcgg ccgccaccgc cgggccccgg ccgtccctgg ctcccctcct gcctcgagaa    60
gggcagggct tctcagaggc ttggcgggaa aaaagaacgg agggagggat cgcgctgagt    120
```

-continued

```
ataaaagccg gttttcgggg ctttatctaa ctcgctgtag taattccagc gagaggcaga    180
gggagcgagc gggcggccgg ctagggtgga agagccgggc gagcagagct gcgctgcggg    240
cgtcctggga agggagatcc ggagcgaata gggggcttcg cctctggccc agccctcccg    300
cttgatcccc caggccagcg gtccgcaacc cttgccgcat ccacgaaact ttgcccatag    360
cagcgggcgg gcactttgca ctggaactta caacacccga gcaaggacgc gactctcccg    420
acgcggggag gctattctgc ccatttgggg acacttcccc gccgctgcca ggacccgctt    480
ctctgaaagg ctctccttgc agctgcttag acgctggatt tttttcgggt agtggaaaac    540
cagcagcctc ccgcgacgat gcccctcaac gttagcttca ccaacaggaa ctatgacctc    600
gactacgact cggtgcagcc gtatttctac tgcgacgagg aggagaactt ctaccagcag    660
cagcagcaga gcgagctgca gccccggcg cccagcgagg atatctggaa gaaattcgag    720
ctgctgccca ccccgcccct gtccctagc cgccgctccg ggctctgctc gccctcctac    780
gttgcggtca caccctttctc ccttcgggga gacaacgacg gcgtggcgg gagcttctcc    840 acggccgacc agctggagat ggtgaccgag ctgctgggag gagacatggt gaaccagagt    900
ttcatctgcg acccggacga cgagaccttc atcaaaaaca tcatcatcca ggactgtatg    960
tggagcggct ctcggccgc cgccaagctc gtctcagaga gctggcctc ctaccaggct   1020 gcgcgcaaag acagcggcag cccgaacccc gcccgcggcc acagcgtctg ctccacctcc   1080
agcttgtacc tgcaggatct gagcgccgcc gcctcagagt gcatcgaccc ctcggtggtc   1140 ttccccctacc ctctcaacga cagcagctcg cccaagtcct gcgcctcgca agactccagc   1200
gccttctctc cgtcctcgga ttctctgctc tcctcgacgg agtcctcccc gcagggcagc   1260
cccgagcccc tggtgctcca tgaggagaca ccgcccacca ccagcagcga ctctgaggag   1320
gaacaagaag atgaggaaga aatcgatgtt gtttctgtgg aaaagaggca ggctcctggc   1380
aaaaggtcag agtctggatc accttctgct ggaggccaca gcaaacctcc tcacagccca   1440
ctggtcctca agaggtgcca cgtctccaca catcagcaca actacgcagc gcctccctcc   1500
actcggaagg actatcctgc tgccaagagg gtcaagttgg acagtgtcag agtcctgaga   1560
cagatcagca acaaccgaaa atgcaccagc cccaggtcct cggacaccga ggagaatgtc   1620
aagaggcgaa cacacaacgt cttggagcgc agaggagga acgagctaaa acggagcttt   1680
tttgccctgc gtgaccagat cccggagttg gaaaacaatg aaaaggcccc caaggtagtt   1740
atccttaaaa aagccacagc atacatcctg tccgtccaag cagaggagca aaagctcatt   1800
tctgaagagg acttgttgcg gaaacgacga gaacagttga acacaaaact tgaacagcta   1860
cggaactctt gtgcgtaagg aaaagtaagg aaaacgattc cttctaacag aaatgtcctg   1920
agcaatcacc tatgaacttg tttcaaatgc atgatcaaat gcaacctcac aaccttggct   1980
gagtcttgag actgaaagat ttagccataa tgtaaactgc ctcaaattgg actttgggca   2040
taaaagaact tttttatgct taccatcttt tttttttctt taacagattt gtatttaaga   2100
attgttttta aaaaattta a                                              2121
```

<210> SEQ ID NO 82
<211> LENGTH: 2121
<212> TYPE: DNA
<213> ORGANISM: Homo sapiens

<400> SEQUENCE: 82

```
ctgctcgcgg ccgccaccgc cgggccccgg ccgtccctgg ctcccctcct gcctcgagaa     60
gggcagggct tctcagaggc ttggcgggaa aaaagaacgg agggagggat cgcgctgagt    120
```

```
ataaaagccg gttttcgggg ctttatctaa ctcgctgtag taattccagc gagaggcaga      180
gggagcgagc gggcggccgg ctagggtgga agagccgggc gagcagagct gcgctgcggg      240
cgtcctggga agggagatcc ggagcgaata gggggcttcg cctctggccc agccctcccg      300
cttgatcccc caggccagcg gtccgcaacc cttgccgcat ccacgaaact ttgcccatag      360
cagcgggcgg gcactttgca ctggaactta caacacccga gcaaggacgc gactctcccg      420
acgcggggag gctattctgc ccatttgggg acacttcccc gccgctgcca ggacccgctt      480
ctctgaaagg ctctccttgc agctgcttag acgctggatt tttttcgggt agtggaaaac      540
cagcagcctc ccgcgacgat gcccctcaac gttagcttca ccaacaggaa ctatgacctc      600
gactacgact cggtgcagcc gtatttctac tgcgacgagg aggagaactt ctaccagcag      660
cagcagcaga gcgagctgca gccccggcg cccagcgagg atatctggaa gaaattcgag      720
ctgctgccca ccccgccct gtccctagc cgccgctccg ggctctgctc gccctcctac      780
gttgcggtca caccctctc ccttcgggga gacaacgacg gcggtggcgg gagcttctcc      840
acggccgacc agctggagat ggtgaccgag ctgctgggag gagacatggt gaaccagagt      900
ttcatctgcg acccggacga cgagaccttc atcaaaaaca tcatcatcca ggactgtatg      960
tggagcggct ctcggccgc cgccaagctc gtctcagaga agctggcctc ctaccaggct     1020
gcgcgcaaag acagcggcag cccgaacccc gcccgcggcc acagcgtctg ctccacctcc     1080
agcttgtacc tgcaggatct gagcgccgcc gcctcagagt gcatcgaccc ctcggtggtc     1140
ttccctacc ctctcaacga cagcagctcg cccagtcct gcgcctcgca agactccagc     1200
gccttctctc cgtcctcgga ttctctgctc tcctcgacgg agtcctcccc gcagggcagc     1260
cccgagcccc tggtgctcca tgaggagaca ccgcccacca ccagcagcga ctctgaggag     1320
gaacaagaag atgaggaaga atcgatgtt gtttctgtgg aaaagaggca ggctcctggc     1380
aaaaggtcag agtctggatc accttctgct ggaggccaca gcaaacctcc tcacagccca     1440
ctggtcctca agaggtgcca cgtctccaca catcagcaca actacgcagc gcctccctcc     1500
actcggaagg actatcctgc tgccaagagg gtcaagttgg acagtgtcag agtcctgaga     1560
cagatcagca acaaccgaaa atgcaccagc cccaggtcct cggacaccga ggagaatgtc     1620
aagaggcgaa cacacaacgt cttggagcgc cagaggagga cgagctaaa acggagcttt     1680
tttgccctgc gtgaccagat cccggagttg gaaaacaatg aaaaggcccc caaggtagtt     1740
atccttaaaa aagccacagc atacatcctg tccgtccaag cagaggagca aaagctcatt     1800
tctgaagagg acttgttgcg gaaacgacga gaacagttga acacaaaact tgaacagcta     1860
cggaactctt gtgcgtaagg aaaagtaagg aaaacgattc cttctaacag aaatgtcctg     1920
agcaatcacc tatgaacttg tttcaaatgc atgatcaaat gcaacctcac aaccttggct     1980
gagtcttgag actgaaagat ttagccataa tgtaaactgc ctcaaattgg actttgggca     2040
taaagaact tttttatgct taccatcttt tttttttctt taacagattt gtatttaaga     2100
attgttttta aaaattttta a                                             2121
```

<210> SEQ ID NO 83
<211> LENGTH: 3597
<212> TYPE: DNA
<213> ORGANISM: Homo sapiens
<400> SEQUENCE: 83

```
ggcgaatgga gcaggggcgc gcagataatt aaagatttac acacagctgg aagaaatcat       60
```

-continued

```
agagaagccg ggcgtggtgg ctcatgccta taatcccagc acttttggag gctgaggcgg      120
gcagatcact tgagatcagg agttcgagac cagcctggtg ccttggcatc tcccaatggg      180
gtggctttgc tctgggctcc tgttccctgt gagctgcctg gtcctgctgc aggtggcaag      240
ctctgggaac atgaaggtct tgcaggagcc cacctgcgtc tccgactaca tgagcatctc      300
tacttgcgag tggaagatga atggtcccac caattgcagc accgagctcc gcctgttgta      360
ccagctggtt tttctgctct ccgaagccca cacgtgtatc cctgagaaca cggaggcgc      420 ggggtgcgtg tgccacctgc tcatggatga cgtggtcagt gcggataact atacactgga      480
cctgtgggct gggcagcagc tgctgtggaa gggctccttc aagcccagcg agcatgtgaa      540
acccagggcc ccaggaaacc tgacagttca caccaatgtc tccgacactc tgctgctgac      600
ctggagcaac ccgtatcccc ctgacaatta cctgtataat catctcacct atgcagtcaa      660
catttggagt gaaaacgacc cggcagattt cagaatctat aacgtgacct acctagaacc      720
ctccctccgc atcgcagcca gcaccctgaa gtctgggatt tcctacaggg cacggggtgag      780 ggcctgggct cagtgctata caccacctg gagtgagtgg agccccagca ccaagtggca      840
caactcctac agggagccct tcgagcagca cctcctgctg ggcgtcagcg tttcctgcat      900
tgtcatcctg gccgtctgcc tgttgtgcta tgtcagcatc accaagatta gaaagaatg      960 gtgggatcag attcccaacc cagcccgcag ccgcctcgtg gctataataa tccaggatgc     1020 tcagggtca cagtgggaga gcggtcccg aggccaggaa ccagccaagt gcccacactg      1080
gaagaattgt cttaccaagc tcttgccctg ttttctggag cacaacatga aaagggatga     1140
agatcctcac aaggctgcca aagagatgcc tttccagggc tctggaaaat cagcatggtg     1200
cccagtggag atcagcaaga cagtcctctg gccagagagc atcagcgtgg tgcgatgtgt     1260
ggagttgttt gaggccccgg tggagtgtga ggaggaggag gaggtagagg aagaaaaagg     1320
gagcttctgt gcatcgcctg agagcagcag ggatgacttc caggagggaa gggagggcat     1380
tgtggcccgg ctaacagaga gcctgttcct ggacctgctc ggagaggaga atggggcctt     1440
ttgccagcag gacatggggg agtcatgcct tcttccacct tcgggaagta cgagtgctca     1500
catgccctgg gatgagttcc caagtgcagg gcccaaggag gcacctccct ggggcaagga     1560
gcagcctctc cacctggagc caagtcctcc tgccagcccg acccagagtc cagacaacct     1620
gacttgcaca gagacgcccc tcgtcatcgc aggcaaccct gcttaccgca gcttcagcaa     1680
ctccctgagc cagtcaccgt gtcccagaga gctgggtcca gacccactgc tggccagaca     1740
cctggaggaa gtagaacccg agatgcctg tgtccccag ctctctgagc caaccactgt     1800
gccccaacct gagccagaaa cctgggagca gatcctccgc cgaaatgtcc tccagcatgg     1860
ggcagctgca gcccccgtct cggcccccac cagtggctat caggagtttg tacatgcggt     1920
ggagcagggt ggcacccagg ccagtgcggt ggtgggcttg ggtccccag gagaggctgg     1980 ttacaaggcc ttctcaagcc tgcttgccag cagtgctgtg tccccagaga aatgtgggtt     2040 tgggggctagc agtggggaag agggggtataa gcctttccaa gacctcattc ctggctgccc     2100 tgggaccct gcccagtcc ctgtcccctt gttcacctt ggactggaca gggagccacc     2160
tcgcagtccg cagagctcac atctcccaag cagctcccca gagcacctgg gtctggagcc     2220 gggggaaag gtagaggaca tgccaaagcc cccacttccc caggagcagg ccacagaccc     2280
ccttgtggac agcctgggca gtggcattgt ctactcagcc cttacctgcc acctgtgcgg     2340
ccacctgaaa cagtgtcatg gccaggagga tggtggccag accctgtca tggccagtcc     2400 ttgctgtggc tgctgctgtg gagacaggtc ctcgcccct acaacccccc tgagggcccc     2460
```

```
agaccoctct ccaggtgggg ttccactgga ggccagtctg tgtccggcct ccctggcacc    2520
ctcgggcatc tcagagaaga gtaaatcctc atcatccttc catcctgccc ctggcaatgc    2580
tcagagctca agccagaccc ccaaaatcgt gaactttgtc tccgtgggac ccacatacat    2640
gagggtctct taggtgcatg tcctcttgtt gctgagtctg cagatgagga ctagggctta    2700
tccatgcctg ggaaatgcca cctcctggaa ggcagccagg ctggcagatt ccaaaagac     2760 ttgaagaacc atggtatgaa ggtgattggc cccactgacg ttggcctaac actgggctgc    2820
agagactgga ccccgcccag cattgggctg ggctcgccac atcccatgag agtagagggc    2880
actgggtcgc cgtgccccac ggcaggcccc tgcaggaaaa ctgaggccct tgggcacctc    2940
gacttgtgaa cgagttgttg gctgctccct ccacagcttc tgcagcagac tgtccctgtt    3000
gtaactgccc aaggcatgtt tgcccacca gatcatggcc cacgtggagg cccacctgcc     3060
tctgtctcac tgaactagaa gccgagccta gaaactaaca cagccatcaa gggaatgact    3120
tgggcggcct tgggaaatcg atgagaaatt gaacttcagg gagggtggtc attgcctaga    3180
ggtgctcatt catttaacag agcttcctta ggttgatgct ggaggcagaa tcccggctgt    3240
caaggggtgt tcagttaagg ggagcaacag aggacatgaa aaattgctat gactaaagca    3300
gggacaattt gctgccaaac acccatgccc agctgtatgg ctgggggctc ctcgtatgca    3360
tggaaccccc agaataaata tgctcagcca ccctgtgggc cgggcaatcc agacagcagg    3420
cataaggcac cagttaccct gcatgttggc ccagacctca ggtgctaggg aaggcgggaa    3480
ccttgggttg agtaatgctc gtctgtgtgt tttagtttca tcacctgtta tctgtgtttg    3540
ctgaggagag tggaacagaa ggggtggagt tttgtataaa taaagtttct ttgtctc       3597

<210> SEQ ID NO 84
<211> LENGTH: 2709
<212> TYPE: DNA
<213> ORGANISM: Homo sapiens

<400> SEQUENCE: 84
gggaatagca gaataggagc aagccagcac tagtcagcta actaagtgac tcaaccaagg      60 cctttttcc ttgttatctt tgcagatact tcattttctt agcgtttctg gagattacaa      120
catcctgcgg ttccgtttct gggaacttta ctgatttatc tccccctca cacaaataag      180 cattgattcc tgcatttctg aagatctcaa gatctggact actgttgaaa aaatttccag     240
tgaggctcac ttatgtctgt aaagatggga aaaaaataca agaacattgt tctactaaaa     300
ggattagagg tcatcaatga ttatcatttt agaatggtta agtccttact gagcaacgat     360
ttaaaactta atttaaaaat gagagaagag tatgacaaaa ttcagattgc tgacttgatg     420
gaagaaaagt tccgaggtga tgctggtttg gcaaactaa taaaaatttt cgaagatata     480
ccaacgcttg aagacctggc tgaaactctt aaaaagaaa agttaaaagt aaaaggacca     540
gccctatcaa gaaagaggaa gaaggaagtg catgctactt cacctgcacc ctccacaagc    600
agcactgtca aaactgaagg agcagaggca actcctggag ctcagaaaag aaaaaaatca    660
accaaagaaa aggctggacc caagggagt aaggtgtccg aggaacagac tcagcctccc     720
tctcctgcag gagccggcat gtccacagcc atgggccgtt ccccatctcc caagacctca    780
ttgtcagctc caccaacag ttcttcaact gagaacccga aaacagtggc caaatgtcag    840
gtaactccca agaaatgt tctccaaaaa cgcccagtga tagtgaaggt actgagtaca      900
acaaagccat ttgaatatga gacccagaa atggagaaaa aaataatgtt tcatgctaca     960
```

-continued

```
gtggctacac agacacagtt cttccatgtg aaggttttaa acaccagctt gaaggagaaa    1020
ttcaatggaa agaaaatcat catcatatca gattatttgg aatatgatag tctcctagag    1080
gtcaatgaag aatctactgt atctgaagct ggtcctaacc aaacgtttga ggttccaaat    1140
aaaatcatca acagagcaaa ggaaactctg aagattgata ttcttcacaa acaagcttca    1200
ggaaatattg tatatggggt atttatgcta cataagaaaa cagtaaatca gaagaccaca    1260
atctacgaaa ttcaggatga tagaggaaaa atggatgtag tggggacagg acaatgtcac    1320
aatatcccct gtgaagaagg agataagctc cagcttttct gctttcgact tagaaaaaag    1380
aaccagatgt caaaactgat ttcagaaatg catagtttta tccagataaa gaaaaaaaca    1440
aacccgagaa acaatgaccc caagagcatg aagctacccc aggaacagcg tcagcttcca    1500
tatccttcag aggccagcac aaccttccct gagagccatc ttcggactcc tcagatgcca    1560
ccaacaactc catccagcag tttcttcacc aagaaaagtg aagacacaat ctccaaaatg    1620
aatgacttca tgaggatgca gatactgaag gaagggagtc attttccagg accgttcatg    1680
accagcatag gcccagctga gagccatccc cacactcctc agatgcctcc atcaacacca    1740
agcagcagtt tcttaaccac gttgaaacca agactgaaga ctgaacctga agaagtttcc    1800
atagaagaca gtgcccagag tgacctcaaa gaagtgatgg tgctgaacgc aacagaatca    1860
tttgtatatg agcccaaaga gcagaagaaa atgtttcatg ccacagtggc aactgagaat    1920
gaagtcttcc gagtgaaggt ttttaatatt gacctaaagg agaagttcac cccaaagaag    1980
atcattgcca tagcaaatta tgtttgccgc aatgggttcc tggaggtata tcctttcaca    2040
cttgtggctg atgtgaatgc tgaccgaaac atggagatcc aaaaggatt gattagaagt    2100 gccagcgtaa ctcctaaaat caatcagctt tgctcacaaa ctaaaggaag ttttgtgaat    2160
ggggtgtttg aggtacataa gaaaaatgta aggggtgaat tcacttatta tgaaatacaa    2220
gataatacag ggaagatgga agtggtggtg catggacgac tgaacacaat caactgtgag    2280
gaaggagata aactgaaact caccagcttt gaattggcac cgaaaagtgg gaataccggg    2340
gagttgagat ctgtaattca tagtcacatc aaggtcatca agaccaggaa aaacaagaaa    2400
gacatactca atcctgattc aagtatggaa acttcaccag actttttctt ctaaaatctg    2460
gatgtcattg acgataatgt ttatggagat aaggtctaag tccctaaaaa aatgtacata    2520
tacctggttg aaatacaaca ctatacatac acaccaccat atatactagc tgttaatcct    2580
atggaatggg ggtattggga gtgctttttt aattttcat agtttttttt taataaaatg    2640
gcatattttg catctacaac ttctataata agaaaaaata aataaacatt atctttttg    2700 tgaaaaaaa                                                          2709
```

<210> SEQ ID NO 85
<211> LENGTH: 777
<212> TYPE: DNA
<213> ORGANISM: Homo sapiens

<400> SEQUENCE: 85

```
ttcttcaaac cctcctcttc cctgtgttct cctacagaga ttgctgattt ctccttaagc      60
aagagattca ctgccgctaa gcatggctca gaccaactcg ttcttcatgc tgatctcctc     120
cctgatgttc ctgtctctga gccaaggcca agaggcccag acagagttgc cccaggcccg     180
gatcagctgc ccagaaggca ccaatgccta tcgctcctac tgctactact ttaatgaaga     240
ccgtgagacc tgggttgatg cagatctcta ttgccgagaa atgaattcgg gcaacctggt     300
gtctgtgctc acccaggccg agggtgcctt tgtggcctca ctgattaagg agagtggcac     360
```

| | |
|---|---|
| tgatgacttc aatgtctgga ttggcctcca tgaccccaaa aagaaccgcc gctggcactg | 420 |
| gagcagtggg tccctggtct cctacaagtc ctggggcatt ggagcccaa gcagtgttaa | 480 |
| tcctggctac tgtgtgagcc tgacctcaag cacaggattc cagaaatgga aggatgtgcc | 540 |
| ttgtgaagac aagttctcct ttgtatgcaa gttcaaaaac tagaggcagc tggaaaatac | 600 |
| atgtctagaa ctgatccagc aattacaacg gagtcaaaaa ttaaaccgga ccatctctcc | 660 |
| aactcaactc aacctggaca ctctcttctc tgctgagttt gccttgttaa tcttcaatag | 720 |
| ttttacctac cccagtcttt ggaaccctaa ataataaaaa taaacatgtt ttccact | 777 |

<210> SEQ ID NO 86
<211> LENGTH: 2043
<212> TYPE: DNA
<213> ORGANISM: Homo sapiens

<400> SEQUENCE: 86

| | |
|---|---|
| gtgcttaggc actgcagttg agtggctcac aaggagctaa aatttcacta atgcgtattc | 60 |
| agtgggtggt tctggtttgc ctgattttg cctctgggca tggctgtttc agcctgagag | 120 |
| gctgttccaa gaatgttgct ttactaggag ctcatgccgc tggtggtaa atatgaagta | 180 |
| cagcagtgca acagaccagt tttactccaa ggaaaccctg tagagatgac agcaatggtt | 240 |
| ggtgatttct gcctcaatta tgaaagtgat ctggtgttac agggccagag aagactaggg | 300 |
| gagttcgggt tttctagacc aaacagacac tcagtcctgg gcctggaggt ctctgcagtg | 360 |
| aggtgctgcc acagacagag ccaccttaac tcctcaggac aaccagtggc ttccgacaca | 420 |
| cactatgcac tggagggcaa gcagctctca gcttgggagc aactgaggat ggtgaacagc | 480 |
| ctgggcaagg agtgctctga ggctaagacc ctgaacagga gaaccgaag tgcagctccc | 540 |
| cacttcaggt aatgtgattc tacccttgc ctgagaaaca tatccatcct aattgccatg | 600 |
| tgctcagctg gaccactaga gggagccatc ctgtaacggg tgaggtcaac ctaacaaatg | 660 |
| gtatcagtcg agtattgatc ggaggccaac gcaagaagtt accagtagcc tatttcagat | 720 |
| ttattaaaaa acacataggt aacgagtcag agctttggct aggaatgatt tggaaaagaa | 780 |
| ctgaaggcat aattccacag gacattcaca gttgtgtgct agagacagag aggagcagga | 840 |
| aagtgtttta gaagcatttg cggtggacaa tggaaggccc ggcttcatcg tattcctgtt | 900 |
| tgctgatcca catctgctgg aaggtggaca gagaggccag gatggagcca ccgatccaga | 960 |
| cagagtattt gcgctccgga ggggcaatga tctgtcagtc aagatgaaaa agaatggtca | 1020 |
| ttaatgtcat cattagtgca gtcgttagtg cggtaggaca gagcctggat gttctaccat | 1080 |
| ggcctagttt cttgttcagc agggacacag gcttgtctgt tagatgccaa ttgtgtccta | 1140 |
| attgtgtcat gttcttggca ggaccgccag agggagccat ggatttagaa attcttcagt | 1200 |
| ggtttcatgg atgccagcag actccatccc tggaaaagag acacaggcca tggtccttaa | 1260 |
| gtggagagta aaacccaggc tagacatgga agaccagact tgaacatctg gatgatcttg | 1320 |
| cagtggactg aggctgggaa gacataataa tctaggaacc acctgtctga gagacaaaag | 1380 |
| ggtcttgtta tgctctatgt cttcctgcct gccttctaat gaggaaggcc tgctgcagca | 1440 |
| tcctgaggtg tgggctacaa cagaaatgct tttggtcttg gggcaaccgt cacttgtctc | 1500 |
| catgttctgg aggctggctt gatatggaag aagacaatga ctccccttcc caggaaaagg | 1560 |
| gcgtttgttg cctaccgatg aaggatggct ggaacagggt ctctgggcag cggaaacgtt | 1620 |
| catttccgat ggtgatcact tgcccatcag gcaactcgta actcttctca agggaggatg | 1680 |

```
aggatgcggc agtggccatc tcattttcaa agtccagagc tacataacac agtttctcct    1740
tgatgtcccg gacaatctca cgctcagctg tcaaccagat acaaacattg tggcaaacat    1800
tagggtctgc acaggtggca aagattcacc tgccctactg cagtctctcc ctcaagacat    1860
gtgccatcaa aaaatgtgtc agttcaatat tctgcaatcc aaaatccaca atgataatga    1920
cgtagtaggg ccaccaggga accacctctg ttcctaggac agtgtctcat gcatagtagg    1980
ccctcagcat gcattgtctg ggaaatgcat aacaagaata aaatgagcta gctagagaaa    2040
ggc                                                                  2043

<210> SEQ ID NO 87
<211> LENGTH: 1501
<212> TYPE: DNA
<213> ORGANISM: Homo sapiens

<400> SEQUENCE: 87
agcgagtcct tcttttcctg actgcagctc ttttcatttt gccatccttc tccagctcca      60
tgatggttct gcaggtttct gcggcccccc ggacagtggc tctgacggcg ttactgatgg     120
tgctgctcac atctgtggtc cagggcaggg ccactccaga gaattacgtg taccagggac     180
ggcaggaatg ctacgcgttt aatgggacac agcgcttcct ggagagatac atctacaacc     240
gggaggagta cgcgcgcttc gacagcgacg tgggggagtt ccgggcggtg acggagctgg     300
ggcggcctgc tgcggagtac tggaacagcc agaaggacat cctggaggag aagcgggcag     360
tgccggacag ggtatgcaga cacaactacg agctggacga ggccgtgacc ctgcagcgcc     420
gagtccagcc taaggtgaac gtttccccct ccaagaaggg gcccctgcag caccacaacc     480
tgcttgtctg ccacgtgaca gatttctacc caggcagcat tcaagtccga tggttcctga     540
atggacagga ggaaacagct ggggtcgtgt ccaccaacct gatccgtaat ggagactgga     600
ccttccagat cctggtgatg ctggaaatga ccccccagca gggagacgtc tacatctgcc     660
aagtggagca caccagcctg gacagtcctg tcaccgtgga gtggaaggca cagtctgatt     720
ctgcccagag taagacattg acgggagctg ggggcttcgt gctggggctc atcatctgtg     780
gagtgggcat cttcatgcac aggaggagca agaaagttca acgaggatct gcataaacag     840
ggttcctgac ctcaccgaaa agactaatgt gccttagaac aagcatttgc tgtgttttgt     900
taacacctgg ttccaggaca gaccctcagc ttcccaagag gatactgctg ccaagaagtt     960
gctctgaagt cagtttctat cgttctgctc tttgattcaa agcactgttt ctctcactgg    1020
gcctccaacc atgttccctt cttcttagca ccacaaataa tcaaaaccca acataagtgt    1080
ttgctttcct ttaaaaatat gcatcaaatc gtctctcatt acttttctct gagggtttta    1140
gtaaacagta ggagttaata agaagttca ttttggttta cacgtaggaa agaagagaag    1200
catcaaagtg gagatatgtt aactattgta taatgtggcc tgttatacat gacactcttc    1260
tgaattgact gtatttcagt gagctgcccc caaatcaagt ttagtgccct catccattta    1320
tgtctcagac cgctattctt aactattcaa tggtgagcag actgcaaatc tgcctgatag    1380
gacccatatt cccacagcac taattcaaca tatatcttac tgagagcatg ttttatcatt    1440
accattaaga agttaaatga acatcagaat ttaaaatcat aaatataatc taatacactt    1500
t                                                                   1501

<210> SEQ ID NO 88
<211> LENGTH: 1096
<212> TYPE: DNA
<213> ORGANISM: Homo sapiens
```

<400> SEQUENCE: 88

```
atgatcctaa acaaagctct gctgctgggg gccctcgctc tgaccaccgt gatgagcccc      60
tgtggaggtg aagacattgt ggctgaccac gttgcctctt gtggtgtaaa cttgtaccag     120
ttttacggtc cctctggcca gtacacccat gaatttgatg gagatgagca gttctacgtg     180
gacctggaga ggaaggagac tgcctggcgg tggcctgagt tcagcaaatt tggaggtttt     240
gacccgcagg gtgcactgag aaacatggct gtggcaaaac acaacttgaa catcatgatt     300
aaacgctaca actctaccgc tgctaccaat gaggttcctg aggtcacagt gttttccaag     360
tctcccgtga cactgggtca gcccaacacc ctcatttgtc ttgtggacaa catctttcct     420
cctgtggtca acatcacatg gctgagcaat gggcagtcag tcacagaagg tgtttctgag     480
accagcttcc tctccaagag tgatcattcc ttcttcaaga tcagttacct caccttcctc     540
ccttctgctg atgagattta tgactgcaag gtggagcact ggggcctgga ccagcctctt     600
ctgaaacact gggagcctga gattccagcc cctatgtcag agctcacaga gactgtggtc     660
tgtgccctgg ggttgtctgt gggcctcatg ggcattgtgg tgggcactgt cttcatcatc     720
caaggcctgc gttcagttgg tgcttccaga caccaagggc cattgtgaat cccatcctgg     780
aagggaaggt gcatcgccat ctacaggagc agaagaatgg acttgctaaa tgacctagca     840
ctattctctg gcccgattta tcatatccct tttctcctcc aaatatttct cctctcacct     900
tttctctggg acttaagctg ctatatcccc tcagagctca caaatgcctt tacattcttt     960
ccctgacctc ctgatttttt ttttcttttc tcaaatgtta cctacaatac atgcctgggg    1020
taagccaccc ggctacctaa ttcctcagta acctccatct aaaatctcca aggaagcaat    1080
aaattccttt tatgag                                                    1096
```

<210> SEQ ID NO 89
<211> LENGTH: 1100
<212> TYPE: DNA
<213> ORGANISM: Homo sapiens

<400> SEQUENCE: 89

```
ctaaagctgg gttggtagct cctacctact gtgtggcaag aaggtatggg tcatgaacag      60
aaccaaggag ctgcgctgct acagatgtta ccacttctgt ggctgctacc ccactcctgg     120
gccgtccctg aagctcctac tccaatgtgg ccagatgacc tgcaaaacca cacattcctg     180
cacacagtgt actgccagga tgggagtccc agtgtgggac tctctgaggc ctacgacgag     240
gaccagcttt tcttcttcga cttttcccag aacactcggg tgcctcgcct gcccgaattt     300
gctgactggg ctcaggaaca gggagatgct cctgccattt tatttgacaa agagttctgc     360
gagtggatga tccagcaaat agggccaaaa cttgatggga aaatcccggt gtccagaggg     420
tttcctatcg ctgaagtgtt cacgctgaag cccctggagt ttggcaagcc caacactttg     480
gtctgttttg tcagtaatct cttcccaccc atgctgacag tgaactggca gcatcattcc     540
gtccctgtgg aaggatttgg gcctactttt gtctcagctg tcgatggact cagcttccag     600
gccttttctt acttaaactt cacaccagaa ccttctgaca ttttctcctg cattgtgact     660
cacgaaattg accgctacac agcaattgcc tattgggtac cccggaacgc actgccctca     720
gatctgctgg agaatgtgct gtgtggcgtg gcctttggcc tgggtgtgct gggcatcatc     780
gtgggcattg ttctcatcat ctacttccgg aagccttgct caggtgactg attcttccag     840
accagagttt gatgccagca gcttcggcca tccaaacaga ggatgctcag atttctcaca     900
```

-continued

| | |
|---|---|
| tcctgcccag gatctcctct tagggtagaa gaagtctctg ggacatccct ggggtgtgtg | 960 |
| tgtagatttc ccacctgggg actctgctgt ccctgggctt gcatcccagg gatcccagag | 1020 |
| tggcctgcct atcacaacca catcccttcc ccccacaagg caataaatct catttcttta | 1080 |
| aaaaaaaaaa aaaaaaaaa | 1100 |

<210> SEQ ID NO 90
<211> LENGTH: 3526
<212> TYPE: DNA
<213> ORGANISM: Homo sapiens

<400> SEQUENCE: 90

| | |
|---|---|
| ccacgcgtcc ggacaggctt aagcatggcc aagaagcttg agagaagaaa aatttcagaa | 60 |
| aaattgtctc aatttgacta gaatatcaat gaaccaggaa aactgaagca ccttccctaa | 120 |
| agaaaacttg ggtatacaat tactccacag acagagctga gggtttttta cccaaatcag | 180 |
| tcactggatt ttgctgcctg atacgtgaat cttcttggaa tttttctcat gtggatctaa | 240 |
| ggggaatgct ttattatggc tgctgttgtc caacagaacg acctagtatt tgaatttgct | 300 |
| agtaacgtca tggaggatga acgacagctt ggtgatccag ctatttttcc tgccgtaatt | 360 |
| gtggaacatg ttcctggtgc tgatattctc aatagttatg ccggtctagc ctgtgtggaa | 420 |
| gagcccaatg acatgattac tgagagttca ctggatgttg ctgaagaaga atcatagac | 480 |
| gatgatgatg atgacatcac ccttacagtt gaagcttctt gtcatgacgg ggatgaaaca | 540 |
| attgaaacta ttgaggctgc tgaggcactc ctcaatatgg attcccctgg ccctatgctg | 600 |
| gatgaaaaac gaataaataa taatatattt agttcacctg aagatgacat ggttgttgcc | 660 |
| ccagtcaccc atgtgtccgt cacattagat gggattcctg aagtgatgga aacacagcag | 720 |
| gtgcaagaaa aatatgcaga ctcaccggga gcctcatcac cagaacagcc taagaggaaa | 780 |
| aaaggaagaa aaactaaacc accacgacca gattccccag ccactacgcc aaatatatct | 840 |
| gtgaagaaga aaacaaaga tggaaaggga aacacaattt atctttggga gttttactg | 900 |
| gcactgctcc aggacaaggc tacttgtcct aaatacatca agtggaccca gcgagagaaa | 960 |
| ggcattttta aattggtgga ttctaaagca gtgtccaggt tgtggggaa gcacaaaaac | 1020 |
| aaacctgata tgaattatga gaccatggga agagcactca ggtactatta ccaaggggt | 1080 |
| attctggcaa aagtggaagg tcagcgcttg gtgtatcagt ttaaagaaat gccaaaagat | 1140 |
| cttatatata taaatgatga ggatccaagt tccagcatag agtcttcaga tccatcacta | 1200 |
| tcttcatcag ccacttcaaa taggaatcaa accagccggt cgagagtatc ttcaagtcca | 1260 |
| ggggtaaaag gaggagccac tacagttcta aaaccaggga attctaaagc tgcaaaaccc | 1320 |
| aaagatcctg tggaagttgc acaaccatca gaagttttga ggacagtgca gcccacgcag | 1380 |
| tctccatatc ctacccagct cttccggact gttcatgtag tacagccagt acaggctgtc | 1440 |
| ccagagggag aagcagctag aaccagtacc atgcaggatg aaacattaaa ttcttccgtt | 1500 |
| cagagtatta ggactataca ggctccaacc caagttccag tggttgtgtc tcctaggaat | 1560 |
| cagcagttgc atacagtaac actccaaaca gtgccactca acacagttat agccagcaca | 1620 |
| gatccatcag caggtactgg atctcagaag tttatttac aagccattcc atcatcacag | 1680 |
| cccatgacag tactgaaaga aaatgtcatg ctgcagtcac aaaaggcggg ctctcctcct | 1740 |
| tcaattgtct gggccctgc ccaggttcag caggtcctta ctagcaatgt tcagaccatt | 1800 |
| tgcaatggaa ccgtcagtgt ggcttcctct ccatccttca gtgctactgc acctgtggtg | 1860 |
| accttttctc ctcgcagttc acagctggtt gctcacccac ctggcactgt aatcacttca | 1920 |

-continued

| | |
|---|---|
| gttatcaaaa ctcaagaaac aaaaactctt acacaggaag tagagaaaaa ggaatctgaa | 1980 |
| gatcatttga aagagaacac tgagaaaacg gagcagcagc cacagcctta tgtgatggta | 2040 |
| gtgtccagtt ccaatggatt tacttctcag gtagctatga aacaaaacga actgctggaa | 2100 |
| cccaactctt tttagttaat ataccaaagc ttatgaataa ttgtttgtta attgaacatt | 2160 |
| ttcaattata tgcagactga ctgattctaa gataaattct aaggaggttt ctaattttgt | 2220 |
| aattgttaaa aatagagtta attttgactt tgttagatga gggaggaaaa ctcaactgtt | 2280 |
| tctctttgtt atctaaatgt ttcagaattc aatcgtgaag gaacaggcat tttacactat | 2340 |
| gaagacattc ttttgagatt tttatttcag ttgctatatc ataagcattt ttaaagtttc | 2400 |
| ttttctaatt ttacattgta ttagattttc tgattctttt gtaaatacag aacttaaata | 2460 |
| gaaggcaaca ggaaatttat ataggaacta ttttcattcc acttgtgtaa gttaagtctt | 2520 |
| gactctttca aatgcaaaaa acctattta tgctttgtta aaattatggt gtcacttaga | 2580 |
| ttgactttag ttgactgcac tatataatat agaactatga atatgtagaa taacatgaaa | 2640 |
| aattggaggt gctggtggta tggctgaccc tgtttcagaa gcaggatagt ataaaagcat | 2700 |
| cagcctaaga atggcactcc cactaactag ctatgtaatc ttgacctctt tgggctttag | 2760 |
| ttcctctcat aaaaggaaga gatgtattgg attagactag attatcacca ctttctcttc | 2820 |
| tagttctaat tttttaatt ctaataccta tattttcaag ttatgtcaat taaatcatta | 2880 |
| tcaggttatt tcctaatgta agaatagcta aaatgttgca gagaaataag tgacccaaca | 2940 |
| aaatttattc atctgttatg ggtaagatct gccataaatt cttcctaaat aatttgttta | 3000 |
| ctaactcttt aggccactgt gctttgcggt ccattagtaa acttgtgttg ctaagtgcta | 3060 |
| aacagaatac tgctattttg agagagtcaa gactctttct taagggccaa gaaagcaact | 3120 |
| tgagccttgg gctaatctgg ctgagtagtc agttataaaa gcataattgc tttatatttt | 3180 |
| ggatcatttt ttactggggg cggacttggg ggggttgca tacaaagata acatatatat | 3240 |
| ccaactttct gaaatgaaat gttttagat tactttttca actgtaaata atgtacattt | 3300 |
| aatgtcacaa gaaaaaatg tcttctgcaa attttctagt ataacagaaa tttttgtaga | 3360 |
| tgaaaaaaat cattatgttt agaggtctaa tgctatgttt tcatattaca gagtgaattt | 3420 |
| gtatttaaac aaaaatttaa attttggaat cctctaaaca tttttgtatc tttaattggt | 3480 |
| ttattattaa ataaatcata taaaaattct caaaaaaaaa aaaaa | 3526 |

<210> SEQ ID NO 91
<211> LENGTH: 1968
<212> TYPE: DNA
<213> ORGANISM: Homo sapiens

<400> SEQUENCE: 91

| | |
|---|---|
| aattccgccg ggcgcttaga acagaggctt gcacaggtgg agatgtggaa gtctgtagtg | 60 |
| ggccatgatg tgtctgtttc cgtggagacc cagggtgatg attgggacac agatcctgac | 120 |
| tttgtgaatg acatctctga aaaggagcaa cgatggggag ccaagaccat cgagggtct | 180 |
| ggacgcacag aacacatcaa catccaccag ctgaggaaca agtatcaga ggagcatgat | 240 |
| gttctcagga agaaagagat ggagtcaggg cccaaagcat cccatggcta tggaggtcgg | 300 |
| tttggagtag aaagagaccg aatggacaag agtgcagtgg gccatgagta tgttgccgag | 360 |
| gtggagaagc actcttctca gacggatgct gccaaaggct ttgggggcaa gtacggagtt | 420 |
| gagagggaca gggcagacaa gtcagcagtc ggctttgatt ataaaggaga agtggagaag | 480 |

```
catacatctc agaaagatta ctctcgtggc tttggtggcc ggtacggggt ggagaaggat      540
aaatgggaca aagcagctct gggatatgac tacaagggag agacggagaa acacgagtcc      600
cagagagatt atgccaaggg ctttggtggc cagtatggaa tccagaagga ccgagtggat      660
aagagcgctg tcggcttcaa tgaaatggag gccccgacca cagcttataa gaagacgacg      720
cccatagaag ccgcttctag tggtgcccgt gggctgaagg cgaaatttga gtccatggct      780
gaggagaaga ggaagcgaga ggaagaggag aaggcacagc aggtggccag gaggcaacag      840
gagcgaaagg ctgtgacaaa gaggagccct gaggctccac agccagtgat agctatggaa      900
gagccagcag taccggcccc actgcccaag aaaatctcct cagaggcctg gcctccagtt      960
gggactcctc catcatcaga gtctgagcct gtgagaacca gcagggaaca cccagtgccc     1020
ttgctgccca ttaggcagac tctcccggag gacaatgagg agcccccagc tctgcccct      1080 aggactctgg aaggcctcca ggtggaggaa gagccagtgt acgaagcaga gcctgagcct     1140
gagcccgagc tgagcccgga gcctgagaat gactatgagg acgttgagga gatggacagg     1200
catgagcagg aggatgaacc agaggggac tatgaggagg tgctcgagcc tgaagattct      1260 tcttttctt ctgctctggc tggatcatca ggctgcccgg ctggggctgg ggctggggct      1320
gtggctctgg ggatctcagc tgtggctcta tatgattacc aaggagaggg aagtgatgag     1380
ctttcctttg atccggacga cgtaatcact gacattgaga tggtgacga gggctggtgg      1440 cggggacgtt gccatggcca cttggactc ttccctgcaa attatgtcaa gcttctggag       1500
tgactagagc tcactgtcta ctgcaactgt gatttcccat gtccaaagtg gctctgctcc      1560
accccctccc tattcctgat gcaaatgtct aaccagatga gtttctggac agacttccct      1620
ctcctgcttc attaagggct tggggcagag acagcatggg gaaggaggtc cccttcccca     1680
agagtcctct ctatcctgga tgagctcatg aacatttctc ttgtgttcct gactccttcc     1740
caatgaacac ctctctgcca ccccaagctc tgctctcctc ctctgtgagc tctgggcttc     1800
ccagtttgtt tacccgggaa agtacgtcta gattgtgtgg tttgcctcat tgtgctattt     1860
gcccactttc cttccctgaa gaaatatctg tgaaccttct ttctgttcag tcctaaaatt     1920
cgaaataaag tgagactatg gttcacctgt aaaaaaaaaa aaggaatt                   1968
```

<210> SEQ ID NO 92
<211> LENGTH: 2088
<212> TYPE: DNA
<213> ORGANISM: Homo sapiens

<400> SEQUENCE: 92

```
gaattcggca cgagcgcgcg gcgaatctca acgctgcgcc gtctgcgggc gcttccgggc       60
caccagtttc tctgctttcc accctggcgc ccccagccc tggctcccca gctgcgctgc       120
cccgggcgtc cacgccctgc gggcttagcg ggttcagtgg gctcaatctg cgcagcgcca      180
cctccatgtt gaccaagcct ctacaggggc ctcccgcgcc ccccgggacc ccacgccgc       240 cgccaggagg caaggatcgg gaagcgttcg aggccgagta tcgactcggc cccctcctgg     300
gtaagggggg ctttggcacc gtcttcgcag gacaccgcct cacagatcga ctccaggtgg      360
ccatcaaagt gattccccgg aatcgtgtgc tgggctggtc cccttgtca gactcagtca       420 catgcccact cgaagtcgca ctgctatgga aagtgggtgc aggtggtggg caccctggcg      480
tgatccgcct gcttgactgg tttgagacac aggaaggctt catgctggtc ctcgagcggc      540 ctttgccccgc ccaggatctc tttgactata tcacagagaa gggcccactg ggtgaaggcc     600
caagccgctg cttctttggc caagtagtgg cagccatcca gcactgccat tcccgtggag      660
```

```
ttgtccatcg tgacatcaag gatgagaaca tcctgataga cctacgccgt ggctgtgcca      720
aactcattga ttttggttct ggtgccctgc ttcatgatga ccctacact gactttgatg       780 ggacaagggt gtacagcccc ccagagtgga tctctcgaca ccagtaccat gcactcccgg      840
ccactgtctg gtcactgggc atcctcctct atgacatggt gtgtgggac attccctttg      900 agagggacca ggagattctg gaagctgagc tccacttccc agcccatgtc tccccagact     960
gctgtgccct aatccgccgg tgcctggccc ccaaaccttc ttcccgaccc tcactggaag    1020
agatcctgct ggaccctggg atgcaaacac cagccgagga tgttacccct caacccctcc    1080
aaaggaggcc ctgccccttt ggcctggtcc ttgctaccct aagcctggcc tggcctggcc    1140
tggcccccaa tggtcagaag agccatccca tggccatgtc acaggataga atggacattt    1200
gttgacttgg ttttacaggt cattaccagt cattaaagtc cagtattact aaggtaaggg    1260
attgaggatc aggggttaga agacataaac caagtttgcc cagttccctt cccaatccta    1320
caaaggagcc ttcctcccag aacctgtggt ccctgatttt ggaggggggaa cttcttgctt   1380 ctcattttgc taaggaagtt tattttggtg aagttgttcc catttttgagc cccgggactc   1440 ttattttgat gatgtgtcac cccacattgg cacctcctac taccaccaca caaacttagt    1500
tcatatgctt ttacttgggc aagggtgctt tccttccaat accccagtag ctttttatttt   1560 agtaaaggga cccttttcccc tagcctaggg tcccatattg ggtcaagctg cttacctgcc   1620
tcagcccagg atttttttatt ttggggggagg taatgccctg ttgttacccc aaggcttctt   1680 ttttttttttt tttttttttg ggtgagggga ccctactttg ttatcccaag tgctcttatt    1740
ctggtgagaa gaaccttaat tccataattt gggaaggaat ggaagatgga caccaccgga    1800
caccaccaga caataggatg ggatggatgg ttttttgggg gatgggctag gggaaataag    1860
gcttgctgtt tgttttcctg gggcgctccc tccaattttg cagattttttg caacctcctc    1920 ctgagccggg attgtccaat tactaaaatg taaataatca cgtattgtgg ggaggggagt    1980
tccaagtgtg ccctccttttt ttttcctgcc tggattattt aaaaagccat gtgtggaaac    2040
ccactattta ataaaagtaa tagaatcaga aaaaaaaaa aaaaaaaa                   2088

<210> SEQ ID NO 93
<211> LENGTH: 415
<212> TYPE: DNA
<213> ORGANISM: Homo sapiens

<400> SEQUENCE: 93
ccgctgcgtg ttttcctctt gatcgggaac tcctgcttct ccttgcctcg aaatggaccc     60
caactgctcc tgctcgcctg ttggctcctg tgcctgtgcc ggctcctgca aatgcaaaga    120
gtgcaaatgc acctcctgca agaagagctg ctgctcctgc tgccctgtgg gctgtgcmaa    180
gtgtgcccag ggctgcatct gcaaagggac gtcagacaag tgcagctgct gtgcctgatg    240
ccaggacagc tgtgctctca gatgtaaata gagcaaccta tataaacctg gattttttttt   300 tttttttttt tgtacaaccc tgacccgttt gctacatctt tttttctatg aaatatgtga    360
atggcaataa attcatctag actaaaaaaa aaaaaaaaaa aaaaaaaaaa aaaaa          415

<210> SEQ ID NO 94
<211> LENGTH: 5725
<212> TYPE: DNA
<213> ORGANISM: Homo sapiens

<400> SEQUENCE: 94
```

-continued

```
cctggaggag ggctctggaa gtcacgtcag gttggctctt caggttcatt tccatagttc    60
cctgcggcct ctgccttggg gagttatgtt ttgttaccga gatccgcgct accagattgc   120
accggggctg atttggggc tgggaatttg ccattctgct gtacagacac tgatttttt    180
ttcttcttt taaaaagcaa ggtttgtttt cattttggat tttaggtgat gggcaagtca   240
gaaagtcaga tggatataac tgatatcaac actccaaagc caagaagaa acagcgatgg   300
actcgactgg agatcagcct ctcggtcctt gtcctgctcc tcaccatcat agctgtgaga   360
atgatcgcac tctatgcaac ctacgatgat ggtatttgca agtcatcaga ctgcataaaa   420
tcagctgctc gactgatcca aaacatggat gccaccactg agccttgtag agactttttc   480
aaatatgctt gcggaggctg gttgaaacgt aatgtcattc ccgagaccag ctcccgttac   540
ggcaactttg acatttaag agatgaacta gaagtcgttt tgaaagatgt ccttcaagaa   600
cccaaaactg aagatatagt agcagtgcag aaagcaaaag cattgtacag gtcttgtata   660
aatgaatctg ctattgatag cagaggtgga gaacctctac tcaaactgtt accagacata   720
tatgggtggc cagtagcaac agaaaactgg gagcaaaaat atggtgcttc ttggacagct   780
gaaaaagcta ttgcacaact gaattctaaa tatgggaaaa aagtccttat taatttgttt   840
gttggcactg atgataagaa ttctgtgaat catgtaattc atattgacca acctcgactt   900
ggcctccctt ctagagatta ctatgaatgc actggaatct ataaagaggc ttgtacagca   960
tatgtggatt ttatgatttc tgtggccaga ttgattcgtc aggaagaaag attgcccatc  1020
gatgaaaacc agcttgcttt ggaaatgaat aaagttatgg aattggaaaa agaaattgcc  1080
aatgctacgg ctaaacctga agatcgaaat gatccaatgc ttctgtataa caagatgaga  1140
ttggcccaga tccaaaataa cttttcacta gagatcaatg ggaagccatt cagctggttg  1200
aatttcacaa atgaaatcat gtcaactgtg aatattagta ttacaaatga ggaagatgtg  1260
gttgtttatg ctccagaata tttaaccaaa cttaagccca ttcttaccaa atattctgcc  1320
agagatcttc aaaatttaat gtcctggaga ttcataatgg atcttgtaag cagcctcagc  1380
cgaacctaca aggagtccag aaatgctttc cgcaaggccc tttatggtac aacctcagaa  1440
acagcaactt ggagacgttg tgcaaactat gtcaatggga atatggaaaa tgctgtgggg  1500
aggctttatg tggaagcagc atttgctgga gagagtaaac atgtggtcga ggatttgatt  1560
gcacagatcc gagaagtttt tattcagact ttagatgacc tcacttggat ggatgccgag  1620
acaaaaaaga gagctgaaga aaaggcctta gcaattaaag aaaggatcgg ctatcctgat  1680
gacattgttt caaatgataa caaactgaat aatgagtacc tcgagttgaa ctacaaagaa  1740
gatgaatact tcgagaacat aattcaaaat ttgaaattca gccaaagtaa acaactgaag  1800
aagctccgag aaaaggtgga caaagatgag tggataagtg gagcagctgt agtcaatgca  1860
ttttactctt caggaagaaa tcagatagtc ttcccagccg gcattctgca gccccccttc  1920
tttagtgccc agcagtccaa ctcattgaac tatggggca tcggcatggt cataggacac  1980
gaaatcaccc atggcttcga tgacaatggc agaaacttta caaagatgg agacctcgtt  2040
gactggtgga ctcaacagtc tgcaagtaac tttaaggagc aatcccagtg catggtgtat  2100
cagtatggaa acttttcctg ggacctggca ggtggacagc accttaatgg aattaataca  2160
ctgggagaaa acattgctga taatggaggt cttggtcaag catacagagc ctatcagaat  2220
tatattaaaa agaatggcga agaaaaatta cttcctggac ttgacctaaa tcacaaacaa  2280
ctatttttct tgaactttgc acaggtgtgg tgtggaacct ataggccaga gtatgcggtt  2340
aactccatta aaacagatgt gcacagtcca ggcaatttca ggattattgg gactttgcag  2400
```

```
aactctgcag agtttcaga agcctttcac tgccgcaaga attcatacat gaatccagaa    2460
aagaagtgcc gggttggtg atcttcaaaa gaagcattgc agcccttggc tagacttgcc    2520
aacaccacag aaatggggaa ttctctaatc gaaagaaaat gggccctagg ggtcactgta    2580
ctgacttgag ggtgattaac agagagggca ccatcacaat acagataaca ttaggttgtc    2640
ctagaaaggg tgtggaggga ggaagggggt ctaaggtcta tcaagtcaat catttctcac    2700
tgtgtacata atgcttaatt tctaaagata atattactgt ttatttctgt ttctcatatg    2760
gtctaccagt ttgctgatgt ccctagaaaa caatgcaaaa cctttgaggt agaccaggat    2820
ttctaatcaa aagggaaaag aagatgttga agaatagagt taggcaccag aagaagagta    2880
ggtgacacta tagtttaaaa cacattgcct aactactagt ttttacttt atttgcaaca    2940
tttacagtcc ttcaaaatcc ttccaaagaa ttcttataca cattggggcc ttggagctta    3000
catagtttta aactcatttt tgccatacat cagttattca ttctgtgatc atttatttta    3060
agcactctta aagcaaaaaa tgaatgtcta aaattgtttt ttgttgtacc tgctttgact    3120
gatgctgaga ttcttcaggc ttcctgcaat tttctaagca atttcttgct ctatctctca    3180
aaacttggta tttttcagag atttatataa atgtaaaaat aataattttt atattaatt    3240
attaactaca tttatgagta actattatta taggtaatca atgaatattg aagtttcagc    3300
ttaaaataaa cagttgtgaa ccaagatcta taaagcgata tacagatgaa aatttgagac    3360
tatttaaact tataaatcat attgatgaaa agatttaagc acaaacttta gggtaaaaat    3420
tgcgattgga cagttgtcta gagatatata tacttgtggt tttcaaattg gacttcaaa    3480
attaaatctg tccctgagag tgtctctgat aaaagggcaa atctgcacct atgtagctct    3540
gcatctcctg tcttttcagg tttgtcatca gatggaaata ttttgataat aaattgaaat    3600
tgtgaactca ttgctcccta agactgtgac aactgtctaa ctttagaagt gcatttctga    3660
atagaaatgg gaggcctctg atggaccttc tagaattata agtcacaaag agttctggaa    3720
aagaactgtt tactgcttga taggaattca tcttttgagg cttctgttcc tctcttttcc    3780
tgttgtattg actatttcg ttcattactt gattaagatt ttacaaaaga ggagcacttc    3840
caaaattctt attttcccta acaaaagatg aaagcaggga atttctatct aaatgatgag    3900
tattagttcc ctgtctcttg aaaaatgccc attgcctttt aaaaaaaaaa gttacagaaa    3960
tactataaca tatgtacata aattgcataa agcataagta tacagttcaa taaacttaac    4020
tttaactgaa caatggccct gtagccagca cctgtaagaa acagagcagt accagcgctc    4080
taaaagcacc tccttgtcac tttattactc ccagaacaac aactatcctg acttctaata    4140
tcattcacta gctttgcctg gttttgtctt ttatgcagat agaatcaatc agtatgtatt    4200
cttttgtgcc tggcttcttt ctctcagcct tacattgtg agattcctct gtattgtgct    4260
gattgtggat cttttcattc tcattgcaga ataatgttct attgtgggac ttattacaat    4320
ttgttcatcc tattgttgat gggcacttga gaactttcca ttttggcgct attacaaata    4380
gtgcaactat gaatgtactg catgttacca tcttacttga gcctttaatg gacttatttc    4440
ttcaaatcct tccaaaaatt attataagca ttgaaattat agtttcaagc caactgtgga    4500
taccctttacc ctttcctcct ttatcacaac caccgttaca agtatactta tatttcccta    4560
aaatacattt aaaacttacc taagtgacat ttgtagttgg agtaatagga gcttccagct    4620
ctaataaaac agctgtctct aacttatttt atttccatca tgtcagagca ggtgaagagc    4680
cagaagtgaa gagtgactag tacaaattat aaaaagccac tagactcttc actgttagct    4740
```

-continued

```
ttttaaaaca ttaggctccc atccctatgg aggaacaact ctccagtgcc tggatcccct    4800
ctgtctacaa atataagatt ttctgggcct aaaggataga tcaaagtcaa aaatagcaat    4860
gcctccctat ccctcacaca tccagacatc atgaattta catggtactc ttgttgagtt    4920
ctatagagcc ttctgatgtc tctaaagcac taccgattct ttggagttgt cacatcagat    4980
aagacatatc tctaattcca tccataaatc cagttctact atggctgagt tctggtcaaa    5040
gaaagaaagt ttagaagctg agacacaaag ggttgggagc tgatgaaact cacaaatgat    5100
ggtaggaaga agctctcgac aatacccgtt ggcaaggagt ctgcctccat gctgcagtgt    5160
tcgagtggat tgtaggtgca agatggaaag gattgtaggg gcaagctgtc cagagaaaag    5220
agtccttgtt ccagccctat tctgccactc ctgacagggt gaccttgggt atttgcaata    5280
ttcctttggg cctctgcttc tctcacctaa aaaagagaa ttagattata ttggtggttc    5340
tcagcaagag aaggagtatg tgtccaatgc tgccttccca tgaatctgtc tcccagttat    5400
gaatcagtgg gcaggataaa ctgaaaactc ccatttaagt gtctgaatcg agtgagacaa    5460
aattttagtc caaataacaa gtaccaaagt tttatcaagt ttgggtctgt gctgctgtta    5520
ctgttaacca tttaagtggg gcaaaacctt gctaattttc tcaaaagcat ttatcattct    5580
tgttgccaca gctggagctc tcaaactaaa agacatttgt tattttggaa agaagaaaga    5640
ctctattctc aaagtttcct aatcagaaat ttttatcagt ttccagtctc aaaaatacaa    5700
aataaaaaca aacgttttta atact                                         5725

<210> SEQ ID NO 95
<211> LENGTH: 3259
<212> TYPE: DNA
<213> ORGANISM: Homo sapiens

<400> SEQUENCE: 95
gacgcgcgcc gggagccggc ggccgggcca gccggcgccg gggcccagtg cgccgcgctc      60
gcagccggta gcgcgccagc cgtaggcgtc gctcggcagc cgcggggccc taggcgtgcc     120
ggggaggggg cgagggcggc caggcgcctg ccgccccgga ggcaggatga gcatcgagat     180
cccggcggga ctgacggagc tgctgcaggg cttcacggtg gaggtgctga ggcaccagcc     240
cgcggacctg ctggagttcg cgctgcagca cttcacccgc ctgcagcagg agaacgagcg     300
caaaggcacc gcgcgcttcg gccatgaggg caggacctgg ggggacctgg gcgccgctgc     360 cggggggcggc accccagca aggggtcaa cttcgccgag gagcccatgc agtccgactc     420
cgaggacggg gaggaggagg aggcggcgcc cgcggacgca ggggcgttca atgctccagt     480
aataaaccga ttcacaaggc gtgcctcagt atgtgcagaa gcttataatc ctgatgaaga     540
agaagatgat gcagagtcca ggattataca tccaaaaact gatgatcaaa gaaataggtt     600
gcaagaggct tgcaaagaca tcctgctgtt taagaatctg gatccggagc agatgtctca     660
agtattagat gccatgtttg aaaaattggt caaagatggg gagcatgtaa ttgatcaagg     720
tgacgatggt gacaactttt atgtaattga tagaggcaca tttgatattt atgtgaaatg     780
tgatggtgtt ggaagatgtg ttggtaacta tgataatcgt gggagtttcg gcgaactggc     840
cttaatgtac aatacaccca gcagctac aatcactgct acctctcctg gtgctctgtg     900
gggtttggac agggtaacct tcaggagaat aatttgtgaaa acaatgcca aaagagaaa     960 aatgtatgaa agctttattg agtcactgcc attccttaaa tctttggagt tttctgaacg    1020
cctgaaagta gtagatgtga taggcaccaa agtatacaac gatggagaac aaatcattgc    1080
tcagggagat tcggctgatt cttttttcat tgtagaatct ggagaagtga aaattactat    1140
```

```
gaaaagaaag ggtaaatcag aagtggaaga gaatggtgca gtagaaatgc ctcgatgctc    1200
gcggggacag tactttggag agcttgccct ggtaactaac aaacctcgag cagcttctgc    1260
ccacgccatt gggactgtca aatgtttagc aatggatgtg caagcatttg aaaggcttct    1320
gggaccttgc atggaaatta tgaaaggaa catcgctacc tatgaagaac agttagttgc     1380
cctgtttgga acgaacatgg atattgttga acccactgca tgaagcaaaa gtatggagca    1440
agacctgtag tgacaaaatt acacagtagt ggttagtcca ctgagaatgt gtttgtgtag    1500
atgccaagca ttttctgtga tttcaggttt tttccttttt ttacatttac aacgtatcaa    1560
taaacagtag tgatttaata gtcataggc tttaacatca ctttctaaag agtagttcat     1620
aaaaaaatca acatactgat aaaatgactt tgtactccac aaaattatga ctgaaaggtt    1680
tattaaaatg attgtaatat atagaaagta tctgtgttta agaagataat taaaggatgt    1740
tatcataggc tatatgtgtt ttacttattc agactgataa tcatattagt gactatcccc    1800
atgtaagagg gcacttggca attaaacatg ctacacagca tggcatcact tttttttata    1860
actcattaaa cacagtaaaa ttttaatcat ttttgtttta aagttttcta gcttgataag    1920
ttatgtgctg ccttggccta ttggtgaaat ggtataaaat atcatatgca gttttaaaac    1980
tttttatatt tttgcaataa agtacatttt gactttgttg gcataatgtc agtaacatac    2040
atattccagt ggttttatgg acaggcaatt tagtcattat gataataagg aaaacagtgt    2100
tttagatgag agatcattaa tgcatttttc cctcatcaag catatatctg cttttttta     2160 ttttgcaatt ctctgtattc tatgtcttta aaaatttgat cttgacattt aatgtcacaa    2220
agttttgttt ttttaaaaag tgatttaaac ttaagatccg acattttttg tattctttaa    2280 gattttcac ctaaaaaatc tctcctatcc caaaataat gtgggatcct tatcagcatg      2340
cccacagttt atttctttgt tcttcactag gcctgcataa tacagtccta tgtagacatc    2400
tgttcccttg ggtttccgtt cttttcttagg atggttgcca acccacaatc tcattgatca    2460
gcagccaata tgggtttgtt tggtttttt aattcttaaa aacatcctct agaggaatag     2520
aaacaaattt ttatgagcat aaccctatat aaagacaaaa tgaatttctg accttaccat    2580
atataccatt aggccttgcc attgctttaa tgtagactca tagttgaaat tagtgcagaa    2640
agaactcaga tgtactagat tttcattgtt cattgatatg ctcagtatgc tgccacataa    2700
gatgaattta attatattca accaaagcaa tatactctta catgatttct aggccccatg    2760
acccagtgtc tagagacatt aattctaacc agttgtttgc ttttaaatga gtgatttcat    2820
tttgggaaac aggtttcaaa tgaatatata tacatgggta aaattactct gtgctagtgt    2880
agtcttacta gagaatgttt atggtcccac ttgtatatga aaatgtggtt agaatgttaa    2940
ttggataatg tatatataag aagttaaagt atgtaaagta taacttcagc cacattttta    3000
gaacactgtt taacatttt gcaaaacctt cttgtaggaa aagagagctc tctacatgaa     3060
gatgacttgt tttatatttc agattttatt ttaaaagcca tgtctgttaa acaagaaaaa    3120
acacaaaaga actccagatt cctggttcat cattctgtat tcttactcac ttttcaagt     3180 tatctatttt gttgcataaa ctaattgtta actattcatg gaacagcaaa cgcctgttta    3240
ataaagaact ttgaccaag                                                 3259
```

<210> SEQ ID NO 96
<211> LENGTH: 2376
<212> TYPE: DNA
<213> ORGANISM: Homo sapiens

```
<400> SEQUENCE: 96
cgagggcagc gccggtcggg agcgcagcgc ggcgcagctc ggcgcgcacg gcgggagcgg      60
cgcgcgagtg gtcgggcctg gcggctggac gggcgcccct cgctgccccg cgcgctcccc     120
gccgcccccc atgagcgcag ccccgcgcgg cccgggtccg taggcggcgg ggcgcccccc     180
atgctgctgc agcccgcgcc gtgcgccccg agcgcgggct tcccgcggcc cctggccgcc     240
cccggcgcca tgcacggctc gcagaaggac accacgttca ccaagatctt cgtgggcggc     300
ctgccgtacc acactaccga cgcctcgctc aggaagtact tcgagggctt cggcgacatc     360
gaggaggccg tggtcatcac cgaccgccag acgggcaagt cccgcggcta cggcttcgtg     420
accatggccg accgggcggc agctgagagg gcttgcaaag acccgaaccc catcatcgac     480
ggccgcaagg ccaacgtgaa cctggcatat ctgggcgcca gccgcggag cctccagacg      540
ggctttgcca ttggggtgca gcagctgcac ccacccttga tccagcggac ttacgggctg     600
accccgcact acatctaccc accagccatc gtgcagccca gcgtggtgat cccagccgcc     660
cctgtcccgt cgctgtcctc gccctacatt gagtacacgc cggccagccc ggcctacgcc     720
cagtacccac cggccaccta tgaccagtac ccatacgccg cctcgcctgc cacggctgcc     780
agcttcgtgg gctacagcta ccctgccgcc gtgccccagg ccctctcagc cgcagcaccc     840
gcgggcacca ctttcgtgca gtaccaggcg ccgcagctgc agcctgacag gatgcagtga     900
ggggcgttcc tgccccgagg actgtggcat tgtcaccttc acagcagaca gagctgccag     960
gccatgatgg gctggcgaca gcccggctga gctttagtga ggtgccacca gcacccgtgc    1020
ctccgaagac cgctcgggca ttccgcctgc gccctgggac agcggagaga tggcttctct    1080
ttaatctagg tcccattgtg tcttgaggga ggactttaag aatgactgag aactatttaa    1140
agacgcaatc ccaggttcct tgcacaccat ggcagcctct tcttgcacct tctcctgcct    1200
ctccacactc caggttccct caggcttgtg tccccactgc tgcatcgtgg cggggtgtca    1260
cagaccctct gcagcccctg gctgccctgg actgtgcaga gatgcctgac tccagggaaa    1320
cctgaaagca agaagttaat ggactgttta ttgtaacttg atcctcccga gctgtgagcg    1380
cagtctgagg tgtgaggaca cggcctcctg ttggagtccc attttctcca tcagggcacg    1440
tgggcggctt cctcaagccc ggaggagctc ccaggcgcac aggggccgcc ggtaacaggg    1500
gccgccggcc aaaggcccct ttccagtcat agcactgaag ttgcaacttt tttcttgtaa    1560
ttgttttgct actaagataa tttcagaagt tcagtctatt ttttcagcgg atactgccgc    1620
caccaagaat ccaaaaccta tttttgactt ggagagactt gcttttgttg gttccgcccg    1680
tggagacgac gacagtgttt ctgtataata aagtgtctgc cggctcgcgg gccaggatcc    1740
tctcggtggg atgggcacca cagacaggag gcccctcagg cccgtgcggg ccactgtctg    1800
ctgccgcctg ccggggtggc agagtgagtt gtctcaggac cccgtcactg cgacgttgac    1860
actctctcct tccttccttc cccaactccc caaacactgt ggaagggaag aaggaagtga    1920
tccacagcat tcaggccact tggggtctag accatggtgg tgccagcctg gggggggcag    1980
tggccctcag ctctgcccgc tggagcggtt gagtgcagaa gggtgcgcct cttccctcta    2040
cccccgcacc acctgctgtg tgccagcctg agacggttcc tgcctgtctt gggggttggt    2100
ggagggtgga ggcagttctg ccagccgtgg cagggctgct atgggcatc cagggctgtg      2160
ggggtctgga ggaggggaca tgaggtgaga ggtatcctgg ccgagggcgg gggcagcgg     2220
ggggtctccc tccggaccta cctcaggag ctgagcgtgc aggcgctcca gggcaggcct      2280
gggacagagt caaggctcag agaataaagg tagctaatct catcataata tttttattag    2340
```

```
-continued aatgttctga tgataaaaat aaaacttgtt ttcttt                                    2376

<210> SEQ ID NO 97
<211> LENGTH: 21
<212> TYPE: DNA
<213> ORGANISM: Artificial Sequence
<220> FEATURE:
<223> OTHER INFORMATION: Primer

<400> SEQUENCE: 97
gttgtaaaac gacggccagt g                                                      21

<210> SEQ ID NO 98
<211> LENGTH: 19
<212> TYPE: DNA
<213> ORGANISM: Artificial Sequence
<220> FEATURE:
<223> OTHER INFORMATION: Primer

<400> SEQUENCE: 98
cacacaggaa acagctatg                                                         19

<210> SEQ ID NO 99
<211> LENGTH: 21
<212> TYPE: DNA
<213> ORGANISM: Artificial Sequence
<220> FEATURE:
<223> OTHER INFORMATION: Primer

<400> SEQUENCE: 99
tttttttttt tttttttttt v                                                      21
```

METHODS FOR ANALYZING HIGH DIMENSIONAL DATA FOR CLASSIFYING, DIAGNOSING, PROGNOSTICATING, AND/OR PREDICTING DISEASES AND OTHER BIOLOGICAL STATES

CROSS REFERENCE TO RELATED APPLICATION

This application is a continuation application of Ser. No. 10/133,937, filed on Apr. 25, 2002, the entire contents of which are incorporated herein by reference.

STATEMENT OF GOVERNMENT RIGHTS

The work performed during the development of this invention utilized U.S. Government Funds. The government has certain rights in the invention.

FIELD OF THE INVENTION

The invention relates generally to the use of supervised pattern recognition methods to classify and diagnose disease. More specifically, the invention relates to the use of supervised pattern recognition methods, such as artificial neural networks for the classification, diagnosis, prognosis and prediction of disease using high dimensional data, such as gene expression profiling data.

BACKGROUND OF THE INVENTION

Disease is generally diagnosed based on a myriad of factors, both objective and subjective, including but not limited to symptoms, laboratory test values, demographic factors and environmental factors. Diagnosis relies on a clinician such as a physician or a veterinarian being able to identify and evaluate the relevant factors. Often this task can be difficult, and becomes exceedingly more so as the number of factors to be considered increases.

An example of a disease whose diagnosis is difficult is tumors. Tumors are currently diagnosed on the basis of clinical presentation, routine histology, immunohistochemistry and electron microscopy. However the histological appearance may not reveal the genetic aberrations or underlying biologic processes that contribute to the malignancy. Monitoring global gene expression levels using DNA microarrays would provide an additional tool for elucidating tumor biology as well as the potential for molecular diagnostic classification of cancers. Several studies have demonstrated that gene expression profiling using DNA microarrays is able to classify tumors with a high accuracy, and discover new cancer classes.

A specific type of tumors which could benefit is the small, round blue cell tumors (SRBCTs) of childhood as a model. SRBCTs include, neuroblastoma (NB), rhabdomyosarcoma (RMS), non-Hodgkin lymphoma (NHL) and the Ewing family of tumors (EWS), are so named because of their similar appearance on routine histology. However, accurate diagnosis of SRBCTs is essential because the treatment options, responses to therapy, and prognoses vary widely depending on the diagnosis. As their name implies, these cancers are difficult to distinguish by light microscopy, and currently no single test can precisely distinguish these cancers.

In clinical practice, several techniques are used for diagnosis, including immunohistochemistry, cytogenetics, interphase fluorescence in situ hybridization and reverse transcription (RT)-PCR. Immunohistochemistry allows the detection of protein expression, but it can only examine one protein at a time. Molecular techniques such as RT-PCR are used increasingly for diagnostic confirmation following the discovery of tumor-specific translocations such as EWS-FLI1; t(11;22)(q24;q12) in EWS, and the PAX3-FKHR; t(2;13)(q35;q14) in alveolar rhabdomyosarcoma (ARMS). However, molecular markers do not always provide a definitive diagnosis, as on occasion there is failure to detect the classical translocations, due to either technical difficulties or the presence of variant translocations.

An example of a diagnostic method replete with such problems is the diagnostic method for Ewing sarcoma. Ewing sarcoma is diagnosed by immunohistochemical evidence of MIC2 expression and lack of expression of the leukocyte common antigen CD45 (excluding lymphoma), muscle-specific actin or myogenin (excluding RMS). However, reliance on detection of MIC2 alone can lead to incorrect diagnosis as MIC2 expression occurs occasionally in other tumor types including RMS and NHL.

One objective factor that can, in certain circumstances, be entirely predictive of a diseased state is the genetic makeup of the individual. Genetic makeup of an individual can also be considered in terms of the level of expression of the genes of that individual through gene expression data.

DNA microarray technology is a recently developed high throughput technology for monitoring gene expression at the transcription level. Its use is akin to performing tens of thousands of northern blots simultaneously, and has the potential for parallel integration of the expression levels of an entire genome. A DNA microarray consists of DNA probes immobilized on a solid support such as a glass microscope slide. The DNA probes can be double stranded cDNA or short (25 mers) or long (50-70 mers) oligonucleotides of known sequences. An ideal DNA microarray should be able to interrogate all of the genes expressed in an organism.

In DNA microarrays using cDNA, the probes are PCR amplified from plasmid cDNA clones that have been purified and robotically printed onto coated glass slides. DNA microarrays using oligonucleotide have an advantage over cDNA microarrays because physical clones are not necessary. The oligonucleotides can either be previously synthesized and printed on glass slides, or can be synthesized directly on the surface of silicon or glass slides. Several print-ready oligonucleotide (60-70 mers) sets are commercially available for human, mouse and other organisms (cgen.com, operon.com).

Another technique for fabricating oligonucleotides microarrays chemically synthesizes the oligonucleotides (25 mers) on a silicon surface using photolithography techniques. (Affymetrix Inc., Santa Clara, Calif.). Originally such arrays were designed to detect single-nucleotide mutations, but now have applications for gene expression profiling studies. Yet another technique delivers single nucleic acids, which ultimately form longer oligonucleotides (60 mers), by ink-jet onto glass surfaces.

One method of utilizing gene expression data from microarrays is given by Tusher et al., PNAS 98(9) p. 5116-21, April, 2001. The method of Tusher et al. is a statistical method titled Significance Analysis of Microarrays ("SAM"). The general approach in SAM is based on commonly used statistical tests, t-tests specifically, to find genes that discriminate between two classes in a gene-by-gene fashion. SAM uses replication of experiments to assign a significance to the discriminating genes in terms of a false discover rate. SAM therefore offers a method of choosing particular genes from a set of gene expression data, but does not offer a diagnosis based on those genes.

DNA microarrays would be an invaluable tool for disease diagnosis. Gene-expression profiling using DNA microarrays permits a simultaneous analysis of multiple markers, and can be used for example to categorize cancers into subgroups. The only limitation associated with the use of DNA microarrays is the vast amount of data generated thereby. A method that would allow for the easy and automated use of DNA microarray data in disease diagnosis is therefore desirable. Despite the many statistical techniques to analyze gene-expression data, none so far has been rigorously tested for their ability to accurately distinguish diseases belonging to several diagnostic categories. Such methods have also not been used to extract the genes or features that are the most important for the classification performance. Such genes would also generally be those that are of use to biologists and physicians as offering avenues to research in investigating cures.

Therefore, there remains a need for a method of using gene expression data to diagnose, predict, or prognosticate about a disease condition.

However, these other methods have not been used to extract the genes or features that are most important for the classification performance and which also will be of interest to cancer biologists.

SUMMARY OF THE INVENTION

In accordance with the invention, there is provided a method of diagnosing, predicting, and/or prognosticating about a disease including obtaining experimental data, wherein the experimental data includes high dimensional data, filtering noise from the data, reducing the dimensionality of the data by using one or more methods of analysis, training a supervised pattern recognition and/or classification method, ranking individual data from the overall data based on the relevance of the individual data to the diagnosis, prediction, prognosis or classification, choosing multiple individual data members, wherein the choice is based on the relative ranking of the individual data, and using the chosen data to determine if an unknown set of experimental data indicates a particular diseased condition, prognosis, prediction, or classification.

The invention offers a method of diagnostic classification of cancers from their gene-expression signatures and also identifies the genes that contributed to this classification. One embodiment of the method diagnoses SRBCTs of childhood, which occasionally present diagnostic difficulties.

The invention also offers a method of diagnosing, predicting, and/or prognosticating about SRBCTs including obtaining gene expression data, filtering noise from the gene expression data, reducing the dimensionality of the data by using principal component analysis (PCA), training an ANN, ranking the individual genes from the gene expression data, choosing multiple genes from the gene expression data, wherein the choice is based on the relative ranking of the individual genes and using the chosen genes to determine if an unknown set of gene expression data indicates a particular diseased condition, prognosis, and/or a prediction.

Methods of the invention can be utilized in a number of different applications. For example, diagnostic chips can be fabricated based on the identification of the diagnostic genes. Such chips would be very useful in clinical settings, as it would allow clinicians to diagnose cancers from a relatively small set of genes instead of purchasing entire gene sets.

Methods of the invention can also be used to define which patients with the same types of cancers are likely to respond to treatment. This would allow a physician to intensify treatment for those with a more negative prognosis based on their gene expression profiles as detected utilizing a method of the invention.

Methods of the invention can also be used for identifying pharmaceutical targets. Pharmaceutical companies can utilize methods of the invention to determine which genes to target in efforts to target specific diseases.

Methods of the invention can also be utilized as a research tool for analyzing all types of gene expression data including cDNA and oligonucleotide microarray data.

Methods of the invention can also be utilized to identify and rank, by importance, the genes that contribute to a diagnosis. A minimal set of genes that can correctly classify and identify diagnostic categories can also be determined using methods of the invention.

Methods of the invention identify the most significant genes, by calculating the sensitivity of the classification to a change in the expression level of each gene. A list of genes, ranked by their significance to the classification, is produced thereby. In an embodiment of the invention utilized for classifying SRBCTs the most important 96 genes reduced the misclassifications to zero. This allows for cost effective fabrication of SRBCT subarrays for diagnostic use. When a method of the invention used the 96 genes on 25 unknown samples, all 20 samples of SRBCTs and 5 non-SRBCTs were correctly classified.

One embodiment of the invention calibrates ANN models on the expression profiles of 63 SRBCTs of 4 diagnostic categories. Preferred embodiments of the invention utilize linear (that is no hidden layers) ANN models because of the high performance achieved. Methods of the invention may utilize other linear methods as well, and methods of the invention can easily accommodate nonlinear features of expression data if required. Hidden layers will be utilized for non linear data. Preferably, both tumor samples and cell line samples are used in order to compensate for heterogeneity within unknown samples (which contain both malignant and stromal cells) based on possible artifacts due to growth of cell lines in tissue culture.

Data from such samples is complementary, because tumor tissue, though complex, provides a gene-expression pattern representative of tumor growth in vivo, while cell lines contain a uniform malignant population without stromal contamination. Despite using only neuroblastoma (NB) cell lines for calibrating the ANN models, all four NB tumors among the test samples were correctly diagnosed with high confidence. This not only demonstrates the high similarity of NB cell lines to the tumors of origin, but also validates the use of cell lines for ANN calibration. One embodiment of a method of the invention accurately classified all 63 training SRBCTs and showed no evidence of over-training, thereby demonstrating the robustness of this method.

BRIEF DESCRIPTION OF THE FIGURES

FIG. 7 represents two projections of the MDS plot of the training samples.

DETAILED DESCRIPTION OF THE PREFERRED EMBODIMENTS

The invention is a method of classifying, diagnosing, prognosticating about, and predicting disease conditions or other biological states using supervised pattern recognition methods to analyze high dimensional data.

Figure 1:
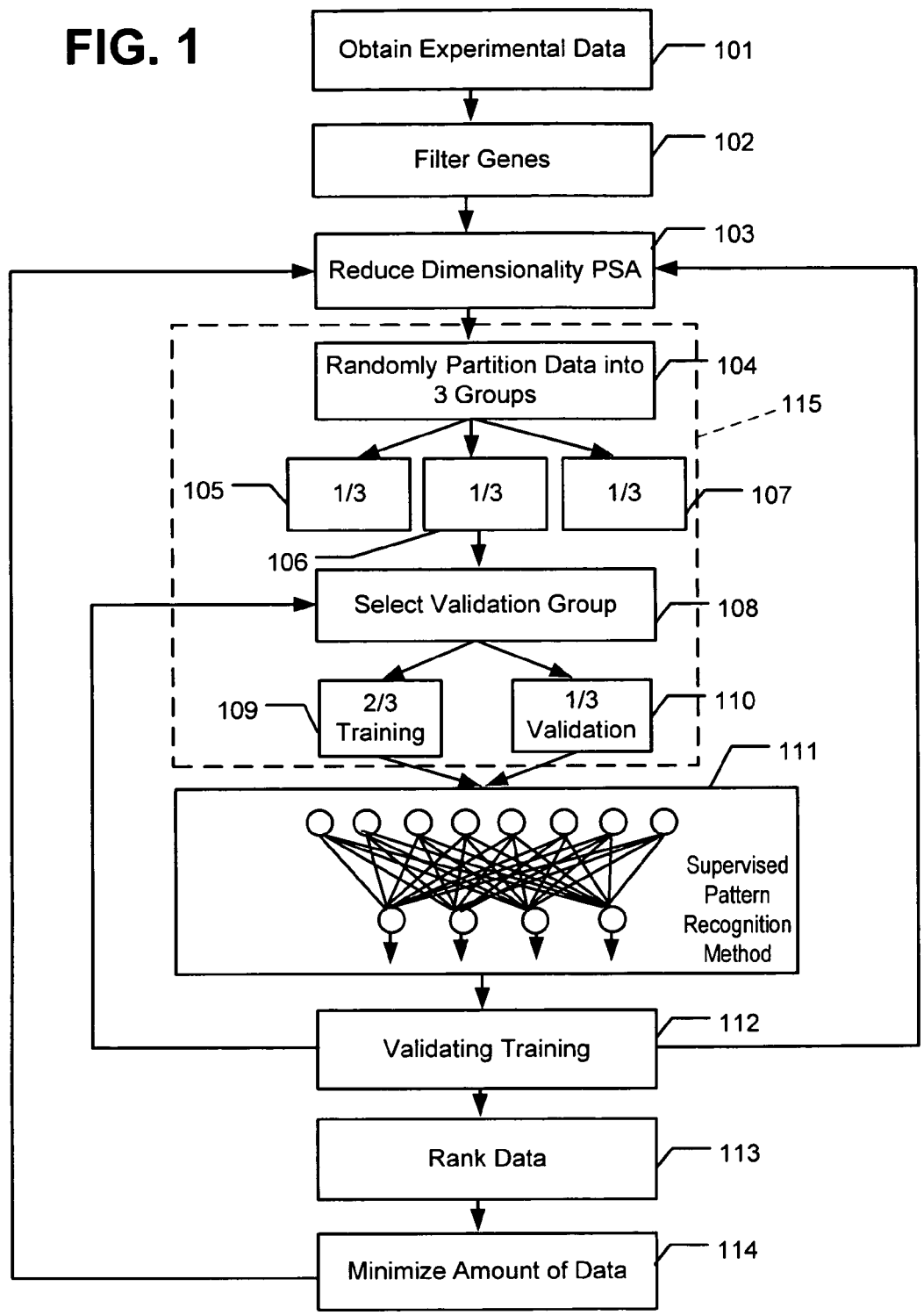
FIG. 1 illustrates a process flow for a method to classify and diagnose diseases using artificial neural networks according to one embodiment of the invention.

One embodiment of the invention is illustrated in FIG. 1. This process flow describes an embodiment of the method that includes obtaining experimental data 101, filtering the data 102, reducing the dimensionality of the data 103, setting up a validation method 115, training a supervised pattern recognition method 111, validating the outcome of the supervised pattern recognition method 112, and once the supervised pattern recognition method is validated, ranking the data based on the outcome of the supervised pattern recognition method 113. Further detail and more specific embodiments of methods of the invention are described below.

Any diagnostic categories can be diagnosed using the technology described here. It includes distinguishing patients with multiple sclerosis, rheumatoid arthritis, and other inflammatory or autoimmune diseases. It may also diagnose other systemic diseases based on gene expression profiles of white cells, including infections with particular organisms, cancer, or myocardial infarctions.

Obtaining Experimental Data

The first step in methods of the invention is to obtain experimental data. Experimental data utilized in methods of the invention is high dimensional data. High dimensional data is data that has at least hundreds of individual pieces of information associated with one sample. An example of high dimensional data useful in methods of the invention is gene expression data. Gene expression data is high dimensional data because each sample or person has a large number of gene expression levels. Generally speaking, gene expression data generally has thousands of gene expression levels for each sample. Other examples of high dimensional data useful in the invention include but are not limited to protein arrays and protein chips, cell array based expression analysis, analysis of patterns of single nucleotide polymorphisms in disease conditions, and comparative genomic hybridization on methaphase, BAC genomic, cDNA and oligonucleotide arrays.

Preferably, the gene expression data is obtained through use of DNA microarray technology. DNA microarrays are preferred as a source of data because they generally offer a more complete picture of the interactions of a large number of genes with a limited number, or even one experiment. An example of a general description of how gene expression data can be obtained by using cDNA microarray technology is given below.

DNA microarrays, although a relatively new technology, have already been saddled with a number of different names, biochip, DNA chip, gene chip, genome chip, cDNA microarray, and gene array. The use of any of these terms herein refers generally to DNA microarrays. The underlying principle of DNA microarrays is base pairing or hybridization i.e., A-T and G-C for DNA, and A-U and G-C for RNA.

DNA microarrays provide a medium for matching known and unknown DNA samples based on the base pairings given above. DNA microarrays can either be fabricated by high-speed robotics or can be fabricated in a laboratory setting. They are generally patterned on glass, but can also be fabricated on nylon substrates. Microarrays generally have sample spot sizes of less than 200 µm diameter, and generally contain thousands of DNA spots on one microarray.

One method of fabricating cDNA microarrays begins by first producing gene-specific DNA by polymerase chain reaction (PCR) amplification of purified template plasmid DNAs from cloned expressed sequence tags (ESTs). The PCR product is then purified, resuspended and printed onto a substrate. cDNA microarrays are also commercially available from a number of sources, including but not limited to Affymetric, Inc. (Santa Clara, Calif.), Agilent Technologies (Palo Alto, Calif.), and Research Genetics (Huntsville, Ala.).

One general procedure for a cDNA microarray experiment begins by preparing DNA samples and arraying them (either with an arraying robot, or by hand), to form a DNA microarray. Next, the RNA samples are extracted from the cells of interest, purified, reverse transcribed into cDNA and differentially fluorescently labeled to create probes. Then, the fluorescently labeled cDNA probes are hybridized to the cDNA microarray. If a probe contains a cDNA whose sequence is complementary to the DNA on a given spot, the cDNA probe will hybridize to that spot. After the cDNA probes are hybridized to the array, and any loose probe has been washed away, the microarray is imaged to determine how much of each probe is hybridized to each spot. This indicates how much of each gene from the microarray is expressed in the two samples.

The experimental high dimensional data, preferably obtained from gene expression experiments, preferably performed using cDNA microarrays, is then further analyzed by a method of the invention.

Filtering the Data

The next step in a method of the invention is filtering the data 102 to remove individual pieces of data that are deemed undesirable. This filtering step functions to eliminate weak and/or problematic data from further use in the method. Accomplishment of the step of filtering depends greatly on the type of high dimensional data utilized. Any method known to those of ordinary skill in the art can be used to eliminate data determined to be undesirable.

One basis for carrying out this filtering, if a DNA microarray is being utilized for obtaining the high dimensional data, is the intensity of the fluorescence from the individual microarray spots. This basis of omitting data is based on failure or error in the imaging of the specific spots. A preferred method of performing initial data filtering on cDNA microarray data to remove those spots where imaging was a problem is to utilize the intensity of the various spots and utilize only those spots that have an intensity over a certain threshold value. Other methods of filtering DNA microarray data include but are not limited to eliminating spots in which the number of pixels represented is less than a threshold defined by the user, eliminating spots in which the standard deviation of the signal on the spots is too large, as defined by the user, eliminating spots in which the background intensity of a single spot is too high, or any combination thereof. In addition quality values based on intensity, can be assigned to each spot, standard deviation of intensity, background and/or size of each spot, then a spot could be eliminated if its quality value falls below a threshold as defined by the user.

Reducing the Dimensionality of the Data

The next step in methods of the invention is reducing the dimensionality of the data 103. The number of samples needed to calibrate a classifier with good predictive ability, depends critically on the number of features used in the design of the classifier. In the case of high-dimensional data, such as microarray data, where the number of samples is much smaller than the number of individual pieces of data there exists a large risk of over-fitting. There are two different solutions to this problem. First, the calibration process can be carefully monitored using a cross-validation scheme to avoid over-fitting (see below). Second, the dimension of the data can be reduced, either by using a dimensional reduction algorithm or by selecting a smaller set of data for input to the supervised pattern recognition method. Dimensionality reduction allows the number of parameters representing each sample to be reduced. This allows for the design of a classifier that has less risk of over-fitting, thereby increasing its predictive ability. Examples of methods of reducing the dimensionality of the data include but are not limited to principal component analysis (PCA), weighted gene analysis, t-test, rank based Wilcoxon or Mann-Whitney tests, signal-to-noise statistic, Fisher's discriminant analysis, or ANOVA tests.

In a preferred embodiment of the invention, PCA is used to reduce the dimensionality of the data.

In the case of PCA on gene expression data, reduction of the dimensionality is achieved by rotating gene expression space, such that the variance of the expression is dominated by as few linear combinations of genes as possible Even though the formal dimension of the problem is given by the number of individual data points, the effective dimension is just one less than the number of samples. Hence the eigenvalue problem underlying PCA can be solved without diagonalizing 2308×2308 matrices by using singular value decomposition. Thus each sample is represented by 88 numbers, which are the results of projections of the data using the PCA eigenvectors.

A potential risk when using PCA on relatively few samples is that components might be singled out due to strong noise in the data. It could be argued that the outputs (labels) should be included in the dimensional reduction, using e.g. the Partial Least Squares (PLS) algorithm, in order to promote components with strong relevance for the output. However, based on explorations with similar data sets, this is not optimal; bias is introduced and implicitly "over-trains" from the outset by including the outputs in the procedure.

Setting up a Validation Method for the Supervised Pattern Recognition Method

Once the data has been filtered 102 and its dimensionality reduced 103, a validation method is set up for monitoring and validating the training of the supervised pattern recognition method 115. Any method commonly used by those of skill in the art for validating the training of a supervised pattern recognition method can be used.

In one embodiment, the first step in setting up a validation method is to randomly divide the data into three groups of data, 105, 106, and 107. Then, one of those groups is chosen as a validation group 108. The first two of the groups 105 and 106 are combined into a training group 109, which is used to train the supervised pattern recognition method 111 and the third group 107 is used to validate the performance of the supervised pattern recognition method 111, once trained, and is called a validation group 110.

In this specific preferred embodiment, the 3-fold cross validation procedure (steps 104 through 110) is performed on all of the samples. A data group having 63 samples is given as an example. The 63 known (labeled) samples are randomly shuffled 104 and split into 3 equally sized groups (105, 106, and 107). The supervised pattern recognition method 111 is then calibrated as discussed below using the training group 109. The third group, a validation group 110, is reserved for testing predictions. Comparisons with the known answers refer to the results from the validation group 110 (i.e. when using a model, the samples used for training the model are never used in predictions). This procedure is repeated 3 times, each time with a different group used for validation. The random shuffling 104 is done about 100 to 10000 times. For each shuffling, one supervised pattern recognition method 111 model is generated. Thus, in total each sample belongs to a validation group 110, 1250 times and 3750 supervised pattern recognition methods 111 have been calibrated.

Training the Supervised Pattern Recognition Method

The supervised pattern recognition method 111 is then trained. The specific method of training the supervised pattern recognition method 111 is dependent on the specific form that the supervised pattern recognition method 111 takes. The choice of the supervised pattern recognition method 111 and the training thereof is well within one of skill in the art, having read this specification.

One example of a supervised pattern recognition method is an artificial neural network (ANN). ANNs are computer-based algorithms that are modeled on the structure and behavior of neurons in the human brain and can be trained to recognize and categorize complex patterns. Pattern recognition is achieved by adjusting parameters of the ANN by a process of error minimization through learning from experience. They can be calibrated using any type of input data, such as gene-expression levels generated by cDNA microarrays, and the output can be grouped into any given number of categories. ANNs have been recently applied to clinical problems such as diagnosing myocardial infarcts and arrhythmias from electrocardiograms and interpreting radiographs and magnetic resonance images. However, ANNs have not been used to decipher gene-expression signatures of SRBCTs or for diagnostic classification.

In embodiments where an artificial neural network (ANN) is employed as the supervised pattern recognition method 111, calibration is preferably performed using JETNET (C. Peterson, T. Roegnvaldsson and L. Loennblad, "JETNET 3.0—A versatile artificial neural network package," Computer Physics Communications 81, 185-220 (1994)). Preferably, the software is used with a learning rate $\eta=0.7$, momentum coefficient $p=0.3$ and the learning rate is decreased with a factor 0.99 after each iteration. Initial weight values are chosen randomly from $[-r, r]$, where $r=0.1/\max_i F_i$ and the "fanin" $F_i$ is the number of nodes connecting to node i. The calibration is performed using a training set and it is monitored both for the training set and a validation set, which is not subject to calibration (see below). The weight values are updated after every 10 samples and the calibration is terminated after 100 passes (epochs) through the entire training set. In one embodiment of a method of the invention, the resulting parameters for the completed training of a supervised pattern recognition method 111 defines a "model".

In preferred embodiments, due to the limited amount of calibration data and the fact that four output nodes are needed (Ewing's sarcoma (EWS), Burkitt's lymphoma (BL), neuroblastoma (NB) and rhabdomyo sarcoma (RMS)), linear perceptrons (LP) with 10 input nodes representing the PCA components described above are utilized. In other words, the supervised pattern recognition method 111 generally contains 44 parameters including four threshold units. Since 10 components could be used without risking "over-training" the optimization of the number of components to a smaller number is generally not necessary.

The possibility of using all the PCA components as inputs followed by a subsequent pruning of weights to avoid "overfitting" is also one alternative. This resulted in the dominant 4-8 PCA components (depending on the composition of the training set 107) being the surviving inputs. Generally, the less dominant PCA components contain variance not related to separating the four cancers, but rather to, for example, experimental conditions (noise) or variance related to sub-groupings within a cancer type.

Verifying the Outcome of the Supervised Pattern Recognition Method

Once the supervised pattern recognition method 111 is trained, the next step is to determine whether the validation of the supervised pattern recognition method 111 is successful 112. This step determines whether the supervised pattern recognition method 111 adequately predicted the results for the validation data set 110 using any number of performance measurements and error measurements.

Any method known to those of ordinary skill in the art can be utilized to evaluate the performance of the training of the supervised pattern recognition method 111. Generally speaking, the performance is evaluated by comparison with some predetermined level of correct predictions that the user has determined is acceptable.

If the performance of the supervised pattern recognition method 111 is sufficiently poor, and a measure of error is greater than an allowable threshold, the processing may return to module 103 where the dimensionality of the data is reduced in a different manner and the entire training and validation process is repeated.

Ranking the Data

Once module 112 determines that the network 111 has been adequately trained, the processing proceeds to rank the output of the supervised pattern recognition method 113.

The outcome of the supervised pattern recognition method 111 can be looked at either independently or in a compiled form. Each supervised pattern recognition method 111 gives a number between 0 (not this disease type) and 1 (this disease type) as an output for each disease type. If the predictions are viewed independently, the maximal output is forced to 1 while the other outputs are forced to 0. Then it is determined how many of the predictions are correct. If the predictions are viewed in a compiled form, all of the predicted outputs are considered in their numerical form, after which all of the numbers are averaged and the resulting average is forced to 0 or 1.

In one embodiment of the method, the predictions, as compiled, are used to classify samples. For validation samples the compilation is based on 1250 models, while for additional unknown samples all 3750 models are used in the compilation.

In one embodiment, each sample is classified as belonging to the disease type corresponding to the largest average in the compilation. In addition, it is desirable to be able to reject the second largest vote as well as test samples that do not belong to any of the disease types. In order to reject those samples that do not belong, a distance $d_c$ from a sample to the ideal vote for each disease type is defined as:

$$d_c = \frac{1}{2}\sum_{i=1}^{4}(o_i - \delta_{i,c})^2 \quad (1)$$

where c is a disease type, $o_i$ is the average from the compilation for disease type i, and $\delta_{i,c}$ is unity if i corresponds to disease type c and zero otherwise. The distance is normalized such that the distance between two ideal samples belonging to different disease categories is unity. Based on the validation group, an empirical probability distribution of its distances is generated for each disease type.

The empirical probability distributions are preferably built using each supervised pattern recognition method 111 independently (not the average from the compilation). Thus, the number of entries in each distribution is given by 1250 multiplied by the number of samples belonging to the disease type. For a given test sample, the possible classifications based on these probability distributions can be rejected. This means that for each disease category a cutoff distance from an ideal sample is defined, within which, based on the validation samples, a sample of this category is expected to be. The distance given by the 95th percentile of the probability distribution is preferably chosen as a cutoff, which means that if a sample is outside of this cutoff distance it cannot be confidently diagnosed. It should be noted that the classification as well as the extraction of important genes (see below) converges using less than 100 supervised pattern recognition method 111 models. 3750 supervised pattern recognition method 111 models are preferred is because sufficient statistics exist for these empirical probability distributions.

For each disease category the sensitivity and specificity of the diagnosis may be calculated (see Table 1 below). Table 1 gives sensitivity, specificity and ROC curve areas for both validation and test samples. Both the sensitivity and the specificity are very high for all categories. It should be noted, that they generally depend on the kind of samples that are used as test samples.

TABLE 1

| Category | Sensitivity | Specificity | ROC curve area |
|---|---|---|---|
| EWS | 93% | 100% | 1.0 |
| BL | 100% | 100% | 1.0 |
| NB | 100% | 100% | 1.0 |
| RMS | 96% | 100% | 1.0 |

For example, in the case of SRBCT classification, using normal muscle samples as tests makes it harder to separate out RMS samples. If only samples from the four categories were used as blind distance cutoffs, it could easily have been designed such that both the sensitivity and the specificity would have been 100% for all diseases. However, it is preferred that the method is tested using a variety of blind tests. If it is desirable to improve rejection of for example normal muscle samples, one could incorporate them as a fifth category in the training process. However, using more samples of all four categories in the training is initially probably the best way to improve the diagnostic separation.

The Receiver Operator Characteristic (ROC) curve area is identical to another more intuitive and easily computed measure of discrimination: the probability that in a randomly chosen pair of samples, one belonging to and one not belonging to the disease category, the one belonging to the category is the one with the closest distance to the ideal for that particular category. Since the ROC curve areas are unity for all disease categories (see Table 1), it is possible to define cutoff distances such that both the sensitivity and the specificity are 100% for all diseases. However, based on the training and validation groups it is difficult to motivate such cutoff distances.

The next step in a method in accordance with the invention is to actually rank the data. This step can in principle be done in two ways; (1) model-independent and (2) model-dependent analysis respectively. Due to the relative small number of samples, the model-dependent analysis is preferred when using ANN models.

The sensitivity (S) of the outputs (o) with respect to any of the 2308 input variables ($x_k$) is defined as:

$$S_k = \frac{1}{N_s} \frac{1}{N_o} \sum_{s=1}^{N_s} \sum_{i=1}^{N_o} \left| \frac{\delta o_i}{\delta x_k} \right| \quad (2)$$

where $N_s$ is the number of samples (63 or 88) and No is the number of outputs (4). The procedure for computing $S_k$ involves a committee of 3750 models. In addition we have defined a sensitivity for each output i ($S_i$), which is analogous to Eq. (2) but without the sum over outputs. Furthermore, a sensitivity can be defined for each sample (or subsets of samples) individually, by only using that sample(s) in the sum over samples in Eq. (2). For all these sensitivities the sign of the sensitivity has also been defined. The sign signals whether the largest contribution to the sensitivity stems from positive or negative terms. A positive sign implies that increasing the expression rate of the gene increases the possibility that the sample belongs to this cancer type, while a negative sign means that decreasing the expression rate of the gene increases the same possibility. In other words, the sign does not tell whether a gene is up- or down-regulated but if it is more or less expressed in this cancer type as compared to the others. This means the genes are ranked not only according to their importance for the total classification, but also according to their importance for the different disease categories separately. The genes are preferably given a total rank as well as a separate rank for each disease category. Based on these ranks each gene is classified according to which disease category it is highly expressed in.

In one embodiment, once ranked, a relevant set of data can be selected module 114 by minimizing the amount of data to be used to classify and identify a particular disease. In one embodiment, a pre-determined amount of data having the highest ranking are selected. Of course, other selection methods may be employed without deviating from the spirit and scope of the present invention as recited in the attached claims.

Implementation of Methods of the Invention

Figure 2:
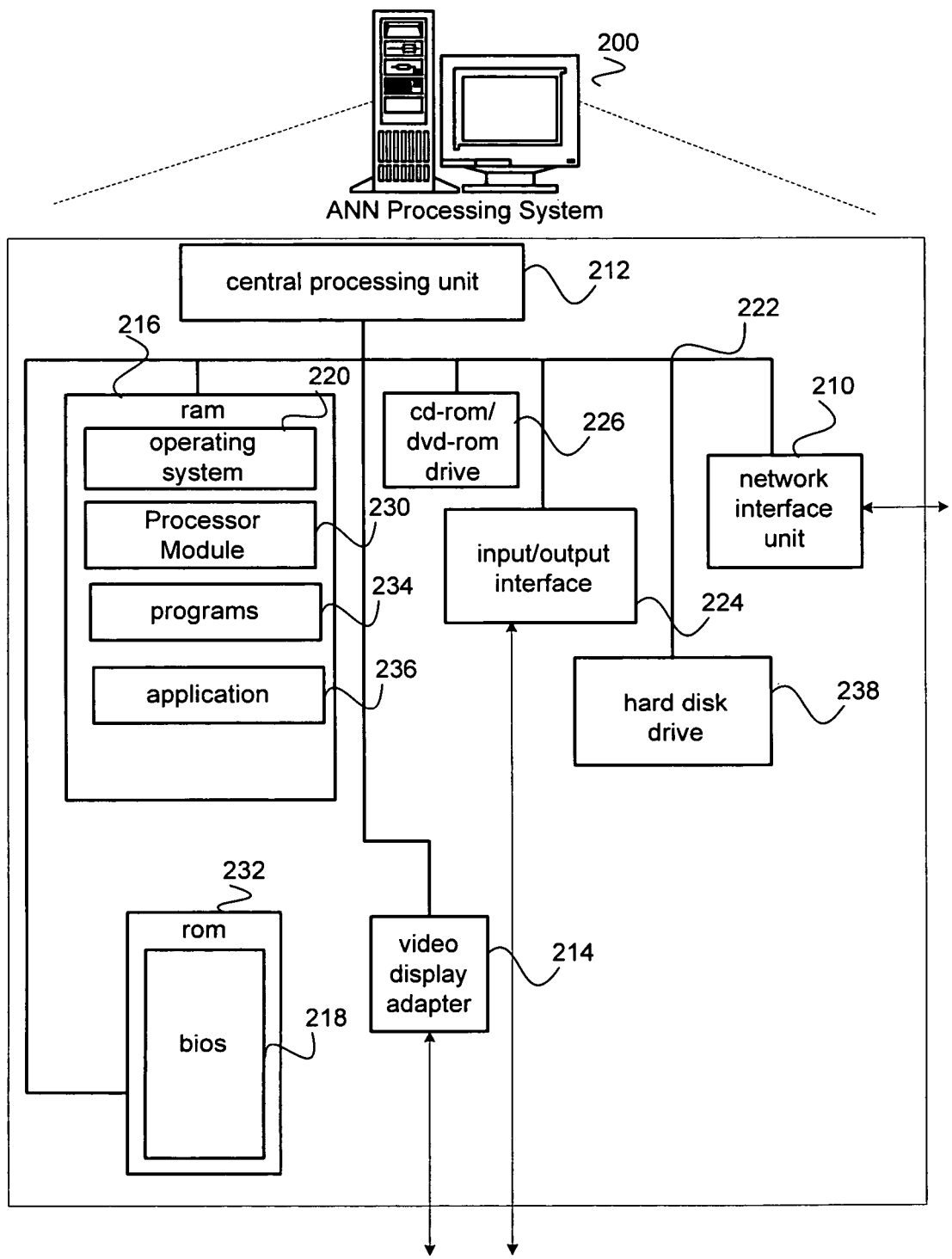
FIG. 2 illustrates a general purpose computing system utilized as part of an artificial neural network according to another embodiment of the invention.

In embodiments of the method in which the supervised pattern recognition method 111 is an artificial neural network, a general purpose computing system as depicted in FIG. 2 can be utilized. An exemplary ANN processing system 200 provides an artificial neural network that also receives experimental data to train the artificial neural network, to verify the output of an artificial neural network, and to identify relevant genes using the neural network.

Those of ordinary skill in the art will appreciate that the ANN processing system 200 may include many more components than those shown in FIG. 2. However, the components shown are sufficient to disclose an illustrative embodiment for practicing the present invention. As shown in FIG. 2, the ANN processing system 200 is connected to a WAN/LAN, or other communications network, via network interface unit 210. Those of ordinary skill in the art will appreciate that network interface unit 210 includes the necessary circuitry for connecting the ANN processing system 200 to a WAN/LAN, and is constructed for use with various communication protocols including the TCP/IP protocol. Typically, network interface unit 210 is a card contained within the ANN processing system 200.

The ANN processing system 200 also includes processing unit 212, video display adapter 214, and a mass memory, all connected via bus 222. The mass memory generally includes RAM 216, ROM 232, and one or more permanent mass storage devices, such as hard disk drive 228, a tape drive, CD-ROM/DVD-ROM drive 226, and/or a floppy disk drive. The mass memory stores operating system 220 for controlling the operation of ANN processing system 200. It will be appreciated that this component may comprise a general purpose server operating system as is known to those of ordinary skill in the art, such as UNIX, LINUX, MAC OS?, or Microsoft WINDOWS NT?. Basic input/output system ("BIOS") 218 is also provided for controlling the low-level operation of ANN processing system 200.

The mass memory as described above illustrates another type of computer-readable media, namely computer storage media. Computer storage media may include volatile and nonvolatile, removable and non-removable media implemented in any method or technology for storage of information, such as computer readable instructions, data structures, program modules or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The mass memory also stores program code and data for providing an ANN processing and network development. More specifically, the mass memory stores applications including ANN processing module 230, programs 234, and other applications 236. ANN processing module 230 includes computer executable instructions which, when executed by ANN processing system 200, performs the logic described above.

The ANN processing system 200 also comprises input/output interface 224 for communicating with external devices, such as a mouse, keyboard, scanner, or other input devices not shown in FIG. 2. Likewise, ANN processing system 200 may further comprise additional mass storage facilities such as CD-ROM/DVD-ROM drive 226 and hard disk drive 228. Hard disk drive 228 is utilized by ANN processing system 200 to store, among other things, application programs, databases, and program data used by ANN processing module 230. For example, customer databases, product databases, image databases, and relational databases may be stored. The operation and implementation of these databases is well known to those skilled in the art.

Figure 3:
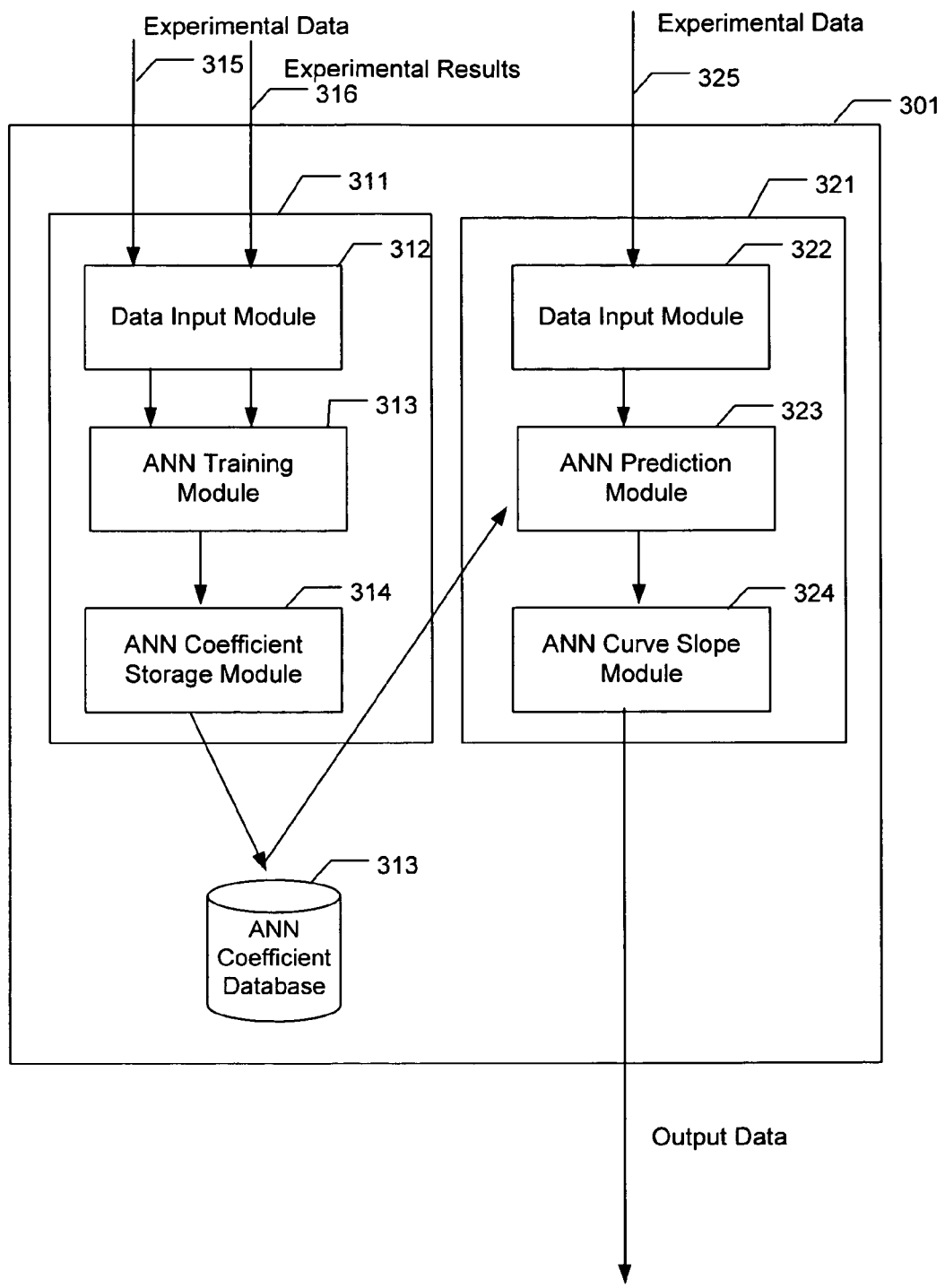
FIG. 3 illustrates a set of processing modules making up an embodiment of an artificial neural network according to the invention.

A set of processing modules making up an embodiment of an artificial neural network according to the invention is illustrated in FIG. 3. The artificial neural network disclosed herein corresponds to a generic neural network of no particular topology for the network of nodes contained therein. The neural network typically utilizes a form of competitive learning for the operation of the nodes within the network. Within competitive learning networks, a large number of data vectors are distributed in a highly dimensional space. These data vectors represent known values for experimental data that typically reflect a probability distribution of the input experimental data. From this probability distribution representation, predictions for unknown values for similar input data may be determined.

In all of these competitive learning networks, the networks are typically presented a set of input data that possesses a corresponding set of results data. From these data values, the network of nodes "learns" a relationship between the input data and its corresponding results data. In this process, the probability distribution relationship is estimated using the multi-dimensional network of nodes. This relationship is represented within a set of artificial neural network coefficients for a particular topology of nodes.

One skilled in the art will recognize that competitive learning networks include a nearly infinite number of network topologies that may be used to represent a particular probability distribution relationship without deviating from the spirit and scope of the present invention as recited within the attached claims. In addition, artificial neural networks may utilize various well-known algorithm architectures, including hard-competitive learning (i.e. "winner-take-all" learning), soft competitive learning without a fixed network dimensionality, and soft competitive learning with a fixed network dimensionality, to specify an artificial neural network according to the invention as recited within the attached claims. Each of these algorithm architectures represents the same probability distribution relationship; however each of the various algorithm architectures better optimize corresponding processing parameters, which are often mutually exclusive with each other. These parameters include error minimization or the minimization of an expected quantization error, entropy maximization for the reference vectors used within a network, and topology-preserving or feature mapping architectures that attempt to map high-dimensional inputs signals onto lower-dimensional structures in a manner that attempts to preserve similar relationships found within the original data within the post-mapping data. As such, any of these types of algorithm architectures may be used to construct an artificial neural network without deviating from the spirit and scope of the present invention as recited within the attached claims.

Now referring to FIG. 3, an artificial neural network processing system 301 comprises a learning module 311, a prediction module 321, and a database of network node coefficients 313. The learning module 311 is used with a set of experimental data 315 that possesses a corresponding set of experimental results 316 to generate a set of network node coefficients that represent a probability distribution relationship for the experimental data 315-experimental result 316 data set for a particular neural network topology and algorithm architecture. The learning module 311 includes a data learning input module 312 that receives the experimental data 315-experimental result 316 data set generated using the process described above. The learning module 311 also includes an ANN training module 313 that processes the experimental data 315-experimental result 316 data set to generate the coefficients used to specify the probability distribution relationship and an ANN coefficient storage module 314 for storing the coefficients that have been previous generated within the database 313 for later use.

The data processing within the learning module 311 may proceed in a batch processing fashion in which all of the vectors within the experimental data 315-experimental result 316 data set are processed at a single time. In such a process, the experimental data 315-experimental result 316 data set is received by the input module 312, processed by the training module 313, and the generated coefficients are placed within the database 313 by the storage module 314. Alternatively, the experimental data 315-experimental result 316 data set may be processed as a sequence of smaller data sets in which the experimental data 315-experimental result 316 data set data values are generated at different times. In such a process, the training module 313 uses the previously stored coefficients retrieved by the storage module along with a new small data set provided by the input module 312 to generate an updated set of coefficients. These updated coefficients may be once again stored within the database 313 for use at a later time.

Once an artificial neural network 301 has been trained, the prediction module 321 may be used to predict, or classify, a particular test data value 325. The prediction module 321 includes a data prediction input module 322, an ANN prediction module 323, and an ANN curve slope module 324. The data prediction input module 322 receives the input test data generated as described above for use in the prediction module. The ANN prediction module 323 receives and utilizes the network coefficient values for the neural network from the ANN coefficient database 313 to predict the possible result for the probability distribution relationship specified within the neural network. This output value is used by the ANN curve slope module 324 to determine all possible values for a given gene, in the manner discussed above, to determine a curve slope value. This slope value is then output for later use in ranking and classifying the individual genes used to determine the presence, or lack there of, for a disease.

The embodiments described herein are implemented as logical operations performed by a computer. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

While the above embodiments of the invention describe the use of an artificial neural network to identify relevant genes associated with diseases and use the identified genes to classify and identify diseases, one skilled in the are will recognize that the use of the processing system discussed above are merely example embodiments of the invention. As long as experimental data is used to self-train a processing system using competitive learning processing, the present invention to would be useable in other data processing systems. It is to be understood that other embodiments may be utilized and operational changes may be made without departing from the scope of the present invention as recited in the attached claims.

WORKING EXAMPLES

The following examples provide a nonlimiting illustration of various embodiments of the invention.

Example 1

Preparation of Microarrays

Preparation of glass cDNA microarrays, probe labeling, hybridization and image acquisition were performed according to the protocol given below, which is a standard NHGRI protocol (nhgri.nih.gov/DIR/LCG/15K/HTML/protocol).

Gene-specific DNA was produced by PCR amplification of purified template plasmid DNAs from cloned ESTs. The PCR product was purified by ethanol precipitation, thoroughly resuspended in 3×SSC, and printed onto a poly-L-lysine coated slide.

The materials, reagents, and solutions used include: 96 well alkaline lysis miniprep kit (Edge BioSystems, Gaithersburg, Md.); LB Broth (Biofluids, Rockville, Md.); Superbroth (Biofluids, Rockville, Md.); dATP, dCTP, dGTP, dTTP, 100 mM each #27-2035-02, store frozen, −20° C. (Pharmacia, Peapack, N.J.); PCR primer AEK M13F (5'-GTTG-TAAAACGACGGCCAGTG-3') (SEQ ID NO. 97) and AEK M13R (5'-CACACAGGAAACAGCTATG-3') (SEQ ID NO. 98) at 1 mM concentration, store frozen, −20° C.; 10× PCR Buffer, # N808-0189, and Ampli-Taq DNA polymerase, #N808-4015 store frozen, −20° C. (Perkin Elmer, Norwalk, Conn.); Carbenicillin (Gibco-BRL, Rockville, Md.); Ethanol (200 Proof USP Ethyl Alcohol); 1M Tris-HCl (pH 8); 0.5M NaEDTA (pH 8); T Low E; Buffer; 20× SSC; Glycerol (enzyme grade); Sodium Acetate (tri-hydrate); Boric Acid; Sodium Hydroxide (1M); Glacial Acetic Acid; Succinic anhydride, #23969-0 and 1-methyl-2-pyrrolidinone, # 32863-4 (Aldrich Chemical Co., St. Louis, Mo.); Diethyl Pyrocarbonate (DEPC) treated $H_2O$ ; Master set of clone-purified, sequence verified human ESTs (e.g. gf211 release, Research Genetics, Huntsville, Ala.); 96 pin inoculating block (#VP 4088, V&P Scientific, Inc, San Diego, Calif.); Airpore Tape Sheets, (# 19571, QIAGEN Inc., Valencia, Calif.); Sterile 96-well plate seals, (e.g. # SEAL-THN-STR (Elkay Products, Inc., Shrewsbury, Mass.); 96-well U-Bottom Microtiter Plates, #3799 and 96-well V-Bottom Microtiter Plates, #3894 (Corning Inc., Corning, N.Y.); Thin wall PCR plate and Cylcleseal PCR plate sealer (e.g. #1038-50-0 and #1044-39-4, Robbins Scientific Corp. Sunnyvale, Calif.); household one-gallon sealable storage bags (e.g. Glad Lock); heat sealable storage bags and heat sealer; 0.2 mm Sterile Filtration unit; Diamond scribe for writing on slides; Pyrex baking dish (~24×34×5 cm); UV transparent plastic wrap (e.g. Glad Cling Wrap); 30 slide rack (stainless steel) #113 and 30 slide glass tank, #122 (Shandon Lipshaw, Pittsburgh, Pa.); 1L glass tank; 1L glass beaker; 1L graduated; cylinder ; Stir bar; Slide Box (plastic with no paper or cork liners), (e.g. #60-6306-02, PGC Scientific, Gaithersburg, Md.); PCR heat cycler (e.g. DNA Engine Tetrad, MJ Research, Waltham, Mass.); Centrifuge with a horizontal ("swinging bucket") rotor with a depth capacity of 6.2 cm for spinning microtiter plates and filtration plates (e.g. Sorvall Super T 21, Sorvall Inc., Newtown, Conn.); 37° C. Shaker incubator with holders for deep-well plates; 37° C. Waterbath; 65° C. Incubator; Vortex mixer; Immunowash microliter plate washer, #1575 (BioRad, Hercules, Calif.); pH Meter; Platform Shaker; UV Stratalinker 2400, (Stratagene La Jolla, Calif.); Stirrer/Hotplate; Robotic slide printer; −80° C. Freezer; −20° C. Freezer; 45% (w/v) Sterile Glycerol ; 450 grams enzyme grade glycerol per liter 9 Autoclave and store at room temperature); T low E Buffer ; 1M Tris-HCl (pH 8.0) 10 mL; 0.5 M EDTA (pH 8.0) 0.2 mL; DEPC treated $H_2O$ 990 mL (Autoclave and store at room temperature); Carbenicillin stock solution (1 gram of carbenicillin in 10 mls of sterile water, Sterile filter with a 0.2 micron filter, Store frozen at −20° C.); LB with 100 µg/ml carbenicillin (Add 1 ml of carbenicillin stock solution to 1 liter of LB, Make fresh); 3M Sodium Acetate pH=6.0 (408.2 grams sodium acetate (tri-hydrate) per liter, 3M acetic acid (172.4 ml per liter),Titrate the pH of the 3M sodium acetate solution to pH 6.0 with the 3M acetic acid solution, Filter sterilize using a 0.2 micron filter, Store at room temperature); Ethanol/acetate mix (Ethanol (100%) 950 ml, Sodium acetate pH=6.0, 50 ml); 1000 ml 3× SSC; DEPC $H_2O$ 42.5 ml; 20× SSC 7.5 ml; 50 ml 70% Ethanol; Ethanol (100%) 350 ml; DEPC $H_2O$ 150 ml; 500 ml.

The first step was to grow the EST clones. The cDNA clones were obtained from Research Genetics (Huntsville, Ala.) and were their standard microarray set, which consisted of 3789 sequence-verified known genes and 2778 sequence-verified ESTs.

The sealed master plates were incubated over night at 37° C. Most suppliers provide low density bacterial cultures. Replicating directly from these dilute stocks frequently results in non-growth in the secondary culture. If making the template from a plate that had previously been cultured to high density before freezing, this initial growth step should not be used, as it will reduce the viability of the cultures.

A set of standard 96 well round (U) bottom plates were then prepared by labeling all plates and placing 100 µl of LB broth containing 100 ?g/ml carbenicillin in each well. These plates were used as working copies. To preserve the master set of plates, it was useful to make replicate copies of the master plate to serve as working copies when the master plate was first replicated. The EST clones were then checked to insure that they were in a vector conferring ampicillin resistance, as is common with human IMAGE clones.

The master plates were spun briefly (about two minutes) at 1000 rpm in a horizontal microtiter plate rotor to remove condensation and droplets from the seals before opening. Bacterial culture fluid on the sealers can easily be transferred from one well to others, cross-contaminating the stocks.

Then a container was partially filled with 100% alcohol. The 96 pin-replicating tool was dipped in the alcohol, removed and then the pins were flamed.

The inoculation block was allowed to cool briefly, then the replicating tool was dipped in the master plate and then into the daughter plate. This was repeated as necessary for each plate inoculated. It is useful to color the plate corner near the A-I well of all master and daughter plates with a marker pen before beginning the replication process in order to reduce mistakes in the relative orientation of the plates. The suggested plates have a notch at this corner as well.

The inoculated LB plates, with the lids on, were placed into a one gallon sealable bag containing a moistened paper towel and grow overnight at 37° C. Many 37° C. incubators tend to dry out microtiter plate cultures. Placing the plates in a highly humidified bag avoids this problem.

Next, deep well plates were filled with 1 ml of Superbroth (100 µg/ml carbenicillin) per well. These plates served as the source of culture for template preparation. Using the replicating tool, the deep well plates were then inoculated directly from the freshly grown LB plates. Next, the openings of the deep well plates were covered with Qiagen Airpore Tape Sheets and the plastic lids were placed over the sheet. The plates were then placed in a 37° C. shaker incubator at 200 RPM for twenty-four hours. 50 µl of 45% (w/v) sterile glycerol was added to each well of any working plates that are to be frozen (−80° C.) and subsequently used as culture sources.

After the EXT clones were grown, the plasmid templates have to be isolated. First, the lysis buffer (Edge Biosystems Kit) was warmed to 37° C. to dissolve the SDS. Then the RNAse solution was added to the resuspension buffer (Edge Biosystems Kit), 1 ml/100 ml, and stored at 4° C. The receiving plates were prepared from the Edge Biosystems Kit by adding 350 µl of ethyl alcohol to each well of the receiving plates. The filter plate was then placed on top and secured with tape. The bacterial cultures in the deep well plates were centrifuged at 1500×g for seven minutes in a centrifuge equipped with a horizontal rotor for 96-well plates. They were then briefly inverted and excess media was tapped out on a clean paper towel. The pellets will loosen and may be lost when pouring off excess media if this step is delayed.

The pellet was then resuspended in 100 µl of Resuspension Buffer, and Vortexed until the entire pellet was re-suspended. This step is critical. Poor resuspension of the cells results in clumps of cells that do not lyse in subsequent steps. This reduces the yield and decreases the purity of the product. 100 µl of Lysis Buffer was then added and the solution was mixed gently by rocking the plates from side to side, to avoid shearing the bacterial chromosomal DNA. 100 µl of Precipitation buffer was added to each well and briefly mixed. Then, 100 µl of Neutralization buffer was added to each well and Vortexed.

The contents of the deep wells were then transferred to the waiting filter plates/receiving plate stacks using the wide bore pipette tips provided in the kits. The stacked plates were then centrifuged at 1500×g for twelve minutes in a centrifuge equipped with a horizontal rotor for 96-well plates. The stacked plates were then removed from the centrifuge. The filter plates were removed and discarded. The alcohol and filtrate were decanted from the receiver plate and the excess alcohol was touched off on clean paper towels. 500 µl of 70% ethanol was added to each well and immediately decanted and excess alcohol was touched off with a clean paper towel. Then, the plates were placed in a clean drawer without their lids, covered with a clean paper towel and allowed to dry overnight.

The next day, the DNA was resuspended in 200 µl of T Low E Buffer. The top was sealed with plate sealer and rehydrated at 4° C. for at least two days before using. They were stored at −20° C. in the interim.

After the plasmid templates have been isolated, the EST inserts were amplified. For each 96 well plate to be amplified, a PCR reaction mixture was prepared containing the following ingredients: 1000 µl of 10×PCR Buffer, 20 ?L of dATP (100 mM), 20?L of dGTP (100 mM), 20 ?L of dCTP (100 mM), 20 ?L of dTTP (100 mM), 5 ?L of AEK M13F primer (1 mM), 5 µL of AEK M13R primer (1 mM), 100 µL of Ampli-Taq polymerase (5 U/µl), and 8800 mL of $H_2O$. The 96-well PCR plates were then labeled and 100 µl of the PCR reaction mixture from above was aliquotted to each well. The plates were then gently tapped to insure that no air bubbles were trapped at the bottom of the wells. 1 µl of purified EST plasmid template from above was then added to each well. The donor and recipient plates were then marked at the corner, near the A1 well to facilitate correct orientation during transfer of the template. It was important to make sure that the pipette tips were all submerged in the PCR reaction mix when delivering the template. Missing the liquid was easier when multi-channel pipettes were used.

The following thermal cycle series was then performed: 1 initial cycle of heating to 96° C. and holding for 30 sec, 25 cycles of denaturing at 94° C. for 30 sec, reannealing at 55° C. for 30 sec, and extending at 72° C. for 150 sec, one final cycle of holding at 72° C. for 5 minutes, then cooling to ambient temperature. After the above cycle, the plates were held at 4° C. while quality controls were performed.

The quality control was done by agarose gel electrophoresis of the ESTs. If this was the first time the template for these ESTs was being amplified, 2 µl of each PCR product was analyzed on a 2% agarose gel. If amplified products from this template had been previously tested, then one row of wells from each plate amplified was analyzed. Gel imaging allowed a rough quantitation of product while giving an excellent characterization of the product. Band size, as well as the number of bands observed in the PCR products, contributed to an understanding of the final results of the hybridization. The use of gel well formats suitable for loading from 96 well plates and programmable pipetters made this form of analysis feasible on a large scale.

The materials, reagents and solutions for the quality control check included: Electrophoresis apparatus with capacity for four 50 well combs, (e.g. #D3, Owl Scientific, Woburn, Mass.); 50× Tris-Acetate Electrophoresis BufferM; Agarose; Dye Solution (Xylene Cyanol/Bromophenol Blue) (e.g. #351-081-030, Quality Biological Inc., Gaithersburg Md.); Glycerol (enzyme grade); Ethidium Bromide solution (10 mg/ml); 100 base-pair ladder size standard; Programmable, 12-channel pipetter (e.g. #2019, Matrix Technologies, Lowell, Mass.); Disposable microtiter mixing trays (e.g. Falcon #353911, Becton Dickinson, Franklin Lake, N.J.); Electrophoresis power supply; 1×TAE Buffer; 50×TAE Buffer 40 ml; Ethidium Bromide (10 mg/ml) 0.1 ml and Water 960 ml; 1000 ml; Loading Buffer; Glycerol (enzyme grade) 4.0 ml, DEPC Water 0.9 ml, and Dye Solution* 0.1 ml for a total of 5.0 ml (*This solution is 0.25% (w/v) Xylene Cyanol and 0.25% (w/v) Bromophenol Blue); 100 bp Size Standards; DNA ladder (1 mg/ml) 50 µL, 1 M Tris-HCl (pH 8.0) 5 µl, 0.5 M EDTA (pH 8.0) 5 µl, and Loading Buffer 440 µl for a total of 500 µl The electrophoresis was carried out with a 2% agarose gel (1×TAE) with four combs (50 tooth) that was submerged in an electrophoresis apparatus with sufficient 1×TAE buffer to just cover the surface of the gel. A reservoir of Loading Buffer was prepared, using 12 wells of a microtiter plate. Then a pipetter was programmed to sequentially carry out the following steps: fill with 2 µl, fill with 1 µL, fill with 2 µl, mix a volume of 5 µl five times, expel 5 µl. Twelve (12) disposable tips were then placed on the pipetter. 2 µl of PCR product from wells A1-A12 of the PCR plate were loaded, followed by 1 µl of air, then 2 µl of Loading Buffer from the reservoir. The tips were then placed in clean wells of a disposable mixing tray and the pipette was allowed to mix the sample and loading dye. The pipette tip was then placed in a 50 well row so that the tip containing the PCR product from well A1 is in the second well of the row, and the other tips are in every other succeeding well.

The process was repeated (changing tips each time), to load PCR plate row B starting in the 3rd well, interleaved with the A row, the C row starting at well 26, and the D row at well 27, interleaved with the C row. Then 5 µl of 100 bp Size Standards were placed in wells 1 and 50. This process was repeated, to load samples from rows E, F, G, and H in the second, 50 well row of gel wells, to load samples from two 96 well PCR plates per gel, or single row samples from 16 PCR plates. To reduce diffusion and mixing, a voltage was applied to the gel for a minute between loading each well strip. This caused the DNA to enter the gel, and reduced band spreading and sample loss.

A voltage was then applied to the gel and it was run until the bromophenol blue (faster band) had nearly migrated to the next set of wells. For a gel that is 14 cm in the running dimension, and 3 cm between each row of wells, 200 volts were applied for 15 minutes. Digital photos of the gel were taken and the images stored for future reference. The gels should show bands of fairly uniform brightness distributed in size between 600 to 2000 base-pairs. Further computer analysis of such images can be carried out with image analysis packages to provide a list of the number and size of bands. Ideally this information can be made available during analysis of the data from hybridizations involving these PCR products.

After the quality control checks are run on the plates, the next step involves purifying the PCR products. 96 well V-bottom plates were filled with 200 µl per well of ethanol/acetate mix. The ethanol acetate solution used for precipitation is less acidic (pH 6) than is typically used. In this instance, more acidic solutions produce precipitates which are harder to resuspend without improving yield.

100 µl per well of PCR product was transferred into V-bottom plates and mixed by pipetting a volume of 75 µl per well four times. The plates were then placed in a −80° C. freezer for one hour or stored overnight at −20° C. The plates were stored at −20° C. if they were to be left for more than one hour, because aggressive precipitation produces precipitates which are hard to resuspend. The plates were then thawed to reduce brittleness and melt any ice, which may have formed in the wells.

The plates were loaded into a centrifuge with a horizontal microtiter plate rotor and spun at 2600×g for 40 minutes at 4° C. Next, the supernatant from each well was aspirated using the Immunowash plate washer. Settings for the depth of aspiration by the plate washer needed to be adjusted to suit the microtiter plates used. It is advisable to leave approximately 10-20 ml in the bottom of the well to avoid disturbing the pellet. 200 µl of 70% ethanol was delivered to each well in the plate using the Immunowash plate washer, and the plates were centrifuged at 2600×g for 40 minutes. The supernatant was aspirated from each well using the Immunowash plate washer, and the plates were dried overnight in a closed drawer. They should not be dried in a speed-vac because desiccated PCR products are hard to resuspend.

After the PCR products were purified, they were then resuspended by adding 40 µl of 3×SSC per well. The plates were then sealed with a foil sealer, taking care to achieve a tight seal over each well. The plates were then placed in heat sealable bags with paper towels moistened with 3×SSC and the bag was sealed with a heat sealer. The high external humidity within the sealed bag helped to keep the volumes in the individual wells from varying. The bags were then placed in a 65° C. incubator for 2 hours. The heat in the incubator was then turned off, and the plates were allowed to cool gradually in the incubator to avoid condensation on the sealers. The plates were stored at −20° C.

The yield of the PCR suspension was then checked by fluorometric determination of DNA concentration. 1 µl of resuspended PCR product from one row of wells from each plate on a 2% agarose gel was analyzed as previously described. Adequate precipitation and resuspension produced very intense bands, with no material failing to leave the loading well, and no smear of material from the band towards the loading well.

While it would be ideal to be able to exactingly quantify each EST PCR product and spot each DNA species at equivalent concentrations, it is impractical for most labs to do so when thousands of ESTs must be prepared. Fortunately, it is possible to use a strategy where excess DNA is spotted, so that the exact quantities used do not produce much variation in the observed results. When using this strategy, it is necessary to track the average productivity of the PCR reactions. Fluorometry provides a simple way to obtain an approximate concentration of the double-stranded PCR product in the PCR reaction mix.

Next, the double stranded DNA was quantified. The materials, reagents, and solutions necessary include: reference double-stranded DNA (0.5 mg/ml) (e.g. #15612-013 Gibco/BRL, Bethesda, Md.), 96 well plates for fluorescent detection (e.g. #7105, Dynex, Chantilly, Va.), Fluorometer (e.g. #LS50B, Perkin Elmer, Norwalk, Conn.), FluoReporter Blue dsDNA Quantitation Kit (#F-2962, Molecular Probes, Eugene, Oreg.), TE, 12 channel multi-pipetters, Computer equipped with Microsoft Excel software, Ds-DNA Standards: 50 µg/ml, 100 µg/ml, 250 µg/ml, 500 µg/ml, µl TE 90, 80, 50, 0 µl ds-DNA (0.5 mg/ml) 10, 20, 50, 100, (It is good practice to check both the integrity (agarose gel) and the concentration (absorbance) of the standard before use); Fluor Buffer (Hoechst 33258 solution (contains the dye at an unspecified concentration in a 1:4 mixture of DMSO:$H_2O$) (from kit) 25 µl, TNE Buffer (TNE Buffer is 10 mM Tris-HCl (pH 7.4), 2 M NaCl, 1 mM EDTA) (from kit) 10 ml.

The double stranded DNA was quantified as follows. 96 well plates were labeled for fluorescence assay. 200 µl of Fluor Buffer was added to each well. 1 µl of PCR product from each well in a row of a PCR plate was added to a row of the fluorometry plate. Samples were added to rows A through G of the fluorometry plate. In the final row of the fluorometry plate 1 µl of each of the series of ds-DNA standards 0 µg/ml (TE only), 50, 100, 250 and 500 µg/ml ds-DNA were added. This series was repeated twice in the final row.

The fluorometer was set for excitation at 346 nm and emission at 460 nm, and adjusted as necessary to read the plate. If the fluorometer used did not support automated analysis, the data table was exported to Excel. The response for the standards was tested to see that it was linear and reproducible from the range of 0 to 500 µg/ml of ds-DNA.

Next, the concentration of ds-DNA in the PCR reactions was calculated using the following equation, after subtracting the average 0 µg/ml value from all other sample and control values:

[$ds$-DNA(µg/ml)]=((PCR sample value)/
(average 100 µg/ml value))*100

Constantly tracking the yields of the PCRs makes it possible to rapidly detect many ways in which PCR can fail or perform poorly. This assay can also be applied after precipitation and resuspension of the PCR products to monitor overall recovery of product. 1 µl of amplified products from one row of wells from each amplified plate by fluorometry was analyzed.

Slides were then coated with poly-L-lysine to have a surface that is both hydrophobic and positively charged. The hydrophobic character of the surface minimizes spreading of the printed spots, and the charge appears to help position the DNA on the surface in a way that makes cross-linking more efficient.

Materials, reagents, and solutions for coating the slides includes: Gold Seal Microscope Slides (#3011, Becton Dickinson, Franklin Lake, N.J.), Ethanol (100%), Poly-L-lysine (#P8920, Sigma, St. Louis, Mo.), 50 Slide Stainless Steel Rack, #900401, and 50 Slide Glass Tank, #900401, (Wheaton Science Products, Millville, N.J.), Sodium Hydroxide, Stir Plate, Stir Bar, Platform Shaker, 30 Slide Rack, #196, plastic, and 30 slide Box, #195, plastic, (Shandon Lipshaw, Pittsburgh, Pa.), Sodium Chloride, Potassium Chloride, Sodium Phosphate Dibasic Heptahydrate, Potassium Phosphate Monobasic, Autoclave, 0.2 mm Filter: Nalgene, Centrifuge: Sorvall Super 20, Slide Box (plastic with no paper or cork liners), (e.g. #60-6306-02, PGC Scientific, Gaithersburg, Md.), lL Glass Beaker; lL Graduated Cylinder, 1M Sodium Borate (pH 8.0) (Dissolve 61.83 g of Boric acid in 900 ml of DEPC $H_2O$. Adjust the pH to 8.0 with 1N NaOH. Bring volume up to one liter. Sterilize with a 0.2 micron filter and store at room temperature), Cleaning Solution ($H_2O$ 400 ml, Ethanol 600 ml, NaOH 100 g —Dissolve NaOH in $H_2O$. Add ethanol and stir until the solution clears. If the solution does not clear, add $H_2O$ until it does), and Poly-L-lysine Solution (poly-L-lysine (0.1% w/v) 35 ml PBS 35 ml $H_2O$ 280 ml 350 ml)

First, the slides are placed into 50 slide racks and the racks are placed in glass tanks with 500 ml of cleaning solution. Gold Seal Slides are highly recommended, as they have been found to have consistently low levels of autofluorescence. It was important to wear powder free gloves when handling the slides to avoid contamination.

The tanks are placed on platform shakers for two hours at 60 rpm. After being shook, the cleaning solution was poured out, and the slides were then washed in $H_2O$ for three minutes. This wash was repeated four times. The slides were then transferred to 30 slide plastic racks and placed into small plastic boxes for coating. The slides were then submerged in 200 ml poly-L-lysine solution per box. The slide boxes were then placed on platform shaker for one hour at 60 rpm. The slides were rinsed three times with $H_2O$, and submerged in $H_2O$ for one minute, and then centrifuged for two minutes at 400×g and the slide boxes used for coating were dried.

The slides were then placed back into the slide box used for coating and allowed to stand overnight before transferring to a new slide box for storage. This allowed the coating to dry before it was handled. The slides were allowed to age for two weeks on the bench, in a new slide box, before they were printing on. The coating dried slowly, becoming more hydrophobic with time.

Slide boxes used for long term storage should be plastic and free of cork lining. The glue used to affix the cork will leach out over time and give slides stored in these types of boxes a greasy film that has a high degree of autofluorescence. All glassware and racks used for slide cleaning and coating should be cleaned with highly purified $H_2O$ only, and detergent should not be used.

Once the slides were coated, they were printed. The variety of printers and pens for transferring PCR products from titer plates to slides precludes highly detailed descriptions of the process. The following steps provide a general description of the processing.

The print pens were pre-cleaned according to the manufacturer's specification. The printer slide deck was then loaded with poly-L-lysine coated slides from above. The plates containing the purified EST PCR products were thawed and centrifuged briefly, (about two minutes) at 1000 rpm in a horizontal microtiter plate rotor to remove condensation and droplets from the seals before being opening. 5 to 10 μl of the purified EST PCR products were transferred to a plate that served as the source of solution for the printer. Printing with quill-type pens usually requires that the volume of fluid in the print source was sufficiently low, so that when the pen was lowered to the bottom of the well, it was submerged in the solution to a depth of less than a millimeter. This keeps the pen from carrying a large amount of fluid on the outside of the pen shaft and producing variable, large spots on the first few slides printed.

A repetitive test print was run on the first slide. In this operation, the pens were loaded with the DNA solution, and then the pens serially deposited this solution on the first slide in the spotting pattern specified for the print. This test was run to check the size and shape of the specified spotting pattern, as well as its placement on the slide. It also served to verify that the pens were loading and spotting, and that a single loading produced as many spots as were required to deliver material to every slide in the printer. If one or more of the pens was not performing at the desired level, it was re-cleaned or substituted with another pen and tested again. If all pens were performing, the full print was carried out.

At the end of the print, the slides were removed from the printer, labeled with the print identifier and the slide number by writing on the edge of the slide with a diamond scribe and placed in a dust free slide box to age for one week. It was useful to etch a line, which outlined the printed area of the slide, onto the first slide. This served as a guide to locate the area after the slides have been processed, and the salt spots were then washed off.

The slides were placed, printed side face up, in a casserole dish and covered with cling wrap. The slides were then exposed to a 450 mJ dose of ultraviolet irradiation in the Stratalinker. Slides should have been and were aged at ambient temperature in a closed slide box for one week prior to blocking. The slides were then transferred to a 30 slide stainless steel rack and the rack was placed into a small glass tank. 6.0 g succinic anhydride was dissolved in 325 ml 1-methyl-2-pyrrolidinone in a glass beaker by stirring with a stir bar. Nitrile gloves were worn and the work was carried out in a chemical fume hood while handling 1-methyl-2-pyrrolidinone (a teratogen).

25 ml 1M sodium borate buffer (pH 8.0) was added to the beaker. The solution was allowed to mix for a few seconds, then rapidly poured into a glass tank with slides. Succinic anhydride hydrolyzed quite rapidly once the aqueous buffer solution was added. To obtain quantitative passivation of the poly-L-lysine coating, it was critical that the reactive solution be brought in contact with the slides as quickly as possible. The glass tank was placed on a platform shaker in a fume hood for 20 minutes. Small particulates resulting from precipitation of reaction products may be visible in the fluid.

While the slides were incubating on the shaker a boiling $H_2O$ bath was prepared to denature the DNA on the slides. After the slides were incubated for 20 minutes, they were transferred into the boiling $H_2O$ bath. The heating element was immediately turned off after the slides were submerged in the bath. The slides were allowed to stand in the $H_2O$ bath for 2 minutes. The slides were then transferred into a glass tank filled with 100% ethanol and incubated for 4 minutes. The slides were removed and centrifuged at 400 rpm for 3 minutes in a horizontal microtiter plate rotor to dry the slides. The slides were then transferred to a clean, dust free slide box and allowed to stand overnight before being used for collection of gene expression data.

Example 2

Cell Culture and Tumor Samples

The source and other information for the cell lines and tumor samples used herein are described in TABLE 2 below for both the training set and the test samples.

TABLE 2

Supplement Table: Known Molecular Characteristics of Samples.

| Sample Label | Histological Diagnosis | Molecular Markers | Source Label | Source |
|---|---|---|---|---|
| EWS-C1 | EWS-C | EWS-FLI1 10-6 | A4573 | NCI |
| EWS-C2 | EWS-C | EWS-FLI1, type I | TC71 | NCI |
| EWS-C3 | EWS-C | EWS-FLI1, type I | TC106 | NCI |
| EWS-C4 | EWS-C | EWS-FLI1, type I | 5838 | NCI |

TABLE 2-continued

Supplement Table: Known Molecular Characteristics of Samples.

| Sample Label | Histological Diagnosis | Molecular Markers | Source Label | Source |
|---|---|---|---|---|
| EWS-C6 | EWS-C | EWS-FLI1, type I | A673 | NCI |
| EWS-C7 | EWS-C | EWS-FLI1, type I | ES-CL1 | MSKCC |
| EWS-C8 | EWS-C | EWS-FLI1, type I | TC32 | NCI |
| EWS-C9 | EWS-C | EWS-FLI1, type II | SK-ES-1 | ATCC |
| EWS-C10 | EWS-C | EWS-FLI1, type II | SK-N-MC | ATCC |
| EWS-C11 | EWS-C | EWS-FLI1, type II | RDES | ATCC |
| EWS-T1 | EWS-T | EWS-FLI1, type I | ES20 | MSKCC |
| EWS-T2 | EWS-T | EWS-FLI1, type II | ES13 | MSKCC |
| EWS-T3 | EWS-T | EWS-FLI1, type I | ES16 | MSKCC |
| EWS-T4 | EWS-T | EWS-FLI1, type I | ES17 | MSKCC |
| EWS-T6 | EWS-T | EWS-FLI1, 7-8 | ES22 | MSKCC |
| EWS-T7 | EWS-T | EWS-ERG, 7-9 | ES25 | MSKCC |
| EWS-T9 | EWS-T | EWS-FLI1, type I | 9602P006 | CHTN |
| EWS-T11 | EWS-T | EWS-FLI1, type I | 9703P152 | CHTN |
| EWS-T12 | EWS-T | EWS-FLI1, type I | 9704P218 | CHTN |
| EWS-T13 | EWS-T | EWS-FLI1, type I | ES23 | MSKCC |
| EWS-T14 | EWS-T | EWS-FLI1, type I | 9605P074 | CHTN |
| EWS-T15 | EWS-T | EWS-FLI1, type I | 9609P027 | CHTN |
| EWS-T19 | EWS-T | EWS-FLI1, type I | SARC75 | CHTN |
| RMS-C2 | ERMS-C | — | RD | ATCC |
| RMS-C3 | ARMS-C | ND | RH4 | NCI |
| RMS-C4 | ARMS-C | PAX3-FKHR | RH3 | NCI |
| RMS-C5 | ARMS-C | PAX3-FKHR | RH5 | NCI |
| RMS-C6 | ARMS-C | PAX3-FKHR | RH28 | NCI |
| RMS-C7 | ARMS-C | ND | RH30 | NCI |
| RMS-C8 | ERMS-C | — | CTR | ATCC |
| RMS-C9 | ARMS-C | PAX3-FKHR | RH4 | NCI |
| RMS-C10 | ARMS-C | PAX3-FKHR | RMS13 | NCI |
| RMS-C11 | ERMS-C | — | TE671 | ATCC |
| RMS.T1 | ARMS-T | PAX3-FKHR | RMS3 | MSKCC |
| RMS.T2 | ARMS-T | PAX3-FKHR | RMS6 | MSKCC |
| RMS.T3 | ERMS-T | — | RMS2 | MSKCC |
| RMS.T4 | ERMS-T | no PAX-FKHR | RMS5 | MSKCC |
| RMS.T5 | ARMS-T | PAX3-FKHR | RMS10 | MSKCC |
| RMS.T6 | RMS-T | ND | RT1 | CHTN |
| RMS.T7 | ERMS-T | — | RT4 | CHTN |
| RMS.T8 | RMS-T | ND | RT5 | CHTN |
| RMS.T10 | RMS-T | ND | RT2 | CHTN |
| RMS.T11 | ERMS-T | — | RHAB2 | CHTN |
| NB-C1 | NB-C | MYCN amp | KCNR | NCI |
| NB-C2 | NB-C | — | GICAN | NCI |
| NB-C3 | NB-C | — | 3K-N-AS | ATCC |
| NB-C4 | NB-C | MYCN amp | LAN5 | NCI |
| NB-C5 | NB-C | MYCN amp | SK-N-BE2 | ATCC |
| NB-C6 | NB-C | MYCN amp | SK-N-DZ | ATCC |
| NB-C7 | NB-C | — | GICAN | NCI |
| NB-C8 | NB-C | — | NGP | NCI |
| NB-C9 | NB-C | — | SH-SY5Y | ATCC |
| NB-C10 | NB-C | MYCN amp | SK-N-FI | ATCC |
| NB-C11 | NB-C | Single copy MYCN | SK-N-SH | ATCC |
| NB-C12 | NB-C, | MYCN amp | CHP-134B | NCI |
| BL-C1 | BL-C | — | RAMOS (RA1) | ATCC |
| BL-C2 | BL-C | — | ST486 | ATCC |
| BL-C3 | BL-C | — | CA46 | ATCC |
| BL-C4 | BL-C | — | ST486 | ATCC |
| BL-C5 | BL-C | — | RAJI | ATCC |
| BL-C6 | BL-C | — | MC116 | ATCC |
| BL-C7 | BL-C | — | DAUDI | ATCC |
| BL-C8 | BL-C | — | SULTAN | ATCC |
| Test1 | NB-C | MYCN amp | IMR32 | ATCC |
| Test2 | EWS-C | ND | CHOP1 | NCI |
| Test3 | Osteosarcoma-C | — | OsA-Cl | ATCC |
| Test4 | ARMS-T | — | ARMD1 | CHTN |
| Test5 | Sarcoma | — | A204 | ATCC |
| Test 6 | EWS-T | EWS-FLI1, type I | 9608P053 | CHTN |
| Test7 | BL-C | — | EB1 | ATCC |
| Test8 | NB-C | — | SMSSAN | NCI |
| Test9 | Sk. Muscle | — | SkM1 | CHTN |
| Test10 | ERMS-T | — | ERDM1 | CHTN |

TABLE 2-continued

Supplement Table: Known Molecular Characteristics of Samples.

| Sample Label | Histological Diagnosis | Molecular Markers | Source Label | Source |
|---|---|---|---|---|
| Test11 | Prostate Ca-C | – | PC3 | ATCC |
| Test12 | EWS-T | – | SARC6Y | CHTN |
| Test13 | Sk. Muscle | – | SkM2 | CHTN |
| Test 14 | NB-T | Single copy MYCN | NBS | DZNSG |
| Test 15 | BL-C | – | EB2 | ATCC |
| Test 16 | NB-T | Single copy MYCN | NB1 | DZNSG |
| Test 17 | ARMS-T | – | ARMD2 | CHTN |
| Test 18 | BL-C | – | GA10 | ATCC |
| Test 19 | EWS-T | ND | ET3 | CHTN |
| Test 20 | EWS-T | EWS-FLI1, type I | 9903P1339 | CHTN |
| Test 21 | EWS-T | EWS-FLI1, type II | ES23 | MSKCC |
| Test 22 | ERMS-T | – | ERMD2 | CHTN |
| Test 23 | NB-T | Single Copy MYCN | NB2 | DZNSG |
| Test 24 | ERMS-T | No PAX-FKHR | RMS4 | MSKCC |
| Test 25 | NB-T | Single copy MYCN | NB4 | DZNSG |

Supplement Table: Known molecular characteristics of samples. Table labels and abbreviations are described in Table 1 in the manuscript. EWS and ARMS samples with noted translocations were verified by RT-PCR. ND; not determined. Amp.: amplification.

All the original histological diagnoses were made at tertiary hospitals, which have reference diagnostic laboratories with extensive experience in the diagnosis of pediatric cancers. Approximately 20% of all samples in each category were randomly selected, blinded and set aside for testing. To augment this test set, we added 4 neuroblastoma tumors and 5 non-SRBCT samples (also blinded to the authors performing the analysis). The EWSs had a spectrum of the expected translocations, and the RMSs were a mixture of both ARMS containing the PAX3-FKHR translocation and embryonal rhabdomyosarcoma (ERMS). The NBs contained both MYCN amplified and single copy samples. The NHLs were cell lines derived from BL. TABLE 2 gives details of these samples as well.

This protocol details the methods used to extract RNA from cells, purify the RNA by a combination of phase extraction and chromatography, and prepare a labeled cDNA copy of the message fraction of the purified RNA. The protocol also describes the process of making fluorescent cDNA representations of the message pools within the isolated total RNA pools. This is accomplished by using the pure total RNA as a substrate for reverse transcription in the presence of nucleotides derivatized with either a Cy3 or a Cy5 fluorescent tag.

The materials, reagents, and solutions needed include: Trizol Reagent (#15596-018, Life Technologies, Rockville, Md.); RNeasy Maxi Kit (# 75162, Qiagen, Valencia, Calif.); Chloroform; Ethanol (200 Proof USP Ethyl Alcohol); DPBS (Dulbecco's phosphate buffered saline); 3M sodium acetate (pH 5.2); dATP, dCTP, dGTP, dTTP, 100 mM each, store frozen, −20° C. (#27-2035-02, Pharmacia, Peapack, N.J.); pd(T)12-18 resuspend at 1 mg/ml, and store frozen −20° C. (#27-7858, Amersham Pharmacia Biotech); Anchored oligo primer (anchored;5'-TTT TTT TTT TTT TTT TTT TTV N-3') (SEQ ID NO. 99); resuspend at 2 mg/ml, store frozen −20° C. (e.g. # 3597-006, Genosys) ; CyTM3-dUTP, 1 mM, and CyTM5-dUTP, 1 mM, store −20° C., light sensitive ; Rnasinâ Rnase inhibitor, store −20° C. (#N211A, Promega) ; SUPERSCRIPT™ II Rnase H' Reverse Transcriptase Kit, store −20° C., (#18064-014, Life Technologies, Rockville, Md.); C0t-1 DNA, 1mg/ml, store frozen −20° C. (#15279-011, Life Technologies, Rockville, Md.); 0.5M EDTA(pH 8.0); 1 N NaOH ; 1M TRIS-HCL; (pH 7.5); TE pH 7.4; DEPC water 50× Tris Acetate Buffer; 15 ml round bottom; polypropylene centrifuge tubes; 50 ml conical polypropylene centrifuge tubes; 1.5 ml; Eppendorf tubes ; 0.2 ml thin wall PCR tube; MicroCon 100 (Amicon Cat No. 42412); High speed centrifuge for 15 ml tubes; Clinical centrifuge with horizontal rotor for 50 ml conical tubes; Tissue homogenizer (e.g. Polytron PT1200 with Polytron-Aggregate-Dispergier-und-Mischtechnik 147a Ch6014 #027-30-520-0, Brinkmann Instruments Inc., Westbury, N.Y.); RPE Buffer (Add 4 volumes of ethanol per volume of RPE concentrate supplied in Quiagen KitO; RW1 Buffer (Supplied in Qiagen Kit) 75% EtOH(Ethanol (100%) 375 ml, and DEPC H2O 125 ml for a total of 500 ml); 10× low T dNTP Mix (25 μL dGTP (100 mM), 25 μL dATP (100 mM), 25 μL dCTP (100 mM), 10 μdTTP (100 mM), and 415 μL DEPC $H_2O$ for a total of 500 μL); 5× First Strand Buffer (Provided with Superscript II); TAE Buffer (50× Tris Acetate Electrophoresis Buffer 20 ml, and DEPC H2O 980 mL for a total of 1000 ml.

If the cells that were used were harvested from tissue culture, the cell pellet was washed twice in DPBS. If the cells that were used were from tissue culture, 1 ml of Trizol was added per $2\times10^7$ cells and mixed by shaking. If tissue was being used, 100 mg of frozen tissue was added directly to 4 ml of Trizol, and dissociate by homogenization with a rotating blade tissue homogenizer.

Whatever the source, 2/10 volume of chloroform was added to the cells and shook for 15 seconds, and then allowed to stand for 3 minutes, followed by centrifugation at 12,000×g for 15 minutes at 4° C. The supernatant was taken off and added to a polypropylene tube, while recording the volume of the supernatant.

Then 0.53 volumes of ethanol were slowly added to the supernatant while vortexing, this produced a final ethanol concentration of 35%. The ethanol was added drop by drop and allowed to mix completely with the supernatant before more ethanol is added. If a high local concentration of ethanol is produced, the RNA in that vicinity will precipitate.

The supernatant from an extraction of $2\times10^7$ to $1\times10^8$ cells was added to an RNeasy maxi column, which is seated in a 50 ml centrifuge tube. The tube was then centrifuged at 2880×g in a clinical centrifuge with a horizontal rotor at room temperature for 5 minutes. The flow-through was then poured back onto the top of the column and centrifuged again. This step is necessary because a significant amount of RNA is not captured by the column matrix in the first pass of the RNA containing solution through the column.

The flow-through was discarded and 15 ml of RW1 buffer was added to the column, followed by centrifugation at 2880×g for 5 minutes. The flow-through was discarded again and then 10 ml of RPE buffer was added, followed again by centrifugation at 2880×g for 5 minutes. Once again, the flow through was discarded and another 10 ml of RPE buffer was added, and the column was centrifuged at 2880×g for 10 minutes.

Next, the column was placed in a fresh 50 ml tube and add 1 ml of DEPC treated water from the kit was added to the column, and the column was allowed to stand for 1 minute.

The column was then centrifuged at 2880×g for 5 minutes, and another 1 ml of water was added to the column. The column was allowed to stand for 1 minute, followed by centrifugation at 2880×g for 10 minutes.

Then, 400 µl portions of the column eluate was aliquotted to 1.5 ml Eppendorf tubes, to which 1/10 volume of 3M sodium acetate (pH 5.2) was added, along with 1 ml of ethanol. The tubes were then allowed to stand for 15 minutes, after which they were centrifuged at 12000×g at 4 C for 15 minutes. The pellet was then washed two times in 75% EtOH and stored at −80° C.

The RNA was resuspended at approximately 1 mg/ml in DEPC $H_2O$. It was then concentrated to greater than 7 mg/ml by centrifugation on a MicroCon 100 filter unit, centrifuged at 500×g, checking as necessary to determine the rate of concentration. This step removes many residual, small to medium sized, molecules that inhibit the reverse transcription reaction in the presence of fluorescently derivatized nucleotides. The concentration of RNA in the concentrated sample was then determined by spectrophotometry, and the sample was stored at −80° C.

If an anchored oligo dT primer was used, the primer was annealed to the RNA in the following 17 µl reaction (a 0.2 ml thin wall PCR tube was used so that incubations could be carried out in a PCR cycler):

| Component | addition for Cy5 labeling | addition for Cy3 labeling |
|---|---|---|
| Total RNA (>7 mg/ml) | 150-200 µg | 50-80 µg |
| Anchored primer (2 µg/µl) | 1 µl | 1 µl |
| DEPC H2O | to 17 µl | to 17 µl |

If an oligo dT(12-18) primer was used, the primer was annealed to the RNA in the following 17 µl reaction:

| Component | addition for Cy5 labeling | addition for Cy3 labeling |
|---|---|---|
| Total RNA (>7 mg/ml) | 150-200 µg | 50-80 µg |
| dT(12-18) primer (1 µg/µl) | 1 µl | 1 µl |
| DEPC H2O | to 17 µl | to 17 µl |

The incorporation rate for Cy5-dUTP is less than that of Cy3-dUTP, so more RNA is labeled to achieve more equivalent signal from each species.

It was then heated to 65° C. for 10 minutes and cooled on ice for 2 minutes. Then, 23 µl (8 µl of 5× first strand buffer, 4 µl of 10× low T dNTPs mix, 4 µl of Cy5 or Cy3 dUTP (1 mM), 4 µl of 0.1 M DTT, 1 µl of Rnasin (30 u/?l), and 2 ?l of Superscript OI (200 u/?l)) of reaction mixture containing either Cy5-dUTP or Cy3-dUTP nucleotides was added, mixed well by pipetting and a brief centrifuge spin was used to concentrate it in the bottom of the tube. Superscript polymerase is very sensitive to denaturation at air/liquid interfaces, so we were careful to suppress foaming in all handling of this reaction.

It was then incubated at 42° C. for 30 min., after which 2 µl Superscript II was added, making sure the enzyme was well mixed in the reaction volume and incubated at 42O C for 30-60 min. Then, 5 µl of 0.5M EDTA was added, making sure the reaction was stopped with EDTA before adding NaOH (the next step), since nucleic acids precipitate in alkaline magnesium solutions.

Then, 10 µl 1N NaOH was added and it was incubated at 65? C for 60 minutes to hydrolyze residual RNA, after which it was cooled to room temperature. The purity of the sodium hydroxide solution used in this step is crucial. Slight contamination or long storage in a glass vessel can produce a solution that will degrade the Cy5 dye molecule, turning the solution yellow. Some researchers achieve better results by reducing the time of hydrolysis to 30 minutes.

It was then neutralized by adding 25 µl of 1M Tris-HCl (pH 7.5). Then, the labeled cDNA was desalted by adding the neutralized reaction, 400 µl of TE pH 7.5 and 20 µg of human C0t-1 DNA to a MicroCon 100 cartridge. It was then pipetted to mix, and spun for 10 minutes at 500×g. 200 µl TE pH 7.5 was added, and the solution was then concentrated to about 20-30 µl (approximately 8-10 min at 500×g). Alternatively, a smaller pore MicroCon 30 was used to speed the concentration step. In this case, the first wash was centrifuged for approximately 4.5 minutes at 16,000×g and the second (200 µl wash) for about 2.5 minutes at 16,000×g.

It was then recovered by inverting the concentrator over a clean collection tube and spinning for 3 min at 500×g. In some cases, the cy5 labeled cDNA formed a gelatinous blue precipitate that was recovered in the concentrated volume. The presence of this material signaled the presence of contaminants. The more extreme the contamination, the greater the fraction of cDNA which will be captured in this gel. Even if heat solubilized, this material tends to produce uniform, non-specific binding to the DNA targets. When concentrating by centrifugal filtration, the times required to achieve the desired final volume were variable. Overly long spins can remove nearly all the water from the solution being filtered. When fluor-tagged nucleic acids are concentrated onto the filter in this fashion, they are very hard to remove, so it is necessary to approach the desired volume by conservative approximations of the required spin times. If control of volumes proves difficult, the final concentration can be achieved by evaporating liquid in the speed-vac. Vacuum evaporation, if not to dryness, does not degrade the performance of the labeled cDNA.

Next, a 2-3 µl aliquot of the Cy5 labeled cDNA was taken for analysis, leaving 18-28 µl for hybridization. This probe was run on a 2% agarose gel (6 cm wide×8.5 cm long, 2 mm wide teeth) in Tris Acetate Electrophoresis Buffer (TAE). For maximal sensitivity when running samples on a gel for fluor analysis, a loading buffer with minimal dye was used and no ethidium bromide was added to the gel or running buffer.

The gel was then scanned on a Molecular Dynamics Storm fluorescence scanner (setting: red fluorescence, 200 micron resolution, 1000 volts on PMT). Successful labeling produces a dense smear of probe from 400 bp to >1000 bp, with little pile-up of low molecular weight transcripts. Weak labeling and significant levels of low molecular weight material indicates a poor labeling. A fraction of the observed low molecular weight material is unincorporated fluor nucleotide.

Next, the fluorescent cDNA had to be hybridized to the microarray. The volume of hybridization solution required was first determined. The rule of thumb is to use 0.033 µl for each mm 2 of slide surface area covered by the cover slip used to cover the array. An array covered by a 24 mm by 50 mm cover slip required 40 µl of hybridization solution. The volume of the hybridization solution is critical. When too little solution is used, it is difficult to seat the cover slip without introducing air bubbles over some portion of the arrayed ESTs, and the cover slip will not sit at a uniform distance from the slide. If the cover slip is bowed toward the slide in the center, there will be less labeled cDNA in that area and hybridization will be non-uniform. When too much volume is applied, the cover slip will move easily during handling, leading to misplacement relative to the arrayed ESTs, and non-hybridization in some areas of the array.

For a 40 μl hybridization, the Cy3 and Cy5 labeled cDNAs were pooled into a single 0.2 ml thin wall PCR tube and the volume was adjusted to 30 μl by either adding DEPC H₂O, or removing water in a SpeedVac. If a vacuum device was used to remove water, high heat or heat lamps were not used to accelerate evaporation because the fluorescent dyes could be degraded.

For a 40 μl hybridization the following components were combined:

|  | High Sample Blocking | High Array Blocking |
| --- | --- | --- |
| Cy5 + Cy3 probe | 30 μl | 28 μl |
| Poly d(A) (8 mg/ml) | 1 μl | 2 μl |
| Yeast tRNA (4 mg/ml) | 1 μl | 2 μl |
| Human C0t-1 DNA (10 mg/ml) | 1 μl | 0 μl |
| 20× SSC | 6 μl | 6 μl |
| 50× Denhardt's blocking solution | 1 μl (optional) | 2 μl |
| Total volume | 40 ul | 40 ul |

Arrays and samples can vary somewhat, making it necessary to vary the composition of the hybridization cocktail. In cases where there is residual hybridization to control repeat DNA samples on the array, more C0t-1 DNA was used, as in the High Sample Blocking formulation. When there is diffuse background or a general haze on all of the array elements, more of the non-specific blocker components was used, as in the High Array Blocking formulation.

The components were mixed well by pipetting, heated at 98° C. for 2 minutes in a PCR cycler, cooled quickly to 25° C. and 0.6 ul of 10% SDS was added. It was then centrifuged for 5 min at 14,000×g. The fluor labeled cDNAs have a tendency to form small, very fluorescent, aggregates which result in bright, punctate background on the array slide. Hard centrifugation will pellet these aggregates, allowing you to avoid introducing them to the array.

The labeled cDNA was applied to a 24 mm×50 mm glass cover slip and then touched with the inverted microarray. Applying the hybridization mix to the array and cover slipping it is an operation which requires some dexterity to get the positioning of the cover slip and the exclusion of air bubbles just right. It was helpful to practice this operation with buffer and plain slides before attempting actual samples. The hybridization solution was added to the cover slip first, since some aggregates of fluor remain in the solution and will bind to the first surface they touch.

The slide was then placed in a microarray hybridization chamber, 5 μl of 3×SSC was added to the reservoir, if the chamber provided one, or at the scribed end of the slide and the chamber was sealed. The chamber was submerged in a 65° C. water bath and the slide was allowed to hybridize for 16-20 hours. There are a wide variety of commercial hybridization chambers. It was worthwhile to prepare a mock hybridization with a blank slide, load it in the chamber and incubate it to test for leaks, or drying of the hybridization fluid, either of which cause severe fluorescent noise on the array.

Next, the unbound fluorescent cDNA was washed off. The hybridization chamber was removed from the water bath, cooled and carefully dried off. The chamber was unsealed and the slide was removed. As there may be negative pressure in the chamber after cooling, it is necessary to remove water from around the seals so that it was not pulled into the chamber and onto the slide when the seals are loosened.

The slide was placed, with the cover slip still affixed, into a Coplin jar filled with 0.5×SSC/0.01% SDS wash buffer. The cover slip was allowed to fall from the slide and then removed from the jar with a forceps. The slide was allowed to wash for 2-5 minutes. The slide was transferred to a fresh Coplin jar filled with 0.06×SSC, and allowed to wash for 2-5 minutes. The sequence of washes may need to be adjusted to allow for more aggressive noise removal, depending on the source of the sample RNA. Useful variations are to add a first wash which is 0.5×SSC/0.1% SDS or to repeat the normal first wash twice.

The slide was then transferred to a slide rack and centrifuged at low rpm (700-1000) for 3 minutes in a clinical centrifuge equipped with a horizontal rotor for microtiter plates. If the slide is simply air dried, it frequently acquires a fluorescent haze. Centrifuging off the liquids results in a lower fluorescent background. As the rate of drying can be quite rapid, it is suggested that the slide be placed in the centrifuge immediately upon removal from the Coplin jar.

Image analysis was performed using DeArray software (Chen, Y., Dougherty, E. R. and Bittner, M. L. Ratio-based decisions and the quantitative analysis of cDNA microarray images, *Biomedical Optics* 2, 364-374 (1997).

Example 3

Data Analysis

To calibrate ANN models to recognize cancers in each of the four SRBCT categories, gene-expression data from cDNA microarrays as obtained via Examples 1 and 2 above were used. The 63 training samples included both tumor biopsy material (13 EWS and 10 RMS) and cell lines (10 EWS, 10 RMS, 12 NB and 8 Burkitt lymphomas (BL; a subset of NHL). For two samples, ST486 (BL-C2 and C4) and GICAN(NB-C2 and C7), we performed two independent microarray experiments to test the reproducibility of the experiments and these were subsequently treated as separate samples.

Genes were filtered based on the intensity of the fluorescence gathered from the cDNA microarray. This type of filtering was designed to remove spots for which image analysis failed. Genes were filtered by requiring that a gene have a red intensity greater than 20 across all experiments. The number of genes that passed this filter was 2308. Each slide was normalized across all experiments. Therefore the expression level was based on a relative (or normalized) red intensity (RRO) for each gene, RRI=mean intensity of that spot/mean intensity of filtered genes. The natural logarithm (ln) of RRI was used as a measure of the expression levels.

Principal component analysis (PCA) further reduced the dimensionality. To allow for a supervised regression model with no over-training (when we have low number of parameters as compared to the number of samples), the dimensionality of the samples was reduced by PCA using centralized ln (RRI) values as input. Thus each sample was represented by 88 numbers, which are the results of projection of the gene expressions using PCA eigenvectors. We used the 10 dominant PCA components for subsequent analysis. These 10 dominant components contained 63% of the variance in the data matrix. The remaining PCA components contained variance unrelated to separating the four cancers.

Figure 5:
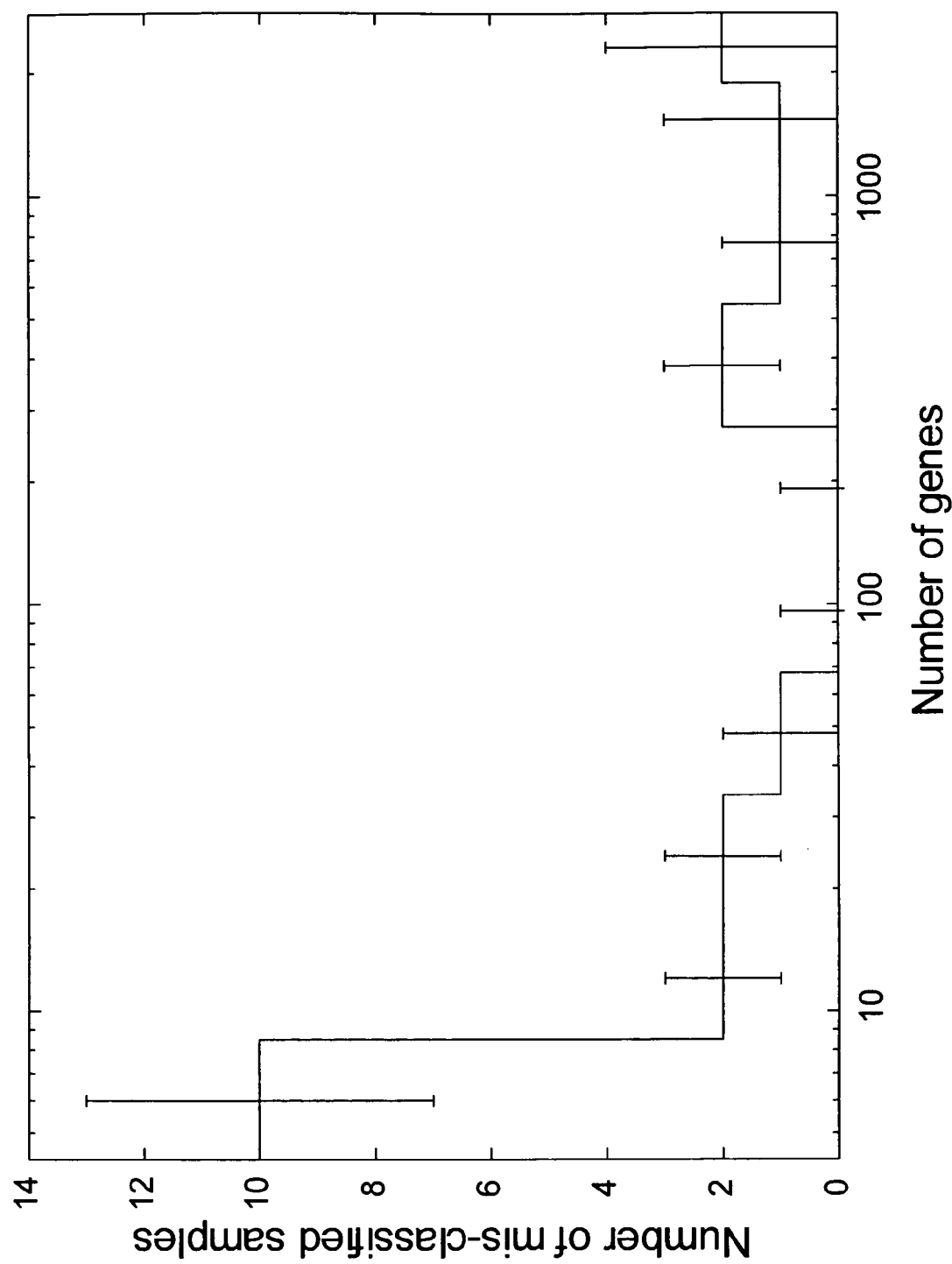
FIG. 5 represents a plot of the average number of misclassified samples for all 3750 models plotted against an increasing number of used genes.

We classified the training samples in the 4 categories using a 3-fold cross validation procedure: the 63 training (labeled) samples were randomly shuffled and split into 3 equally sized groups. Each linear ANN model was then calibrated with the 10 PCA input variables (normalized to centralized z-scores) using 2 of the groups, with the third group reserved for testing predictions (validation). This procedure was repeated 3 times, each time with a different group used for validation. The random shuffling was redone 1250 times and for each shuffling we analyzed 3 ANN models. Thus, in total, each sample belonged to a validation set 1250 times, and 3750 ANN models were calibrated. The three-fold cross-validation procedure produced at total of 3750 ANN models, and the training and validation was successful, see FIG. 5.

Figure 4:
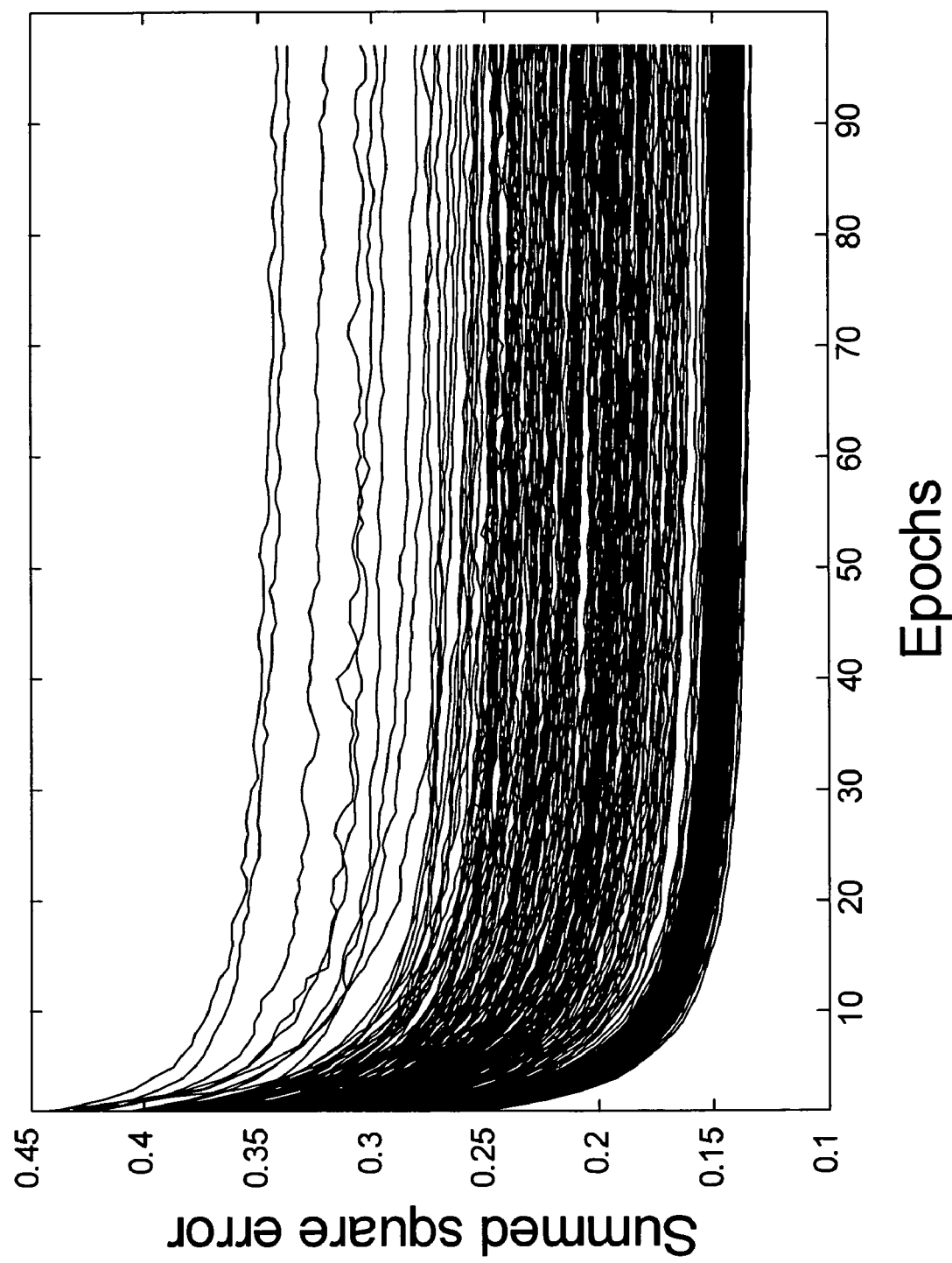
FIG. 4 represents a plot of the average classification error per sample (using a summed square error function) plotted during the training iterations (epochs) for both the training and validation samples.

In addition, there was no sign of 'over-training' of the models, as would be shown by a rise in the summed square error for the validation set with increasing training iterations or 'epochs', see FIG. 4.

For each diagnostic category (EWS, RMS, NB or BL), each ANN model gave an output between 0 (not this category) and 1 (this category). The 1250 outputs for each validation sample were used as a committee as follows. We calculated the average of all the predicted outputs (a committee vote) and then a sample was classified as a particular cancer if it received the highest committee vote for that cancer. In clinical settings, it is important to be able to reject a diagnostic classification including samples not belonging to any of the four diagnoses. Therefore, to be able to reject classification we did as follows. A squared Euclidean distance was computed for each cancer type, between the committee vote for a sample and the 'ideal' output for that cancer type; normalized such that it is unity between cancer types as described above. Using the 1250 ANN models for each validation sample we constructed for each cancer type an empirical probability distribution for the distances. Using these distributions, samples are only diagnosed as a specific cancer if they lie within the 95th percentile. All 3750 models were used to classify the additional 25 test samples.

Using these ANN models, all of the 63 training samples were correctly assigned/classified to their respective categories, having received the highest committee vote (average output) for that category.

Diagnostic results for the 63 training samples can be seen in TABLE 3 below.

TABLE 3

Training sample characteristics

| Sample Label | Source Label | Histological Diagnosis | ANN EWS | Committee Vote RMS | NB | BL | Source |
|---|---|---|---|---|---|---|---|
| EWS-C1 | A4573 | EWS-C | 0.91 | 0.02 | 0.27 | 0.04 | NCI |
| EWS-C2 | TC71 | EWS-C | 0.85 | 0.03 | 0.16 | 0.08 | NCI |
| EWS-C3 | TC106 | EWS-C | 0.89 | 0.04 | 0.10 | 0.08 | NCI |
| EWS-C4 | 5838 | EWS-C | 0.87 | 0.09 | 0.08 | 0.04 | NCI |
| EWS-C6 | A673 | EWS-C | 0.93 | 0.11 | 0.03 | 0.05 | NCI |
| EWS-C7 | ES-CL1 | EWS-C | 0.94 | 0.06 | 0.08 | 0.04 | MSKCC |
| EWS-C8 | TC32 | EWS-C | 0.98 | 0.05 | 0.04 | 0.04 | NCI |
| EWS-C9 | SK-ES-1 | EWS-C | 0.94 | 0.10 | 0.03 | 0.05 | ATCC |
| EWS-C10 | SK-N-MC | EWS-C | 0.81 | 0.22 | 0.03 | 0.06 | ATCC |
| EWS-C11 | RDES | EWS-C | 0.93 | 0.05 | 0.03 | 0.07 | ATCC |
| EWS-T1 | ES20 | EWS-T | 0.99 | 0.04 | 0.03 | 0.06 | MSKCC |
| EWS-T2 | ES13 | EWS-T | 0.95 | 0.08 | 0.06 | 0.04 | MSKCC |
| EWS-T3 | ES16 | EWS-T | 0.97 | 0.10 | 0.05 | 0.03 | MSKCC |
| EWS-T4 | ES17 | EWS-T | 0.93 | 0.14 | 0.11 | 0.02 | MSKCC |
| EWS-T6 | ES22 | EWS-T | 0.97 | 0.12 | 0.04 | 0.04 | MSKCC |
| EWS-T7 | ES25 | EWS-T | 0.99 | 0.04 | 0.03 | 0.04 | MSKCC |
| EWS-T9 | 9602P006 | EWS-T | 0.95 | 0.13 | 0.03 | 0.03 | CHTN |
| EWS-T11 | 9703P152 | EWS-T | 0.99 | 0.03 | 0.06 | 0.03 | CHTN |
| EWS-T12 | 9704P218 | EWS-T | 1.00 | 0.02 | 0.03 | 0.03 | CHTN |
| EWS-T13 | ES23 | EWS-T | 0.67 | 0.28 | 0.16 | 0.04 | MSKCC |
| EWS-T14 | 9605P074 | EWS-T | 0.99 | 0.02 | 0.04 | 0.05 | CHTN |
| EWS-T15 | 9609P027 | EWS-T | 0.99 | 0.03 | 0.06 | 0.03 | CHTN |
| EWS-T19 | SARC75 | EWS-T | 0.93 | 0.06 | 0.09 | 0.04 | CHTN |
| RMS-C2 | RD | ERMS-C | 0.06 | 0.81 | 0.11 | 0.03 | ATCC |
| RMS-C3 | RH4 | ARMS-C | 0.04 | 0.84 | 0.05 | 0.03 | NCI |
| RMS-C4 | RH3 | ARMS-C | 0.00 | 0.88 | 0.11 | 0.05 | NCI |
| RMS-C5 | RH5 | ARMS-C | 0.01 | 0.91 | 0.09 | 0.04 | NCI |
| RMS-C6 | RH28 | ARMS-C | 0.00 | 0.87 | 0.07 | 0.07 | NCI |
| RMS-C7 | RH30 | ARMS-C | 0.01 | 0.88 | 0.09 | 0.03 | NCI |
| RMS-C8 | CTR | ERMS-C | 0.03 | 0.86 | 0.07 | 0.03 | ATCC |
| RMS-C9 | RH4 | ARMS-C | 0.05 | 0.86 | 0.03 | 0.05 | NCI |
| RMS-C10 | RMS13 | ARMS-C | 0.01 | 0.90 | 0.14 | 0.03 | NCI |
| RMS-C11 | TE671 | ERMS-C | 0.07 | 0.77 | 0.08 | 0.03 | ATCC |
| RMS-T1 | RMS3 | ARMS-T | 0.02 | 0.93 | 0.03 | 0.06 | MSKCC |
| RMS-T2 | RMS6 | ARMS-T | 0.06 | 0.86 | 0.03 | 0.04 | MSKCC |
| RMS-T3 | RMS2 | ERMS-T | 0.08 | 0.80 | 0.07 | 0.02 | MSKCC |
| RMS-T4 | RMS5 | ERMS-T | 0.07 | 0.93 | 0.03 | 0.03 | MSKCC |
| RMS-T5 | RMS10 | ARMS-T | 0.05 | 0.84 | 0.08 | 0.03 | MSKCC |
| RMS-T6 | RT1 | RMS-T | 0.04 | 0.93 | 0.05 | 0.03 | CHTN |
| RMS-T7 | RT4 | ERMS-T | 0.10 | 0.75 | 0.05 | 0.05 | CHTN |
| RMS-T8 | RT5 | RMS-T | 0.06 | 0.90 | 0.05 | 0.02 | CHTN |
| RMS-T10 | RT2 | RMS-T | 0.02 | 0.93 | 0.06 | 0.03 | CHTN |
| RMS-T11 | RHAB2 | ERMS-T | 0.03 | 0.76 | 0.06 | 0.03 | CHTN |
| NB-C1 | KCNR | NB-C | 0.00 | 0.08 | 0.93 | 0.03 | NCI |
| NB-C2 | GICAN | NB-C | 0.03 | 0.10 | 0.70 | 0.03 | NCI |
| NB-C3 | SK-N-AS | NB-C | 0.01 | 0.26 | 0.64 | 0.04 | ATCC |
| NB-C4 | LAN5 | NB-C | 0.02 | 0.03 | 0.85 | 0.06 | NCI |
| NB-C5 | SK-N-BE2 | NB-C | 0.02 | 0.02 | 0.92 | 0.06 | ATCC |
| NB-C6 | SK-N-DZ | NB-C | 0.02 | 0.02 | 0.89 | 0.09 | ATCC |
| NB-C7 | GICAN | NB-C | 0.07 | 0.05 | 0.80 | 0.08 | NCI |
| NB-C8 | NGP | NB-C | 0.00 | 0.06 | 0.96 | 0.04 | NCI |
| NB-C9 | SH-SY5Y | NB-C | 0.06 | 0.04 | 0.85 | 0.04 | ATCC |
| NB-C10 | SK-N-FI | NB-C | 0.00 | 0.12 | 0.91 | 0.03 | ATCC |
| NB-C11 | SK-N-SH | NB-C | 0.06 | 0.01 | 0.95 | 0.05 | ATCC |
| NB-C12 | CHP-134B | NB-C | 0.02 | 0.24 | 0.41 | 0.06 | NCI |
| BL-C1 | RAMOS(RA1) | BL-C | 0.03 | 0.06 | 0.08 | 0.90 | ATCC |
| BL-C2 | ST486 | BL-C | 0.04 | 0.12 | 0.04 | 0.82 | ATCC |
| BL-C3 | CA46 | BL-C | 0.07 | 0.09 | 0.02 | 0.89 | ATCC |
| BL-C4 | ST486 | BL-C | 0.04 | 0.06 | 0.08 | 0.80 | ATCC |
| BL-C5 | RAJI | BL-C | 0.10 | 0.04 | 0.04 | 0.87 | ATCC |
| BL-C6 | MC116 | BL-C | 0.10 | 0.02 | 0.09 | 0.87 | ATCC |
| BL-C7 | DAUDI | BL-C | 0.09 | 0.04 | 0.02 | 0.93 | ATCC |
| BL-C8 | SULTAN | BL-C | 0.20 | 0.03 | 0.03 | 0.89 | ATCC |

Source label refers to the original name of the sample as labeled by the source. Histological diagnosis is defined as cancer type suffixed with -T for a tumor sample and -C for a cell line. Highlighted in gray is the ANN classification of the samples. NCI: National Cancer Institute, National Institutes of Health, ATCC: American Type Culture Collection, MSKCC: Memorial Sloan-Kettering Cancer Center, CHTN: Cooperative Human Tissue Network.

Example 4

Optimization of Genes Utilized for Classification

The contribution of each gene to the classification by the ANN models was determined by measuring the sensitivity of the classification to a change in the expression level of each gene, using the 3750 previously calibrated models.

The sensitivity to the different genes was determined by the absolute value of the partial derivative of the output with respect to the gene expressions, averaged over samples and ANN models. A large sensitivity implied that changing the expression influences the output significantly.

In this way the genes were ranked according to their significant for the classification. We then determined the classification error rate using increasing numbers of these ranked genes. The classification error rate minimized to 0% at 96 genes, see FIG. 5. The 10 dominant PCA components for these 96 genes contained 79% of the variance in the data matrix. Using only these 96 genes, we recalibrated the ANN models and again correctly classified all 63 samples, see FIG.

Figure 8:
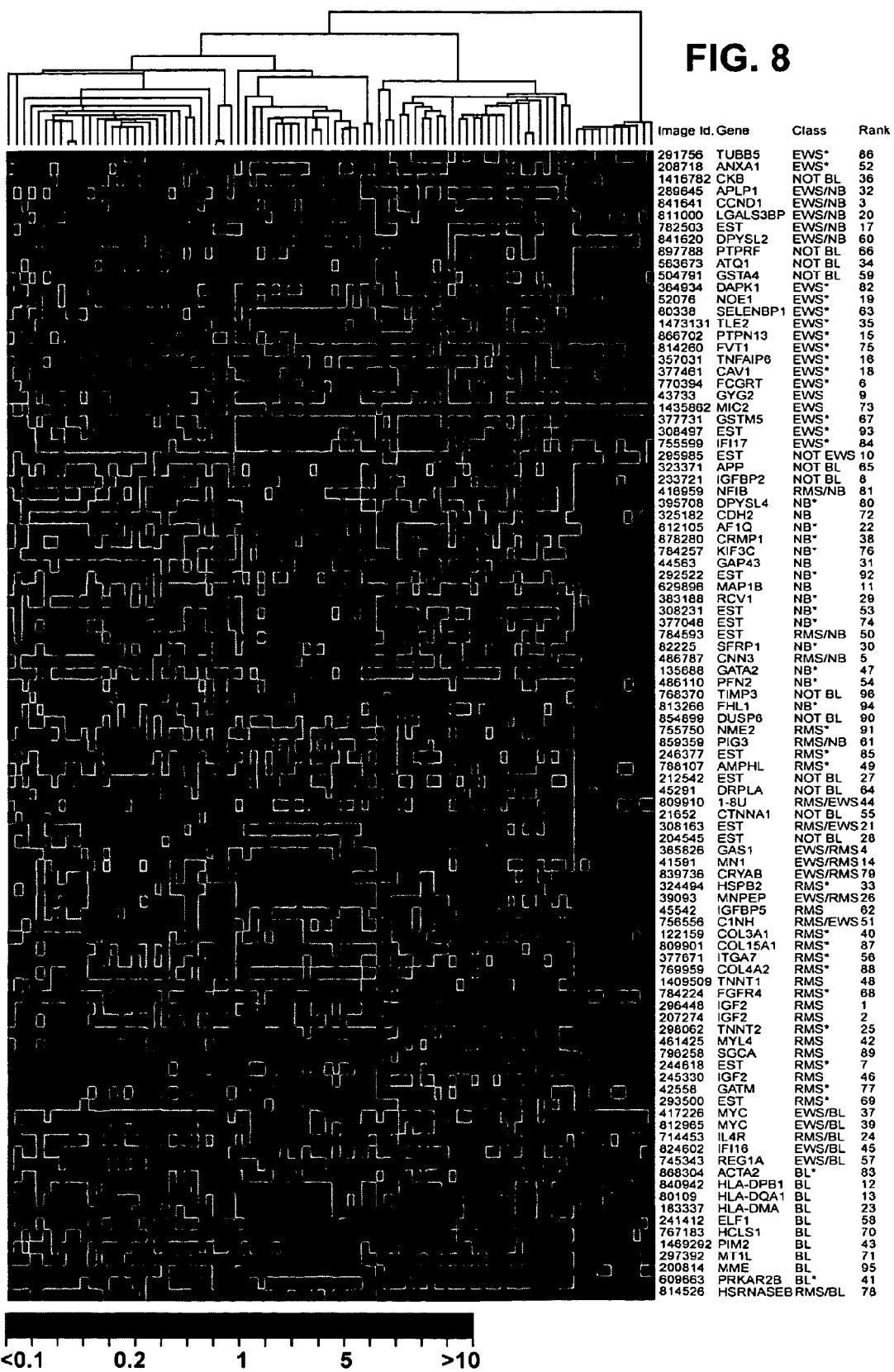
FIG. 8 represents a hierarchical clustering of the samples and genes, where each row represents one of the 96 cDNA clones, and each column represents a separate sample.

6. Moreover, multidimensional scaling (MDS) analysis using these 96 genes clearly separated the four cancer types, see FIG. 7. The top 96 discriminators represented 93 unique genes, see FIG. 8, as IGF2 was represented by three independent clones and MYC by two.

Of the 96 genes, 13 were anonymous expressed sequence tags (ESTs); 16 genes were specifically expressed in EWS, 20 in RMS, 15 in NB and 10 in BL. Twelve genes were good discriminators on the basis of lack of expression in BL and variable expression in the other three types. One gene (EST; Clone ID 295985) discriminated EWS from other cancer types by its lack of expression in this cancer. The remainder of the genes was expressed in two of the four cancer types. To our knowledge, of the 61 genes that were specifically expressed in cancer type, 41 have not been previously reported as associated with these diseases.

Example 5

Diagnostic Classification and Hierarchical Clustering

The diagnostic classification capabilities of these ANN models were then tested on a set of 25 blinded test samples. Samples were classified to a diagnostic category if they received the highest vote for that category. As this classifier had only four possible outputs, all samples were classified to one of the four categories. We therefore established a diagnostic classification method based on a statistical cutoff to enable us to reject a diagnosis of a sample classified to a given category. If a sample falls outside the 95th percentile of the probability distribution of distances between samples and their ideal output (for example for EWS it is EWS=1, RMS=NB=BL=0), its diagnosis is rejected.

TABLE 4

| Sample label | ANN committee vote EWS | RMS | NB | BL | ANN classification | ANN diagnosis | Histological diagnosis | Source label | Source |
|---|---|---|---|---|---|---|---|---|---|
| Test 1 | 0.01 | 0.07 | 0.76 | 0.06 | NB | NB | NB-C | IMR32 | ATCC |
| Test 2 | 0.67 | 0.06 | 0.08 | 0.09 | EWS | EWS | EWS-C | CHOP1 | NCI |
| Test 3 | 0.11 | 0.17 | 0.16 | 0.11 | RMS | — | Osteosarcoma-C | OsA-CI | ATCC |
| Test 4 | 0.00 | 0.95 | 0,06 | 0.03 | RMS | RMS | ARMS-T | ARMD1 | CHTN |
| Test 5 | 0.11 | 0.11 | 0.25 | 0.10 | NB | — | Sarcoma-C | A204 | ATCC |
| Test 6 | 0.98 | 0.04 | 0.10 | 0.03 | EWS | EWS | EWS-T | 9608P053 | CHTN |
| Test 7 | 0.05 | 0.02 | 0.05 | 0.93 | BL | BL | BL-C | EB1 | ATCC |
| Test 8 | 0.00 | 0.05 | 0.94 | 0.04 | NB | NB | NB-C | SMSSAN | NCI |
| Test 9 | 0.22 | 0.60 | 0.03 | 0.06 | RMS | — | Sk. Muscle | SkM1 | CHTN |
| Test 10 | 0.10 | 0.68 | 0.11 | 0,04 | RMS | — | ERMS-T | ERDM1 | CHTN |
| Test 11 | 0.39 | 0.04 | 0.28 | 0.15 | EWS | — | Prostate Ca.-C | PC3 | ATCC |
| Test 12 | 0.89 | 0.05 | 0.14 | 0.03 | EWS | EWS | EWS-T | SARC67 | CHTN |
| Test 13 | 0.20 | 0.7 | 0.03 | 0.05 | RMS | — | Sk. Muscle | SkM2 | CHTN |
| Test 14 | 0.03 | 0.02 | 0.90 | 0.07 | NB | NB | NB-T | NB3 | DZNSG |
| Test 15 | 0.06 | 0.03 | 0,05 | 0.91 | BL | BL | BL-C | EB2 | ATCC |
| Test 16 | 0.03 | 0.02 | 0.93 | 0.05 | NB | NB | NB-T | NB1 | DZNSG |
| Test 17 | 0,01 | 0.90 | 0.05 | 0.03 | RMS | RMS | ARMS-T | ARMD2 | CHTN |
| Test 18 | 0.06 | 0.04 | 0,04 | 0.88 | BL | BL | BL-C | GA10 | ATCC |
| Test 19 | 0.99 | 0.02 | 0.04 | 0.05 | EWS | EWS | EWS-T | ET3 | CHTN |
| Test 20 | 0.40 | 0.30 | 0,10 | 0.06 | EWS | — | EWS-T | 9903P1339 | CHTN |
| Test 21 | 0.81 | 0.19 | 0.12 | 0,04 | EWS | EWS | EWS-T | ES23 | MSKCC |
| Test 22 | 0.01 | 0.88 | 0.09 | 0.04 | RMS | RMS | ERMS-T | ERMD2 | CHTN |
| Test 23 | 0.07 | 0.08 | 0.70 | 0.06 | NB | NB | NB-T | NB2 | DZNSG |

TABLE 4-continued

| Sample label | ANN committee vote | | | | ANN classification | ANN diagnosis | Histological diagnosis | Source label | Source |
|---|---|---|---|---|---|---|---|---|---|
| | EWS | RMS | NB | BL | | | | | |
| Test 24 | 0.05 | 0.87 | 0.06 | 0.03 | RMS | RMS | ERMS-T | RMS4 | MSKCC |
| Test 25 | 0.05 | 0.02 | 0.89 | 0.06 | NB | NB | NB-T | NB4 | DZNSG |

Source label refers to the original name of the sample as designated by the source. Histological diagnosis is defined as cancer type suffixed with -T for a tumor sample and -C for a cell line. Normal skeletal muscle (Sk. Muscle) is also included in the test set. The ANN classification as determined by the committee vote is bolded, NCI: National Cancer Institate, National Institutes of Health, ATCC: American Type Culture Collection, MSKCC: Memorial Sloan-KetteringCancer Center. CHTN: Cooperative Human Tissue Network, DZNSG: German Cancer Research Center, Heidelberg.

Figure 6:
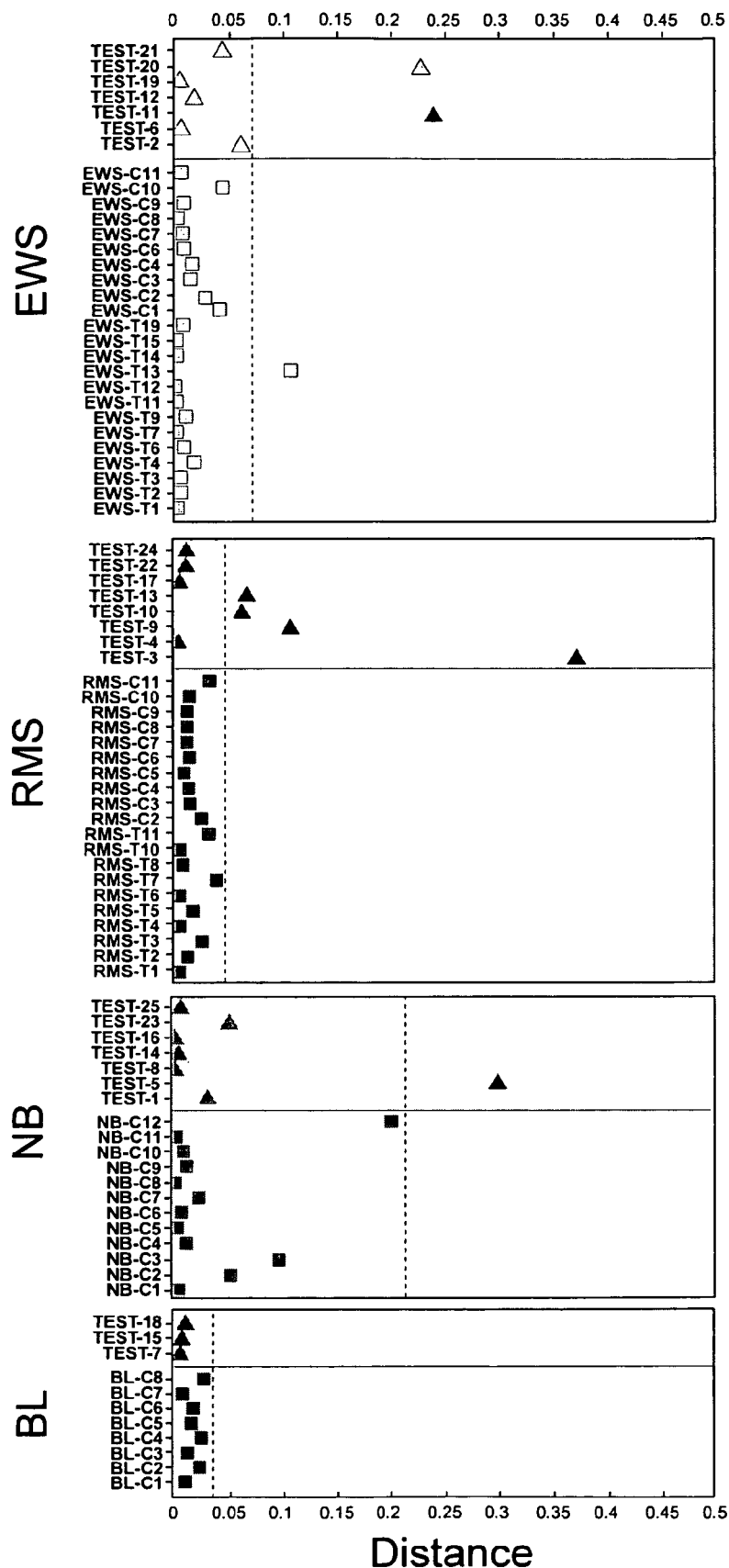
FIG. 6 represents a plot of the distance from the samples committee vote to the ideal vote for that diagnostic category.

The test samples contained both tumors (5 EWS, 5 RMS and 4 NB) and cell lines (1 EWS, 2 NB and 3 BL). The ability of these models to reject a diagnosis on 5 non-SRBCTs was also tested (consisting of 2 normal muscle tissues (Tests 9 and 13) and 3 cell lines including an undifferentiated sarcoma (Test 5), osteosarcoma (Test 3) and a prostate carcinoma (Test 11)). Using the 3750 ANN models calibrated with the 96 genes, we correctly classified 100% of the 20 SRBCT tests (FIG. 6 and TABLE 4) as well as all 63 training samples, see TABLE 2. Three of these samples, Test 10, Test 20 and EWS-T13 were correctly assigned to their categories (RMS, EWS and EWS respectively), having received the highest vote for their respective categories. However, their distance from a perfect vote was greater than the expected 95th percentile distance (FIG. 6); therefore, we could not confidently diagnose them by this criterion. All of the five non-SRBCT samples were excluded from any of the four diagnostic categories, since they fell outside the 95th percentiles. Using these criteria for all 88 samples, the sensitivity of the ANN models for diagnostic classification was 93% for EWS, 96% for RMS and 100% for both NB and BL. The specificity was 100% for all four diagnostic categories.

Figure 9:
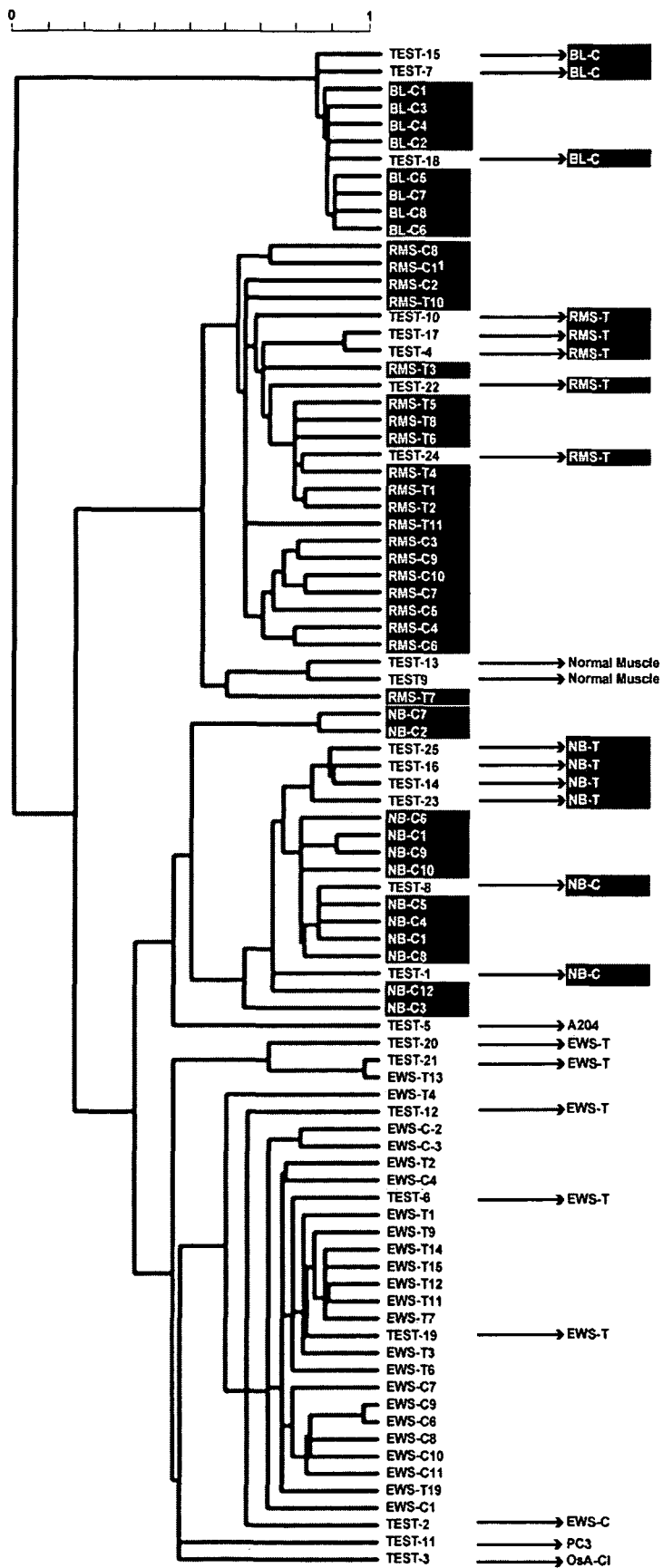
FIG. 9 represents a hierarchical clustering dendrogram of the samples in FIG. 8.

Also, hierarchical clustering using the 96 genes, identified from the ANN models, correctly clustered all 20 of the test samples (FIG. 9). Moreover, the two pairs of samples that were derived from two cell lines, BL-C2 and C4 (ST486) and NB-C2 and C7 (GICAN), were adjacent to one another in the same cluster.

Example 6

Expression of FGFR4 on SRBCT Tissue Array

To confirm the effectiveness of the ANN models to identify genes that show preferential high expression in specific cancer types at the protein level, we performed immunohistochemistry on SRBCT tissue arrays for the expression of fibroblast growth factor receptor 4 (FGFR4). This tyrosine kinase receptor is expressed during myogenesis but not in adult muscle, and is of interest because of its potential role in tumor growth and in prevention of terminal differentiation in muscle. Moderate to strong cytoplasmic immunostaining for FGFR4 was seen in all 26 RMSs tested (17 alveolar, 9 embryonal). We also observed generally weaker staining in EWS and NHL in agreement with the microarray results, except for one of anaplastic large cell lymphoma that was strongly positive (data not shown).

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. The present invention is presently embodied as a method, apparatus, and a computer data product containing a computer program for classifying and diagnosing disease using artificial neural networks.

The above specification, examples and data provide a complete description of the manufacture and use of the composition of the invention. Since many embodiments of the invention can be made without departing from the spirit and scope of the invention, the invention resides in the claims hereinafter appended.

The claimed invention is:

1. A method of diagnosing a disease by distinguishing a first disease from a second disease comprising the steps of:
   (a) obtaining high dimensional experimental data from a first biological sample known to be of the first disease and a second biological sample known to be of the second disease by isolating nucleic acids or proteins from each biological sample and detecting the nucleic acids or protein from each sample to determine gene expression levels, protein expression levels, single nucleotide polymorphisms, or comparative genomic analysis of each sample;
   (b) filtering said data by removing data that does not meet a predetermined threshold;
   (c) reducing the dimensionality of said data by selecting the features of the data;
   (d) training a supervised pattern recognition method using data obtained from the first biological sample and the second biological sample to obtain a probability distribution relationship between the data obtained from the first biological sample and the first disease and between the data obtained from the second biological sample and the second disease;
   (e) ranking individual data points from said high dimensional data by determining the sensitivity of the data point to the classification to the first disease or second disease, wherein said ranking is dependent on an outcome of said supervised pattern recognition method;
   (f) choosing a first set of multiple data points from said high dimensional data as predictive for the first disease and choosing a second set of multiple data points from said high dimensional data as predictive for the second disease, wherein said choice is based on said relative ranking of said individual data points; and
   (g) determining whether the subject whose disease condition is unknown has the first or second disease by identifying the presence of said first or second set of multiple data points in experimental data obtained from a biological sample from the subject whose disease condition is unknown.

2. The method of claim 1, wherein said high dimensional data is gene expression data.

3. The method of claim 2, wherein said gene expression data is obtained by using a cDNA or an oligonucleotide microarray.

4. The method of 3, wherein said step of filtering said gene expression data is based on the intensity of the spots on said microarray.

5. The method of claim 1, wherein said method of reducing the dimensionality of said data is accomplished by principal component analysis.

6. The method of claim 1, wherein said multiple data points chosen from said data comprise at least 96 individual data points.

7. The method of claim 1, wherein said first and second disease are chosen from the group consisting of multiple sclerosis, rheumatoid arthritis, and different types of cancer.

8. The method of claim 7, wherein said first and second disease are cancer.

9. The method of claim 8, wherein said first and second disease are selected from the group consisting of neuroblastoma, rhabdomyosarcoma, non-Hodgkin lymphoma, and a Ewing family of tumors.

10. A computer-based method of determining a set of multiple data points for use in diagnosing, predicting, or prognosticating about a disease, the computer-based method comprising:

(a) obtaining high dimensional experimental data from a biological sample known to be of the disease by isolating nucleic acids or proteins from each biological sample and detecting the nucleic acids or protein from each sample to determine gene expression levels, protein expression levels, single nucleotide polymorphisms, or comparative genomic analysis of each sample, and receiving the experimental data representing high dimensional data by a receiver module of the computer;

(b) filtering the experimental data by removing data that does not meet a predetermined threshold by a filter module;

(c) reducing the dimensionality of the experimental data using one or more methods;

(d) dividing the experimental data into a training data set and a validation data set;

(e) generating a probability distribution relationship between the gene expression data and the disease using the training data and a training module;

(f) validating the performance of the probability distribution relationship using the validation data set;

(g) generating a ranking data value for each gene corresponding to a relative ranking for individual data points using the data from a trained artificial neural network by using a ranking module; and (h) choosing a set of multiple data points from the data using the ranking data values that is predictive of the presence of the disease; and (i) using the set of data points to detect the presence of the disease in a patient by obtaining high dimensional experimental data from a biological sample from the patient and determining whether the set of multiple data points are present in the biological sample from the patient.

11. A computer readable storage medium comprising:

a receiver module for receiving data representing experimental gene expression data obtained from a biological sample known to be of the disease;

a filter module encoded to filter the gene expression data;

a module that reduces the dimensionality of the gene expression data using principle component analysis;

a training module encoded to train and validate a probability distribution relationship using a training data set to generate the probability distribution relationship between the gene expression data and the disease and using a validation data set to validate the probability distribution relationship;

a ranking module encoded to generate a ranking data value corresponding to a relative ranking for individual genes using the training module and encoded to choose a set of data points that correspond to multiple genes from the gene expression data using the ranking data value for each gene; and a diagnostic module encoded to diagnose the presence of the disease in the subject by detecting the presence of the set of data points for multiple genes in experimental gene expression data obtained from a biological sample from the subject.

* * * * *